(12) United States Patent
Yoshinaga et al.

(10) Patent No.: US 9,522,914 B2
(45) Date of Patent: Dec. 20, 2016

(54) AZOLE DERIVATIVE

(71) Applicant: TAISHO PHARMACEUTICAL CO., LTD, Toshima-ku, Tokyo (JP)

(72) Inventors: Mitsukane Yoshinaga, Tokyo (JP); Takeshi Kuwada, Tokyo (JP); Naoki Miyakoshi, Tokyo (JP); Tomoko Ishizaka, Tokyo (JP); Daisuke Wakasugi, Tokyo (JP); Shin-ichi Shirokawa, Tokyo (JP); Nobutaka Hattori, Tokyo (JP); Youichi Shimazaki, Tokyo (JP)

(73) Assignee: TAISHO PHARMACEUTICAL CO., LTD, Tokyo (JP)

( * ) Notice: Subject to any disclaimer, the term of this patent is extended or adjusted under 35 U.S.C. 154(b) by 223 days.

(21) Appl. No.: 14/353,447

(22) PCT Filed: Oct. 25, 2012

(86) PCT No.: PCT/JP2012/077541
§ 371 (c)(1),
(2) Date: Apr. 22, 2014

(87) PCT Pub. No.: WO2013/062027
PCT Pub. Date: May 2, 2013

(65) Prior Publication Data
US 2014/0275006 A1 Sep. 18, 2014

(30) Foreign Application Priority Data

Oct. 27, 2011 (JP) .................................. 2011-236487

(51) Int. Cl.
| | | |
|---|---|---|
| C07D 491/107 | (2006.01) | |
| C07D 471/08 | (2006.01) | |
| C07D 403/10 | (2006.01) | |
| C07D 498/08 | (2006.01) | |
| C07D 233/64 | (2006.01) | |
| C07D 401/10 | (2006.01) | |
| C07D 231/12 | (2006.01) | |
| C07D 233/70 | (2006.01) | |
| C07D 233/90 | (2006.01) | |
| C07D 401/04 | (2006.01) | |
| C07D 403/04 | (2006.01) | |
| C07D 403/06 | (2006.01) | |
| C07D 413/10 | (2006.01) | |
| C07D 249/08 | (2006.01) | |
| C07D 451/06 | (2006.01) | |
| C07D 249/10 | (2006.01) | |

(Continued)

(52) U.S. Cl.
CPC ......... C07D 471/08 (2013.01); C07D 207/444 (2013.01); C07D 231/12 (2013.01); C07D 233/64 (2013.01); C07D 233/70 (2013.01); C07D 233/90 (2013.01); C07D 249/08 (2013.01); C07D 249/10 (2013.01); C07D 249/12 (2013.01); C07D 263/32 (2013.01); C07D 277/20 (2013.01); C07D 277/30 (2013.01); C07D 401/04 (2013.01); C07D 401/10 (2013.01); C07D 403/04 (2013.01); C07D 403/06 (2013.01); C07D 403/10 (2013.01); C07D 413/10 (2013.01); C07D 451/06 (2013.01); C07D 491/107 (2013.01); C07D 498/08 (2013.01)

(58) Field of Classification Search
None
See application file for complete search history.

(56) References Cited

U.S. PATENT DOCUMENTS

2006/0276449 A1 12/2006 Kumagai et al.
2007/0037822 A1 2/2007 Letourneau et al.

(Continued)

FOREIGN PATENT DOCUMENTS

JP 2000-63363 A 2/2000
JP 2008-542444 A 11/2008

(Continued)

OTHER PUBLICATIONS

Lemmens-Gruber et al., Drugs of the future: Review, Vasopressin antagonists. Cellular and Molecular Life Sciences, 2006, 63, 1766-1779.*

(Continued)

Primary Examiner — Rebecca Anderson
Assistant Examiner — Po-Chih Chen
(74) Attorney, Agent, or Firm — Sughrue Mion, PLLC

(57) ABSTRACT

The present invention provides agents for treating or preventing diseases such as mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, alopecia, and so forth. Specifically, the invention provides azole derivatives represented by general formula (I), or pharmaceutically acceptable salts thereof that have an antagonistic action against the arginine-vasopressin (AVP) V1b receptor:

[Chem. 1]

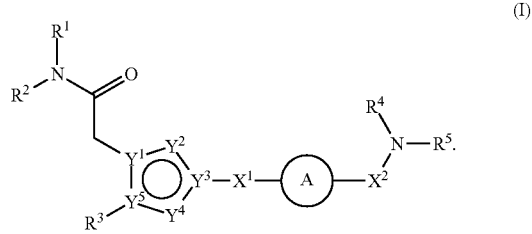

(I)

14 Claims, No Drawings

(51) Int. Cl.
*C07D 249/12* (2006.01)
*C07D 263/32* (2006.01)
*C07D 277/20* (2006.01)
*C07D 277/30* (2006.01)
*C07D 207/444* (2006.01)

(56) References Cited

U.S. PATENT DOCUMENTS

| | | |
|---|---|---|
| 2009/0312381 A1 | 12/2009 | Meier et al. |
| 2013/0190330 A1 | 7/2013 | Furstner et al. |
| 2013/0197217 A1 | 8/2013 | Kuwada et al. |

FOREIGN PATENT DOCUMENTS

| | | |
|---|---|---|
| JP | 2009-537581 A | 10/2009 |
| WO | 01/55130 A2 | 8/2001 |
| WO | 2005/021534 A1 | 3/2005 |
| WO | 2005/030755 A1 | 4/2005 |
| WO | 2006/095014 A1 | 9/2006 |
| WO | 2006/102308 A2 | 9/2006 |
| WO | 2006/133242 A2 | 12/2006 |
| WO | 2007/109098 A2 | 9/2007 |
| WO | 2007/134862 A1 | 11/2007 |
| WO | 2008/025736 A1 | 3/2008 |
| WO | 2008/033757 A2 | 3/2008 |
| WO | 2008/033764 A2 | 3/2008 |
| WO | 2009/017236 A1 | 2/2009 |
| WO | 2009/130231 A1 | 10/2009 |
| WO | 2009/130232 A1 | 10/2009 |
| WO | 2011/096461 A1 | 8/2011 |
| WO | 2011/104322 A1 | 9/2011 |
| WO | 2012/043791 A1 | 4/2012 |

OTHER PUBLICATIONS

Ferrier et al., Proinflammatory role of vasopressin through V1b receptors in hapten-induced experimental colitis in rodents: implication in IBD. The American Journal of Physiology—Gastrointestinal and Liver Physiology, 2010, 299, G1298-G1307.*

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Communication for European Application No. 12843663.1 dated Jan. 15, 2015, with Supplementary European Search Report (dated Dec. 22, 2014).

Russell et al., "In vitro and in vivo pharmacological characterisation of the potent and selective vasopressin V1A receptor antagonist 4-[4-(4-Chlorophenyl)-5-[1,2,3]triazol-2-ylmethyl-4H-[1,2,4]triazol-3-yl]piperdin-1-yl-(3,5-difluoro-phenyl)methanone.", European Journal of Pharmacology, 670:347-355 (2011).

Malhotra et al., "Substituted imidazole derivatives as novel cardiovascular agents", Bioorganic and Medicinal Chemistry Letters, 21:936-939 (2010).

Toru Sugimoto, et al., "Molecular Cloning and Functional Expression of a cDNA Encoding the Human V1b Vasopressin Receptor", The Journal of Biological Chemistry, 1994, pp. 27088-27092, vol. 269, No. 43.

Stephen J. Lolait, et al., "Extrapituitary expression of the rat V1b vasopressin receptor gene", National Institute of Mental Health, Proc. Natl. Acad. Sci. USA, Jul. 1995, pp. 6783-6787, vol. 92.

Christopher Vaccari, et al., "Comparative Distribution of Vasopressin V1b and Oxytocin Receptor Messenger Ribonucleic Acids in Brain", Endocrinology, 1998, pp. 5015-5033, vol. 139, No. 12.

Fernando Hernando, et al., "Immunohistochemical Localization of the Vasopressin V1b Receptor in the Rat Brain and Pituitary Gland: Anatomical Support for Its Involvement in the Central Effects of Vasopressin", Endocrinology, 2001, pp. 1659-1668, vol. 142, No. 4.

SR Wersinger, et al., "Vasopressin V1b receptor knockout reduces aggressive behavior in male mice", Molecular Psychiatry, 2002, pp. 975-984, vol. 7.

Gudrun Liebsch, et al., "Septal vasopressin modulates anxiety-related behaviour in rats", Neuroscience Letters, 1996, pp. 101-104, vol. 217.

Claudine Serradeil-Le Gal, et al., "Characterization of (2S, 4R)-1-[5-Chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist", The Journal of Pharmacology and Experimental Therapeutics, 2002, pp. 1122-1130, vol. 300, No. 2.

Guy Griebel, et al., "Anxiolytic-and antidepressant-like effects of the non-peptide vasopressin V1b receptor antagonist, SSR149415, suggest and innovative approach for the treatment of stress-related disorders", PNAS, Apr. 30, 2002, pp. 6370-6375, vol. 99, No. 9.

Jack D. Scott, et al., "Tetrahydroquinoline sulfonamides as vasopressin 1b receptor anatgonists", Bioorganic & Medicinal Chemistry Letters, 2009, pp. 6018-6022, vol. 19.

Chris A. Smethurst, et al., "The characterization of a novel V1b antagonist lead series", Bioorganic & Medicinal Chemistry Letters, 2011, pp. 92-96, vol. 21.

James Baker, et al., "Identification and optimisation of novel sulfonamide, selective vasopressin V1b receptor antagonists", Bioorganic & Medicinal Chemistry Letters, 2011, pp. 3603-3607, vol. 21.

International Search Report of PCT/JP2012/077541, dated Dec. 4, 2012.

* cited by examiner

AZOLE DERIVATIVE

CROSS REFERENCE TO RELATED APPLICATIONS

This application is a National Stage of International Application No. PCT/JP2012/077541 filed Oct. 25, 2012, claiming priority based on Japanese Patent Application No. 2011-236487, filed Oct. 27, 2011.

TECHNICAL FIELD

The present invention relates to a compound with an azole skeleton that has an antagonistic action against the arginine-vasopressin (AVP) V1b receptor and to pharmaceutical compositions comprising the compound as an active ingredient, in particular, to agents for treating or preventing diseases such as mood disorder (including depression), anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, and alopecia.

BACKGROUND ART

The arginine-vasopressin (AVP) is a peptide composed of nine amino acids that is biosynthesized mainly in the hypothalamus and closely involved as a posterior pituitary hormone in the regulation of plasma osmolality, blood pressure, and body fluid volume.

The AVP receptors have so far been cloned in three subtypes, V1a, V1b, and V2 receptors, all of which are known to be seven-transmembrane receptors. The V2 receptor is coupled to Gs to increase the cAMP level. The V1a receptor is coupled to Gq/11 to facilitate PI response and increase the intracellular Ca level. The V1a receptor is expressed in the brain, liver, adrenal gland, and vascular smooth muscle, for example, and is involved in the vasoconstrictive action. As is the V1a receptor, the V1b receptor is also coupled to Gq/11 to facilitate PI response (see Non-Patent Documents 1 and 2). The V1b receptor is found most commonly in the pituitary gland (expressed in 90% or more of ACTH secreting cells of the anterior lobe) and is estimated to participate in the AVP-mediated secretion of ACTH from the anterior pituitary. Other than in the pituitary gland, the V1b receptor is widely distributed in the brain and occurs in large amounts not only in the limbic cortex system including the hippocampus, amygdala and entorhinal cortex but also in the cerebral cortex, the olfactory bulb, and the raphe nuclei which are the nuclei of origin of the serotonin nervous system (see Non-Patent Documents 3 and 4).

In recent years, involvement of the V1b receptor in mood disorder or anxiety disorder has been suggested, and usefulness of V1b receptor antagonists is being studied. The V1b receptor KO mice exhibit reduced aggressive behavior (see Non-Patent Document 5). In addition, injection of a V1b receptor antagonist into the septal area prolonged the time spent in the open arms (anxiolytic-like action) in an elevated plus-maze test (see Non-Patent Document 6). In recent years, a peripherally administrable 1,3-dihydro-2H-indol-2-one compound has been created as a V1b receptor specific antagonist (see Patent Documents 1 to 3). Furthermore, the 1,3-dihydro-2H-indol-2-one compound has been reported to show antidepressant and anxiolytic actions in a variety of animal models (see Non-Patent Documents 7 and 8). The compound disclosed in Patent Document 1 has high affinity for the V1b receptor ($1 \times 10^{-9}$ mol/L to $4 \times 10^{-9}$ mol/L) on which it selectively acts; this compound, however, antagonizes AVP, AVP+CRF, and restraint stress-induced ACTH increases.

Recently, V1b receptor antagonists having different structures from the 1,3-dihydro-2H-indol-2-one compound have been reported and they are quinazolin-4-one derivatives (see Patent Documents 4 and 10), β-lactam derivatives (see Patent Documents 5 and 7), azinon/diazinon derivatives (see Patent Document 6), benzimidazolone derivatives (Patent Document 8), isoquinolinone derivatives (see Patent Documents 9 and 10), pyridopyrimidin-4-one derivatives (see Patent Document 11), pyrrolo[1,2-a]pyrazine derivatives (see Patent Document 12), pyrazolo[1,2-a]pyrazine derivatives (see Patent document 13), quinoline derivatives (see Patent Document 14), tetrahydroquinoline sulfonamide derivatives (see Non-Patent Document 9), thiazole derivatives (see Non-Patent Document 10), and sulfonamide derivatives (see Non-Patent Document 11). However, no report has been made of the compounds disclosed in the present invention that have an azole skeleton.

CITATION LIST

Patent Documents

Patent Document 1: WO2001/055130
Patent Document 2: WO2005/021534
Patent Document 3: WO2005/030755
Patent Document 4: WO2006/095014
Patent Document 5: WO2006/102308
Patent Document 6: WO2006/133242
Patent Document 7: WO2007/109098
Patent Document 8: WO2008/025736
Patent Document 9: WO2008/033757
Patent Document 10: WO2008/033764
Patent Document 11: WO2009/017236
Patent Document 12: WO2009/130231
Patent Document 13: WO2009/130232
Patent Document 14: WO2011/096461

Non-Patent Documents

Non-Patent Document 1: Sugimoto T, Kawashima G, J. Biol. Chem., 269, 27088-27092, 1994
Non-Patent Document 2: Lolait S, Brownstein M, PNAS, 92, 6783-6787, 1995
Non-Patent Document 3: Vaccari C, Ostrowski N, Endocrinology, 139, 5015-5033, 1998
Non-Patent Document 4: Hernando F, Burbach J, Endocrinology, 142, 1659-1668, 2001
Non-Patent Document 5: Wersinger S R, Toung W S, Mol. Psychiatry, 7, 975-984, 2002
Non-Patent Document 6: Liebsch G, Engelmann M, Neurosci. Lett., 217, 101-104, 1996
Non-Patent Document 7: Gal C S, Le Fur G, 300, JPET, 1122-1130, 2002
Non-Patent Document 8: Griebel G, Soubrie P, PNAS, 99, 6370-6375, 2002
Non-Patent Document 9: Jack D. Scott, et al., Bioorganic & Medicinal Chemistry Letters, 19, 21, 6018-6022, 2009
Non-Patent Document 10: Chris A S, et. al., Bioorganic & Medicinal Chemistry Letters, 21, 92-96, 2011
Non-Patent Document 11: James B, et. al., Bioorganic & Medicinal Chemistry Letters, 21, 3603-3607, 2011.

SUMMARY OF INVENTION

Technical Problem

It is an object of the present invention to find novel compounds having a V1b receptor antagonistic action and to provide agents for treating or preventing diseases such as mood disorder (including depression), anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, and alopecia.

Solution to Problem

As a result of diligent studies, the present inventors have found novel compounds with a novel azole skeleton that have a V1b receptor antagonistic action (the compounds are hereinafter referred to as "azole derivatives") and this has led to the accomplishment of the present invention.

Thus, the present invention includes the following embodiments:
(1) An azole derivative represented by Formula (I):

[Chem. 1]

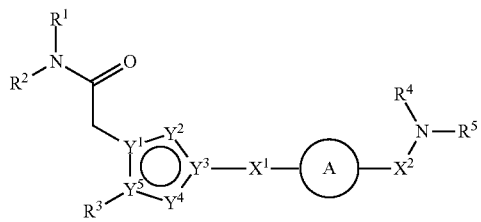

(I)

[in Formula (I),
$R^1$ represents a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocycle;
$R^2$ represents a hydrogen atom or $C_{1-5}$ alkyl;
$R^3$ represents aryl or heteroaryl (the aryl and heteroaryl are optionally substituted by one or two groups selected from the group consisting of $C_{1-5}$ alkoxy, $C_{1-5}$ alkyl, halogen atoms, trifluoromethyl, trifluoromethoxy, cyano, hydroxy, difluoromethoxy, and $C_{1-5}$ alkylsulfonyl);
$R^4$ and $R^5$ which may be the same or different each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or a 4- to 8-membered saturated or unsaturated heterocycle containing one or more nitrogen, oxygen or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or
$R^4$ and $R^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, trifluoromethyl, amino, mono-$C_{1-5}$ alkylamino, di-$C_{1-5}$ alkylamino and $C_{2-5}$ alkanoylamino, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl or 7-oxa-2-azaspiro[3.5]non-2-yl;
the optionally substituted azole ring which is represented by the following formula (α):

[Chem. 2]

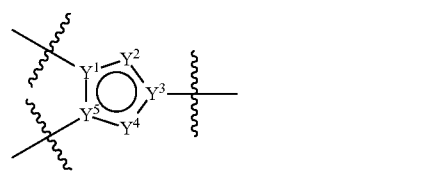

(α)

has any one of the structrures in the following formula group (II):

[Chem. 3]

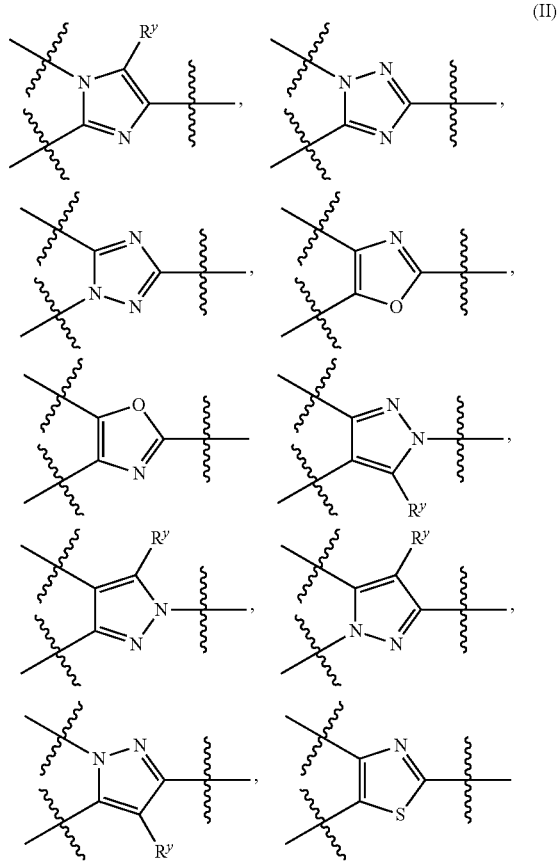

(II)

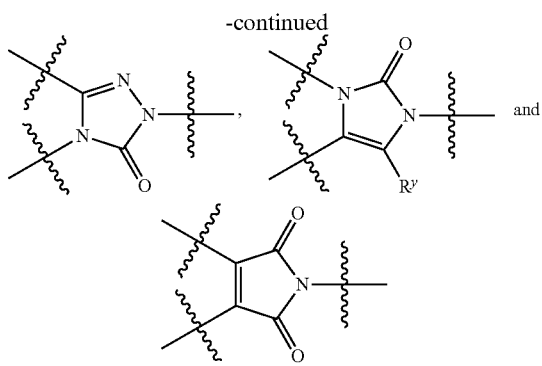

where $R^y$ represents a hydrogen atom or $C_{1-5}$ alkyl;

$X^1$ and $X^2$ are such that i) when $X^1$ is a single bond or the formula —CO—, $X^2$ represents —$C_{1-5}$ alkylene- or —O—$C_{1-5}$ alkylene-; and ii) when $X^1$ is the formula —CONR$^{x1}$—, $X^2$ represents a single bond;

$R^{x1}$ represents a hydrogen atom or $C_{1-5}$ alkyl; and the ring A represents a benzene ring, a 6-membered aromatic heterocycle (the benzene ring and the 6-membered aromatic heterocycle are optionally substituted by one or two groups selected from the group consisting of halogen atoms and $C_{1-5}$ alkoxy), a 4- to 8-membered saturated or partially unsaturated heterocycle containing one or two nitrogen atoms (the 4- to 8-membered saturated or unsaturated heterocycle is optionally substituted by one oxo) or $C_{3-7}$ cycloalkane] or a pharmaceutically acceptable salt of the azole derivative.

(2) The azole derivative or pharmaceutically acceptable salt thereof according to embodiment (1), wherein in the above Formula (I), $R^4$ and $R^5$ which may be the same or different each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or a 4- to 8-membered saturated or unsaturated heterocycle containing one or more nitrogen, oxygen or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl or 7-oxa-2-azaspiro[3.5]non-2-yl.

(3) The azole derivative or pharmaceutically acceptable salt thereof according to embodiment (1) or (2), wherein in the above Formula (I), $X^1$ represents a single bond;

$X^2$ represents —$C_{1-5}$ alkylene- or —O—$C_{1-5}$ alkylene-; and the ring A represents a benzene ring, a 6-membered aromatic heterocycle (the benzene ring and the 6-membered aromatic heterocycle are optionally substituted by one or two groups selected from the group consisting of halogen atoms and $C_{1-5}$ alkoxy) or a 4- to 8-membered saturated or unsaturated heterocycle containing one or two nitrogen atoms (the 4- to 8-membered saturated or unsaturated heterocycle is optionally substituted by one oxo).

(4) The azole derivative or pharmaceutically acceptable salt thereof according to any one of embodiments (1) to (3), wherein in the above Formula (I), the ring A represents a benzene ring or a 6-membered aromatic heterocycle (the benzene ring and the 6-membered aromatic heterocycle are optionally substituted by one or two groups selected from the group consisting of halogen atoms and $C_{1-5}$ alkoxy).

(5) The azole derivative or pharmaceutically acceptable salt thereof according to any one of embodiments (1) to (4), wherein in the above Formula (I), the ring A represents a benzene ring or a pyridine ring (the benzene ring and the pyridine ring are optionally substituted by one or two groups selected from the group consisting of halogen atoms and $C_{1-5}$ alkoxy).

(6) The azole derivative or pharmaceutically acceptable salt thereof according to any one of embodiments (1) to (5), wherein in the above Formula (I), $R^1$ is a $C_{1-5}$ alkyl;

$R^2$ is a hydrogen atom; and $R^3$ is phenyl or pyridyl (the phenyl and pyridyl are optionally substituted by one or two groups selected from the group consisting of $C_{1-5}$ alkyl, $C_{1-5}$ alkoxy, halogen atoms, cyano, trifluoromethyl, difluoromethoxy, trifluoromethoxy, and $C_{1-5}$ alkylsulfonyl).

(7) The azole derivative or pharmaceutically acceptable salt thereof according to any one of embodiments (1) to (6), wherein in the above Formula (I), the optionally substituted azole ring which is represented by the following formula (α):

[Chem. 4]

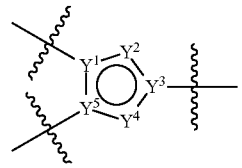

(α)

has any one of the structrures in the following formula group (III):

[Chem. 5]

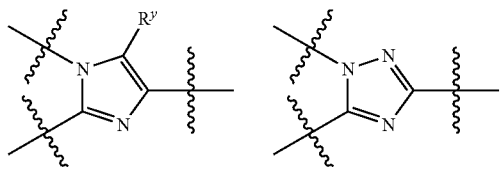

(III)

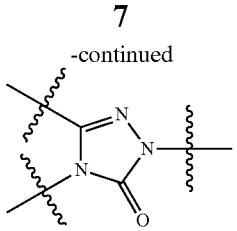

where
$R^y$ represents a hydrogen atom or a methyl group.
(8) The azole derivative or pharmaceutically acceptable salt thereof according to any one of embodiments (1) to (7), wherein in the above Formula (I),
$X^1$ is a single bond;
$X^2$ is ethylene or methylethylene; and
$R^4$ and $R^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl.
(9) The azole derivative or pharmaceutically acceptable salt thereof according to any one of embodiments (1) to (8), wherein in the above Formula (I),
$R^4$ and $R^5$, together with the adjoining nitrogen atom, form a 5- or 6-membered saturated heterocycle optionally containing one or more oxygen atoms in the ring in addition to the adjoining nitrogen atom (the 6-membered saturated heterocycle is optionally substituted by one or two groups selected from the group consisting of hydroxyl and $C_{1-5}$ alkyl, and the 6-membered saturated heterocycle optionally has a $C_{1-5}$ alkylene group crosslinking two different carbon atoms in the ring) or form 2-oxa-6-azaspiro[3.3]hept-6-yl.
(10) A pharmaceutical composition comprising the azole derivative or pharmaceutically acceptable salt thereof according to any one of embodiments (1) to (9) as an active ingredient.
(11) An agent for treating or preventing mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, or alopecia, comprising the azole derivative or pharmaceutically acceptable salt thereof according to any one of embodiments (1) to (9) as an active ingredient.

Advantageous Effects of Invention

It has now become clear that the novel azole derivatives of the present invention not only show an affinity for the V1b receptor but also exhibit an antagonistic action against a stimulus to the receptor by a physiological ligand.

DESCRIPTION OF EMBODIMENTS

The terms used in the specification have the following meanings.

The term "halogen atom" refers to a fluorine atom, a chlorine atom, a bromine atom, or an iodine atom.

The term "$C_{1-5}$ alkyl" refers to a linear or branched alkyl group having 1 to 5 carbon atoms, and examples thereof include methyl, ethyl, n-propyl, isopropyl, n-butyl, isobutyl, sec-butyl, tert-butyl, n-pentyl, isopentyl, neopentyl, and tert-pentyl.

The term "$C_{3-7}$ cycloalkyl" may be exemplified by a cyclopropyl, cyclobutyl, cyclopentyl, cyclohexyl, or cycloheptyl group.

The term "$C_{1-5}$ alkoxy" refers to a linear or branched alkoxy group having 1 to 5 carbon atoms, and examples thereof include methoxy, ethoxy, n-propoxy, isopropoxy, n-butoxy, isobutoxy, sec-butoxy, tert-butoxy, n-pentyloxy, isopentyloxy, neopentyloxy, and tert-pentyloxy.

The term "$C_{1-5}$ alkylsulfonyl" refers to a sulfonyl group substituted by the "$C_{1-5}$ alkyl" defined above, and examples thereof include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, and tert-pentylsulfonyl.

The term "$C_{2-5}$ alkanoyl" refers to a linear or branched alkanoyl group having 2 to 5 carbon atoms, and examples thereof include acetyl, propionyl, butyryl, isobutyryl, valeryl, isovaleryl, and pivaloyl.

The term "$C_{2-5}$ alkanoylamino" refers to an amino group having one "$C_{2-5}$ alkanoyl" defined above as a substituent and examples thereof include acetylamino, propionylamino, butyrylamino, isobutyrylamino, valerylamino, isovalerlylamino, and pivaloylamino.

The term "mono-$C_{1-5}$ alkylaminocarbonyl" refers to a carbonyl group substituted by an amino having one "$C_{1-5}$ alkyl" group defined above as a substituent, and examples thereof include methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, isopentylaminocarbonyl, and neopentylaminocarbonyl.

The term "mono-$C_{1-5}$ alkylamino" refers to an amino group having one "$C_{1-5}$ alkyl" group defined above as a substituent, and examples thereof include methylamino, ethylamino, n-propylamino, isopropylamino, n-butylamino, isobutylamino, sec-butylamino, tert-butyamino, n-pentylamino, isopentylamino, and neopentylamino.

The term "di-$C_{1-5}$ alkylaminocarbonyl" refers to a carbonyl group substituted by an amino having two identical or different "$C_{1-5}$ alkyl" groups defined above as substituents, and examples thereof include dimethylaminocarbonyl, diethylaminocarbonyl, di(n-propyl)aminocarbonyl, di(isopropyl)aminocarbonyl, ethylmethylaminocarbonyl, methyl(n-propyl)aminocarbonyl, and isopropyl(methyl)aminocarbonyl.

The term "di-$C_{1-5}$ alkylamino" refers to an amino group having two identical or different "$C_{1-5}$ alkyl" groups defined above as substituents, and examples thereof include dimethylamino, diethylamino, di(n-propyl)amino, di(isopropyl)amino, ethylmethylamino, methyl(n-propyl)amino, and isopropyl(methyl)amino.

The term "aryl" refers to a monocyclic or bicyclic aromatic carbocycle, and examples thereof include phenyl, 1-naphthyl, and 2-naphthyl.

The term "heteroaryl" refers to a mono- or bi-cyclic aromatic group having 1 to 9 carbon atoms and also having at least one hetero atom selected from the group consisting of oxygen, nitrogen, and sulfur atoms, and examples thereof include thienyl, furyl, pyrazolyl, imidazolyl, triazolyl, tetrazolyl, thiazolyl, isothiazolyl, thiadiazolyl, oxazolyl, isoxazolyl, oxadiazolyl, pyridyl, pyrimidinyl, quinolyl, indolyl, and benzofuranyl.

The term "4- to 8-membered saturated heterocycle" may be exemplified by oxetan-3-yl, azetidin-1-yl, 1-pyrrolidinyl, piperidino, 2-piperidyl, 3-piperidyl, 1-piperazinyl, morpholin-4-yl, morpholin-3-yl, thiomorpholin-4-yl, thiomorpholin-3-yl, azepan-1-yl, 1,4-oxazepan-4-yl, and azocan-1-yl.

The term "4- to 8-membered saturated or unsaturated heterocycle containing one or more nitrogen, oxygen or sulfur atoms in the ring" may be exemplified by oxetan-3-yl, azetidin-1-yl, 1-pyrrolidinyl, piperidino, 2-piperidyl, 3-piperidyl, 1-piperazinyl, morpholin-4-yl, morpholin-3-yl, thiomorpholin-4-yl, thiomorpholin-3-yl, azepan-1-yl, 1,4-oxazepan-4-yl, and azocan-1-yl.

The term "a 4- to 8-membered saturated or unsaturated heterocycle formed together with the adjoining nitrogen atom and optionally containing one or more nitrogen, oxygen or sulfur atoms in the ring in addition to the adjoining nitrogen atom" may be exemplified by azetidin-1-yl, 1-pyrrolidinyl, piperidino, 1-piperazinyl, morpholin-4-yl, thiomorpholin-4-yl, azepan-1-yl, 1,4-oxazepan-4-yl, azocan-1-yl, 5,6-dihydropyridin-1(2H)-yl, 1,4-diazepan-1-yl, and 1,2,3,6-tetrahydropyridin-1-yl. The heterocycle under consideration is preferably a 5- or 6-membered saturated heterocycle that is formed together with the adjoining nitrogen atom and which may optionally contain one or more oxygen atoms in the ring in addition to the adjoining nitrogen atom, and examples thereof include 1-pyrrolidinyl, piperidino, morpholin-4-yl, 5,6-dihydropyridin-1(2H)-yl, and 1,2,3,6-tetrahydropyridin-1-yl.

The term "$C_{1-5}$ alkylene" refers to a divalent group having one hydrogen atom removed from the "$C_{1-5}$ alkyl" defined above, and examples thereof include methylene, ethylene, methylmethylene, trimethylene, methylethylene, propylene, tetramethylene, ethylethylene, and pentamethylene.

The term "4- to 8-membered saturated or unsaturated heterocycle having a $C_{1-5}$ alkylene group crosslinking two different carbon atoms in the ring" as referred to in connection with the "4- to 8-membered saturated or unsaturated heterocycle formed together with the adjoining nitrogen atom and optionally containing one or more nitrogen, oxygen or sulfur atoms in the ring in addition to the adjoining nitrogen atom" defined above, may be exemplified by 8-azabicyclo[3.2.1]oct-8-yl (tropinyl), 8-oxa-3-azabicyclo[3.2.1]oct-3-yl, 3-oxa-8-azabicyclo[3.2.1]oct-8-yl, and octahydroisoquinolin-2(1H)-yl. Preferred are 8-azabicyclo[3.2.1]oct-8-yl (tropinyl), 8-oxa-3-azabicyclo[3.2.1]oct-3-yl, and 3-oxa-8-azabicyclo[3.2.1]oct-8-yl. Examples of the 8-azabicyclo[3.2.1]oct-8-yl that is substituted by hydroxy include 3-hydroxy-8-azabicyclo[3.2.1]oct-8-yl.

The term "6-membered aromatic heterocycle" may be exemplified by pyridine and pyrimidine rings The term "4- to 8-membered saturated or partially unsaturated heterocycle containing one or two nitrogen atoms" may be exemplified by azetidine, pyrrolidine, piperidine, piperazine, azepane, 1,4-diazepane, 1,2-dihydropyridine, and 1,2,3,6-tetrahydropyridine rings.

The term "$C_{3-7}$ cycloalkane" may be exemplified by cyclopropane, cyclobutane, cyclopentane, cyclohexane, and cycloheptane rings.

In the present invention, $R^1$ is preferably $C_{1-5}$ alkyl and more preferably isopropyl or tert-butyl.

In the present invention, $R^2$ is preferably a hydrogen atom.

In the present invention, $R^3$ is preferably phenyl or pyridyl (the phenyl and pyridyl are optionally substituted by one or two groups selected from the group consisting of $C_{1-5}$ alkyl, $C_{1-5}$ alkoxy, halogen atoms, cyano, hydroxy, trifluoromethyl, difluoromethoxy, trifluoromethoxy, and $C_{1-5}$ alkylsulfonyl).

More preferably, $R^3$ is phenyl (the phenyl is optionally substituted by one or two groups selected from the group consisting of $C_{1-5}$ alkyl, $C_{1-5}$ alkoxy, halogen atoms, cyano, trifluoromethyl, difluoromethoxy, trifluoromethoxy, and $C_{1-5}$ alkylsulfonyl) or pyridyl (the pyridyl is optionally substituted by one or two groups selected from the group consisting of $C_{1-5}$ alkyl, $C_{1-5}$ alkoxy, halogen atoms, cyano, hydroxy, trifluoromethyl, difluoromethoxy, and trifluoromethoxy).

Still more preferably, $R^3$ is phenyl (the phenyl is optionally substituted by one or two groups selected from the group consisting of $C_{1-5}$ alkoxy, chlorine atom, fluorine atom, cyano, and $C_{1-5}$ alkylsulfonyl) or pyridyl (the pyridyl is optionally substituted by $C_{1-5}$ alkoxy).

In a particularly preferred case, $R^3$ is a group represented by any one of the structures in the following formula group (IV).

[Chem. 6]

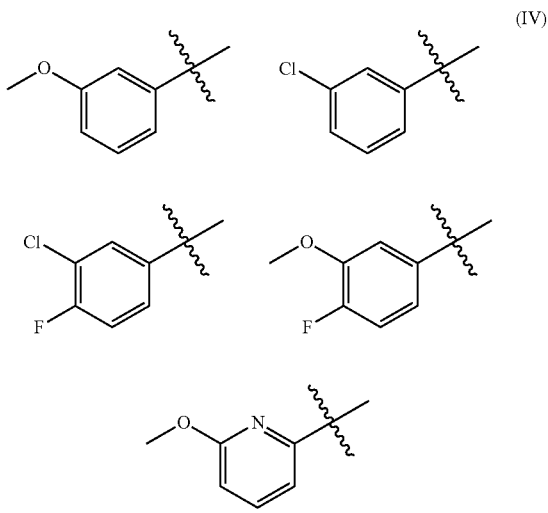

(IV)

In a preferred embodiment of the present invention, the optionally substituted azole ring represented by the following formula (α)

[Chem. 7]

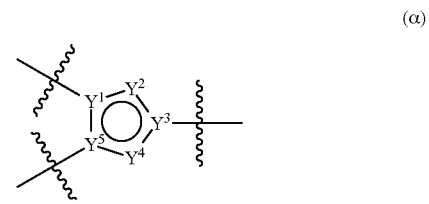

(α)

is a ring that is represented by any one of the structures in the following formula group (V).

[Chem. 8]

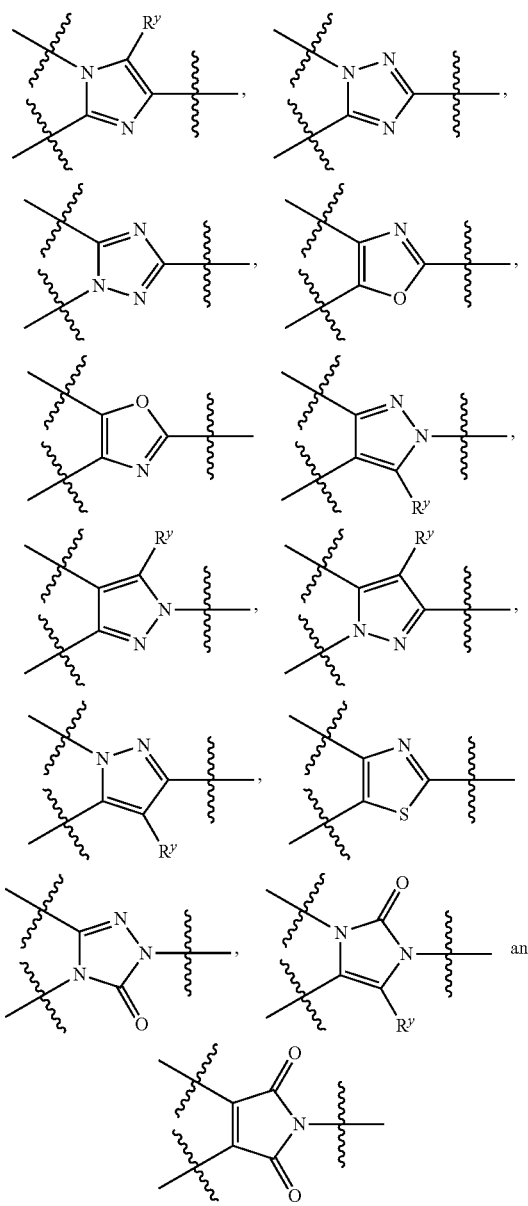

(V)

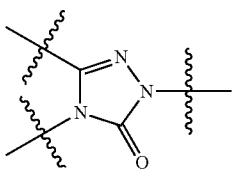

In the present invention, $R^y$ is preferably a hydrogen atom or a methyl group.

In the present invention, $X^1$ is preferably a single bond.

In the present invention, $X^2$ is preferably —$C_{1-5}$ alkylene- or —O—$C_{1-5}$ alkylene-.

More preferably, $X^2$ is —$C_{1-5}$ alkylene-.

Still more preferably, $X^2$ is ethylene or methylethylene.

In the present invention, the ring A is preferably benzene or pyridine (the benzene ring and the pyridine are optionally substituted by one or two groups selected from the group consisting of halogen atoms and $C_{1-5}$ alkoxy) or a 4- to 8-membered saturated or partially unsaturated heterocycle having one or two nitrogen atoms (the 4- to 8-membered saturated or unsaturated heterocycle is optionally substituted by one oxo).

More preferably, the ring A is a ring represented by any one of the structures in the following formula group (VII).

[Chem. 10]

(VII)

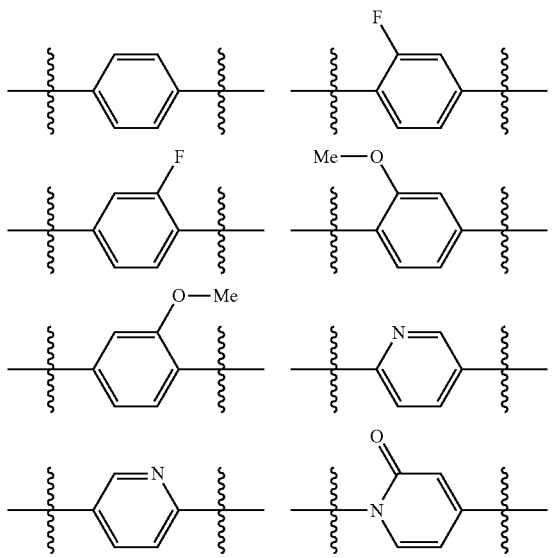

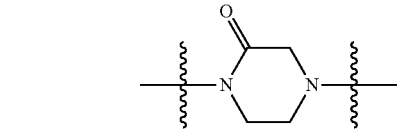

In a further preferred embodiment, the optionally substituted azole ring represented by the above formula (α) is a ring that is represented by any one of the structures in the following formula group (VI).

[Chem. 9]

(VI)

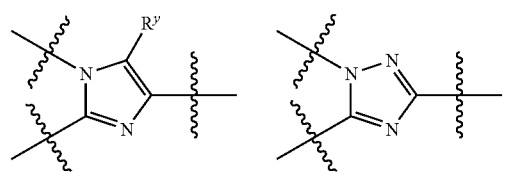

Still more preferably, the ring A is a ring represented by any one of the structures in the following formula group (VIII).

[Chem. 11]

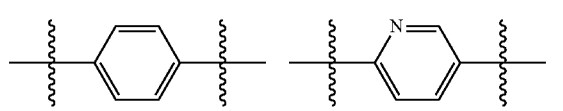

(VIII)

In the present invention, $R^4$ and $R^5$ preferably, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl.

More preferably, $R^4$ and $R^5$, together with the adjoining nitrogen atom, form a 5- or 6-membered saturated heterocycle optionally containing one or more oxygen atoms in the ring in addition to the adjoining nitrogen atom (the 6-membered saturated heterocycle is optionally substituted by one or two groups selected from the group consisting of hydroxyl and $C_{1-5}$ alkyl, and the 6-membered saturated heterocycle optionally has a $C_{1-5}$ alkylene group crosslinking two different carbon atoms in the ring) or form 2-oxa-6-azaspiro[3.3]hept-6-yl. Particularly preferred examples of the ring which $R^4$ and $R^5$ form together with the adjoining nitrogen atom are 1-pyrrolidinyl, piperidino (where the 1-pyrrolidinyl and piperidino are optionally substituted by one or two hydroxyl groups), morpholin-4-yl (where morpholine is optionally substituted by one or two $C_{1-5}$ alkyl groups, as in 3-methyl-morpholin-4-yl), 1,4-oxazepan-4-yl, thiomorpholin-4-yl, 8-azabicyclo[3.2.1]oct-8-yl (tropinyl), 3-hydroxy-8-azabicyclo[3.2.1]oct-8-yl, 8-oxa-3-azabicyclo[3.2.1]oct-3-yl, 3-oxa-8-azabicyclo[3.2.1]oct-8-yl, 2-oxa-6-azaspiro[3.3]hept-6-yl, and 7-oxa-2-azaspiro[3.5]non-1-yl.

Among the compounds of the present invention, the following may be listed as preferred examples:

2-[2-(3-chlorophenyl)-4-{4-[2-(piperidin-1-yl)ethyl]phenyl}-1H-imidazol-1-yl]-N-(propan-2-yl)acetamide;
2-[2-(3-chlorophenyl)-4-{4-[2-(morpholin-4-yl)ethyl]phenyl}-1H-imidazol-1-yl]-N-(propan-2-yl)acetamide;
2-[2-(3-chlorophenyl)-4-(4-{2-[3-(hydroxymethyl)pyrrolidin-1-yl]ethyl}phenyl)-1H-imidazol-1-yl]-N-(propan-2-yl)acetamide;
2-[2-(3-chlorophenyl)-4-{4-[2-(3-oxa-8-azabicyclo[3.2.1]oct-8-yl)ethyl]phenyl}-1H-imidazol-1-yl]-N-(propan-2-yl)acetamide;
2-[2-(4-fluoro-3-methoxyphenyl)-4-{4-[2-(piperidin-1-yl)ethyl]phenyl}-1H-imidazol-1-yl]-N-(propan-2-yl)acetamide;
2-[2-(4-fluoro-3-methoxyphenyl)-4-{4-[2-(morpholin-4-yl)ethyl]phenyl}-1H-imidazol-1-yl]-N-(propan-2-yl)acetamide;
2-[2-(4-fluoro-3-methoxyphenyl)-4-{4-[2-(pyrrolidin-1-yl)ethyl]phenyl}-1H-imidazol-1-yl]-N-(propan-2-yl)acetamide;
2-[2-(4-fluoro-3-methoxyphenyl)-4-(4-{2-[(2R)-2-methylpyrrolidin-1-yl]ethyl}phenyl)-1H-imidazol-1-yl]-N-(propan-2-yl)acetamide;
2-[2-(4-fluoro-3-methoxyphenyl)-4-{4-[2-(3-hydroxy-8-azabicyclo[3.2.1]oct-8-yl)ethyl]phenyl}-1H-imidazol-1-yl]-N-(propan-2-yl)acetamide;
2-[2-(4-fluoro-3-methoxyphenyl)-4-{4-[2-(3-methoxypiperidin-1-yl)ethyl]phenyl}-1H-imidazol-1-yl]-N-(propan-2-yl)acetamide;
2-[4-{4-[2-(2,6-dimethylmorpholin-4-yl)ethyl]phenyl}-2-(4-fluoro-3-methoxyphenyl)-1H-imidazol-1-yl]-N-(propan-2-yl)acetamide;
2-[2-(4-fluoro-3-methoxyphenyl)-4-{4-[2-(3-methylpyrrolidin-1-yl)ethyl]phenyl}-1H-imidazol-1-yl]-N-(propan-2-yl)acetamide;
2-[2-(4-fluoro-3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide;
2-[2-(4-fluoro-3-methoxyphenyl)-4-{4-[2-(1,4-oxazepan-4-yl)ethyl]phenyl}-1H-imidazol-1-yl]-N-(propan-2-yl)acetamide;
2-[4-{4-[2-(3,5-dimethylmorpholin-4-yl)ethyl]phenyl}-2-(4-fluoro-3-methoxyphenyl)-1H-imidazol-1-yl]-N-(propan-2-yl)acetamide;
2-[2-(3-chlorophenyl)-4-{5-[2-(morpholin-4-yl)ethyl]pyridin-2-yl}-1H-imidazol-1-yl]-N-(propan-2-yl)acetamide;
2-[2-(3-chlorophenyl)-4-{5-[2-(3-oxa-8-azabicyclo[3.2.1]oct-8-yl)ethyl]pyridin-2-yl}-1H-imidazol-1-yl]-N-(propan-2-yl)acetamide;
2-[2-(3-chlorophenyl)-4-{6-[2-(morpholin-4-yl)ethyl]pyridin-3-yl}-1H-imidazol-1-yl]-N-(propan-2-yl)acetamide;
2-[2-(3-methoxyphenyl)-5-methyl-4-{4-[2-(morpholin-4-yl)ethyl]phenyl}-1H-imidazol-1-yl]-N-(propan-2-yl)acetamide;
2-[2-(3-methoxyphenyl)-4-{4-[2-(morpholin-4-yl)ethyl]phenyl}-1H-imidazol-1-yl]-N-(propan-2-yl)acetamide;
2-[2-(3-chloro-4-fluorophenyl)-4-{4-[2-(morpholin-4-yl)ethyl]phenyl}-1H-imidazol-1-yl]-N-(propan-2-yl)acetamide;
2-[2-(3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide;
2-[2-(3-chlorophenyl)-4-{2-fluoro-4-[2-(morpholin-4-yl)ethyl]phenyl}-1H-imidazol-1-yl]-N-(propan-2-yl)acetamide;
2-[2-(3-chlorophenyl)-4-{4-[2-(morpholin-4-yl)propyl]phenyl}-1H-imidazol-1-yl]-N-(propan-2-yl)acetamide;
2-[5-(3-chlorophenyl)-3-{4-[2-(3-oxa-8-azabicyclo[3.2.1]oct-8-yl)ethyl]phenyl}-1H-1,2,4-triazol-1-yl]-N-(propan-2-yl)acetamide;
2-[5-(3-chlorophenyl)-3-{4-[2-(morpholin-4-yl)ethyl]phenyl}-1H-1,2,4-triazol-1-yl]-N-(propan-2-yl)acetamide;
2-[5-(3-chlorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;
2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;
2-[5-(4-fluoro-3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;
N-tert-butyl-2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]acetamide;
2-[5-(3-chloro-4-fluorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;
N-tert-butyl-2-[5-(3-chlorophenyl)-3-{5-[2-(3-oxa-8-azabicyclo[3.2.1]oct-8-yl)ethyl]pyridin-2-yl}-1H-1,2,4-triazol-1-yl]acetamide;

2-[5-(3-chlorophenyl)-3-{5-[2-(morpholin-4-yl)ethyl]pyridin-2-yl}-1H-1,2,4-triazol-1-yl]-N-(propan-2-yl)acetamide;

N-tert-butyl-2-[5-(3-chlorophenyl)-3-{5-[2-(morpholin-4-yl)ethyl]pyridin-2-yl}-1H-1,2,4-triazol-1-yl]acetamide;

2-[5-(3-chloro-4-fluorophenyl)-3-{5-[2-(morpholin-4-yl)ethyl]pyridin-2-yl}-1H-1,2,4-triazol-1-yl]-N-(propan-2-yl)acetamide;

2-[5-(4-fluoro-3-methoxyphenyl)-3-{5-[2-(morpholin-4-yl)ethyl]pyridin-2-yl}-1H-1,2,4-triazol-1-yl]-N-(propan-2-yl)acetamide;

N-tert-butyl-2-[5-(3-methoxyphenyl)-3-{5-[2-(morpholin-4-yl)ethyl]pyridin-2-yl}-1H-1,2,4-triazol-1-yl]acetamide;

2-[5-(3-methoxyphenyl)-3-{4-[2-(morpholin-4-yl)ethyl]phenyl}-1H-1,2,4-triazol-1-yl]-N-(propan-2-yl)acetamide;

2-[5-(3-methoxyphenyl)-3-{4-[2-(3-oxa-8-azabicyclo[3.2.1]oct-8-yl)ethyl]phenyl}-1H-1,2,4-triazol-1-yl]-N-(propan-2-yl)acetamide;

2-[3-{2-fluoro-4-[2-(morpholin-4-yl)ethyl]phenyl}-5-(3-methoxyphenyl)-1H-1,2,4-triazol-1-yl]-N-(propan-2-yl)acetamide;

2-[3-{3-fluoro-4-[2-(morpholin-4-yl)ethyl]phenyl}-5-(3-methoxyphenyl)-1H-1,2,4-triazol-1-yl]-N-(propan-2-yl)acetamide;

2-[5-(3-methoxyphenyl)-3-{4-[2-(3-oxa-8-azabicyclo[3.2.1]oct-8-yl)propyl]phenyl}-1H-1,2,4-triazol-1-yl]-N-(propan-2-yl)acetamide;

2-[5-(3-methoxyphenyl)-3-{4-[2-(7-oxa-2-azaspiro[3.5]non-2-yl)ethyl]phenyl}-1H-1,2,4-triazol-1-yl]-N-(propan-2-yl)acetamide;

2-[5-(3-methoxyphenyl)-3-{4-[2-(2-oxa-6-azaspiro[3.3]hept-6-yl)ethyl]phenyl}-1H-1,2,4-triazol-1-yl]-N-(propan-2-yl)acetamide;

2-[1-(3-chlorophenyl)-3-{4-[2-(morpholin-4-yl)ethyl]phenyl}-1H-1,2,4-triazol-5-yl]-N-(propan-2-yl)acetamide;

2-[1-(3-chlorophenyl)-3-{4-[2-(3-oxa-8-azabicyclo[3.2.1]oct-8-yl)ethyl]phenyl}-1H-1,2,4-triazol-5-yl]-N-(propan-2-yl)acetamide;

2-[5-(3-chlorophenyl)-3-{4-[2-(morpholin-4-yl)ethyl]phenyl}-2-oxo-2,3-dihydro-1H-imidazol-1-yl]-N-(propan-2-yl)acetamide;

2-[4-(3-chlorophenyl)-2-{4-[2-(piperidin-1-yl)ethyl]phenyl}-1,3-oxazol-5-yl]-N-(propan-2-yl)acetamide;

2-[4-(3-chlorophenyl)-2-{4-[2-(morpholin-4-yl)ethyl]phenyl}-1,3-oxazol-5-yl]-N-(propan-2-yl)acetamide;

2-[4-(3-chlorophenyl)-2-{4-[2-(2-oxa-6-azaspiro[3.3]hept-6-yl)ethyl]phenyl}-1,3-oxazol-5-yl]-N-(propan-2-yl)acetamide;

2-[5-(3-chlorophenyl)-2-{4-[2-(piperidin-1-yl)ethyl]phenyl}-1,3-thiazol-4-yl]-N-(propan-2-yl)acetamide;

2-[5-(3-chlorophenyl)-2-{4-[2-(morpholin-4-yl)ethyl]phenyl}-1,3-thiazol-4-yl]-N-(propan-2-yl)acetamide;

2-[3-(3-chlorophenyl)-1-{4-[2-(piperidin-1-yl)ethyl]phenyl}-1H-pyrazol-4-yl]-N-(propan-2-yl)acetamide;

2-[3-(3-chlorophenyl)-1-{4-[2-(morpholin-4-yl)ethyl]phenyl}-1H-pyrazol-4-yl]-N-(propan-2-yl)acetamide;

2-[5-(3-chlorophenyl)-3-{4-[2-(morpholin-4-yl)ethyl]phenyl}-1H-pyrazol-1-yl]-N-(propan-2-yl)acetamide;

2-[4-(3-chlorophenyl)-1-{4-[2-(morpholin-4-yl)ethyl]phenyl}-2,5-dioxo-2,5-dihydro-1H-pyrrol-3-yl]-N-(propan-2-yl)acetamide;

2-[4-(3-chlorophenyl)-1-{4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

N-tert-butyl-2-[4-(4-fluoro-3-methoxyphenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-methoxyphenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(4-fluoro-3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

N-tert-butyl-2-[4-(3-chlorophenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

2-[4-(3-chlorophenyl)-1-{4-[2-(morpholin-4-yl)propyl]phenyl}-5-oxo-4,5-dihydro-1H-1,2,4-triazol-3-yl]-N-(propan-2-yl)acetamide;

2-[4-(3-chlorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

2-[4-(3-chlorophenyl)-1-{3-fluoro-4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{3-fluoro-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl) acetamide;

2-[4-(3-chlorophenyl)-1-{3-methoxy-4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[4-(3-chloro-4-fluorophenyl)-1-{4-[2-(morpholin-4-yl)ethyl]phenyl}-5-oxo-4,5-dihydro-1H-1,2,4-triazol-3-yl]-N-(propan-2-yl)acetamide;

2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

N-tert-butyl-2-[4-(3-chloro-4-fluorophenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(3-chloro-4-fluorophenyl)-1-{5-[2-(morpholin-4-yl)ethyl]pyridin-2-yl}-5-oxo-4,5-dihydro-1H-1,2,4-triazol-3-yl]acetamide;

N-tert-butyl-2-[4-(3-chloro-4-fluorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

2-[4-(3-chlorophenyl)-1-{5-[2-(3-oxa-8-azabicyclo[3.2.1]oct-8-yl)propyl]pyridin-2-yl}-5-oxo-4,5-dihydro-1H-1,2,4-triazol-3-yl]-N-(propan-2-yl)acetamide;

2-(1-{4-[2-(morpholin-4-yl)ethyl]phenyl}-5-oxo-4-[3-(trifluoromethyl)phenyl]-4,5-dihydro-1H-1,2,4-triazol-3-yl)-N-(propan-2-yl)acetamide;

2-[4-(3-chloro-4-fluorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[4-(4-fluoro-3-methoxyphenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[1-{3-methoxy-4-[2-(3-oxa-8-azabicyclo[3.2.1]oct-8-yl)ethyl]phenyl}-4-(3-methoxyphenyl)-5-oxo-4,5-dihydro-1H-1,2,4-triazol-3-yl]-N-(propan-2-yl)acetamide;

2-[4-(3-chloro-4-fluorophenyl)-5-oxo-1-{4-[2-(pyrrolidin-1-yl)ethyl]phenyl}-4,5-dihydro-1H-1,2,4-triazol-3-yl]-N-(propan-2-yl)acetamide;

2-[4-(3-chloro-4-fluorophenyl)-5-oxo-1-{4-[2-(piperidin-1-yl)ethyl]phenyl}-4,5-dihydro-1H-1,2,4-triazol-3-yl]-N-(propan-2-yl)acetamide; and 2-[2-(3-chlorophenyl)-4-{4-[2-(2-oxa-6-azaspiro[3.3]hept-6-yl)ethyl]phenyl}-1H-imidazol-1-yl]-N-(propan-2-yl)acetamide, or pharmaceutically acceptable salts of these compounds.

Examples of the "pharmaceutically acceptable salt" include salts with inorganic acids, such as sulfuric acid, hydrochloric acid, hydrobromic acid, phosphoric acid, and nitric acid; salts with organic acids such as formic acid, trifluoroacetic acid, acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, and naphthalene-2-sulfonic acid; salts with one or more metal ions such as lithium, sodium, potassium, calcium, magnesium, zinc, and aluminum ions; and salts with amines such as ammonia, arginine, lysine, piperazine, choline, diethylamine, 4-phenylcyclohexylamine, 2-aminoethanol, and benzathine.

The compounds of the present invention can also occur in the form of various solvates. From the aspect of applicability as medicines, the compounds may also occur in the form of hydrates.

The compounds of the present invention encompass all possible forms including their enantiomers, diastereomers, equilibrium compounds, mixtures thereof at any proportions, and racemates.

The compounds of the present invention can be formulated into pharmaceutical preparations together with one or more pharmaceutically acceptable carriers, excipients, or diluents. Examples of the carrier, excipient, and diluent include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzosorbate, talc, magnesium stearate, stearic acid, glycerin, and various oils such as sesame oil, olive oil, and soybean oil.

The above-mentioned carrier, excipient, or diluent is optionally mixed with commonly used additives, such as a bulking agent, a binder, a disintegrant, a pH adjuster, or a solubilizer, and can be prepared in the form of oral or parenteral medicines, such as tablet, pill, capsule, granule, powder, liquid, emulsion, suspension, ointment, injection, or skin plasters and pressure-sensitive adhesives tapes, by common preparation technology. The compounds of the present invention can be orally or parenterally administered to adult patients in a unit dosage of 0.001 to 500 mg once or several times per day. The dosage can be appropriately adjusted depending on, for example, the type of the disease to be treated and the age, weight, and symptoms of the patient.

The compounds of the present invention may include those in which one or more of the hydrogen, fluorine, carbon, nitrogen, oxygen, and sulfur atoms are replaced with radioisotopes or stable isotopes thereof. These labeled compounds are useful, for example, for metabolic or pharmacokinetic study or as ligands of receptors in biological analysis.

The compounds of the present invention can, for example, be produced in accordance with the methods shown below.

The compounds represented by Formula (I) and pharmaceutically acceptable salts thereof can be produced by various organic synthesis techniques known to those skilled in the art. For example, they can be produced by the following synthetic processes to which the present invention is by no means limited.

The term "inert solvents" as used herein covers, for example, aromatic solvents such as benzene, toluene, xylene, and pyridine; hydrocarbon solvents such as hexane, pentane, and cyclohexane; halogenated hydrocarbon solvents such as dichloromethane, chloroform, 1,2-dichloroethane, and carbon tetrachloride; ether solvents such as tetrahydrofuran, diethyl ether, 1,2-dimethoxyethane, and 1,4-dioxane; ester solvents such as ethyl acetate and ethyl formate; alcoholic solvents such as methanol, ethanol, isopropyl alcohol, tert-butyl alcohol, and ethylene glycol; ketonic solvents such as acetone and methyl ethyl ketone; amide solvents such as N,N-dimethylformamide, N-methylpyrrolidone, and N,N-dimethylactamide; sulfoxide solvents such as dimethyl sulfoxide; nitrile solvents such as acetonitrile and propionitrile; water; as well as homogeneous and heterogeneous mixed solvents thereof. These inert solvents may be chosen as appropriate depending on various reaction conditions known to those skilled in the art.

The term "bases" as used herein covers, for example, hydrides of alkali metals or alkaline earth metals such as lithium hydride, sodium hydride, potassium hydride, and calcium hydride; amides of alkali metals or alkaline earth metals such as lithium amide, sodium amide, lithium diisoproylamide, lithium dicyclohexylamide, lithium hexamethyldisilazide, sodium hexamethyldisilazide, and potassium hexamethyldisilazide; lower alkoxides of alkali metals or alkaline earth metals such as sodium methoxide, sodium ethoxide, and potassium tert-butoxide; alkyl lithium compounds such as butyl lithium, sec-butyl lithium, tert-butyl lithium, and methyl lithium; hydroxides of alkali metals or alkaline earth metals such as sodium hydroxide, potassium hydroxide, lithium hydroxide, and barium hydroxide; carbonates of alkali metals or alkaline earth metals such as sodium carbonate, potassium carbonate, and cesium carbonate; hydrogencarbonates of alkali metals or alkaline earth metals such as sodium hydrogencarbonate and potassium hydrogencarbonate; amines such as triethylamine, N-methylmorpholine, N,N-diisopropylethylamine, 1,8-diazabicyclo[5.4.0]undec-7-ene (DBU), 1,5-diazabicyclo[4.3.0]non-5-ene (DBN), and N,N-dimethylaniline; and basic heterocyclic compounds such as pyridine, imidazole, and 2,6-lutidine. These bases may be chosen as appropriate depending on various reaction conditions known to those skilled in the art.

The term "acids" as used herein covers, for example, inorganic acids such as hydrochloric acid, hydrobromic acid, sulfuric acid, nitric acid, and phosphoric acid, and organic acids such as p-toluenesulfonic acid, methanesulfonic acid, trifluoroacetic acid, formic acid, and acetic acid. These acids may be chosen as appropriate depending on various reaction conditions known to those skilled in the art.

The compounds of the present invention can, for example, be produced in accordance with the methods shown below.

The compound represented by Formula (I) can be produced by the synthetic process shown in Scheme 1:

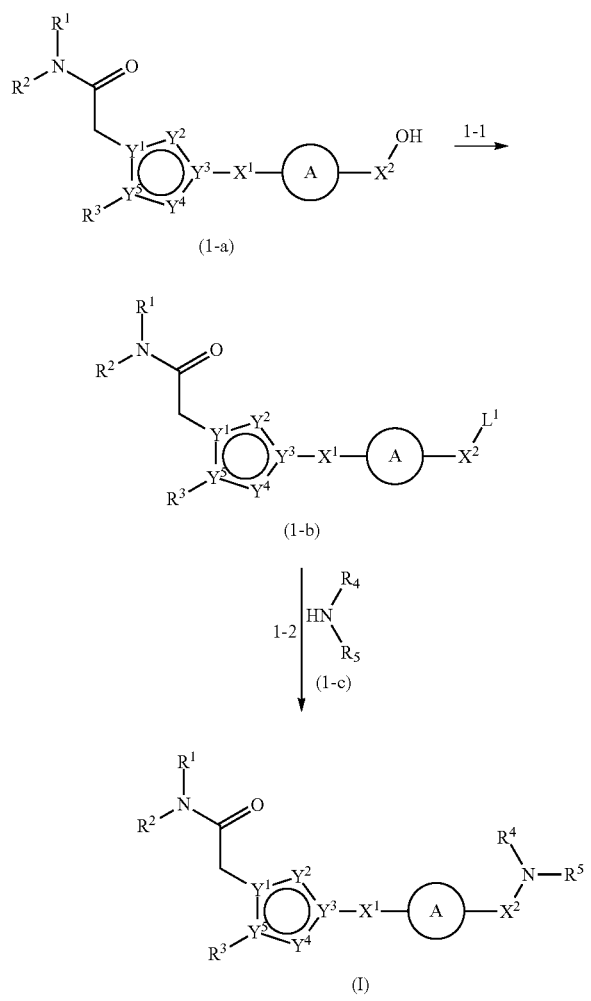

(wherein, $R^1$, $R^2$, $R^3$, $R^4$, $R^5$, $X^1$, $X^2$, $Y^1$, $Y^2$, $Y^3$, $Y^4$, $Y^5$ and A are the same as above, and $L^1$ represents a leaving group; the term "leaving group" means a p-toluenesulfonyloxy group, a methanesulfonyloxy group, a halogen atom, etc.)

The compound represented by Formula (I) can be obtained by conversion of the hydroxyl group of a compound represented by Formula (1-a) into a common leaving group so as to give a compound represented by Formula (1-b) (Step 1-1), which is then reacted with a corresponding amine (1-c) (Step 1-2). The reaction in Step 1-1 (conversion to a leaving group) is performed by, for example, chlorination, bromination, iodination, methanesulfonylation, or p-toluenesulfonylation.

Examples of the chlorination include a method of using carbon tetrachloride and triphenylphosphine, a method of using thionyl chloride or phosphorus oxychloride, and a method of introducing a leaving group using p-toluenesulfonyl chloride or the like and then performing substitution using lithium chloride or the like. These reactions can be performed using a solvent such as tetrahydrofuran, dioxane, dichloromethane, chloroform, N,N-dimethylformamide, or mixed solvents thereof. These reactions can be performed at −50 to 100° C.

Examples of the bromination include a method of using carbon tetrabromide and triphenylphosphine. This reaction can be performed in a solvent such as tetrahydrofuran, dioxane, dichloromethane, chloroform, N,N-dimethylformamide, or mixed solvents thereof at −50 to 50° C.

Examples of the iodination include a method of using iodine, triphenylphosphine, and imidazole. This reaction can be performed using a solvent such as tetrahydrofuran, dioxane, dichloromethane, chloroform, N,N-dimethylformamide, or mixed solvents thereof under the temperature condition of −50 to 100° C.

The methanesulfonylation and the p-toluenesulfonylation can be performed using, for example, methanesulfonyl chloride and p-toluenesulfonyl chloride, respectively. These reactions may be performed in the presence of an appropriate added base. Examples of the base to be added include organic amines such as triethylamine and diisopropylethylamine; and inorganic bases such as potassium carbonate. The reactions can be performed in a reaction solvent such as N,N-dimethylformamide, tetrahydrofuran, dioxane, dichloromethane, chloroform, 1,2-dichloroethane, or mixed solvents thereof under the temperature condition of −50 to 50° C.

The reaction in Step 1-2 proceeds in the absence of a solvent, or in a solvent such as tetrahydrofuran, acetonitrile, N,N-dimethylformamide, dimethyl sulfoxide, ethanol, isopropyl alcohol, or mixed solvents thereof under the temperature condition of from room temperature to near the boiling point of the solvent. The reaction will proceed more smoothly in the presence of sodium iodide or potassium iodide if this is added in addition to an inorganic base such as potassium carbonate or cesium carbonate, or an organic base such as triethylamine or diisopropylethylamine.

Among the compounds represented by the above Formula (1-a), a compound represented by Formula (2-g) can be produced by the synthetic process shown in Scheme 2:

Scheme 2

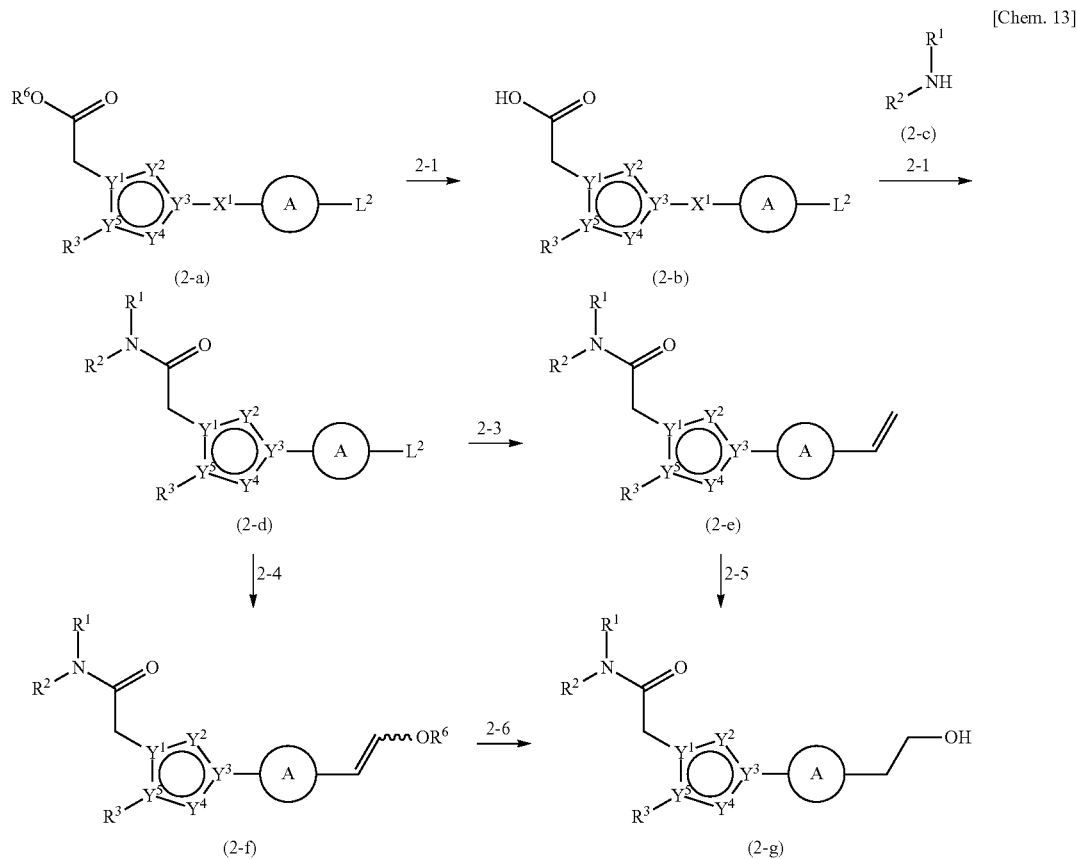

(wherein, $R^1$, $R^2$, $R^3$, $Y^1$, $Y^2$, $Y^3$, $Y^4$, $Y^5$ and A are the same as above; $R^6$ represents a $C_{1-5}$ alkyl; $L^2$ represents a chlorine atom, a bromine atom, an iodine atom, or a trifluoromethanesulfonyloxy group).

The compound represented by Formula (2-b) can be prepared by hydrolyzing the compound represented by Formula (2-a) (Step 2-1). The reaction in Step 2-1 proceeds in a solvent such as water, methanol, ethanol, or a mixed solvent thereof in the presence of a base such as sodium hydroxide, potassium hydroxide, lithium hydroxide or barium hydroxide under the temperature condition of from near 0° C. to near the boiling point of the solvent.

The compound represented by Formula (2-d) can be prepared by subjecting the compound represented by Formula (2-b) to amidation reaction with the compound represented by Formula (2-c) (Step 2-2). Here the amidation reaction may, for example, be performed by a method using a dehydration-condensation agent. Examples of the dehydration-condensation agent include 1-ethyl-3-(3-dimethylaminopropyl)carbodiimide hydrochlroride, dicyclohexylcarbodiimide, diphenylphosphonylazide, and carbonyldiimidazole; if necessary, activators may be used as exemplified by 1-hydroxybenzotriazole and hydroxysuccinimide. Exemplary reaction solvents include dichloromethane, chloroform, 1,2-dichloroethane, N,N-dimethylformamide, tetrahydrofuran, dioxane, toluene, ethyl acetate, and mixed solvents thereof. The reaction may be performed using a base and examples of the base include organic amines such as triethylamine and diisopropylethylamine, organic acid salts such as sodium 2-ethylhexanoate and potassium 2-ethylhexanoate, and inorganic bases such as potassium carbonate. The reaction can be performed at from −50° C. to near the boiling point of the reaction solvent.

The compound represented by Formula (2-e) can be obtained from the compound represented by Formula (2-d) by means of introducing vinyl through the Migita-Kosugi-Stille cross coupling reaction or the Suzuki-Miyaura cross coupling reaction (Step 2-3). The comprehensive review of the Migita-Kosugi-Stille cross coupling reaction is found in Angew. Chem. Int., Ed. 2004, 43, 4704-4734. The comprehensive review of the Suzuki-Miyaura cross coupling reaction is found in Chem. Rev., 1995, 95, 2457-2483.

The compound represented by Formula (2-g) can be obtained from the compound represented by Formula (2-e) by means of common hydroboration and subsequent oxidation reaction (Step 2-5). The reaction in Step 2-5 proceeds in two stages, where the alkene moiety of the compound represented by Formula (2-e) is hydroborated with, for example, a borane-tetrahydrofuran complex, 9-borabicyclo[3.3.1]nonane, disiamylborane, or thexylborane in a solvent such as tetrahydrofuran, toluene, acetonitrile, or mixed solvents thereof under the temperature condition of −10° C. to near room temperature and subsequently hydrogen peroxide or the like is used in the presence of a base such as sodium peroxoborate (monohydrate or tetrahydrate) or sodium hydroxide. The comprehensive review of the hydroboration is found in J. Am. Chem. Soc., 1956, 78, 5694-5695 and J. Org. Chem., 1986, 51, 439-445.

The compound represented by Formula (2-f) can be obtained from the compound represented by Formula (2-d) by means of introducing alkoxyvinyl through the Migita-Kosugi-Stille cross coupling reaction or the Suzuki-Miyaura cross coupling reaction (Step 2-4). Step 2-4 proceeds under the same reaction conditions as those in Step 2-3.

The compound represented by Formula (2-g) can be obtained from the compound represented by Formula (2-f) by means of converting it to a formyl compound through hydrolysis reaction in a hydrous solvent in the presence of an acid catalyst and then subjecting the resulting formyl compound to reduction reaction with a reducing agent. The comprehensive review of the hydrolysis reaction is found in Protective Groups in Organic Synthesis, Fourth Edition, John Wiley & Sons, INC. The comprehensive review of the reduction reaction is found in Comprehensive Organic Transformations, Second Edition, 1999, John Wiley & Sons, INC. The reducing agent is a reagent that is capable of converting a formyl compound to an alcoholic compound through reduction and may be exemplified by lithium borohydride, sodium borohydride, calcium borohydride, zinc borohydride, lithium aluminum hydride, sodium aluminum hydride, diisobutylaluminum hydride, etc.

Among the compounds represented by the above Formula (2-a), a compound represented by Formula (3-h) can be produced by the synthetic process shown in Scheme 3:

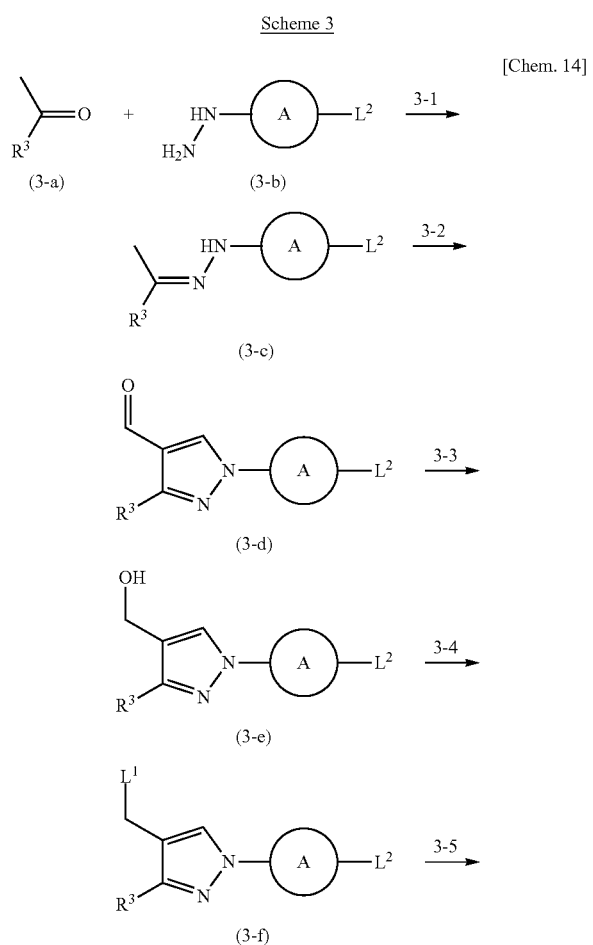

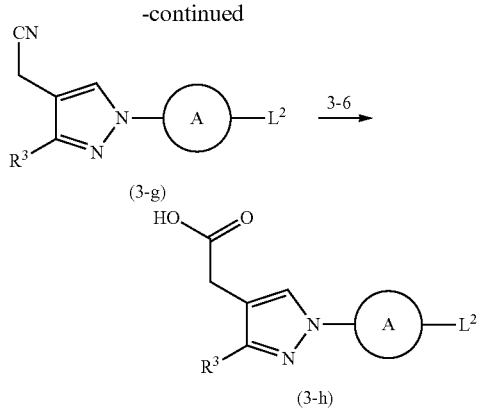

(wherein, $R^3$, $L^1$, $L^2$, and A are the same as above).

The compound represented by Formula (3-c) can be obtained by reacting a ketone compound represented by Formula (3-a) with a hydrazine compound represented by Formula (3-b) in the presence or absence of an acid catalyst (Step 3-1). Here, the ketone compound (3-a) and the hydrazine compound (3-b) are available as commercial compounds or known compounds; alternatively, they may be compounds that are synthesized from commercial compounds or known compounds using various organic synthesis techniques known to those skilled in the art.

The compound represented by Formula (3-d) can be obtained by reacting the compound represented by Formula (3-c) with phosphoryl chloride either in an inert solvent or in a solventless manner (Step 2-3).

The compound represented by Formula (3-e) can be obtained from the compound represented by Formula (3-d) by means of reacting it with a reducing agent in an inert solvent (Step 3-3). The comprehensive review of the reduction reaction is found in Comprehensive Organic Transformations, Second Edition, 1999, John Wiley & Sons, INC. The reducing agent is a reagent that is capable of converting a formyl compound to an alcoholic compound through reduction and may be exemplified by lithium borohydride, sodium borohydride, calcium borohydride, zinc borohydride, lithium aluminum hydride, sodium aluminum hydride, diisobutylaluminum hydride, etc.

The alcoholic compound (3-e) can be converted to a compound (3-f) by the same technique as in Step 1-1 of Scheme 1 (Step 3-4).

The compound represented by Formula (3-g) can be obtained from the compound represented by Formula (3-f) by means of reacting it with a cyanation agent in an inert solvent (Step 3-5). Examples of the cyanation agent include potassium cyanide and sodium cyanide. The comprehensive review of the cyanation reaction is found in Comprehensive Organic Transformations, Second Edition, 1999, John Wiley & Sons, INC.

The compound represented by Formula (3-h) can be obtained by hydrolyzing a compound represented by Formula (3-g) (Step 3-6). The hydrolysis reaction in this step proceeds in a solvent such as water, methanol, ethanol or mixed solvents thereof in the presence of a base such as sodium hydroxide, potassium hydroxide, lithium hydroxide or barium hydroxide under the temperature condition of from near 0° C. to near the boiling point of the solvent. Alternatively, the hydrolysis reaction proceeds in a solvent such as methanol, or ethanol, or mixed solvents thereof in the presence of an acid such as hydrochloric acid or sulfuric acid, under the temperature condition of from near 0° C. to near the boiling point of the solvent. The comprehensive review of the hydrolysis reaction is found in Comprehensive Organic Transformations, Second Edition, 1999, John Wiley & Sons, INC.

Among the compounds represented by the above Formula (2-e), a compound represented by Formula (4-1) can be produced by the synthetic process shown in Scheme 4:

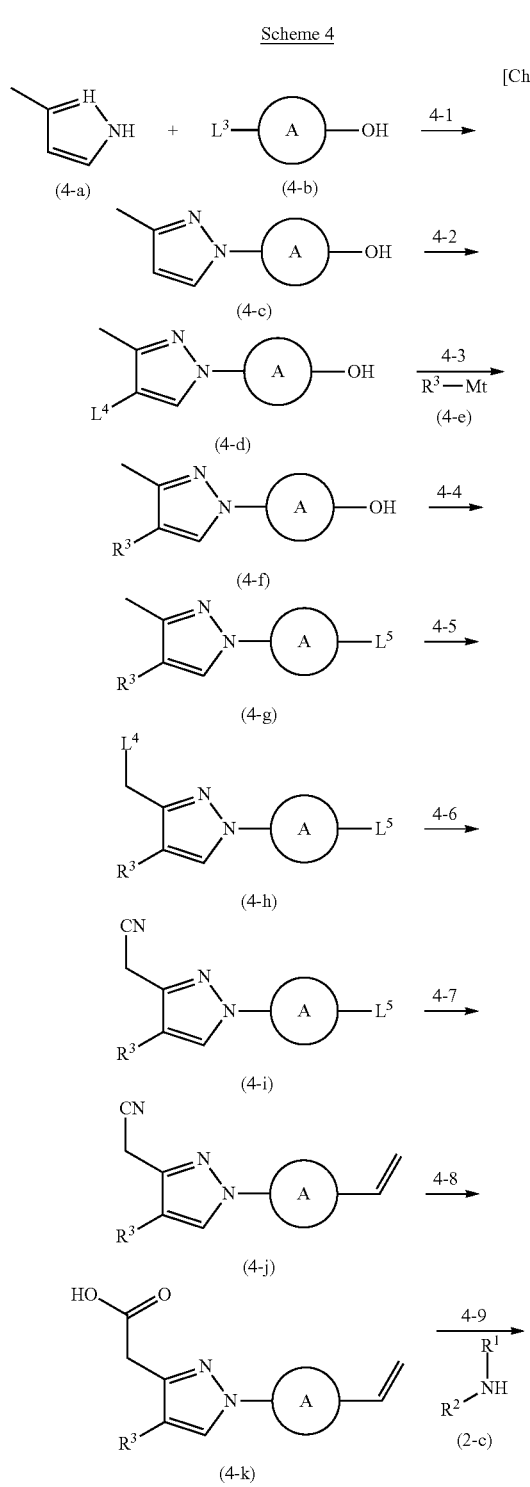

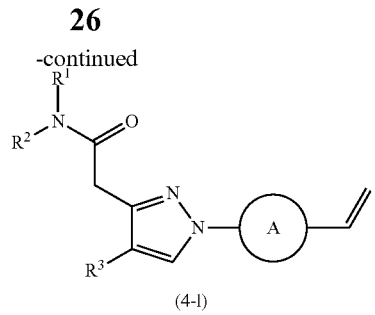

(wherein, $R^1$, $R^2$, $R^3$, and A are the same as above; $L^3$ represents a bromine atom or an iodine atom; $L^4$ represents a halogen atom such as a chlorine atom, a bromine atom or an iodine atom; $L^5$ represents a chlorine atom, a bromine atom, an iodine atom, or a trifluoromethanesulfonyloxy group; Mt represents a metal atom or a metal atomic group that are used in a coupling reaction; examples of the compound (4-e) include a magnesium reactant, a zinc reactant, or a boron reactant having boric acid or a boric acid ester attached thereto, and a tin reactant).

The compound represented by Formula (4-c) can be obtained by the Ullmann reaction between the compound represented by Formula (4-a) and the compound represented by formula (4-b) (Step 4-1). Here the compound represented by Formula (4-b) is available as a commercial compound or a known compound; alternatively, it may be a compound that is synthesized from commercial compounds or known compounds using various organic synthesis techniques known to those skilled in the art. The comprehensive review of the Ullmann reaction is found in Ley, S. V.; Thomas, A. W. Angew. Chem., Int. Ed. 2003, 42, 5400-5449.

The compound represented by Formula (4-d) can be obtained by subjecting the compound (4-c) to an electrophilic substitution reaction with a halogenating agent. Here the electrophilic substitution reaction proceeds in an inert solvent or in a solventless manner in the presence or absence of an acid and in the presence of a halogenating agent such as chlorine, bromine, iodine or N-chlorosuccinimide, N-bromosuccinimide or N-iodosuccinimide under the temperature condition of from near 0° C. to near the boiling point of the solvent (Step 4-2). The comprehensive review of the electrophilic substitution reaction is found in Comprehensive Organic Transformations, Second Edition, 1999, John Wiley & Sons, INC.

The compound represented by Formula (4-f) can be obtained from the compound represented by Formula (4-d) and the compound represented by Formula (4-e) through the Migita-Kosugi-Stille cross coupling reaction or the Suzuki-Miyaura cross coupling reaction (Step 4-3). The comprehensive review of the Migita-Kosugi-Stille cross coupling reaction is found in Angew. Chem. Int., Ed. 2004, 43, 4704-4734. The comprehensive review of the Suzuki-Miyaura cross coupling reaction is found in Chem. Rev., 1995, 95, 2457-2483.

The compound represented by Formula (4-g) can be obtained from the compound represented by Formula (4-f) by means of halogenating or trifluoromethanesulfonylating the hydroxyl group of the latter compound (Step 4-4). The comprehensive review of the halogenation or trifluoromethanesulfonylation reaction can be found in Comprehensive Organic Transformations, Second Edition, 1999, John Wiley & Sons, INC.

The compound represented by Formula (4-h) can be obtained from the compound represented by Formula (4-g) by means of subjecting it to halogenation reaction with a halogenating agent either in the presence of an initiator of radical reaction or under irradiation with light (Step 4-5). Here the initiator of radical reaction may be exemplified by azobisisobutyronitrile, benzoyl peroxide or the like. Examples of the halogenating agent include chlorine, bromine, or N-chlorosuccinimide and N-bromosuccinimide. The comprehensive review of the halogenation reaction can be found in Comprehensive Organic Transformations, Second Edition, 1999, John Wiley & Sons, INC.

The halogen compound (4-h) can be converted to a cyano compound (4-i) by the same technique as in Step 3-5 of Scheme 3 (Step 4-6). The compound (4-i) can be converted to a compound (4-j) by the same technique as in Step 2-3 of Scheme 2 (Step 4-7). The compound (4-j) can be converted to a compound (4-k) by the same technique as in Step 3-6 of Scheme 3 (Step 4-8). The compound (4-k) can be converted to an amide compound (4-l) by the same technique as in Step 2-2 of Scheme 2 (Step 4-9).

Among the compounds represented by the above Formula (2-d), a compound represented by Formula (5-1) can be produced by the synthetic process shown in Scheme 5.

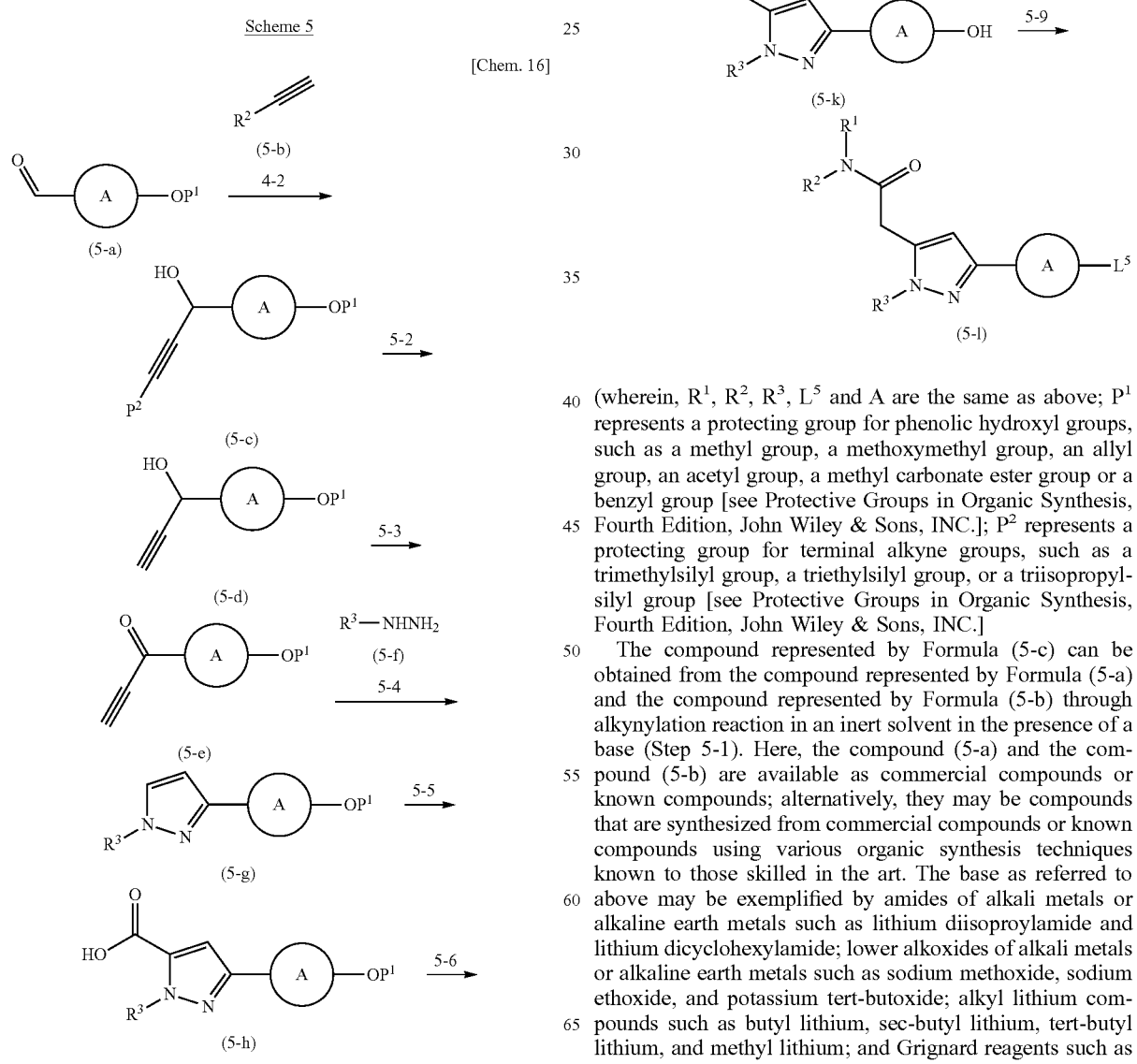

(wherein, $R^1$, $R^2$, $R^3$, $L^5$ and A are the same as above; $P^1$ represents a protecting group for phenolic hydroxyl groups, such as a methyl group, a methoxymethyl group, an allyl group, an acetyl group, a methyl carbonate ester group or a benzyl group [see Protective Groups in Organic Synthesis, Fourth Edition, John Wiley & Sons, INC.]; $P^2$ represents a protecting group for terminal alkyne groups, such as a trimethylsilyl group, a triethylsilyl group, or a triisopropylsilyl group [see Protective Groups in Organic Synthesis, Fourth Edition, John Wiley & Sons, INC.]

The compound represented by Formula (5-c) can be obtained from the compound represented by Formula (5-a) and the compound represented by Formula (5-b) through alkynylation reaction in an inert solvent in the presence of a base (Step 5-1). Here, the compound (5-a) and the compound (5-b) are available as commercial compounds or known compounds; alternatively, they may be compounds that are synthesized from commercial compounds or known compounds using various organic synthesis techniques known to those skilled in the art. The base as referred to above may be exemplified by amides of alkali metals or alkaline earth metals such as lithium diisoproylamide and lithium dicyclohexylamide; lower alkoxides of alkali metals or alkaline earth metals such as sodium methoxide, sodium ethoxide, and potassium tert-butoxide; alkyl lithium compounds such as butyl lithium, sec-butyl lithium, tert-butyl lithium, and methyl lithium; and Grignard reagents such as ethylmagnesium bromide.

The compound represented by Formula (5-d) can be obtained by removing the protective group P² on the terminal alkyne of the compound (5-c) using various organic synthesis techniques known to those skilled in the art [see Protective Groups in Organic Synthesis, Fourth Edition, John Wiley & Sons, INC.](Step 5-2).

The compound represented by Formula (5-e) can be obtained from the compound represented by Formula (5-d) by means of subjecting it to oxidation reaction (Step 5-3). The oxidizing agent for use in the oxidation reaction may be exemplified by manganese dioxide, chromic acid compounds such as pyridinium chlorochromate or pyridinium dichromate, and a Dess-Martin reagent (1,1,1-triacetoxy-1,1-dihydro-1,2-benziodoxol-3(1H)-one). The reaction solvent may be exemplified by dichloromethane and chloroform, with the reaction temperature ranging from 0° C. to near the boiling point of the reaction solvent. In another case, the reaction may be performed using IBX (1-hydroxy-1,2-benziodoxol-3(1H)-one 1-oxide), for example. Dimethyl sulfoxide, for example, may be used as the reaction solvent and reaction can be performed by further diluting it with a solvent that does not participate in the reaction, such as tetrahydrofuran, dichloromethane, or chloroform. The reaction temperature may range from 0° C. to 40° C. This oxidation reaction is not particularly limited and aside from the above-described methods, it may be performed by any method that can oxidize alcohol into aldehyde. Examples include a reaction of dimethyl sulfoxide with an activating agent (e.g., oxalyl chloride, N-chlorosuccinimide, or dicyclohexyl carbodiimide) or an oxidation method using tetra-n-propylammonium perruthenate(VII) and N-methylmorpholine oxide. The comprehensive review of the oxidation reaction under consideration can be found in Richard C. Larock, Comprehensive Organic Transformation, WILEY-VCH, 1999, 604.

The compound represented by Formula (5-g) can be obtained from the compound represented by Formula (5-e) by means of subjecting it to a pyrazole ring formation reaction through the reaction with a hydrazine compound (5-f) (Step 5-4). Here the hydrazine compound (5-f) is available as a commercial compound or a known compound; alternatively, it may be a compound that is synthesized from commercial compounds or known compounds using various organic synthesis techniques known to those skilled in the art.

The compound represented by Formula (5-h) can be obtained from the compound represented by Formula (5-g) through a homologation reaction with carbon dioxide in an inert solvent in the presence of a base such as lithium diisopropylamide (Step 5-5).

The compound represented by Formula (5-i) can be obtained from the compound represented by Formula (5-h) through homologation by the Arndt-Eistert reaction (Step 5-6). The comprehensive review of the Arndt-Eistert reaction can be found in Chem. Ber., 1927, 60, 1364.

The compound (5-i) can be converted to an amide compound (5-j) by the same technique as in Step 2-2 of Scheme 2 (Step 5-7).

The protective group P¹ in the compound represented by Formula (5-j) is then removed by various organic synthesis techniques known to those skilled in the art (see Protective Groups in Organic Synthesis, Fourth Edition, John Wiley & Sons, INC.), to give a compound represented by Formula (5-k) can be obtained (Step 5-8).

The compound represented by Formula (5-k) can be converted to a compound represented by Formula (5-1) by the same technique as in Step 4-4 of Scheme 4 (Step 5-9).

Among the compounds represented by the above Formula (2-a), a compound represented by Formula (6-f) can be produced by the synthetic process shown in Scheme 6.

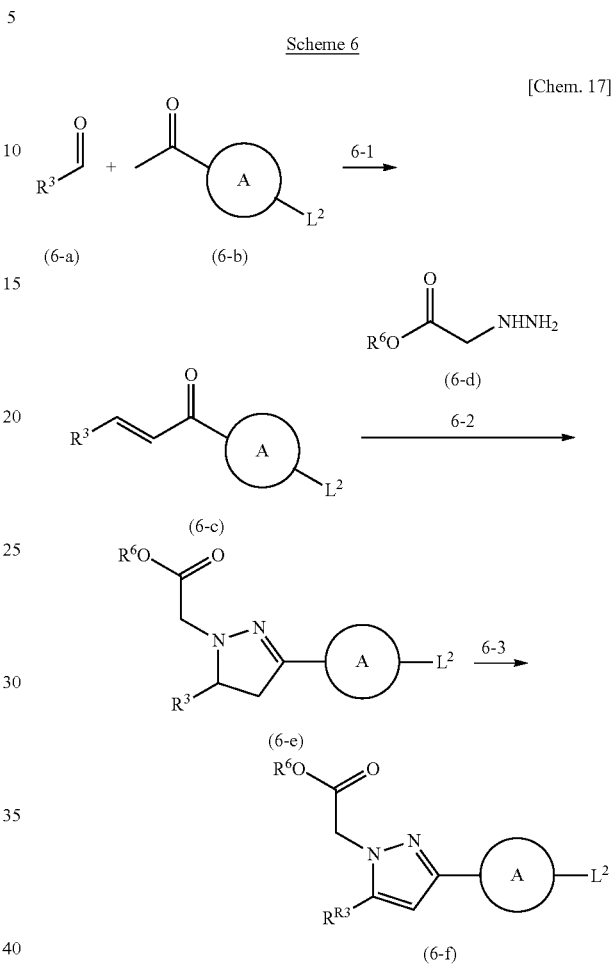

(wherein, $R^3$, $R^6$, $L^2$ and A are the same as above.)

The compound represented by Formula (6-c) can be obtained by the aldol reaction between the compound represented by Formula (6-a) and the compound represented by Formula (6-b) (Step 6-1). The comprehensive review of the aldol reaction can be found in Comprehensive Organic Transformations, Second Edition, 1999, John Wiley & Sons, INC. Here the compound represented by Formula (6-a) and the compound represented by Formula (6-b) are available as commercial compounds or known compounds; alternatively, they may be compounds that are synthesized from commercial compounds or known compounds using various organic synthesis techniques known to those skilled in the art.

The compound represented by Formula (6-e) can be obtained from the compound represented by Formula (6-c) and the hydrazine compound represented by Formula (6-d) through a dihydropyrazole ring forming reaction based on the reaction between the two compounds in an inert solvent in the presence or absence of an acid catalyst (Step 6-2). Here the hydrazine compound (6-d) is available as a commercial compound or a known compound; alternatively, it may be a compound that is synthesized from commercial compounds or known compounds using various organic synthesis techniques known to those skilled in the art.

The compound represented by Formula (6-f) can be obtained from the compound represented by Formula (6-e) through oxidation reaction with an oxidizing agent (Step 6-3). The oxidizing agent that may be used is 2,3-dichloro-5,6-dicyano-p-benzoquinone, manganese dioxide or potassium permanganate, for example. Exemplary reaction solvents include toluene, dichloromethane, and chloroform, with the reaction temperature ranging from 0° C. to near the boiling point of the reaction solvent.

Among the compounds represented by the above Formula (2-a), a compound represented by Formula (7-f) can be produced by the synthetic process shown in Scheme 7.

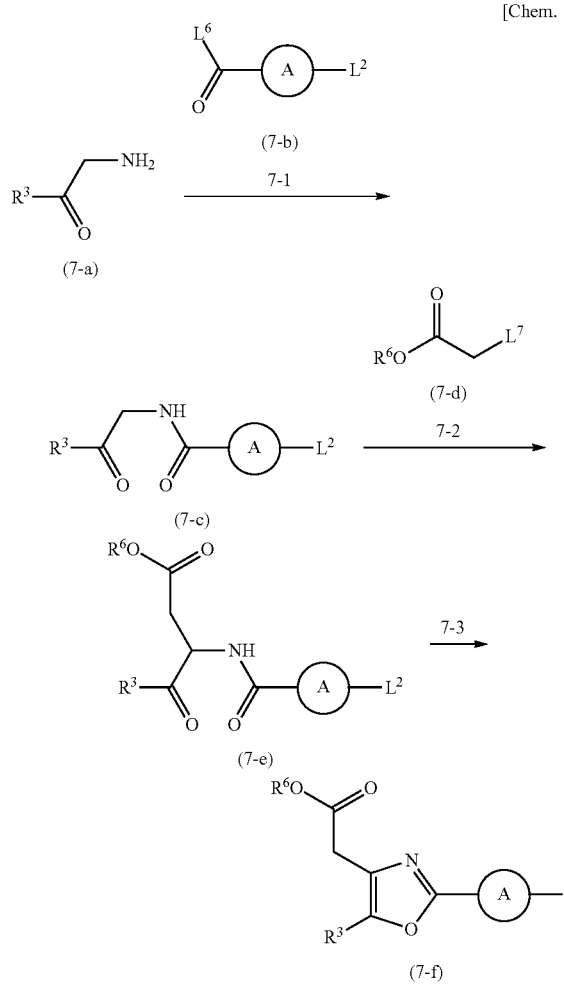

(wherein, $R^3$, $R^6$, $L^2$ and A are the same as above; $L^6$ represents a chlorine atom, a bromine atom or a hydroxyl group; $L^7$ represents a chlorine atom or a bromine atom).

The compound represented by Formula (7-c) can be produced from the compound represented by Formula (7-a) and a compound represented by Formula (7-b) in which $L^6$ is a halogen atom through amidation reaction between the two compounds in an inert solvent in the presence or absence of a base; alternatively, the compound represented by Formula (7-c) can be produced from the compound represented by Formula (7-a) and a compound represented by Formula (7-b) in which $L^6$ is a hydroxyl group through various amidation reactions known to those skilled in the art (Step 7-1). The compound represented by Formula (7-a) and the compound represented by Formula (7-b) are available as commercial compounds or known compounds; alternatively, they may be compounds that are synthesized from commercial compounds or known compounds using various organic synthesis techniques known to those skilled in the art. The amidation reaction of the compound (7-b) wherein $L^6$ is a hydroxyl group may be exemplified by a condensation reaction in an inert solvent in the presence or absence of a base using a condensation agent such as O-(7-azabenzotriazol-1-yl)-N,N,N',N'-tetramethyl uronium hexafluorophosphate (HATU), O-(benzotriazol-1-yl)-N,N,N',N'-tetramethyl uronium hexafluorophosphate (HBTU), N,N'-dicyclohexylcarbodiimide (DCC), 1-ethyl-3-(3-dimethylaminopropyl) carbodiimide hydrochloride (EDC.HCl), diphenylphosphoryl azide (DPPA) or carbonyldiimidazole (CDI), or by a condensation reaction again in an inert solvent in the presence or absence of a base but via a mixed acid anhydride using ethyl chloroformate, isobutyl chloroformate, trimethylacetyl chloride, or the like. In the case of amidation reaction using a condensation agent, an additive such as 1-hydroxybenzotriazole (HOBt) or hydroxysuccinimide (HOSu) may be used depending on the need.

The compound represented by Formula (7-e) can be obtained from the compound represented by Formula (7-c) and the compound represented by Formula (7-d) through alkylation reaction in an inert solvent in the presence of a base (Step 7-2).

The compound represented by (7-f) can be obtained from the compound represented by Formula (7-e) through intramolecular ring closing reaction in an inert solvent in the presence of phosphoryl chloride (Step 7-3).

Among the compounds represented by Formula (2-a), a compound represented by Formula (8-c) can be produced by the synthetic process shown in Scheme 8.

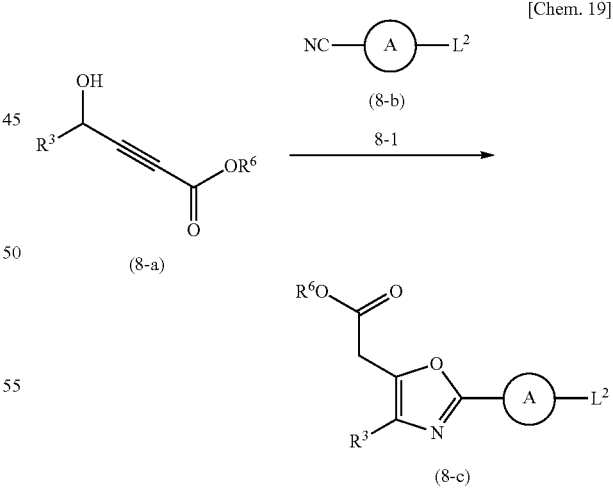

(wherein, $R^3$, $R^6$, $L^2$ and A are the same as above.)

The compound represented by (8-c) can be obtained from the compound represented by Formula (8-a) and the compound represented by Formula (8-b) through an oxazole ring forming reaction in the presence of an acid (Step 8-1). Here the acid may be exemplified by conc. sulfuric acid. Here the compound represented by Formula (8-a) and the compound represented by Formula (8-b) are available as commercial compounds or known compounds; alternatively, they may be compounds that are synthesized from commercial compounds or known compounds using various organic synthesis techniques known to those skilled in the art.

Among the compounds represented by the above Formula (2-b), a compound represented by Formula (9-e) can be produced by the synthetic process shown in Scheme 9.

Scheme 9

[Chem. 20]

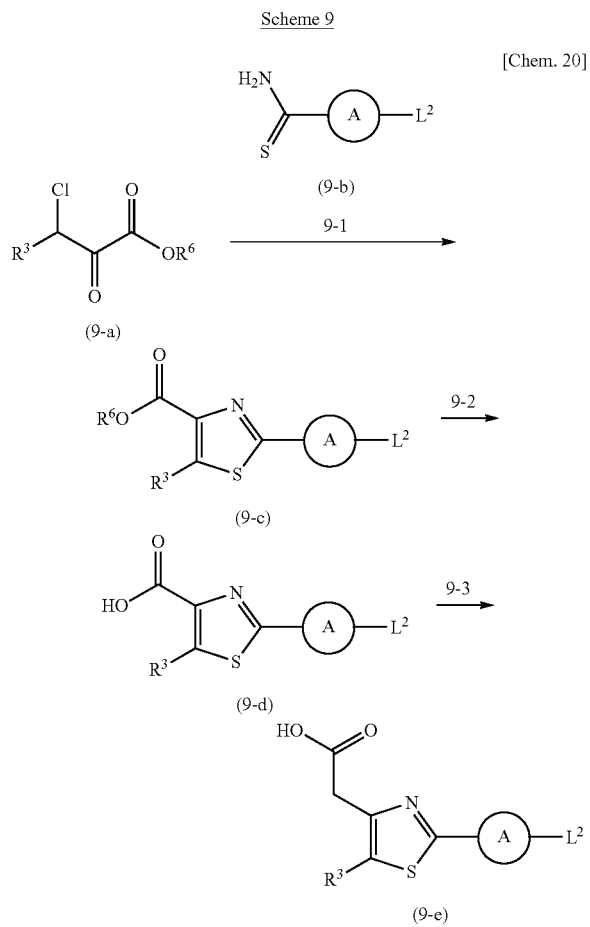

Among the compounds represented by the above Formula (2-d), a compound represented by Formula (10-e) can be produced by the synthetic process shown in Scheme 10.

Scheme 10

[Chem. 21]

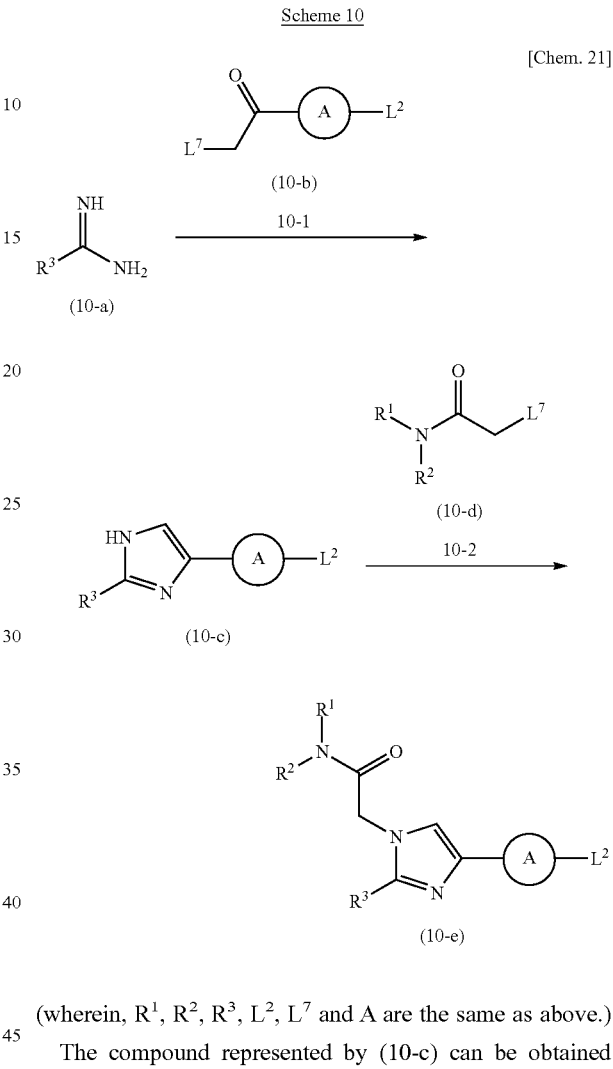

(wherein, $R^3$, $R^6$, $L^2$ and A are the same as above.)

The compound represented by (9-c) can be obtained from the compound represented by Formula (9-a) and the compound represented by Formula (9-b) through a thiazole ring forming reaction in an inert solvent (Step 9-1). Here the compound represented by Formula (9-a) and the compound represented by Formula (9-b) may be available as commercial compounds or known compounds; alternatively, they may be compounds that are synthesized from commercial compounds or known compounds using various organic synthesis techniques known to those skilled in the art. The compound represented by Formula (9-d) can be obtained from the compound represented by Formula (9-c) by means of the same technique as that in Step 2-1 shown in Scheme 2. The compound represented by Formula (9-e) can be obtained from the compound represented by Formula (9-d) by means of the same technique as that in Step 5-6 shown in Scheme 5.

(wherein, $R^1$, $R^2$, $R^3$, $L^2$, $L^7$ and A are the same as above.)

The compound represented by (10-c) can be obtained from the compound represented by Formula (10-a) and the compound represented by Formula (10-b) through an imidazole ring forming reaction in an inert solvent in the presence of a base (Step 10-1). Here the compound represented by Formula (10-a) and the compound represented by Formula (10-b) are available as commercial compounds or known compounds; alternatively, they may be compounds that are synthesized from commercial compounds or known compounds using various organic synthesis techniques known to those skilled in the art.

The compound represented by Formula (10-e) can be obtained from the compound represented by Formula (10-c) and the compound represented by Formula (10-d) through an alkylation reaction in an inert solvent in the presence of a base (Step 10-2).

Among the compounds represented by the above Formula (1-a), a compound represented by Formula (11-i) can be produced by the synthetic process shown in Scheme 11.

Scheme 11

[Chem. 22]

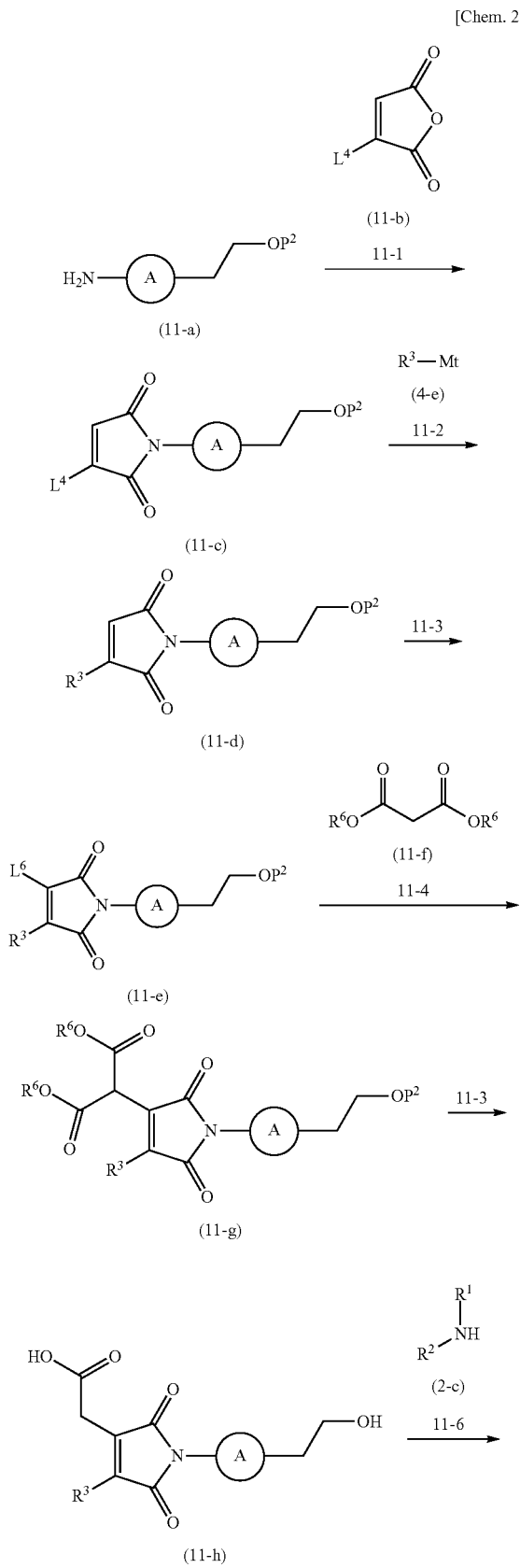

(wherein, $R^1$, $R^2$, $R^3$, $R^6$, $L^4$, Mt and A are the same as above; $P^2$ represents a protecting group for a hydroxyl group, such as a methoxymethyl group, a tert-butyldimethylsilyl group, an acetyl group, a benzyl group, a tetrahydropyranyl group, or a 2-(trimethylsilyl)ethoxymethyl group [see Protective Groups in Organic Synthesis, Fourth Edition, John Wiley & Sons, INC.] or a hydrogen atom).

The compound represented by Formula (11-c) can be obtained from the compound represented by Formula (11-a) and the compound represented by Formula (11-b) through a cyclization reaction in an inert solvent or without a solvent in the presence or absence of an acid (Step 11-1). Here the compound represented by Formula (11-a) and the compound represented by Formula (11-b) are available as commercial compounds or known compounds; alternatively, they may be compounds that are synthesized from commercial compounds or known compounds using various organic synthesis techniques known to those skilled in the art.

The compound (11-c) can be converted to the compound represented by Formula (11-d) by means of the same technique as that in Step 4-3 of Scheme 4 (Step 11-2).

The compound (11-d) is then subjected to a halogenation reaction with chlorine, bromine, iodine or N-chlorosuccinimide, N-bromosuccinimide, N-iodosuccinimide, thionyl chloride or the like, to convert it to the compound (11-e) having a halogen atom introduced thereinto (Step 11-3).

The compound represented by Formula (11-g) can be obtained from the compound represented by Formula (11-e) and the compound represented by Formula (11-f) through a nucleophilic substitution reaction in an inert solvent in the presence of a base (Step 11-4). Here the compound represented by Formula (11-f) is available as a commercial compound or a known compound; alternatively, it may be a compound as synthesized from commercial compounds or known compounds using various organic synthesis techniques known to those skilled in the art.

The compound represented by Formula (11-h) can be obtained from the compound represented by Formula (11-g) through hydrolysis of the ester in an inert solvent in the presence of an acid, followed by subsequent decarboxylation reaction and the removal of the protective group $P^2$ (Step 11-5).

The compound (11-h) can be converted to the amide compound (11-i) by the same technique as in Step 2-2 of Scheme 2 (Step 11-6).

Among the compounds represented by the above Formula (2-d), a compound represented by Formula (12-e) can be produced by the synthetic process shown in Scheme 12.

Scheme 12

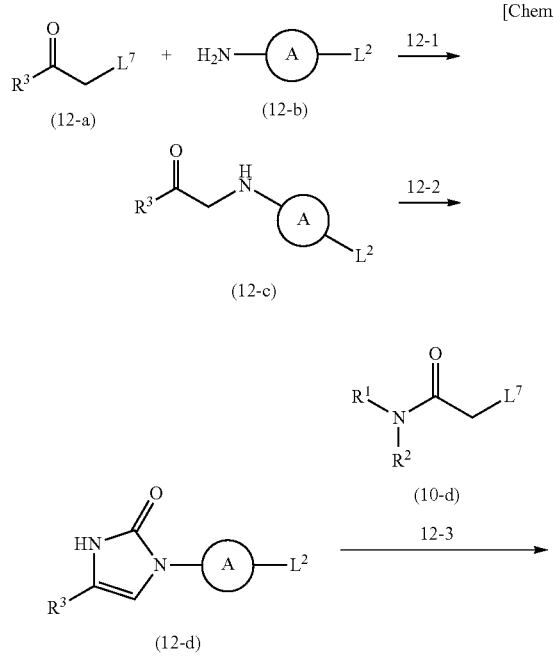

The compound represented by (12-c) can be obtained from the compound represented by Formula (12-a) and the compound represented by Formula (12-b) through an alkylation reaction in an inert solvent or in a solventless manner in the presence of a base (Step 12-1). Here the compound represented by Formula (12-a) and the compound represented by Formula (12-b) are available as commercial compounds or known compounds; alternatively, they may be compounds as synthesized from commercial compounds or known compounds using various organic synthesis techniques known to those skilled in the art.

The compound represented by Formula (12-d) can be obtained from the compound represented by Formula (12-c) and potassium cyanate, sodium cyanate or the like through a ring closing reaction either within or in the absence of an inert solvent in the presence or absence of an acid (Step 12-2).

The compound (12-d) can be converted to an amide compound (12-e) by the same technique as in Step 10-2 of Scheme 10 (Step 12-3).

Among the compounds represented by the above Formula (2-d), a compound represented by Formula (13-d) can be produced by the synthetic process shown in Scheme 13.

Scheme 13

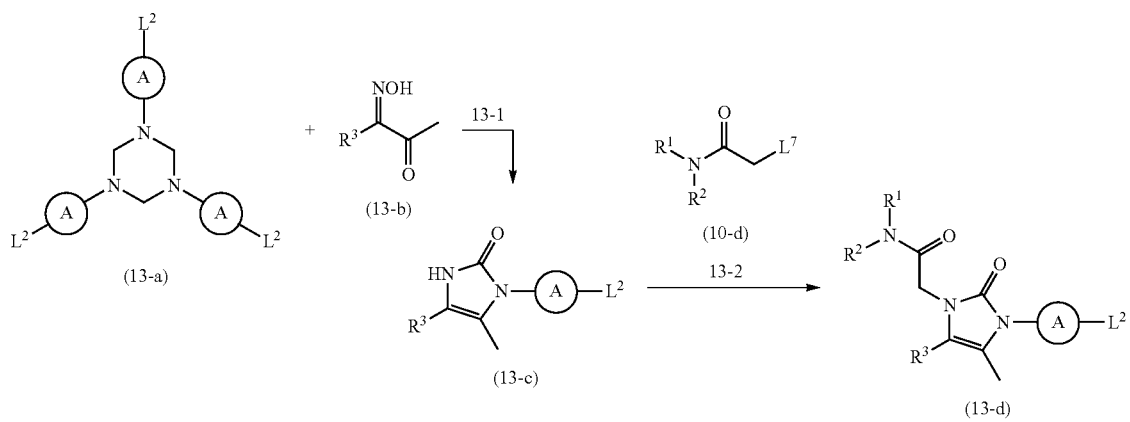

-continued

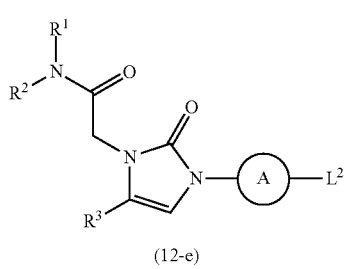

(wherein, $R^1$, $R^2$, $R^3$, $L^2$, $L^7$ and A are the same as above).

(wherein, $R^1$, $R^2$, $R^3$, $L^2$, $L^7$ and A are the same as above).

The compound represented by Formula (13-c) can be obtained from the compound represented by Formula (13-a) and the compound represented by Formula (13-b) through reaction in an inert solvent (Step 13-1). Here the compound represented by Formula (13-a) and the compound represented by Formula (13-b) are available as commercial compounds or known compounds; alternatively, they may be compounds as synthesized from commercial compounds or known compounds using various organic synthesis techniques known to those skilled in the art.

The compound (13-c) can be converted to the compound (13-d) by the same technique as in Step 10-2 of Scheme 10 (Step 13-2).

Among the compounds represented by the above Formula (2-a), a compound represented by Formula (14-f) can be produced by the synthetic process shown in Scheme 14.

Scheme 14

[Chem. 25]

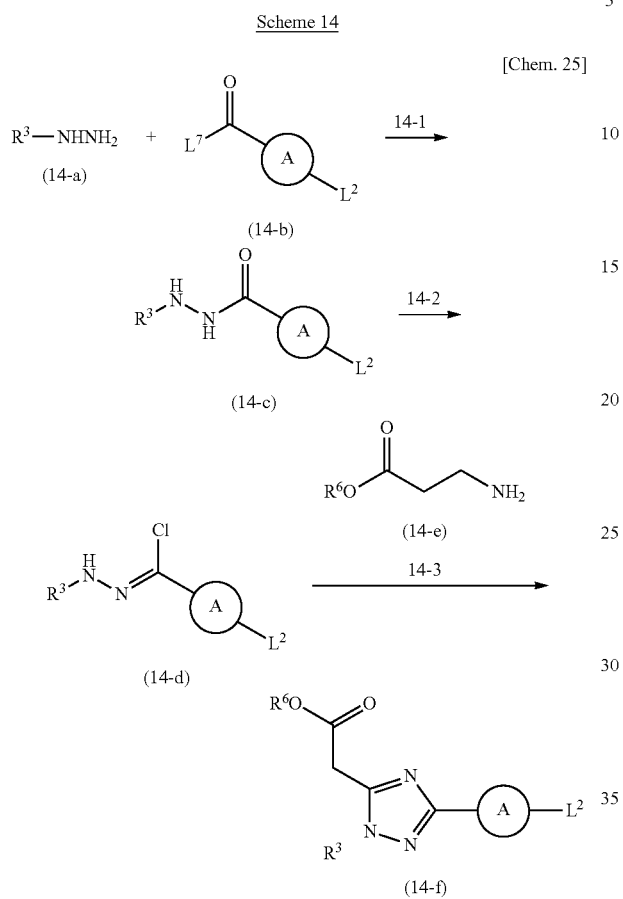

(wherein, $R^3$, $R^6$, $L^2$, $L^7$ and A are the same as above).

The compound represented by Formula (14-c) can be obtained by reacting the compound represented by Formula (14-a) with an acid halide represented by Formula (14-b) (Step 14-1). The reaction in Step 14-1 proceeds in a solvent such as chloroform, toluene, tetrahydrofuran, acetonitrile or mixed solvents thereof in the presence of a base such as triethylamine or diisopropylethylamine under the temperature condition of from near 0° C. to near room temperature. Here the compound represented by Formula (14-a) and the compound represented by Formula (14-b) are available as commercial compounds or known compounds; alternatively, they may be compounds that are synthesized from commercial compounds or known compounds using various organic synthesis techniques known to those skilled in the art.

The compound represented by Formula (14-d) can be obtained by a halogenation reaction of the compound represented by Formula (14-c) (Step 14-2). Examples of the halogenation reaction include a method using carbon tetrachloride and triphenylphosphine, and a method using thionyl chloride or phosphorus oxychloride. These reactions may employ solvents such as tetrahydrofuran, dioxane, dichloromethane, chloroform, N,N-dimethylforamide, or mixed solvents thereof. These reactions can be performed at −50 to 100° C.

The compound represented by Formula (14-f) can be obtained from the compound represented by Formula (14-d) and the amine compound represented by Formula (14-e) through reaction in the presence of an oxidizing agent (Step 14-3). Examples of the oxidizing agent include silver carbonate, hydrogen peroxide, sodium hypochlorite, Dess-Martin reagent (1,1,1-triacetoxy-1,1-dihydro-1,2-benziodoxol-3 (1H)-one), etc.

Among the compounds represented by the above Formula (1-a), a compound represented by Formula (15-g) can be produced by the synthetic process shown in Scheme 15.

Scheme 15

[Chem. 26]

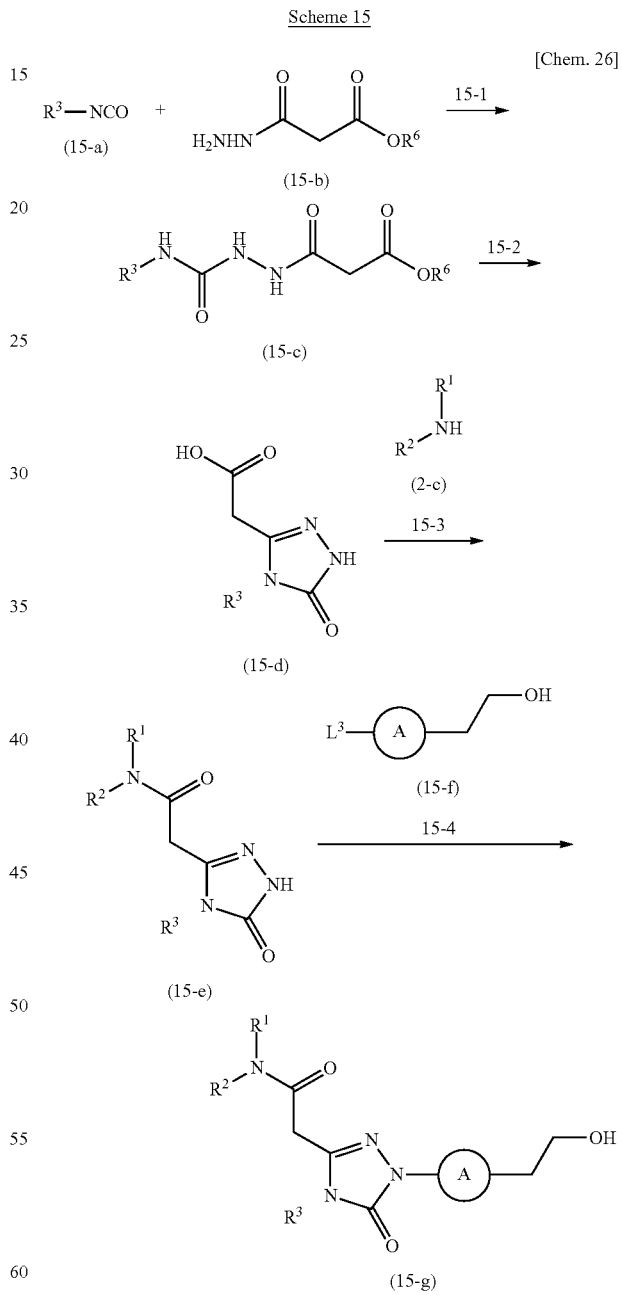

(wherein, $R^1$, $R^2$, $R^3$, $R^6$, $L^3$ and A are the same as above).

The compound represented by Formula (15-c) can be obtained from the isocyanate derivative represented by Formula (15-a) and the compound represented by Formula (15-b) by means of allowing the latter to act on the former (Step 15-1). The reaction in Step 15-1 proceeds in a solvent such as chloroform, toluene, tetrahydrofuran, acetonitrile or mixed solvents thereof under the temperature condition of from a temperature near room temperature to near the boiling point of the solvent. Here the compound represented by Formula (15-a) and the compound represented by Formula (15-b) are available as commercial compounds or known compounds; alternatively, they may be compounds that are synthesized from commercial compounds or known compounds using various organic synthesis techniques known to those skilled in the art. The compound represented by Formula (15-d) can be obtained from the compound represented by Formula (15-c) through reaction under a basic condition (Step 15-2). The reaction in Step 15-2 proceeds in a solvent such as water, tetrahydrofuran, 1,4-dioxane, N,N-dimethylforamide, or mixed solvents thereof in the presence of an inorganic base such as sodium hydroxide, potassium hydroxide, lithium hydroxide or barium hydroxide under the temperature condition of from near room temperature to near the boiling point of the solvent. The compound represented by Formula (15-e) can be obtained by an amidation reaction of the compound represented by Formula (15-d) with an amine (2-c) (Step 15-3). Examples of the amidation reaction that can be used in Step 15-3 include a method using a dehydration-condensation agent. Examples of the dehydration-condensation agent include 1-ethyl-3-(3-dimethylaminopropyl)carbodiimide hydrochloride, dicyclohexyl carbodiimide, diphenylphosphonyl azide, and carbonyldiimidazole; if necessary, an activating agent, such as 1-hydroxybenzotriazole or hydroxysuccinimide may be used. Examples of the reaction solvent include dichloromethane, chloroform, 1,2-dichloroethane, N,N-dimethylformamide, tetrahydrofuran, dioxane, toluene, ethyl acetate, and mixed solvents thereof. The process can be performed using a base, examples of which include organic amines such as triethylamine and diisopropylethylamine; organic acid salts such as sodium 2-ethylhexanoate and potassium 2-ethylhexanoate; and inorganic bases such as potassium carbonate. The reaction can be performed at a temperature ranging from −50° C. to near the boiling point of the reaction solvent. Conversion to the compound (15-g) can be achieved through the Ullmann reaction between the compound (15-e) and the compound (15-f) by the same technique as in Step 4-1 of Scheme 4.

Among the compounds represented by the above Formula (1-a), a compound represented by Formula (16-e) can be prepared by the synthetic process shown in Scheme 16.

Scheme 16

[Chem. 27]

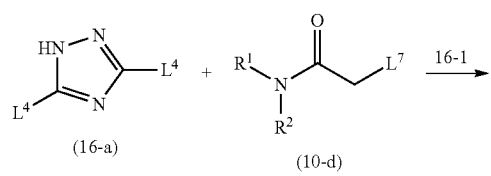

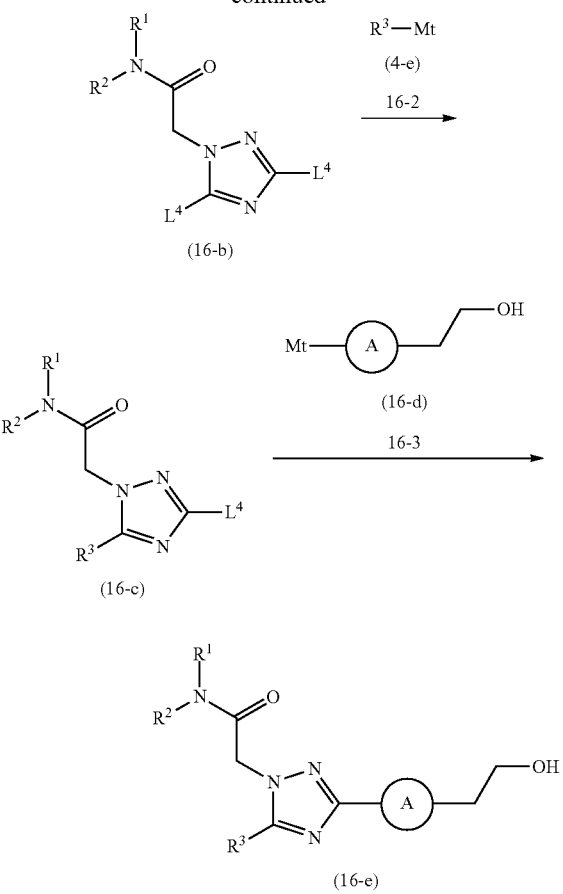

(wherein, $R^1$, $R^2$, $R^3$, $L^4$, $L^7$, Mt and A are the same as above).

The compound represented by Formula (16-b) can be obtained from the compound represented by Formula (16-a) and the compound represented by Formula (10-d) through alkylation reaction by means of the same technique as that in Step 10-2 of Scheme 10. Here the compound represented by Formula (16-a) and the compound represented by Formula (10-d) are available as commercial compounds or known compounds; alternatively, they may be compounds as synthesized from commercial compounds or known compounds using various organic synthesis techniques known to those skilled in the art.

The compound (16-b) can be converted to the compound represented by Formula (16-c) by means of the same technique as that in Step 4-3 of Scheme 4 (Step 16-2). The compound represented by Formula (16-e) can be obtained from the compound represented by Formula (16-c) and the compound represented by Formula (16-d) through coupling reaction by the same technique as in Step 4-3 of Scheme 4 (Step 16-3).

Among the compounds represented by the above Formula (I), a compound represented by Formula (17-b) can be prepared by the synthetic process shown in Scheme 17.

Scheme 17

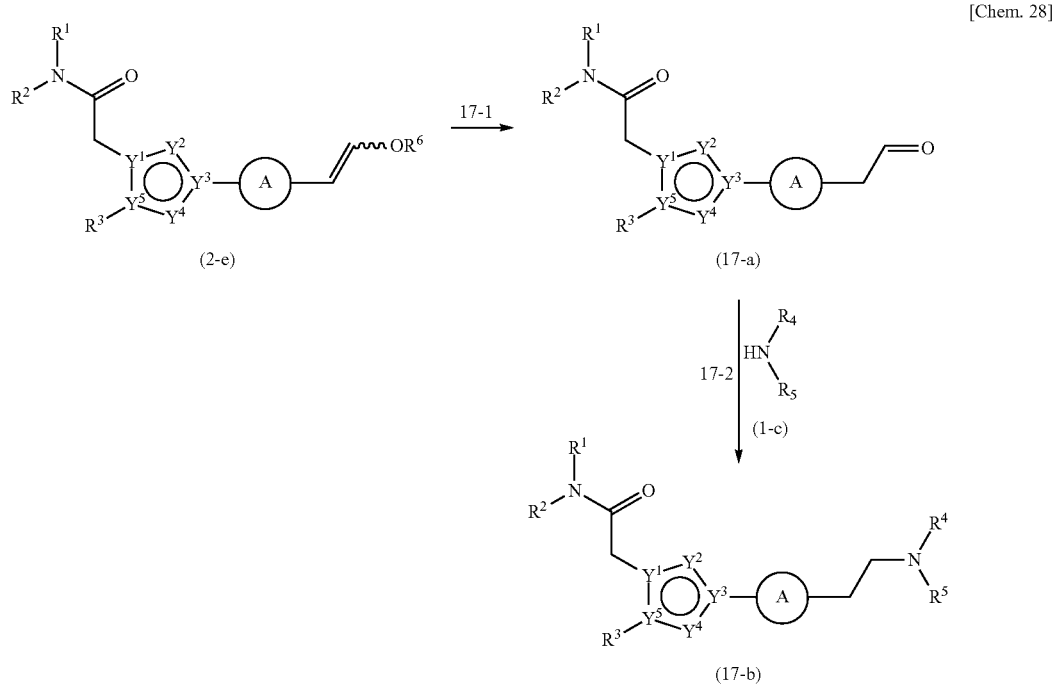

(wherein, $R^1$, $R^2$, $R^3$, $R^4$, $R^5$, $R^6$, $Y^1$, $Y^2$, $Y^3$, $Y^4$, $Y^5$ and A are the same as above).

The compound represented by Formula (17-a) can be obtained from the compound represented by Formula (2-f) through hydrolysis reaction in a hydrous solvent in the presence of an acid catalyst. The comprehensive review of the hydrolysis reaction is found in Protective Groups in Organic Synthesis, Fourth Edition, John Wiley & Sons, INC. (Step 17-1)

The compound represented by Formula (17-b) can be obtained from the compound represented by Formula (17-a) and the compound represented by Formula (1-c) through reductive amination reaction (Step 17-2). The reductive amination reaction is accomplished by reacting the aldehyde (17-a) with a corresponding amine (1-c) to generate an imine derivative, which is then reduced with a reducing agent such as, for example, sodium triacetoxyborohydride. This reaction proceeds in an inert solvent such as methanol, ethanol, tetrahydrofuran, dichloromethane, chloroform, or mixed solvents thereof in the presence or absence of an acid catalyst under the temperature condition of from −70° C. to room temperature. Alternatively, the reaction may employ hydrogen gas with palladium-on-carbon or the like being used as a catalyst; alternatively, the reaction may be performed using other boron reagents such as borohydride, sodium borohydride, and sodium cyanoborohydride.

Among the compounds represented by the above Formula (I), a compound represented by Formula (18-1) can be prepared by the synthetic process shown in Scheme 18.

Scheme 18

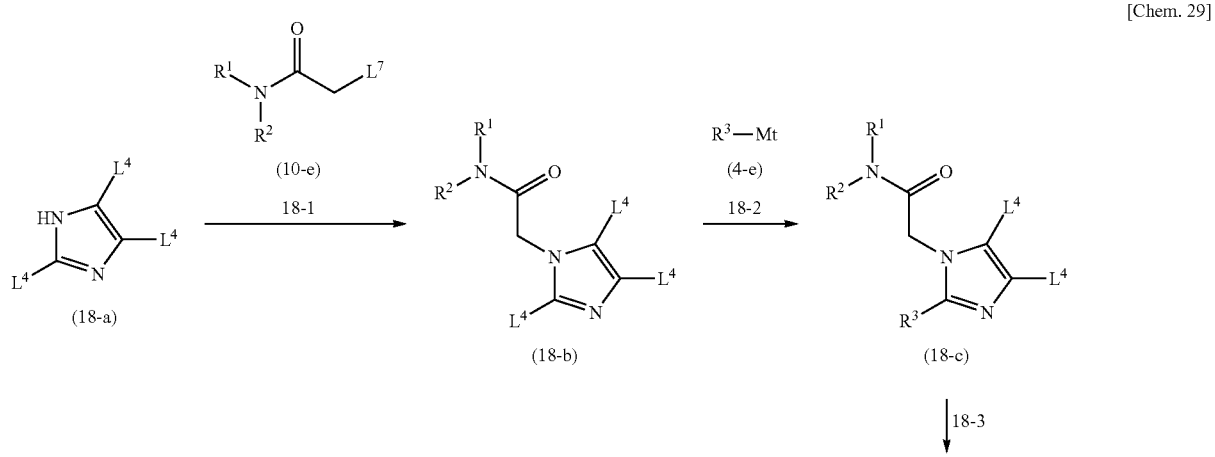

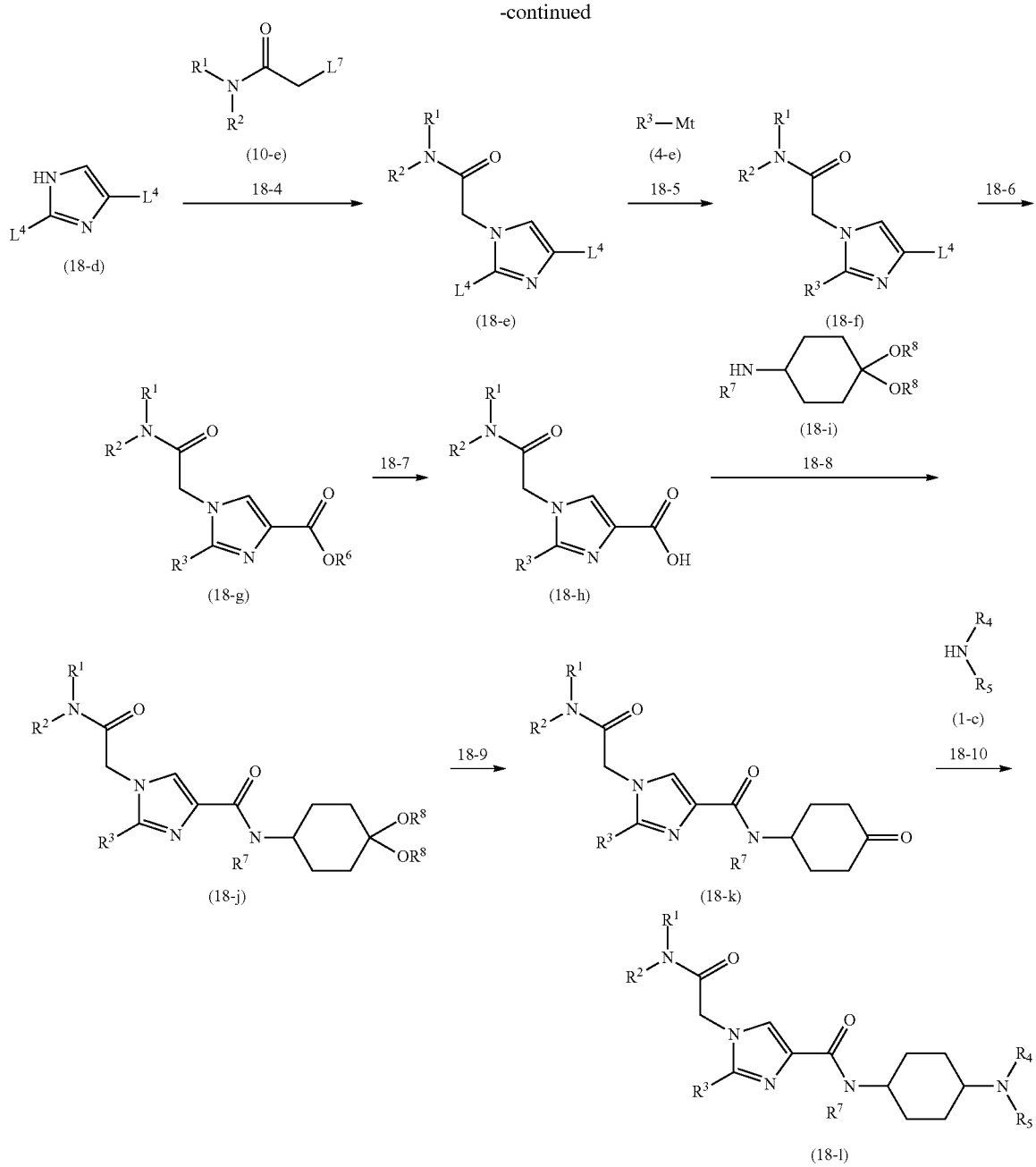

(wherein, $R^1$, $R^2$, $R^3$, $R^4$, $R^5$, $L^4$, $L^7$ and A are the same as above; $R^7$ represents a hydrogen atom or a $C_{1-5}$ alkyl group; $R^8$ represents a protecting group for a carbonyl group, such as a methyl group or an ethyl group; alternatively, adjacent $R^8$ groups may combine to form a ring [see Protective Groups in Organic Synthesis, Fourth Edition, John Wiley & Sons, INC.])

The compound (18-a) can be converted to the compound represented by Formula (18-b) by means of the same technique as that in Step 10-2 of Scheme 10 (Step 18-1). Here the compound (18-a) is available as a commercial compound or a known compound; alternatively, it may be a compound as synthesized from commercial compounds or known compounds using various organic synthesis techniques known to those skilled in the art.

The compound represented by Formula (18-b) can be converted to the compound represented by Formula (18-c) by means of the same technique as that in Step 4-2 of Scheme 4 (Step 18-2).

The compound represented by Formula (18-f) can be obtained from the compound represented by Formula (18-c) through dehalogenation reaction in an inert solvent in the presence of a base (Step 18-3).

The compound represented by Formula (18-d) can be converted to the compound represented by Formula (18-e) by means of the same technique as that in Step 10-2 of Scheme 10 (Step 18-4). Here the compound represented by Formula (18-d) is available as a commercial compound or a known compound; alternatively, it may be a compound as synthesized from commercial compounds or known compounds using various organic synthesis techniques known to those skilled in the art.

The compound represented by Formula (18-e) can be converted to the compound represented by Formula (18-f) by means of the same technique as that in Step 4-2 of Scheme 4 (Step 18-5).

The compound represented by Formula (18-g) can be produced by reacting the compound represented by Formula (18-f) with carbon monoxide and R⁶OH in an inert solvent in the presence or absence of a base and in the presence of a palladium catalyst, optionally using a ligand for the palladium catalyst (Step 18-6) (see Comprehensive Organic Transformations, Second Edition, 1999, John Wiley & Sons, INC.) Examples of the palladium catalyst here mentioned include palladium(II) acetate, dichlorobis(triphenylphosphine)palladium(II), dichlorobisacetonitrilepalladium(II), and tetraquistriphenylphosphine palladium(0). Examples of the ligand include triphenylphosphine, tributylphosphine, 2,2-bis(diphenylphosphino)-1,1-binaphthyl (BINAP), 2-(di-tert-butylphosphino)biphenyl, 1,1'-bis(diphenylphosphino)ferrocene (dppf), and 1,3-bis(diphenylphosphino)propane (dppp).

The compound represented by Formula (18-g) can be converted to the compound represented by Formula (18-h) by means of the same technique as that in Step 2-1 of Scheme 2 (Step 18-7). The compound represented by Formula (18-j) can be obtained from the compound represented by Formula (18-h) and the compound represented by Formula (18-i) through amidation reaction by the same technique as in Step 2-2 of Scheme 2 (Step 18-8).

The compound (18-k) can be produced from the compound (18-j) by removing the protecting groups R⁸ for a carbonyl group, using various organic synthesis techniques known to those skilled in the art [see Protective Groups in Organic Synthesis, Fourth Edition, John Wiley & Sons, INC.](Step 18-9).

The compound (18-k) can be converted to the compound represented by Formula (18-1) by means of the same technique as that in Step 17-2 of Scheme 17 (Step 18-10).

Among the compounds represented by the above Formula (I), a compound represented by Formula (19-c) can be prepared by the synthetic process shown in Scheme 9.

Scheme 19

[Chem. 30]

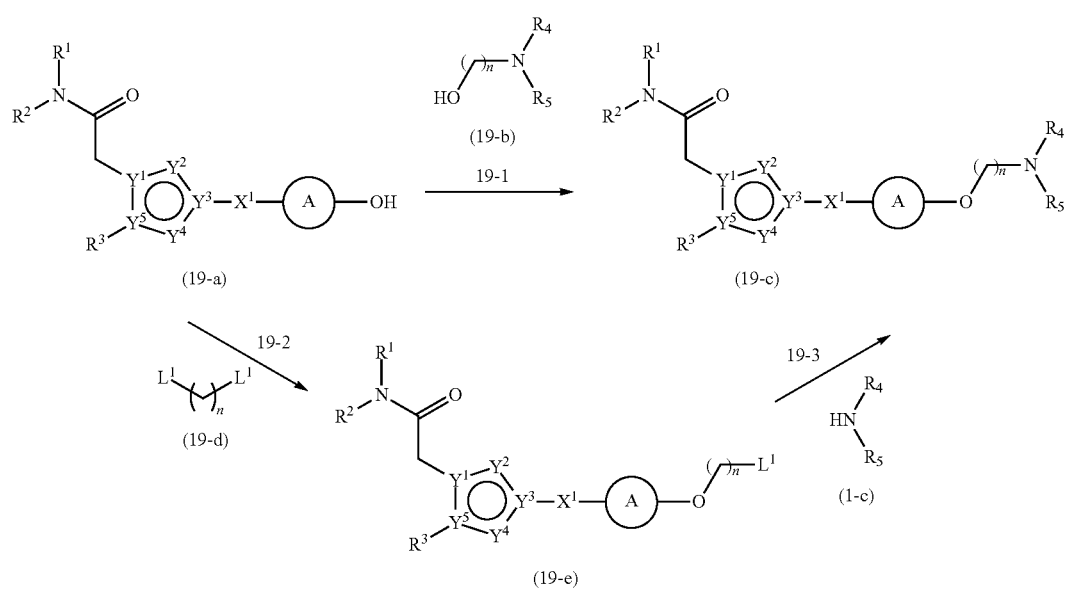

(wherein, $R^1$, $R^2$, $R^3$, $R^4$, $R^5$, $Y^1$, $Y^2$, $Y^3$, $Y^4$, $Y^5$, $L^1$, $X^1$ and A are the same as above; n is an integer of 1 to 5).

The compound represented by Formula (19-c) can be obtained from the compound represented by Formula (19-a) and the compound represented by Formula (19-b) through reaction under the conditions of the Mitsunobu reaction (Step 19-1). The comprehensive review of the Mitsunobu reaction is found in Synthesis. 1981, 1-28; Chem. Asian J. 2007, 2, 1340-1355; Chem. Pharm. Bull. 2003, 51(4), 474-476.

The compound represented by Formula (19-e) can be obtained from the compound represented by Formula (19-a) and the compound represented by Formula (19-d) through reaction under a basic condition (Step 19-2). The reaction in Step 19-2 proceeds in a solvent such as N,N-dimethylformamide, dimethyl sulfoxide, tetrahydrofuran, acetonitrile, ethanol, isopropyl alcohol or mixed solvents thereof in the presence of an inorganic base such as potassium carbonate or cesium carbonate or an organic base such as triethylamine or diisopropylethylamine under the temperature condition of from near 0° C. to near the boiling point of the solvent.

The compound represented by Formula (19-c) can be obtained by reacting the compound represented by Formula (19-e) with a compound in the class of amines which is represented by Formula (1-c) (Step 19-3). The reaction in Step 19-3 proceeds under the same conditions as those in Step 1-2.

Among the compounds represented by the above Formula (19-a), a compound represented by Formula (20-d) can be prepared by the synthetic process shown in Scheme 20.

Scheme 20

[Chem. 31]

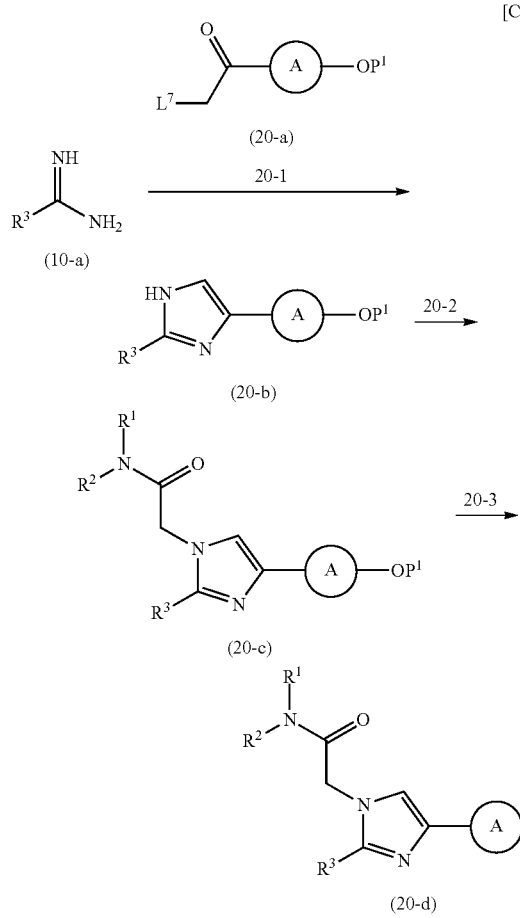

(wherein, $R^1$, $R^2$, $R^3$, $L^7$, $P^1$ and A are the same as above).

The compound represented by Formula (10-a) can be converted to the compound represented by Formula (20-b) by means of the same technique as that in Step 10-1 of Scheme 10 (Step 20-1). The compound represented by Formula (20-b) can be converted to the compound represented by Formula (20-c) by means of the same technique as that in Step 10-2 of Scheme 10 (Step 20-2). The compound represented by Formula (20-c) can be converted to the compound represented by Formula (20-d) by means of the same technique as that in Step 5-8 of Scheme 5 (Step 20-3).

Among the compounds represented by the above Formula (19-a), a compound represented by Formula (21-a) can be prepared by the synthetic process shown in Scheme 21.

Scheme 21

[Chem. 32]

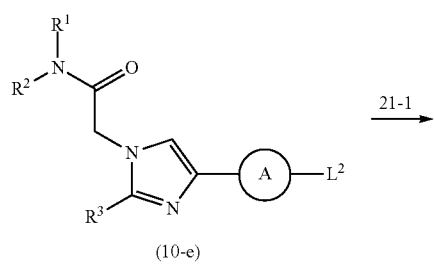

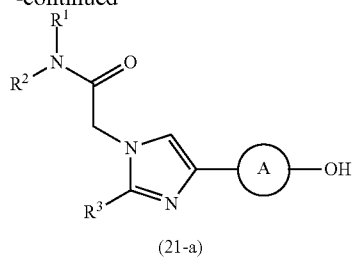

(wherein, $R^1$, $R^2$, $R^3$, $L^2$ and A are the same as above).

The compound represented by Formula (21-a) can be obtained by first preparing a boronic acid derivative from the compound represented by Formula (10-e) and then hydroxylating the derivative with a peracid (Step 21-1). This step can be carried out in accordance with the method described in WO 2006/021886.

Among the compounds represented by the above Formula (I), a compound represented by Formula (22-b) can be prepared by the synthetic process shown in Scheme 22.

Scheme 22

[Chem. 33]

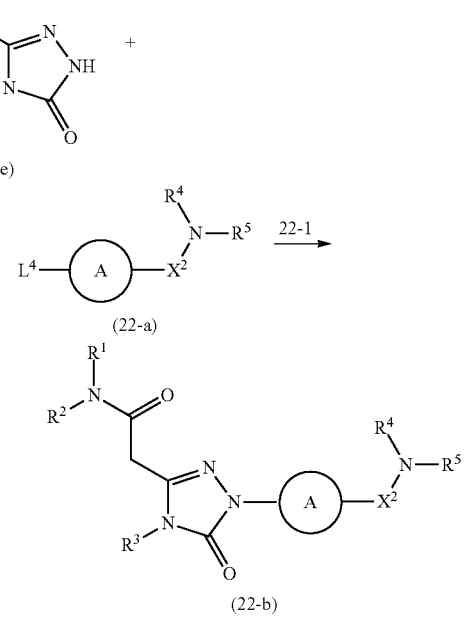

(wherein, $R^1$, $R^2$, $R^3$, $R^4$, $R^5$, $L^4$, $X^2$ and A are the same as above).

The compound represented by Formula (22-b) can be obtained by reacting the compound represented by Formula (15-e) with the compound represented by Formula (22-a) (Step 22-1). The reaction in Step 22-1 proceeds under the same conditions as those in Step 15-4.

Among the compounds represented by the above Formula (I), a compound represented by Formula (23-c) can be prepared by the synthetic process shown in Scheme 23.

Scheme 23

[Chem. 34]

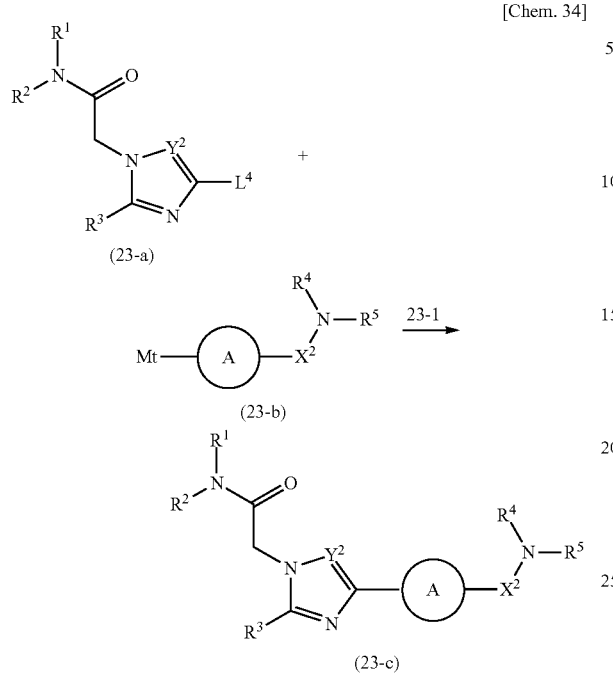

(wherein, $R^1$, $R^2$, $R^3$, $R^4$, $R^5$, $L^4$, $X^2$, $Y^2$, Mt and A are the same as above).

The compound represented by Formula (23-c) can be obtained by reacting the compound represented by Formula (23-a) with the compound represented by Formula (23-b) (Step 23-1). The reaction in Step 23-1 proceeds under the same conditions as those in Step 4-3.

Among the compounds represented by the above Formula (23-a), a compound represented by Formula (24-a) can be prepared by the synthetic process shown in Scheme 24.

Scheme 24

[Chem. 35]

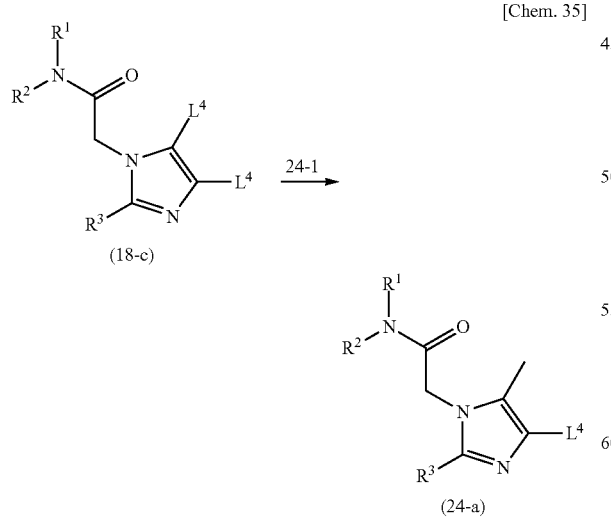

(wherein, $R^1$, $R^2$, $R^3$ and $L^4$ A are the same as above).

The compound represented by Formula (24-a) can be obtained by reacting the compound represented by Formula (18-c) with a methylating agent such as methyl iodide in the presence of a base (Step 24-1).

Among the compounds represented by the above Formula (I), a compound represented by Formula (25-b) can be prepared by the synthetic process shown in Scheme 25.

Scheme 25

[Chem. 36]

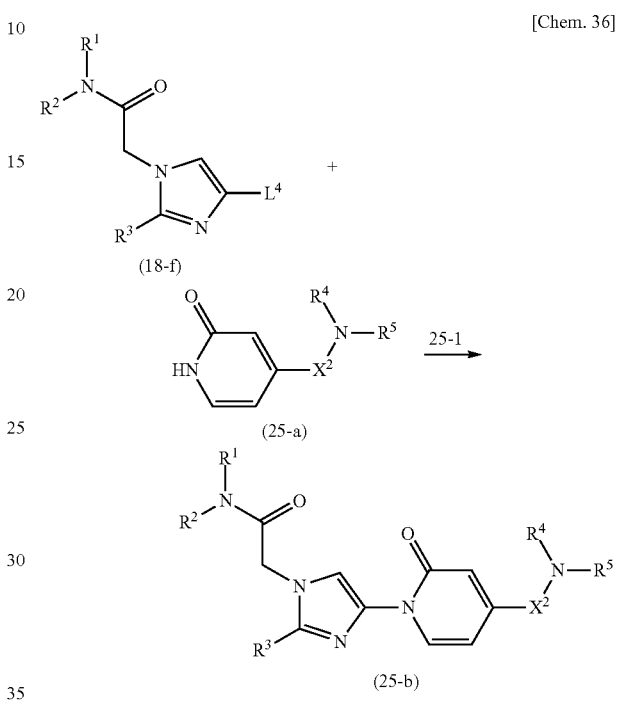

(wherein, $R^1$, $R^2$, $R^3$, $R^4$, $R^5$, $L^4$ and $X^2$ are the same as above).

The compound represented by Formula (25-b) can be obtained by reacting the compound represented by Formula (18-f) with the compound represented by Formula (25-a) (Step 25-1). The reaction in Step 25-1 proceeds under the same conditions as those in Step 4-1.

Among the compounds represented by the above Formula (I), a compound represented by Formula (26-f) can be prepared by the synthetic process shown in Scheme 26.

Scheme 26

[Chem. 37]

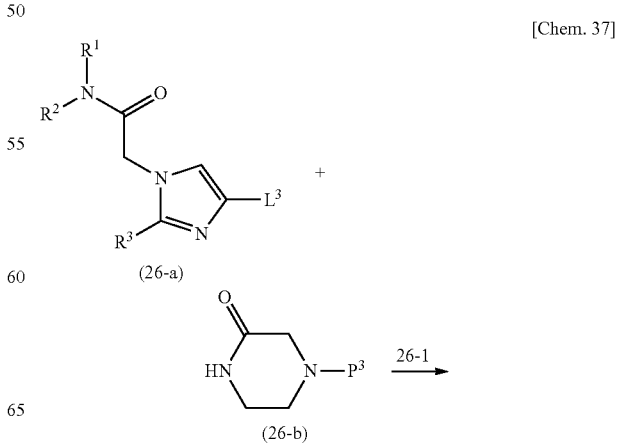

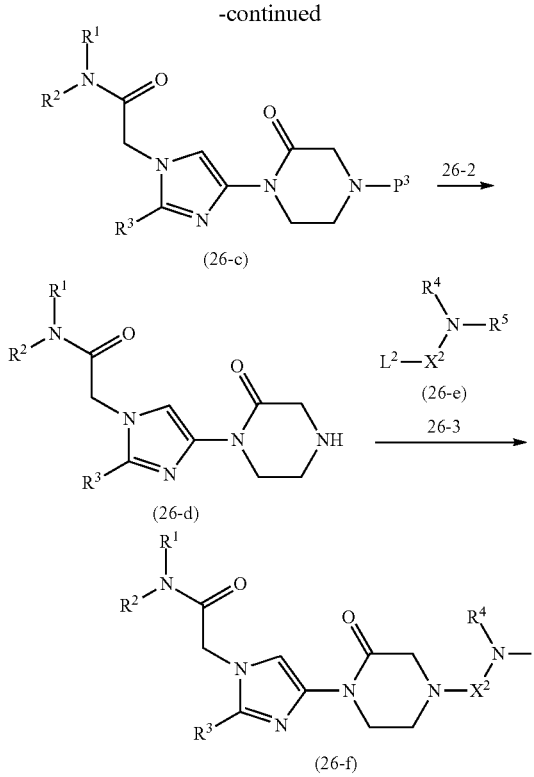

(wherein, $R^1$, $R^2$, $R^3$, $R^4$, $R^5$, $L^4$ and $X^2$ are the same as above; $P^3$ represents a protecting group for amino groups, such as a benzyloxycarbonyl group, an allyloxycarbonyl group, a tert-butylcarbonyl group or a p-toluenesulfonyl group [see Protective Groups in Organic Synthesis, Fourth Edition, John Wiley & Sons, INC.])

The compound represented by Formula (26-c) can be obtained by reacting the compound represented by Formula (26-a) with the compound represented by Formula (26-b) (Step 26-1). The reaction in Step 26-1 proceeds under the same conditions as those in Step 4-1. Here the compound represented by Formula (26-b) is available as a commercial compound or a known compound; alternatively, it may be a compound as synthesized from commercial compounds or known compounds using various organic synthesis techniques known to those skilled in the art.

The compound represented by Formula (26-d) can be obtained from the compound represented by Formula (26-c) by means of removing the protective group $P^3$ using various organic synthesis techniques known to those skilled in the art [see Protective Groups in Organic Synthesis, Fourth Edition, John Wiley & Sons, INC.](Step 26-2).

The compound represented by Formula (26-f) can be obtained by reacting the compound represented by Formula (26-d) with the compound represented by Formula (26-e) (Step 26-3). The reaction in Step 26-3 proceeds under the same conditions as those in Step 1-2.

Among the compounds represented by Formula (22-a), compounds represented by Formula (27-e) and Formula (27-j) can be prepared by the synthetic process shown in Scheme 27.

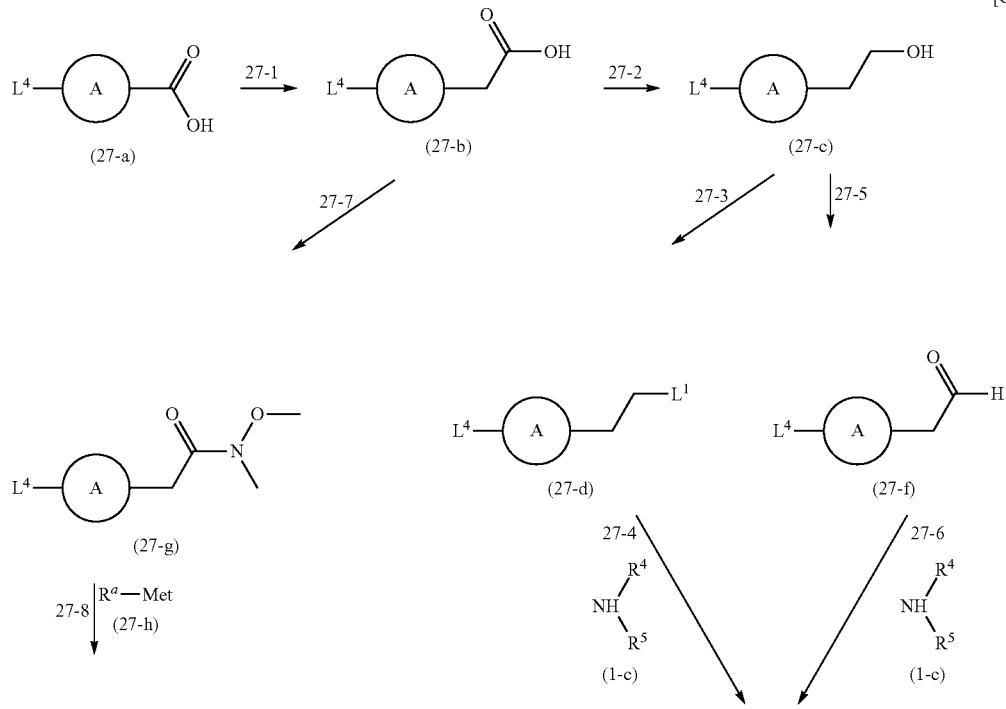

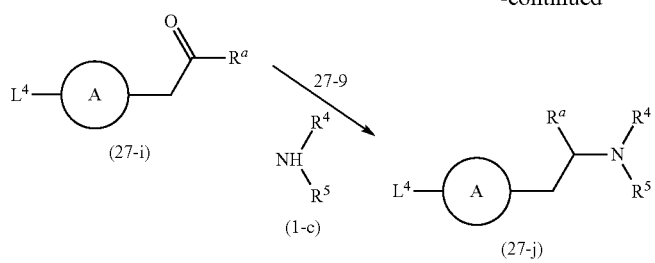

(wherein, $R^4$, $R^5$, $R^7$, $L^1$, $L^4$ and A are the same as above; Met represents a metal such as —MgBr, MgCl, or —Li; and $R^a$ represents a methyl or ethyl group).

The compound represented by Formula (27-b) can be obtained from the compound represented by Formula (27-a) through homologation by the Arndt-Eistert reaction (Step 27-1). The comprehensive review of the Arndt-Eistert reaction can be found in Chem. Ber., 1927, 60, 1364. Here the compound (27-a) is available as a commercial compound or a known compound; alternatively, it may be a compound as synthesized from commercial compounds or known compounds using various organic synthesis techniques known to those skilled in the art. The compound represented by Formula (27-c) can be obtained by reducing the compound represented by Formula (27-b) (Step 27-2). The reduction reaction in Step 27-2 proceeds in a solvent such as tetrahydrofuran, 1,4-dioxane, diethyl ether, diisopropyl ether, or mixed solvents thereof in the presence of a reducing agent such as a borane-THF complex or lithium aluminum hydride under the temperature condition of from −78° C. to near room temperature. The compound represented by Formula (27-e) can be prepared from the compound represented by Formula (27-c) by means of converting the hydroxyl group to a leaving group (Step 27-3) and then allowing an amine (1-c) to act on the resulting compound (Step 27-4). The compound represented by Formula (27-e) can also be obtained by oxidizing the hydroxyl group of the compound represented by Formula (27-c) into an aldehyde group through a common oxidation reaction (Step 27-5) and then performing a reductive amination reaction with the amine (1-c) (Step 27-6). Step 27-3, Step 27-4 and Step 27-6 proceed under the same reaction conditions as those for Step 1-1, Step 1-2 and Step 17-2, respectively. The compound represented by Formula (27-j) can be obtained by converting the compound represented by Formula (27-b) into a Weinreb amide (Step 27-7), then allowing a corresponding organometallic reagent (e.g., a Grignard reagent or an organolithium reagent) to act on the amide so that it is converted into a ketonic form (27-i) (Step 27-8), and thereafter subjecting the ketonic form to a reductive amination reaction with the amine (1-c) (Step 27-9). The reaction in Step 27-7 proceeds in the presence of N,O-dimethylhydroxylamine under the same amidation conditions as those in Step 2-2. The reaction in Step 27-8 is one in which the compound represented by Formula (27-h) (a metallic reagent such as a Grignard reagent or an organioithium reagent) is allowed to act in a solvent such as tetrahydrofuran, 1,4-dioxane, diethyl ether, diisopropyl ether, or mixed solvents thereof under the temperature condition of from −78° C. to near room temperature.

The compound represented by Formula (23-b) can be prepared by the synthetic process shown in Scheme 28.

Scheme 28

[Chem. 39]

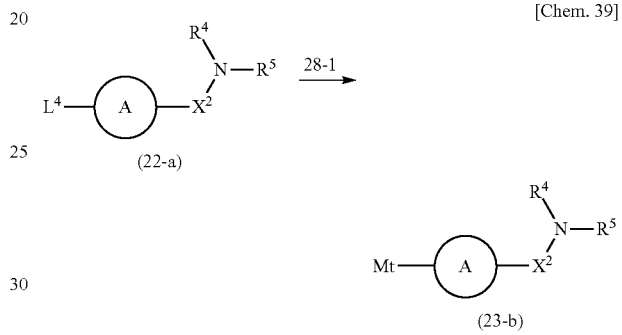

(wherein, $R^4$, $R^5$, $L^4$, $X^2$, Mt and A are the same as above).

The compound represented by the above Formula (23-b) can be synthesized from the compound represented by Formula (22-a) through a metal exchange reaction in the presence or absence of a transition metal catalyst and in the presence or absence of a base (Step 28-1). Here the "metal exchange reaction" may be exemplified by such a reaction that (22-a) is treated with pinacolato borane or bispinacol diborane in an inert solvent in the presence of a palladium catalyst, optionally using a ligand for the palladium catalyst, in the presence of a base such as potassium acetate or triethylamine (see Comprehensive Organic Transformations, Second Edition, 1999, John Wiley & Sons, INC.) Examples of the palladium catalyst here mentioned include palladium(II) acetate, dichlorobis(triphenylphosphine)palladium(II), dichlorobisacetonitrilepalladium(II), and tetraquistriphenylphosphine palladium(0). Examples of the ligand include triphenylphosphine, tributylphosphine, 2,2-bis(diphenylphosphino)-1,1-binaphthyl (BINAP), 2-(di-tert-butylphosphino)biphenyl, 1,1'-bis(diphenylphosphino)ferrocene (dppf), and 1,3-bis(diphenylphosphino)propane (dppp). Another example of the metal exchange reaction that may be given is one in which (22-a) is converted to a Grignard reagent, an organolithium reagent or the like in an inert solvent using various organic synthesis techniques known to those skilled in the art and thereafter the reagent is treated with trimethyl borate, triethyl borate, triisopropyl borate or the like.

The compound represented by Formula (27-c) can be prepared by the synthetic process shown in Scheme 29.

Scheme 29

[Chem. 40]

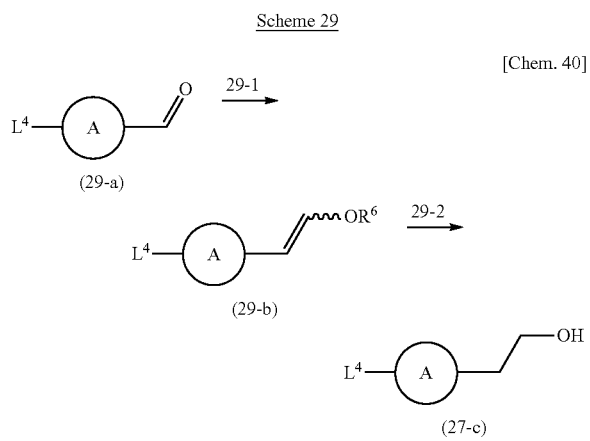

(wherein, $R^6$, $L^4$ and A are the same as above).

The compound represented by Formula (29-b) can be obtained from the compound represented by Formula (29-a) through homologation by the Wittig reaction (Step 29-1). The comprehensive review of the Wittig reaction can be found in Comprehensive Organic Transformations, Second Edition, 1999, John Wiley & Sons, Inc.

The compound (29-b) can be converted to the compound represented by Formula (27-c) by means of the same technique as that in Step 2-6 of Scheme 2 (Step 29-2).

EXAMPLES

The present invention will now be described in more detail by Reference Examples, Examples, and Test Examples, which are by no means intended to limit the present invention and may be modified without departing from the scope of the present invention.

In Reference Examples and Examples, the "phase separator" in post-treatment is an ISOLUTE (registered trademark) Phase Separator of Biotage Inc. In purification by column chromatography, for "SNAP Cartridge KP-NH", SNAP Cartridge KP-NH of Biotage Inc. was used, for "SNAP Cartridge KP-Sil", SNAP Cartridge KP-Sil of Biotage Inc. was used, for "SNAP Cartridge HP-Sil" SNAP Cartridge HP-Sil of Biotage Inc., and for "Chromatorex (registered trademark) NH" Chromatorex (registered trademark) NH of Fuji Silysia Chemical Ltd. was used. In purification by preparative thin-layer chromatography (PTLC), Silica Gel 60F$_{254}$, 20 cm×20 cm, of Merck was used. In purification by "reverse-phase column chromatography", Waters SunFire prep C18 OBD, 5.0 μm, φ30×50 mm or YMC-Actus Triart C18, 5.0 μm, φ30×50 mm was used.

The data described in the Reference Examples and Examples below were obtained by measurement with the following instruments:

NMR spectrometer: JNM-ECA 600 (600 MHz, JEOL Ltd.), JNM-ECA 500 (500 MHz, JEOL Ltd.), UNITY NOVA 300 (300 MHz, Varian, Inc.), or GEMINI 2000/200 (200 MHz, Varian, Inc.);

MS spectrometer: LCMS-2010EV (Shimadzu Corporation) or Platform LC (Micromass, Ltd.).

In the Reference Examples and Examples below, high-performance liquid chromatography-mass spectrometry (LCMS) was performed under the following conditions of measurement:

Condition 1
Instrument: Platform LC (Micromass, Ltd.) and Agilent 1100 (Agilent Technologies, Inc.);
Column: SunFire C18, 2.5 μm, φ4.6×50 mm (Waters Corporation);
Solvent: Solution A, water containing 0.1% trifluoroacetic acid; Solution B, acetonitrile containing 0.1% trifluoroacetic acid;
Gradient: 0 min (Solution A/Solution B=90/10), 0.5 min (Solution A/Solution B=90/10), 5.5 min (Solution A/Solution B=20/80), 6.0 min (Solution A/Solution B=1/99), and 6.3 min (Solution A/Solution B=1/99);
Flow rate: 1 mL/min, Detection: 254 nm; and
Ionization: electron spray ionization (ESI).
Condition 2-1
Instrument: Agilent 2900 and Agilent 6150;
Column: Waters Acquity CSH C18, 1.7 μm, φ2.1×50 mm;
Solvent: Solution A, water containing 0.1% formic acid; Solution B, acetonitrile containing 0.1% formic acid;
Gradient: 0 min (Solution A/Solution B=80/20), 1.2 to 1.4 min (Solution A/Solution B=1/99); and
Flow rate: 0.8 mL/min, Detection: 254 nm.
Condition 2-2
Instrument, column, and solvent are the same as those in Condition 2-1;
Gradient and flow rate: 0.8 mL/min for 0 min (Solution A/Solution B=95/5), 1.20 min (Solution A/Solution B=50/50), and 1.0 mL/min for 1.38 min (Solution A/Solution B=3/97); and
Detection: 254 nm.

In the Reference Examples and Examples below, compounds were named using ACD/Name (ACD/Labs 12.01, Advanced Chemistry Development Inc.)

Terms and reagent names in the Examples are denoted by the following abbreviations:

Brine (saturated brine), MeOH (methanol), MgSO$_4$ (anhydrous magnesium sulfate), K$_2$CO$_3$ (potassium carbonate), Na$_2$CO$_3$ (sodium carbonate), Na$_2$SO$_4$ (anhydrous sodium sulfate), NaHCO$_3$ (sodium hydrogencarbonate), NaOH (sodium hydroxide), KOH (potassium hydroxide), HCl (hydrogen chloride), IPE (diisopropyl ether), THF (tetrahydrofuran), DMF (N,N-dimethylformamide), Et$_2$O (diethyl ether), EtOH (ethanol), NH$_4$OH (25 to 28% aqueous ammonia), EtOAc (ethyl acetate), CHCl$_3$ (chloroform), DMSO (dimethyl sulfoxide), MeCN (acetonitrile), n-Hexane (n-hexane), Et$_3$N (triethylamine), iPr$_2$NEt (diisopropylethylamine), Pd(PPh$_3$)$_4$ [tetrakistriphenylphosphine palladium (0)], HATU [O-(7-azabenzotriazol-1-yl)-N,N,N',N'-tetramethyluronium hexafluorophosphate], DPPA (diphenylphosphoryl azide), BH$_3$.THF (borane-tetrahydrofuran complex), NaBO$_3$.4H$_2$O (sodium perborate tetrahydrate), 9-BBN (9-borabicyclo[3.3.1]nonane), IBX (1-hydroxy-1,2-benziodoxol-3(1H)-one 1-oxide), BBr$_3$ (boron tribromide), MsCl (methanesulfonyl chloride), TMSCH$_2$N$_2$ (trimethylsilyl diazomethane), n-BuLi (n-butyllithium), EDC.HCl [1-ethyl-3-(3-dimethylaminopropyl)carbodiimide hydrochloride], HOBt.H$_2$O (1-hydroxybenzotriazole monohydrate), Cs$_2$CO$_3$ (cesium carbonate), PdCl$_2$(PPh$_3$)$_2$ [bis(triphenylphosphine)palladium(II) dichloride], NaBH$_4$ (sodium borohydride), Na$_2$SO$_3$ (sodium sulfite), PdCl$_2$(dppf) CH$_2$Cl$_2$ {[1,1'-bis(diphenylphosphino)ferrocene]palladium (II) dichloride/dichloromethane complex (1:1)}, AcOK (potassium acetate), Boc (tert-butoxycarbonyl), NBS (N-bromosuccinimide), NIS (N-iodosuccinimide), Tf$_2$O

Reference Example P-A01

Synthesis of 4-(4-bromophenyl)-2-(3-chlorophenyl)-1H-imidazole

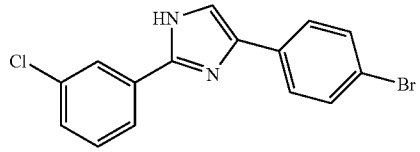

[Chem. 41]

A mixture of 3-chloro-benzamidine (3.53 g), NaHCO₃ (7.67 g), THF (35 mL) and water (14 mL) was refluxed. Under continued refluxing, a solution of 2,4′-dibromoacetophenone (5.23 g) in THF (14 mL) was added and the resulting mixture was refluxed for 2 hours. After leaving the mixture to cool, the solvent was distilled off under reduced pressure and water was added for extraction with CHCl₃. After drying the organic layer with Na₂SO₄, the desiccant was filtered off and the solvent distilled off under reduced pressure. The resulting residue was purified by silica gel column chromatography (Chromatorex NH; mobile phase: EtOAc/n-Hexane=0/100-50/50; v/v) to give the titled compound (4.18 g as a yellow solid).

MS (ESI pos.) m/z: 333, 335 ([M+H]⁺).

Reference Example P-A02

Synthesis of 2-[4-(4-bromophenyl)-2-(3-chlorophenyl)-1H-imidazol-1-yl]-N-(propan-2-yl)acetamide

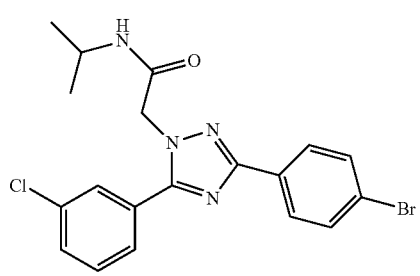

[Chem. 42]

A mixture of the compound (4.18 g) obtained in Reference Example P-A01, 2-bromo-N-isopropylacetamide (3.39 g), K₂CO₃ (3.46 g), and DMF (84 mL) was stirred overnight at room temperature. Water was added and the solid precipitating upon addition of IPE was recovered by filtration to give the titled compound (4.14 g as a pale brown solid).

MS (ESI pos.) m/z: 432, 434 ([M+H]⁺).

Reference Example P-A03

Synthesis of 2-[2-(3-chlorophenyl)-4-(4-ethenylphenyl)-1H-imidazol-1-yl]-N-(propan-2-yl)acetamide

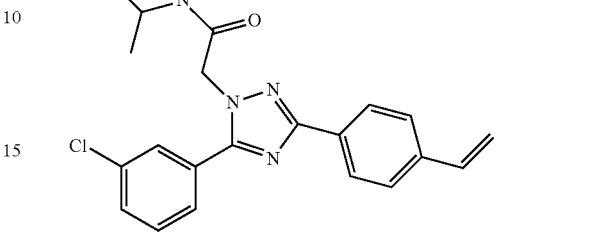

[Chem. 43]

A mixture of the compound (1.03 g) obtained in Reference Example P-A02, tributyl(vinyl)tin (0.76 mL), Pd(PPh₃)₄ (274 mg) and toluene (20 mL) was stirred at an external temperature of 100° C. Tributyl(vinyl)tin (0.76 mL) and Pd(PPh₃)₄ (274 mg) were further added and the mixture was stirred at an external temperature of 100° C. for 7 hours. After allowing the mixture to cool, the solvent was distilled off under reduced pressure and the resulting residue was purified by column chromatography (Chromatorex NH; mobile phase: n-Hexane/CHCl₃=90/10-50/50; v/v) to give the titled compound (660 mg as a colorless solid).

MS (ESI pos.) m/z: 380 ([M+H]⁺).

Reference Example P-A04

Synthesis of 2-{2-(3-chlorophenyl)-4-[4-(2-hydroxyethyl)phenyl]-1H-imidazol-1-yl}-N-(propan-2-yl)acetamide

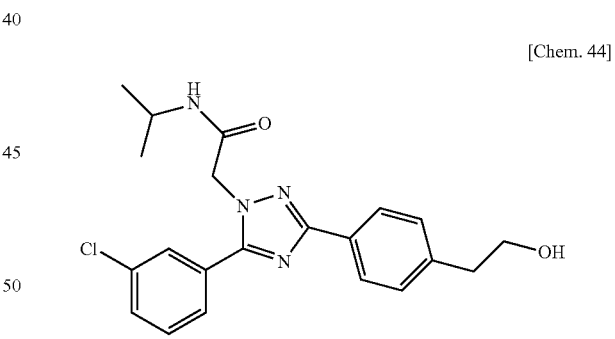

[Chem. 44]

To a THF solution (20 mL) of the compound (658 mg) obtained in Reference Example P-A03, 1.09 mol/L BH₃.THF-THF solution (2.38 mL) was added dropwise under an ice bath and after stirring the mixture for an hour under cooling with ice, water (26 mL) and NaBO₃.4H₂O (1.20 g) were added and the mixture was stirred for 6 hours under cooling with ice. After adding Na₂SO₃, the organic solvent was distilled off under reduced pressure and extraction was conducted with CHCl₃. The solvent was distilled off under reduced pressure and the residue was washed with a mixed solvent (EtOAc/n-Hexane=1/6; v/v); the solid was recovered by filtration to give the titled compound (536 mg as a colorless solid).

MS (ESI pos.) m/z: 398 ([M+H]⁺).

Reference Example P-A05

Synthesis of 4-(4-bromophenyl)-2-(4-fluoro-3-methoxyphenyl)-1H-imidazole

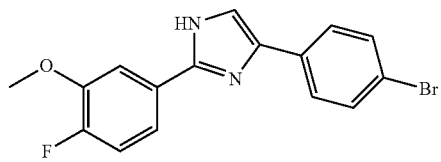

[Chem. 45]

Starting from 4-fluoro-3-methoxybenzamidine (8.00 g) and 2,4'-dibromoacetophenone (10.8 g), the same procedure as in Reference Example P-A01 was applied to give the titled compound (13.3 g as a pale yellow amorphous product).

MS (ESI pos.) m/z: 347, 349 ([M+H]$^+$).

Reference Example P-A06

Synthesis of 2-[4-(4-bromophenyl)-2-(4-fluoro-3-methoxyphenyl)-1H-imidazol-1-yl]-N-(propan-2-yl)acetamide

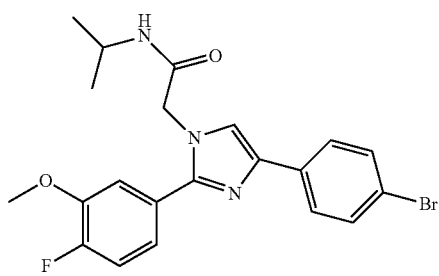

[Chem. 46]

Starting from the compound (13.3 g) obtained in Reference Example P-A05, the same procedure as in Reference Example P-A02 was applied to give the titled compound (14.7 g as a pale red solid).

MS (ESI pos.) m/z: 446, 448 ([M+H]$^+$).

Reference Example P-A07

Synthesis of 2-[4-(4-ethenylphenyl)-2-(4-fluoro-3-methoxyphenyl)-1H-imidazol-1-yl]-N-(propan-2-yl)acetamide

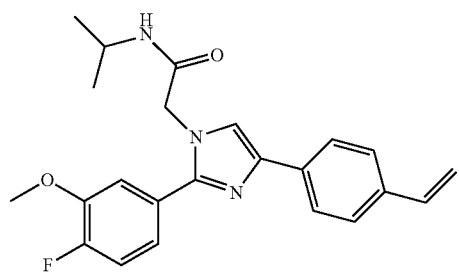

[Chem. 47]

Starting from the compound (5.00 g) obtained in Reference Example P-A06, the same procedure as in Reference Example P-A03 was applied to give the titled compound (3.06 g as a pale yellow amorphous product).

MS (ESI pos.) m/z: 394 ([M+H]$^+$).

Reference Example P-A08

Synthesis of 2-{2-(4-fluoro-3-methoxyphenyl)-4-[4-(2-hydroxyethyl)phenyl]-1H-imidazol-1-yl}-N-(propan-2-yl)acetamide

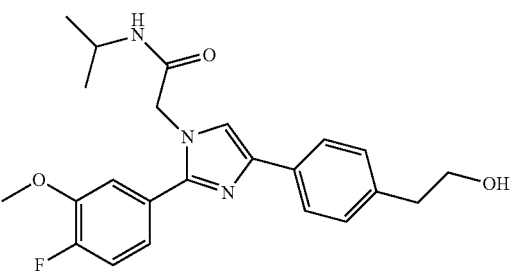

[Chem. 48]

Starting from the compound (3.06 g) obtained in Reference Example P-A07, the same procedure as in Reference P-A04 was applied to give the titled compound (3.20 g as a pale yellow solid).

MS (ESI pos.) m/z: 412 ([M+H]$^+$).

Reference Example P-A09

Synthesis of 5-bromo-2-[2-(3-chlorophenyl)-1H-imidazol-4-yl]pyridine

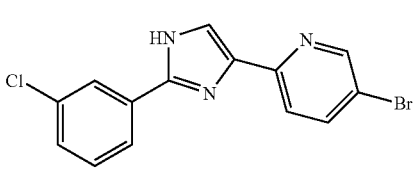

[Chem. 49]

Starting from 3-chloro-benzamidine (1.65 g) and 2-bromo-1-(5-bromopyridin-2-yl)ethanone (2.97 g), the same procedure as in Reference Example P-A01 was applied to give the titled compound (2.65 g as a reddish brown amorphous product).

MS (ESI pos.) m/z: 334, 336 ([M+H]$^+$).

Reference Example P-A10

Synthesis of 2-[4-(5-bromopyridin-2-yl)-2-(3-chlorophenyl)-1H-imidazol-1-yl]-N-(propan-2-yl)acetamide

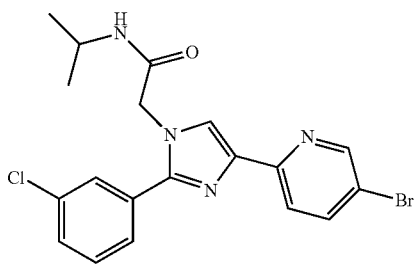

[Chem. 50]

Starting from the compound (2.64 g) obtained in Reference Example P-A09, the same procedure as in Reference Example P-A02 was applied to give the titled compound (2.54 g as a pale reddish brown solid).

MS (ESI pos.) m/z: 433, 435 ([M+H]$^+$).

Reference Example P-A11

2-[2-(3-chlorophenyl)-4-(5-ethenylpyridin-2-yl)-1H-imidazol-1-yl]-N-(propan-2-yl)acetamide

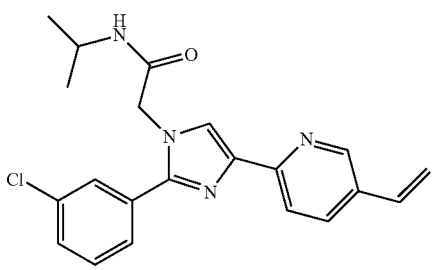

[Chem. 51]

Starting from the compound (1.50 g) obtained in Reference Example P-A10, the same procedure as in Reference Example P-A03 was applied to give the titled compound (768 mg as an orange-colored solid).

MS (ESI pos.) m/z: 381 ([M+H]$^+$).

Reference Example P-A12

Synthesis of 2-{2-(3-chlorophenyl)-4-[5-(2-hydroxyethyl)pyridin-2-yl]-1H-imidazol-1-yl}-N-(propan-2-yl)acetamide

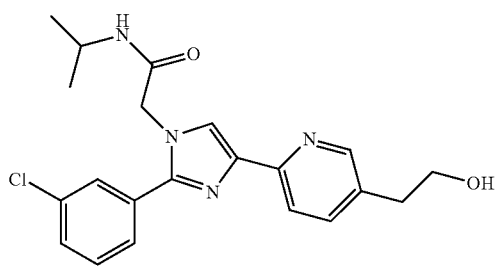

[Chem. 52]

Starting from the compound (760 mg) obtained in Reference Example P-A11, the same procedure as in Reference Example P-A04 was applied to give the titled compound (362 mg as a pale brown solid).

MS (ESI pos.) m/z: 399 ([M+H]$^+$).

Reference Example P-A13

Synthesis of 2-[4-(4-bromophenyl)-1H-imidazol-2-yl]-6-methoxypyridine

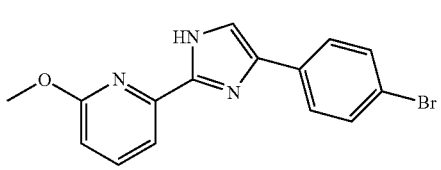

[Chem. 53]

Starting from 6-methoxypicolinimidamide hydrochloride (3.00 g) and 2,4'-dibromoacetophenone (4.45 g), the same procedure as in Reference Example P-A01 was applied to give the titled compound (2.23 g as a colorless solid).

MS (ESI pos.) m/z: 330, 332 ([M+H]$^+$).

Reference Example P-A14

Synthesis of 2-[4-(4-bromophenyl-2-(6-methoxypyridin-2-yl)-1H-imidazol-1-yl]-N-(propan-2-yl)acetamide

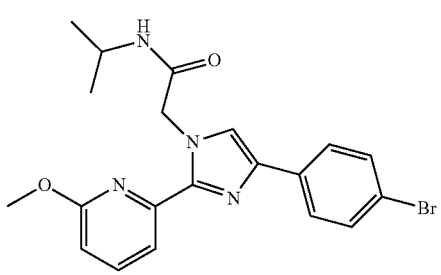

[Chem. 54]

Starting from the compound (2.23 g) obtained in Reference Example P-A13, the same procedure as in Reference Example P-A02 was applied to give the titled compound (2.85 g as a pale pink solid).

MS (ESI pos.) m/z: 429, 431 ([M+H]$^+$).

Reference Example P-A15

Synthesis of 2-[4-{4-[(Z)-2-ethoxyethenyl]phenyl}-2-(6-methoxypyridin-2-yl)-1H-imidazol-1-yl]-N-(propan-2-yl)acetamide

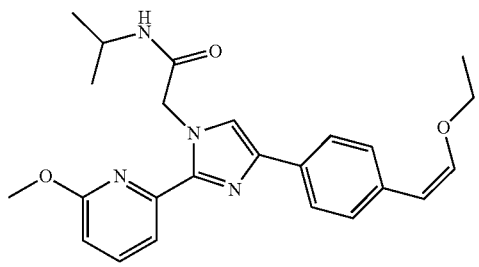

[Chem. 55]

Starting from the compound (500 mg) obtained in Reference Example P-A14 and (Z)-1-ethoxy-2-(tributylstannyl)ethane (0.47 mL), the same procedure as in Reference Example P-A03 was applied to give the titled compound (180 mg as a pale yellow solid).

MS (ESI pos.) m/z: 421 ([M+H]$^+$).

Reference Example P-A16

Synthesis of 2-{2-(6-methoxypyridin-2-yl)-4-[4-(2-oxoethyl)phenyl]-1H-imidazol-1-yl}-N-(propan-2-yl)acetamide

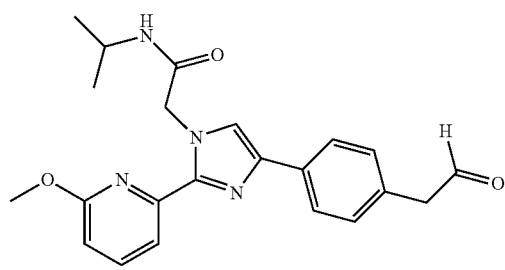

[Chem. 56]

A mixture of the compound (180 mg) obtained in Reference Example P-A15, a 1 M HCl aqueous solution (2 mL) and THF (10 mL) was refluxed overnight at an external temperature of 80° C. After leaving the mixture to cool, a 1 M HCl aqueous solution (2 mL) was further added and the mixture was refluxed for 6 hours at an external temperature of 80° C. After leaving the mixture to cool, the solvent was distilled off under reduced pressure; subsequently, the residue was neutralized with a saturated aqueous NaHCO$_3$ solution, followed by extraction with CHCl$_3$. The organic layer was filtered with Phase Separator and the solvent was distilled off under reduced pressure to give the titled compound (180 mg as a pale yellow solid).

MS (ESI pos.) m/z: 393 ([M+H]$^+$).

Reference Example P-A17

Synthesis of 2-bromo-5-[2-(3-chlorophenyl)-1H-imidazol-4-yl]pyridine

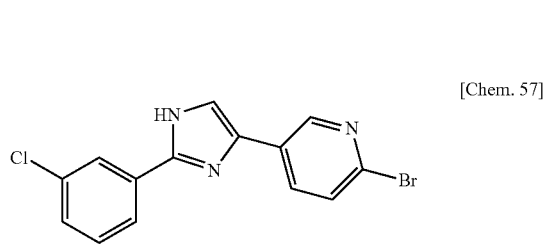 [SMILES: Clc1cccc(-c2nc(-c3ccc(Br)nc3)c[nH]2)c1]

[Chem. 57]

Starting from 3-chlorobenzamidine (4.00 g) and 2-bromo-1-(6-bromopyrid-3-yl)ethanone (7.29 g), the same procedure as in Reference Example P-A01 was applied to give the titled compound (4.02 g as a powder).

MS (ESI pos.) m/z: 334, 336 ([M+H]$^+$).

Reference Example P-A18

Synthesis of 2-[4-(6-bromonopyridin-3-yl)-2-(3-chlorophenyl)-1H-imidazol-1-yl]-N-(propan-2-yl)acetamide

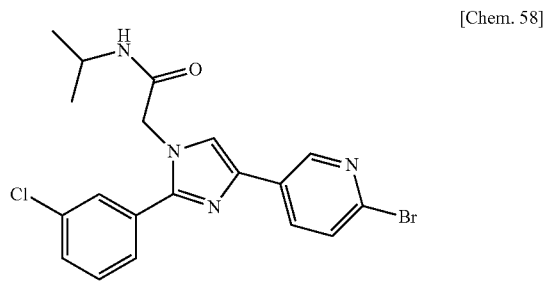 [SMILES: CC(C)NC(=O)Cn1cc(-c2ccc(Br)nc2)nc1-c1cccc(Cl)c1]

[Chem. 58]

Starting from the compound (3.52 g) obtained in Reference Example P-A17, the same procedure as in Reference Example P-A02 was applied to give the titled compound (4.11 g as a powder).

MS (ESI pos.) m/z: 433, 435 ([M+H]$^+$).

Reference Example P-A19

Synthesis of 2-[2-(3-chlorophenyl)-4-{6-[(Z)-2-ethoxyethenyl]pyridin-3-yl}-1H-imidazol-1-yl]-N-(propan-2-yl)acetamide

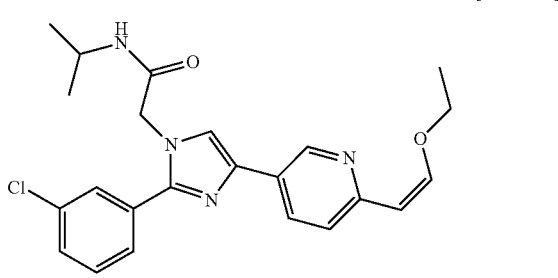

[Chem. 59]

Starting from the compound (2.04 g) obtained in Reference Example P-A18, the same procedure as in Reference Example P-A15 was applied to give the titled compound (863 mg as a colorless solid).

MS (ESI pos.) m/z: 425 ([M+H]$^+$).

Reference Example P-A20

Synthesis of 2-{2-(3-chlorophenyl)-4-[6-(2-oxoethyl)pyridin-3-yl]-1H-imidazol-1-yl}-N-(propan-2-yl)acetamide

[Chem. 60]

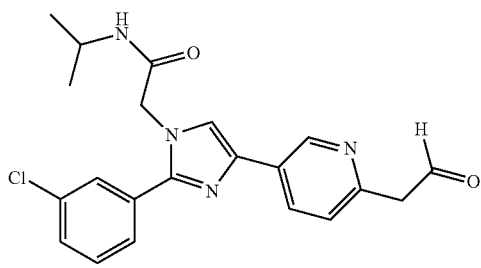

Starting from the compound (211 mg) obtained in Reference Example P-A19, the same procedure as in Reference Example P-A16 was applied to give the titled compound (290 mg as a red oil).

MS (ESI pos.) m/z: 397 ([M+H]$^+$).

Reference Example P-A21

Synthesis of 2-[4-{4-[(Z)-2-ethoxyethenyl]phenyl}-2-(4-fluoro-3-methoxyphenyl)-1H-imidazol-1-yl]-N-(propan-2-yl)acetamide

[Chem. 61]

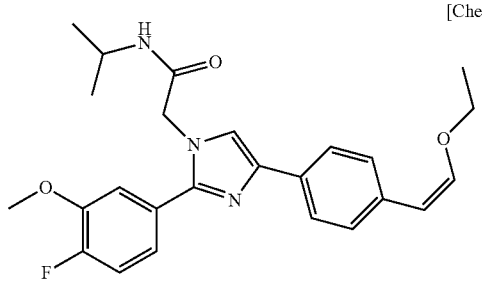

Starting from the compound (2.00 g) obtained in Reference Example P-A06, the same procedure as in Reference Example P-A15 was applied to give the titled compound (1.12 g as a colorless solid.)

MS (ESI pos.) m/z: 438 ([M+H]$^+$).

Reference Example P-A22

Synthesis of 2-{2-(4-fluoro-3-methoxyphenyl)-4-[4-(2-oxoethyl)phenyl]-1H-imidazol-1-yl}-N-(propan-2-yl)acetamide

[Chem. 62]

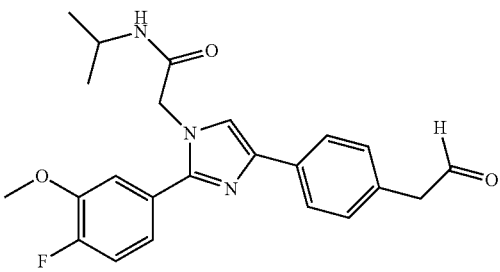

Starting from the compound (1.12 g) obtained in Reference Example P-A21, the same procedure as in Reference Example P-A16 was applied to give the titled compound (1.00 g as a yellow solid).

MS (ESI pos.) m/z: 410 ([M+H]$^+$).

Reference Example P-A23

Synthesis of 2-{2-(3-chlorophenyl)-4-[4-(4,4,5,5-tetramethyl-1,3,2-dioxaborolan-2-yl)phenyl]-1H-imidazol-1-yl}-N-(propan-2-yl)acetamide

[Chem. 63]

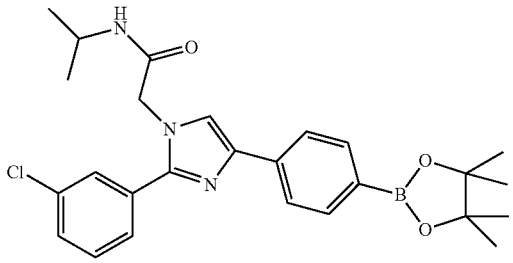

A mixture of the compound (500 mg) obtained in Reference Example P-A02, 4,4,4',4',5,5,5',5'-octamethyl-2,2'-bi-1,3,2-dioxaborolane (381 mg), PdCl$_2$(dppf).CH$_2$Cl$_2$ (95 mg), AcOK (342 mg) and DMSO (8 mL) was stirred at an external temperature of 100° C. for 1.5 hours under a nitrogen atmosphere. After leaving the mixture to cool, water and IPE were added and after continuing the stirring for a while, the precipitating solid was recovered by filtration to give the titled compound (610 mg as a dark gray solid).

MS (ESI pos.) m/z: 480 ([M+H]$^+$).

Reference Example P-A24

Synthesis of 2-[2-(3-chlorophenyl)-4-(4-hydroxyphenyl)-1H-imidazol-1-yl]-N-(propan-2-yl)acetamide

[Chem. 64]

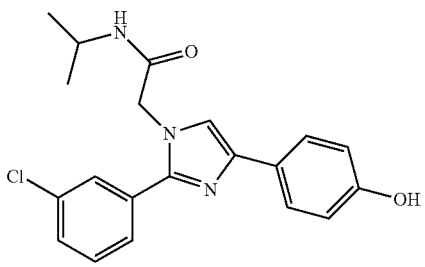

To an EtOH (2 mL) solution of the compound (255 mg) obtained in Reference Example P-A23, a 30% aqueous $H_2O_2$ solution (2 mL) was added and the mixture was stirred at room temperature for one day. Water was added for extraction with $CHCl_3$. The organic layer was washed with Brine and dried over $Na_2SO_4$; subsequently, the desiccant was filtered off and the solvent was distilled off under reduced pressure. The resulting residue was purified by silica gel column chromatography (SNAP Cartridge KP-Sil 25 g; mobile phase: $CHCl_3$/MeOH=99/1-95/5; v/v). The purified product was washed with $Et_2O$ to give the titled compound (123 mg as a colorless solid).

MS (ESI pos.) m/z: 370 ([M+H]$^+$).

Reference Example P-A25

Synthesis of 2-(3-chlorophenyl)-4-(3-methoxyphenyl)-1H-imidazole

[Chem. 65]

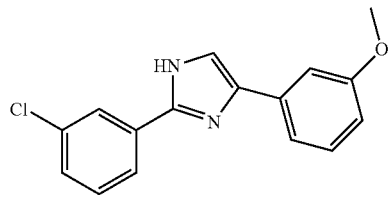

Starting from 3-chloro-benzamidine (943 mg) and 3'-methoxyphenacyl bromide (1.03 g), the same procedure as in Reference Example P-A01 was applied to give the titled compound (760 mg as a pale pink solid).

MS (ESI pos.) m/z: 285 ([M+H]$^+$).

Reference Example P-A26

Synthesis of 2-[2-(3-chlorophenyl)-4-(3-methoxyphenyl)-1H-imidazol-1-yl]-N-(propan-2-yl)acetamide

[Chem. 66]

Starting from the compound (760 mg) obtained in Reference Example P-A25, the same procedure as in Reference Example P-A02 was applied to give the titled compound (910 mg as a colorless solid).

MS (ESI pos.) m/z: 384 ([M+H]$^+$).

Reference Example P-A27

Synthesis of 2-[2-(3-chlorophenyl)-4-(3-hydroxyphenyl)-1H-imidazol-1-yl]-N-(propan-2-yl)acetamide

[Chem. 67]

To a $CHCl_3$ (10 mL) solution of the compound (910 mg) obtained in Reference Example P-A26, 1 M $BBr_3$/n-Hexane (6.0 mL) was added dropwise in an ice bath under a nitrogen atmosphere and the mixture was stirred at room temperature for one day. In a salt ice bath, a saturated aqueous $NaHCO_3$ solution was gradually added. After adding EtOAc and IPE, the mixture was stirred for a while at room temperature. The precipitating solid was recovered by filtration to give the titled compound (658 mg as a colorless solid).

MS (ESI pos.) m/z: 370 ([M+H]$^+$).

Reference Example P-A28

Synthesis of N-(propan-2-yl)-2-(2,4,5-tribromo-1H-imidazol-1-yl)acetamide

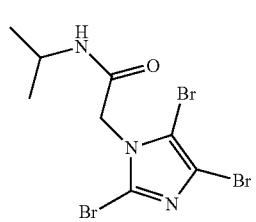

[Chem. 68]

Starting from 2,4,5-tribromoimidazole (3.00 g), the same procedure as in Reference Example P-A02 was applied to give the titled compound (2.65 g as a pale red solid).

MS (ESI pos.) m/z: 402 ([M+H]$^+$).

Reference Example P-A29

Synthesis of 2-[4,5-dibromo-2-(3-methoxyphenyl)-1H-imidazol-1-yl]-N-(propan-2-yl)acetamide

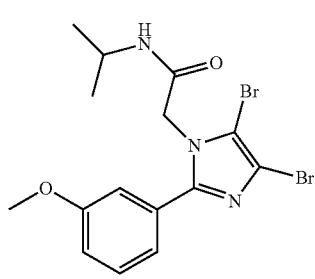

[Chem. 69]

A mixture of the compound (2.00 g) obtained in Reference Example P-A28, 3-methoxyphenylboronic acid (790 mg), Pd(PPh$_3$)$_4$ (572 mg), a 2 M Na$_2$CO$_3$ aqueous solution (4.95 mL) and a mixed solvent (50 mL, toluene/MeOH=5/1; v/v) was stirred at an external temperature of 60° C. for 4 hours. After being left to cool, the mixture was diluted with CHCl$_3$ and washed with water. After being dried over MgSO$_4$, the organic layer was concentrated under reduced pressure. The resulting residue was purified by silica gel (neutral OH form) column chromatography (mobile phase: CHCl$_3$/EtOAc=95/5-70/30; v/v) to give the titled compound (1.05 g as a colorless oil).

MS (ESI pos.) m/z: 430 ([M+H]$^+$).

Reference Example P-A30

Synthesis of 2-[4-bromo-2-(3-methoxyphenyl)-5-methyl-1H-imidazol-1-yl]-N-(propan-2-yl)acetamide

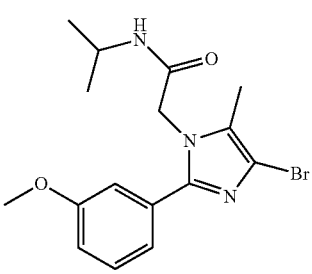

[Chem. 70]

To a THF (7.0 mL) solution of the compound (300 mg) obtained in Reference Example P-A29, 2.66 M nBuLi/n-Hexane (0.37 mL) was added at −78° C. and the mixture was stirred for 10 minutes. After adding methyl iodide (0.087 mL), the mixture was stirred for an additional 30 minutes. The reaction was quenched with MeOH and after dilution with EtOAc, the reaction mixture was washed with water and Brine. After being dried over MgSO$_4$, the organic layer was concentrated under reduced pressure. The resulting residue was purified by silica gel (OH form) column chromatography (mobile phase: CHCl$_3$/EtOAc=97/3-90/10; v/v) to give the titled compound (86 mg as a pale yellow oil).

MS (ESI pos.) m/z: 366 ([M+H]$^+$).

Reference Example P-A31

Synthesis of 2-(2,4-dibromo-1H-imidazol-1-yl)-N-(propan-2-yl)acetamide

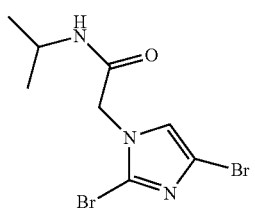

[Chem. 71]

Starting from 2,4-dibromo-1H-imidazole (2.36 g), the same procedure as in Reference Example P-A02 was applied to give the titled compound (2.65 g as a colorless solid).

MS (ESI pos.) m/z: 324 ([M+H]$^+$).

Starting from the compound obtained in Reference Example P-A31, the same procedure as in Reference Example P-A29 was applied to give the following compounds.

Reference Example P-A32

2-[4-bromo-2-(3-methoxyphenyl)-1H-imidazol-1-yl]-N-(propan-2-yl)acetamide

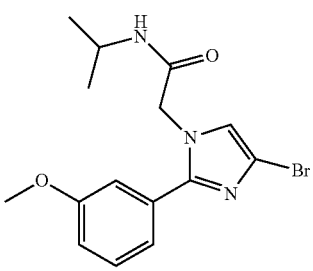

MS (ESI pos.) m/z: 352 ([M+H]⁺).

Reference Example P-A33

2-[4-bromo-2-(3-chloro-4-fluorophenyl)-1H-imidazol-1-yl]-N-(propan-2-yl)acetamide

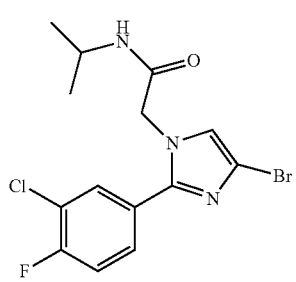

MS (ESI pos.) m/z: 374 ([M+H]⁺).

Reference Example P-A34

2-[4-bromo-2-(5-methoxypyridin-3-yl)-1H-imidazol-1-yl]-N-(propan-2-yl)acetamide

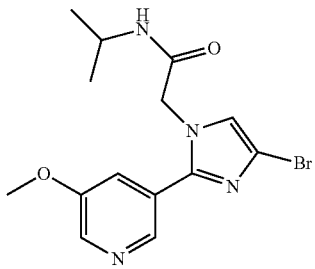

MS (ESI pos.) m/z: 353 ([M+H]⁺).

Reference Example P-A35

2-[4-bromo-2-(2-methoxypyridin-4-yl)-1H-imidazol-1-yl]-N-(propan-2-yl)acetamide

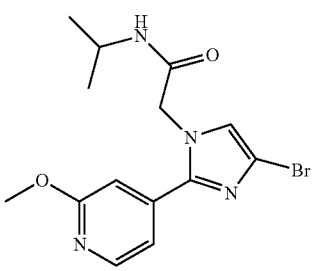

MS (ESI pos.) m/z: 353 ([M+H]⁺).

Reference Example P-A36

2-[4-bromo-2-(3-chlorophenyl)-1H-imidazol-1-yl]-N-(propan-2-yl)acetamide

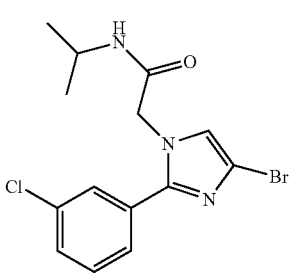

MS (ESI pos.) m/z: 356 ([M+H]⁺).

Reference Example P-A37

Synthesis of 2-[2-(3-chlorophenyl)-4-(2-oxopiperazin-1-yl)-1H-imidazol-1-yl]-N-(propan-2-yl)acetamide

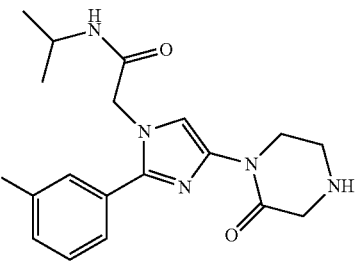

A mixture in 1,4-dioxane (6.0 mL) of the compound (300 mg) obtained in Reference Example P-A36, 1-Boc-3-oxopiperazine (177 mg), copper iodide (160 mg), tripotassium phosphate (357 mg) and trans-N,N'-bismethyl-1,2-cyclohexanediamine (0.13 mL) was stirred overnight at an external temperature of 90° C. under a nitrogen stream. After leaving the mixture to cool, 20% aqueous ammonia was added and extraction was conducted with toluene (containing 10% EtOAc); after drying over $Na_2SO_4$, the desiccant was filtered off and the filtrate was concentrated under reduced pressure. The resulting residue was purified by silica gel column chromatography (SNAP Cartridge KP-NH 28 g; mobile phase: n-Hexane/$CHCl_3$=80/20-0/100; v/v) to give a purified product (206 mg as a colorless solid).

To a solution of this purified product (192 mg) in 1,4-dioxane (6.0 mL), 4 M HCl/EtOAc (0.5 mL) was added and the mixture was stirred at room temperature for two days. After the solvent was distilled off under reduced pressure, the residue was neutralized with a saturated aqueous $NaHCO_3$ solution in an ice bath and the precipitating solid was recovered by filtration to give the titled compound (100 mg as a colorless solid).

MS (ESI pos.) m/z: 376 ([M+H]$^+$).

Reference Example P-A38

Synthesis of sodium 2-(3-chlorophenyl)-1-[2-oxo-2-(propan-2-ylamino)ethyl]-1H-imidazole-4-carboxylate

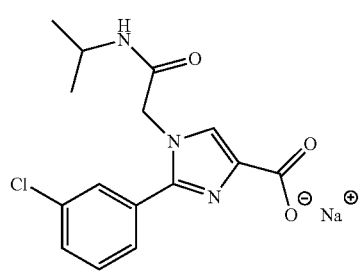

[Chem. 78]

A mixture of the compound (2.52 g) obtained in Reference Example P-A36, Pd(PPh$_3$)$_4$ (816 mg), $K_2CO_3$ (1.47 g) and a mixed solvent (35 mL, DMF/EtOH=2/1; v/v) was stirred at an external temperature of 100° C. for 17 hours under a carbon monoxide atmosphere. The reaction mixture was filtered through Celite (registered trademark) and the filtrate was extracted with EtOAc; after being dried over MgSO$_4$, the organic layer was concentrated under reduced pressure. The resulting residue was purified by silica gel (OH form) column chromatography (mobile phase: CHCl$_3$/EtOAc=90/10-50/50; v/v) to give a purified product (435 mg as a pale yellow solid).

To a suspension of this purified product (300 mg) in THF (4.5 mL), a 1M NaOH aqueous solution (0.9 mL) was added and the mixture was heated under reflux for 5 hours. Subsequent concentration under reduced pressure gave the titled compound (307 mg as a colorless solid).

$^1$H-NMR (600 MHz, DMSO-d$_6$) δ (ppm); 1.06 (6H, d, J=6.6 Hz), 3.79-3.88 (1H, m), 4.62 (2H, s), 7.31 (1H, s), 7.42-7.47 (2H, m), 7.59-7.64 (1H, m), 7.69-7.72 (1H, m), 8.22 (1H, d, J=7.4 Hz).

Reference Example P-A39

Synthesis of 2-(3-chlorophenyl)-N-(4-oxocyclohexyl)-1-[2-oxo-2-(propan-2-ylamino)ethyl]-1H-imidazol-4-carboxamide

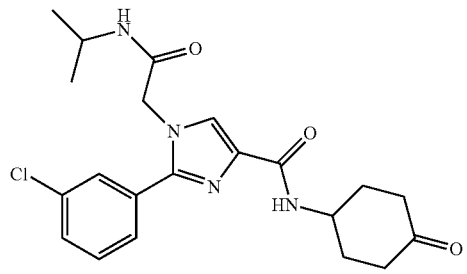

[Chem. 79]

To a CHCl$_3$ (4.0 mL) solution of the compound (201 mg) obtained in Reference Example P-A38 and 1,4-dioxa-spiro [4.5]dec-8-ylamine (92 mg) in, HOBt.H$_2$O (108 mg) and EDC.HCl (135 mg) were added and the mixture was stirred overnight. After adding water and performing extraction with CHCl$_3$, the extract was purified by silica gel (OH form) column chromatography (mobile phase: CHCl$_3$/MeOH=100/0-95/5; v/v) to give a purified product (237 mg as a colorless solid).

A mixture of this purified product (237 mg), THF (3.5 mL) and a 2 M HCl aqueous solution (3.5 mL) was refluxed overnight. After adding a saturated aqueous NaHCO$_3$ solution, the solvent was distilled off under reduced pressure and water was added for extraction with CHCl$_3$. The solvent was then distilled off under reduced pressure to give the titled compound (194 mg as a colorless amorphous product).

MS (ESI pos.) m/z: 417 ([M+H]$^+$).

Reference Example P-A40

Synthesis of 2-(3-chlorophenyl)-N-methyl-N-(4-oxocyclohexyl)-1-[2-oxo-2-(propan-2-ylamino) ethyl]-1H-imidazole-4-carboxamide

[Chem. 80]

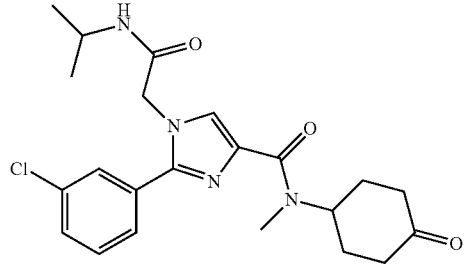

Starting from the compound (206 mg) obtained in Reference Example P-A38 and 4-(methylamino)cyclohexanone 2,2-dimethyltrimethylene ketal (165 mg), the same procedure as in Reference Example P-A39 was applied to give the titled compound (213 mg as a pale yellow oil).

MS (ESI pos.) m/z: 431 ([M+H]$^+$).

Reference Example P-A41

Synthesis 2-[2-(3-chlorophenyl)-4-{[3-(2-hydroxyethyl)pyrrolidin-1-yl]carbonyl}-1H-imidazol-1-yl]-N-(propan-2-yl)acetamide

[Chem. 81]

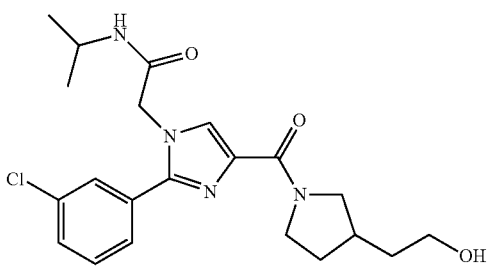

To a CHCl₃ (4.0 mL) solution of the compound (206 mg) obtained in Reference Example P-A38 and 3-pyrrolidine ethanol (0.08 mL) in, HOBt H₂O (110 mg) and EDC.HCl (138 mg) were added and the mixture was stirred overnight. After adding water for extraction with CHCl₃, the extract was purified by silica gel (OH form) column chromatography (mobile phase: CHCl₃/MeOH=100/0-95/5; v/v) to give the titled compound (156 mg as a colorless amorphous product).

MS (ESI pos.) m/z: 419 ([M+H]⁺).

Reference Example P-A42

Synthesis of 8-[2-(4-bromophenyl)ethyl]-3-oxa-8-azabicyclo[3.2.1]octane

[Chem. 82]

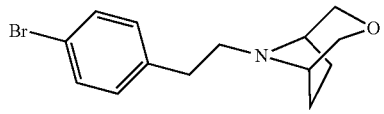

To a solution of 2-(4-bromophenyl)ethanol (1.50 g) in CHCl₃ (10 mL), Et₃N (1.30 mL) and MsCl (0.64 mL) were added sequentially under cooling with ice and the mixture was stirred at room temperature for 2 hours. After adding water under cooling with ice, extraction with CHCl₃ was conducted. The organic layer was filtered with Phase Separator and the filtrate was concentrated under reduced pressure.

A mixture of the resulting residue (2.40 g as a pale yellow oil), 3-oxa-8-azabicyclo[3.2.1]octane (904 mg), 2,2,6,6-tetramethylpiperidine (2.0 mL) and MeCN (10 mL) was stirred at an external temperature of 95° C. for 4 days. After leaving the mixture to cool, water was added for extraction with CHCl₃. The organic layer was filtered with Phase Separator and the solvent was distilled off under reduced pressure. The resulting residue was purified by silica gel column chromatography (SNAP Cartridge HP-Sil 50 g; mobile phase: EtOAc/MeOH=99/1-90/10; v/v) to give the titled compound (1.47 g as a pale brown solid).

MS (ESI pos.) m/z: 296, 298 ([M+H]⁺).

Reference Example P-A43

Synthesis of {4-[2-(3-oxa-8-azabicyclo[3.2.1]oct-8-yl)ethyl]phenyl}boronic acid

[Chem. 83]

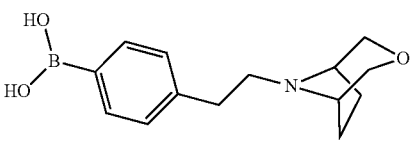

To a THF (8.0 mL) solution of the compound (800 mg) obtained in Reference Example P-A42, 2.64 M nBuLi/n-Hexane (1.2 mL) was added at −78° C. under a nitrogen atmosphere and the mixture was stirred for 30 minutes. After adding triisopropyl borate (0.74 mL), the mixture was stirred for 2 hours in an ice bath. After neutralization with a saturated aqueous NaHCO₃ solution, the mixture was extracted with EtOAc. After drying the organic layer over Na₂SO₄, the desiccant was filtered off and the solvent was distilled off under reduced pressure. The resulting residue was washed with IPE (containing 10% AcOEt) to give the titled compound (190 mg as a colorless solid).

MS (ESI pos.) m/z: 262 ([M+H]⁺).

Reference Example P-A44

Synthesis of 2-(4-bromo-3-fluorophenyl)ethanol

[Chem. 84]

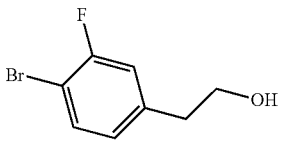

To a solution of 4-bromo-3-fluorophenylacetic acid (3.45 g) in THF (70 mL), 1.08 M BH₃.THF (20.5 mL) was added under cooling with ice and the mixture was stirred for 1.5 hours. Under cooling with ice, MeOH was added until there was no foaming in the system and the solvent was distilled off under reduced pressure; to the resulting residue, water was added for extraction with CHCl₃ and the solvent was distilled off under reduced pressure. The resulting residue was purified by silica gel (OH form) column chromatography (mobile phase: CHCl₃/EtOAc=95/5; v/v) to give the titled compound (2.74 g as a yellow oil).

MS (ESI pos.) m/z: 218, 220 (M+).

Reference Example P-A45

Synthesis of 4-[2-(4-bromo-3-fluorophenyl)ethyl]morpholine

[Chem. 85]

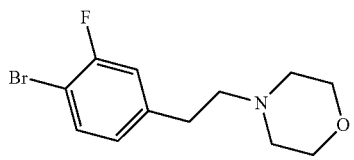

Starting from the compound (500 mg) obtained in Reference Example P-A44 and morpholine (0.6 mL), the same procedure as in Reference Example P-A42 was applied to give the titled compound (564 mg as a pale brown oil).

MS (ESI pos.) m/z: 288, 290 ([M+H]$^+$).

Reference Example P-A46

Synthesis of {2-fluoro-4-[2-(morpholin-4-yl)ethyl]phenyl}boronic acid

[Chem. 86]

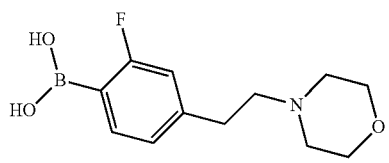

Starting from the compound (785 mg) obtained in Reference Example P-A45, the same procedure as in Reference Example P-A43 was applied to give the titled compound (493 mg as a yellow solid).

MS (ESI pos.) m/z: 254 ([M+H]$^+$).

Reference Example P-A47

Synthesis of 8-[2-(4-bromo-3-fluorophenyl)ethyl]-3-oxa-8-azabicyclo[3.2.1]octane

[Chem. 87]

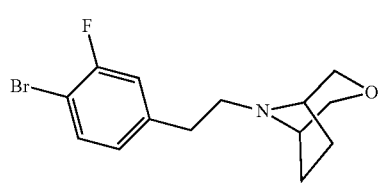

Starting from the compound (543 mg) obtained in Reference Example P-A44 and 3-oxa-8-azabicyclo[3.2.1]octane (421 mg), the same procedure as in Reference Example P-A42 was applied to give the titled compound (207 mg as a pale yellow solid).

MS (ESI pos.) m/z: 314, 316 ([M+H]$^+$).

Reference Example P-A48

Synthesis of 2-(4-bromo-2-fluorophenyl)ethanol

[Chem. 88]

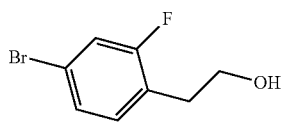

Starting from 4-bromo-2-fluorophenylacetic acid (2.46 g), the same procedure as in Reference Example P-A44 was applied to give the titled compound (1.93 g as a colorless oil).

MS (ESI pos.) m/z: 218, 220 (M+).

Reference Example P-A49

Synthesis of 4-[2-(4-bromo-2-fluorophenyl)ethyl]morpholine

[Chem. 89]

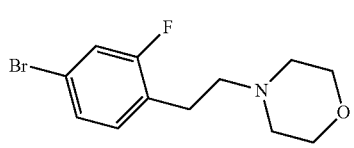

Starting from the compound (500 mg) obtained in Reference Example P-A48 and morpholine (0.20 mL), the same procedure as in Reference Example P-A42 was applied to give the titled compound (315 mg as a pale brown oil).

MS (ESI pos.) m/z: 288, 290 ([M+H]$^+$).

Reference Example P-A50

Synthesis of 8-[2-(4-bromo-2-fluorophenyl)ethyl]-3-oxa-8-azabicyclo[3.2.1]octane

[Chem. 90]

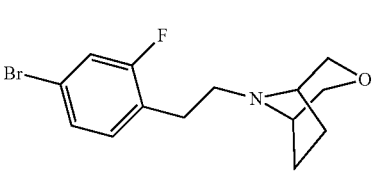

Starting from the compound (500 mg) obtained in Reference Example P-A48 and 3-oxa-8-azabicyclo[3.2.1]octane (194 mg), the same procedure as in Reference Example P-A42 was applied to give the titled compound (330 mg as a colorless solid).

MS (ESI pos.) m/z: 314, 316 ([M+H]$^+$).

Reference Example P-A51

Synthesis of 2-(4-bromo-3-methoxyphenyl)ethanol

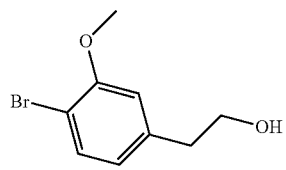
[Chem. 91]

Starting from 4-bromo-3-methoxyphenylacetic acid (1.20 g), the same procedure as in Reference Example P-A44 was applied to give the titled compound (941 mg as a yellow oil).

MS (ESI pos.) m/z: 227, 229 ([M−H]$^-$).

Reference Example P-A52

Synthesis of 8-[2-(4-bromo-3-methoxyphenyl)ethyl]-3-oxa-8-azabicyclo[3.2.1]octane

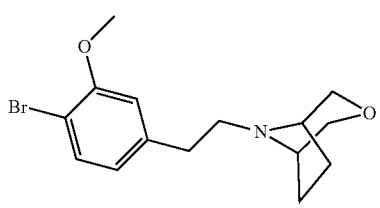
[Chem. 92]

Starting from the compound (308 mg) obtained in Reference Example P-A51 and 3-oxa-8-azabicyclo[3.2.1]octane (226 mg), the same procedure as in Reference Example P-A42 was applied to give the titled compound (401 mg as a pale yellow oil).

MS (ESI pos.) m/z: 326, 328 ([M+H]$^+$).

Reference Example P-A53

Synthesis of 2-(4-bromo-2-methoxyphenyl)ethanol

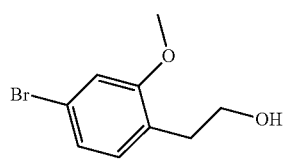
[Chem. 93]

Starting from 2-(4-bromo-2-methoxyphenyl)acetic acid (1.02 g), the same procedure as in Reference Example P-A44 was applied to give the titled compound (828 mg as a yellow oil).

MS (ESI pos.) m/z: 231 ([M+H]$^+$).

Reference Example P-A54

Synthesis of 4-[2-(4-bromo-2-methoxyphenyl)ethyl]morpholine

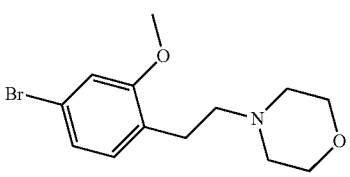
[Chem. 94]

Starting from the compound (500 mg) obtained in Reference Example P-A53 and morpholine (0.6 mL), the same procedure as in Reference Example P-A42 was applied to give the titled compound (586 mg as a pale yellow oil).

MS (ESI pos.) m/z: 300, 302 ([M+H]$^+$).

Reference Example P-A55

Synthesis of 8-[2-(4-bromo-2-methoxyphenyl)ethyl]-3-oxa-8-azabicyclo[3.2.1]octane

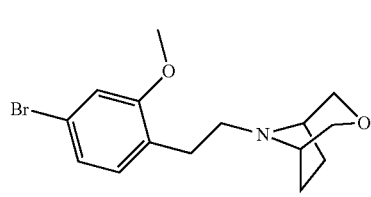
[Chem. 95]

Starting from the compound (100 mg) obtained in Reference Example P-A53 and 3-oxa-8-azabicyclo[3.2.1]octane (146 mg), the same procedure as in Reference Example P-A42 was applied to give the titled compound (147 mg as a pale brown oil).

MS (ESI pos.) m/z: 326, 328 ([M+H]$^+$).

Reference Example P-A56

Synthesis of 4-[2-(6-chloropyridin-3-yl)ethyl]morpholine

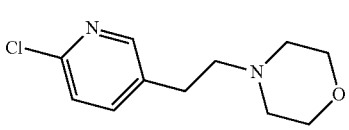
[Chem. 96]

Starting from 2-(6-chloropyridin-3-yl)ethanol (900 mg) and morpholine (0.32 mL), the same procedure as in Reference Example P-A42 was applied to give the titled compound (518 mg as a dark orange-colored amorphous product).

MS (ESI pos.) m/z: 227 ([M+H]$^+$).

Reference Example P-A57

Synthesis of 8-[2-(6-chloropyridin-3-yl)ethyl]-3-oxa-8-azabicyclo[3.2.1]octane

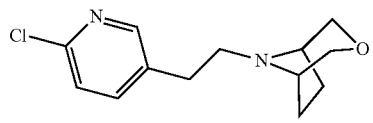

[Chem. 97]

Starting from 2-(6-chloropyridin-3-yl)ethanol (400 mg) and 3-oxa-8-azabicyclo[3.2.1]octane (310 mg), the same procedure as in Reference Example P-A42 was applied to give the titled compound (280 mg as a pale brown solid).

MS (ESI pos.) m/z: 253 ([M+H]$^+$).

Reference Example P-A58

Synthesis of 2-(6-bromopyridin-3-yl)ethanol

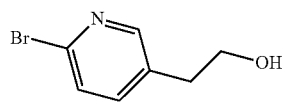

[Chem. 98]

To a suspension of (methoxymethyl)triphenylphosphonium chloride (6.63 g) in THF (25 mL), 2.66 M nBuLi/n-Hexane (7.28 mL) was added dropwise under cooling with ice and the mixture was stirred for an hour. To the stirred mixture, a suspension of 6-bromonicotinaldehyde (3.00 g) in THF (10 mL) was added and the mixture was stirred for an hour. To the reaction mixture, water was added for extraction with EtOAc and thereafter the organic layer was washed with Brine. After drying the organic layer over MgSO$_4$, the desiccant was filtered off and the solvent was distilled off under reduced pressure. The resulting residue was purified by silica gel (OH form) column chromatography (mobile phase: n-Hexane/EtOAc=90/10-70/30; v/v) to give a purified product (1.98 g as a pale yellow oil).

To 4 M HCl/1,4-dioxane, a solution of the resulting purified product (2.28 g) in MeCN—H$_2$O (10:1) was added dropwise and the mixture was stirred at room temperature for 2 hours. After being concentrated, the reaction mixture was diluted with CHCl$_3$ and washed with water. After drying the organic layer over MgSO$_4$, the desiccant was filtered off and the solvent was distilled off under reduced pressure.

After adding MeOH (35 mL) to the resulting residue, NaBH$_4$ (636 mg) was added under cooling with ice and the mixture was stirred for an hour. After being concentrated, the reaction mixture was diluted with CHCl$_3$ and washed with water. After drying the organic layer over MgSO$_4$, the desiccant was filtered off and the solvent was distilled off under reduced pressure. The resulting residue was purified by silica gel (OH form) column chromatography (mobile phase: CHCl$_3$/MeOH=97/3-93/7; v/v) to give the titled compound (1.25 g as a pale yellow solid).

MS (ESI pos.) m/z: 202 ([M+H]$^+$).

Reference Example P-A59

Synthesis of 4-[2-(6-bromopyridin-3-yl)ethyl]morpholine

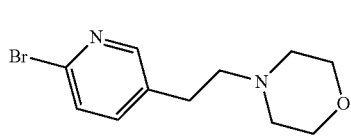

[Chem. 99]

Starting from the compound (1.00 g) obtained in Reference Example P-A58 and morpholine (0.25 mL), the same procedure as in Reference Example P-A42 was applied to give the titled compound (537 mg as a pale yellow solid).

MS (ESI pos.) m/z: 271, 273 ([M+H]$^+$).

Reference Example P-A60

Synthesis of 4-{2-[6-(tributylstannyl)pyridin-3-yl]ethyl}morpholine

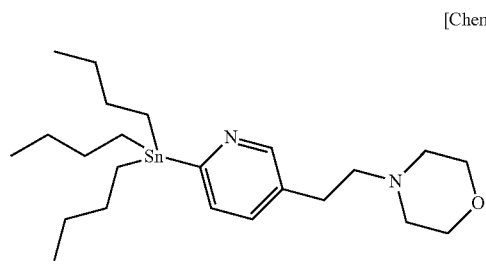

[Chem. 100]

To a THF (12 mL) solution of the compound (600 mg) obtained in Reference Example P-A58, 2.6 M n-BuLi/n-Hexane (1.05 mL) was added dropwise at −78° C. and the mixture was immediately stirred for an hour. To the stirred mixture, tributyltin chloride (0.74 mL) was added dropwise and the mixture was stirred as its temperature was raised to room temperature. Water was added for extraction with EtOAc. After washing the organic layer with Brine and drying the same over Na$_2$SO$_4$, the desiccant was filtered off and the solvent was distilled off under reduced pressure to give the titled compound (766 mg as a pale orange-colored amorphous product).

MS (ESI pos.) m/z: 481 ([M+H]$^+$).

Reference Example P-A61

Synthesis of 8-[2-(6-bromopyridin-3-yl)ethyl]-3-oxa-8-azabicyclo[3.2.1]octane

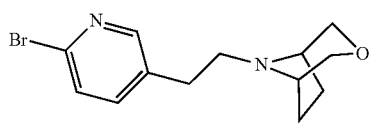

[Chem. 101]

Starting from the compound (1.00 g) obtained in Reference Example P-A58 and 3-oxa-8-azabicyclo[3.2.1]octane (490 mg), the same procedure as in Reference Example P-A42 was applied to give the titled compound (838 mg as a pale yellow solid).

MS (ESI pos.) m/z: 297, 299 ([M+H]$^+$).

Reference Example P-A62

Synthesis of 8-{2-[6-(tributylstannyl)pyridin-3-yl]ethyl}-3-oxa-8-azabicyclo[3.2.1]octane

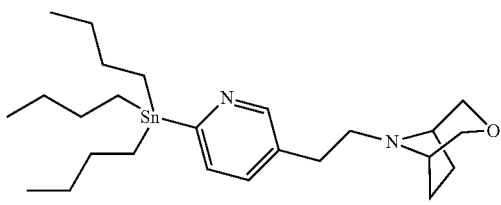

[Chem. 102]

Starting from the compound (200 mg) obtained in Reference Example P-A61, the same procedure as in Reference Example P-A60 was applied to give the titled compound (245 mg as a pale brown oil).

MS (ESI pos.) m/z: 509 ([M+H]$^+$).

Reference Example P-A63

Synthesis of 8-[1-(4-bromophenyl)propan-2-yl]-3-oxa-8-azabicyclo[3.2.1]octane

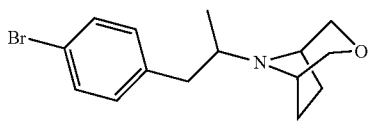

[Chem. 103]

A solution of 4-bromophenyl acetone (1.00 g) and 3-oxa-8-azabicyclo[3.2.1]octane (560 mg) in MeOH/AcOH (10:1, 15 mL) was stirred at room temperature for 30 minutes and, thereafter, 2-picoline borane complex (1.00 g) was added and the mixture was stirred at an external temperature of 60° C. for 8 hours. After leaving the reaction mixture to cool, it was added to a saturated aqueous NaHCO$_3$ solution for neutralization under cooling with ice and extraction with CHCl$_3$ was conducted. The organic layer was filtered with Phase Separator and the solvent was distilled off under reduced pressure. The resulting residue was purified by silica gel column chromatography (SNAP Cartridge HP-Sil 25 g; mobile phase: CHCl$_3$/MeOH=99/1-90/10; v/v) to give the titled compound (418 mg as a pale yellow oil).

MS (ESI pos.) m/z: 310, 312 ([M+H]$^+$).

Reference Example P-A64

Synthesis of 4-[1-(4-bromophenyl)propan-2-yl]morpholine

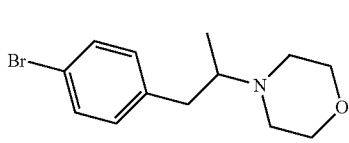

[Chem. 104]

Starting from 4-bromophenyl acetone (2.00 g) and morpholine (1.64 mL), the same procedure as in Reference Example P-A63 was applied to give the titled compound (755 mg as a colorless oil).

MS (ESI pos.) m/z: 284, 286 ([M+H]$^+$).

Reference Example P-A65

Synthesis of {4-[2-(morpholine-4-yl)propyl]phenyl}boronic acid

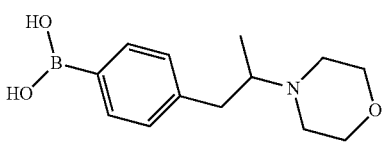

[Chem. 105]

Starting from the compound (1.61 g) obtained in Reference Example P-A64, the same procedure as in Reference Example P-A43 was applied to give the titled compound (1.09 g as a colorless solid).

MS (ESI pos.) m/z: 250 ([M+H]$^+$).

Reference Example P-A66

Synthesis of 8-[1-(6-chloropyridin-3-yl)propan-2-yl]-3-oxa-8-azabicyclo[3.2.1]octane

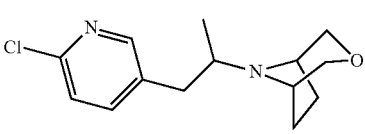

[Chem. 106]

Starting from (6-chloropyridin-3-yl)propan-2-one (235 mg) and 3-oxa-8-azabicyclo[3.2.1]octane (165 mg), the same procedure as in Reference Example P-A63 was applied to give the titled compound (166 mg as a pale yellow oil).

MS (ESI pos.) m/z: 267 ([M+H]$^+$).

Reference Example P-A67

Synthesis of
4-[1-(6-chloropyridin-3-yl)propan-2-yl]morpholine

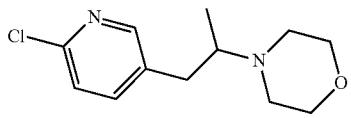
[Chem. 107]

Starting from (6-chloro-pyridin-3-yl)propan-2-one (200 mg) and morpholine (0.21 mL), the same procedure as in Reference Example P-A63 was applied to give the titled compound (216 mg as a pale yellow oil).

MS (ESI pos.) m/z: 241 ([M+H]$^+$).

Reference Example P-A68

Synthesis of
4-[2-(2-methoxypyridin-4-yl)ethyl]morpholine

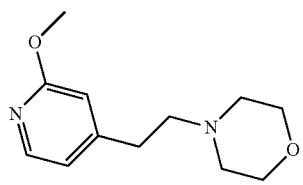
[Chem. 108]

Starting from 2-(2-methoxypyridin-4-yl)ethanol (1.30 g) and morpholine (1.3 mL), the same procedure as in Reference Example P-A42 was applied to give the titled compound (1.39 g as a colorless solid).

$^1$H-NMR (600 MHz, CDCl$_3$) δ (ppm); 2.47-2.54 (4H, m), 2.58-2.63 (2H, m), 2.73-2.77 (2H, m), 3.71-3.75 (4H, m), 3.93 (3H, s), 6.60 (1H, s), 6.72-6.76 (1H, m), 8.06 (1H, d, J=5.4 Hz).

Reference Example P-A69

Synthesis of
4-[2-(morpholin-4-yl)ethyl]pyridin-2(1H)-one

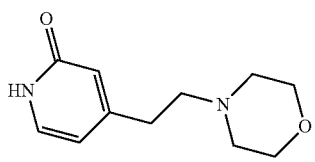
[Chem. 109]

To a THF (2.8 mL) of the compound (300 mg) obtained in Reference Example P-A68, a 6 M HCl aqueous solution (5.6 mL) was added dropwise. The mixture was stirred at 60° C. for 6 hours. After distilling off the solvent under reduced pressure, azeotropic distillation with toluene was conducted twice. The resulting residue was washed with EtOAc and the solids were recovered by filtration to give the titled compound (375 mg as a colorless solid).

$^1$H-NMR (600 MHz, DMSO-d$_6$) δ (ppm); 3.00-3.14 (4H, m), 3.30-3.39 (2H, m), 3.45 (2H, d, J=12.4 Hz), 3.76-3.83 (2H, m), 3.97 (2H, d, J=12.4 Hz), 6.77 (1H, s), 6.89-6.96 (1H, m), 8.13 (1H, d, J=5.4 Hz), 11.24-11.37 (1H, m).

Reference Example P-B01

Synthesis of 2-(3,5-dibromo-1H-1,2,4-triazol-1-yl)-
N-(propan-2-yl)acetamide

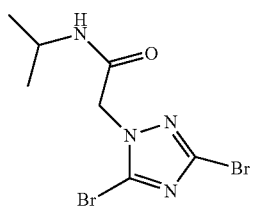
[Chem. 110]

Starting from 3,5-dibromo-1H-1,2,4-triazole (1.00 g), the same procedure as in Reference Example P-A02 was applied to give the titled compound (1.06 g as a pale yellow solid).

MS (ESI pos.) m/z: 325, 327 ([M+H]$^+$).

Starting from the compound obtained in Reference Example P-B01, the same procedure as in Reference Example P-A29 was applied to synthesize the following compounds.

Reference Example P-B02

2-[3-bromo-5-(3-chlorophenyl)-1H-1,2,4-triazol-1-yl]-N-(propan-2-yl)acetamide

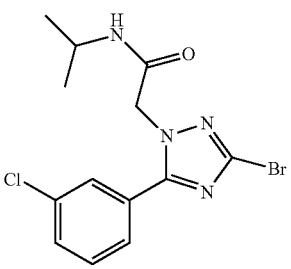
[Chem. 111]

MS (ESI pos.) m/z: 357, 359 ([M+H]$^+$).

Reference Example P-B03

2-[3-bromo-5-(4-fluoro-3-methoxyphenyl)-1H-1,2,4-triazol-1-yl]-N-(propan-2-yl)acetamide

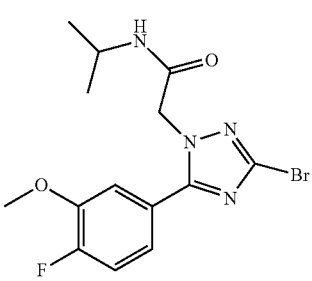

[Chem. 112]

MS (ESI pos.) m/z: 371 ([M+H]$^+$).

Reference Example P-B04

2-[3-bromo-5-(3-methoxyphenyl)-1H-1,2,4-triazol-1-yl]-N-(propan-2-yl)acetamide

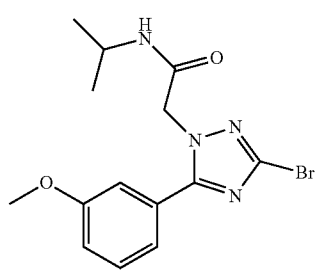

[Chem. 113]

MS (ESI pos.) m/z: 353, 355 ([M+H]$^+$).

Reference Example P-B05

2-[3-bromo-5-(3-chloro-4-fluorophenyl)-1H-1,2,4-triazol-1-yl]-N-(propan-2-yl)acetamide

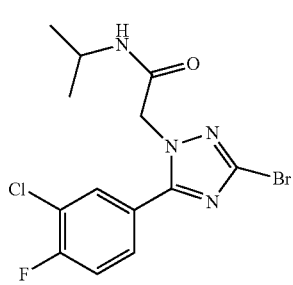

[Chem. 114]

$^1$H-NMR (600 MHz, CDCl$_3$) δ (ppm); 1.18-1.23 (6H, m), 4.10-4.17 (1H, m), 4.76 (2H, s), 5.86-5.93 (1H, m), 7.31 (1H, t, J=8.7 Hz), 7.63-7.67 (1H, m), 7.90 (1H, dd, J=6.6, 2.1 Hz).

Reference Example P-B06

Synthesis of N-tert-butyl-2-(3,5-dibromo-1H-1,2,4-triazol-1-yl)acetamide

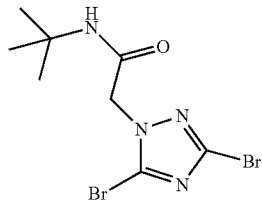

[Chem. 115]

Starting from 3,5-dibromo-1H-1,2,4-triazole (5.0 g) and 2-bromo-N-tert-butylacetamide (5.14 g), the same procedure as in Reference Example P-A02 was applied to give the titled compound (5.4 g as a colorless solid).
$^1$H-NMR (600 MHz, DMSO-d$_6$) δ (ppm); 1.27 (9H, s), 4.81 (2H, s), 8.03 (1H, s).
Starting from the compound obtained in Reference Example P-B06, the same procedure as in Reference Example P-A29 was applied to synthesize the following compounds.

Reference Example P-B07

2-[3-bromo-5-(3-chlorophenyl)-1H-1,2,4-triazol-1-yl]-N-tert-butylacetamide

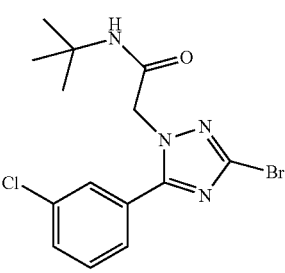

[Chem. 116]

$^1$H-NMR (600 MHz, CDCl$_3$) δ (ppm); 1.36-1.39 (9H, m), 4.73 (2H, s), 5.88-5.95 (1H, m), 7.45-7.49 (1H, m), 7.51-7.55 (1H, m), 7.58-7.62 (1H, m), 7.74-7.77 (1H, m).

Reference Example P-B08

2-[3-bromo-5-(3-methoxyphenyl)-1H-1,2,4-triazol-1-yl]-N-tert-butylacetamide

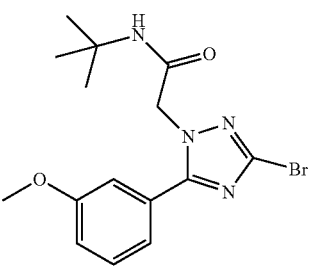

[Chem. 117]

$^1$H-NMR (600 MHz, CDCl$_3$) δ (ppm); 1.32-1.40 (9H, m), 3.86 (3H, s), 4.74 (2H, s), 5.97-6.06 (1H, m), 7.06-7.11 (1H, m), 7.22-7.25 (1H, m), 7.39-7.44 (1H, m), 7.52-7.58 (1H, m).

Starting from the compound obtained in Reference Example P-B04, the same procedure as in Reference Example P-A29 was applied to synthesize the following compound.

Reference Example P-B09

2-{3-[4-(2-hydroxyethyl)phenyl]-5-(3-methoxyphenyl)-1H-1,2,4-triazol-1-yl}-N-(propan-2-yl)acetamide

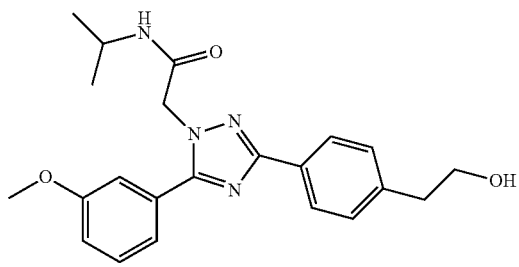

[Chem. 118]

MS (ESI pos.) m/z: 395 ([M+H]$^+$).

Reference Example P-C01

Synthesis of 4-(3-methyl-1H-pyrazol-1-yl)phenol

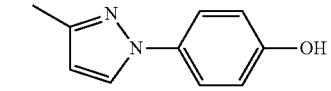

[Chem. 119]

A suspension of 3-methylpyrazole (3.0 g), 4-iodophenol (6.3 g), copper iodide (350 mg), potassium carbonate (2.1 g) and trans-N,N'-bismethyl-1,2-cyclohexanediamine (1.0 g) in toluene (18 mL) was stirred at an external temperature of 100° C. for 60 hours under a nitrogen stream. After leaving the reaction mixture to cool, EtOAc was added and after filtering off the insoluble matter, the organic layer was washed with water and Brine. After drying the organic layer over MgSO$_4$, the desiccant was filtered off and the filtrate was concentrated under reduced pressure. The resulting residue was purified by silica gel column chromatography (SNAP Cartridge KP-Sil; mobile phase: n-Hexane/EtOAc=80/20-40/60; v/v); after washing the resulting compound with IPE, the solids were recovered by filtration to give the titled compound (2.7 g as a pale red solid).

MS (ESI pos.) m/z: 175 ([M+H]$^+$).

Reference Example P-C02

Synthesis of 4-(4-iodo-3-methyl-1H-pyrazol-1-yl)phenol

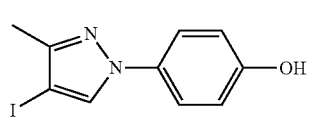

[Chem. 120]

To a DMF solution of the compound (2.7 g) obtained in Reference Example P-C01, NIS (5.9 g) was added and the mixture was stirred at room temperature for 4 hours. To the reaction mixture, EtOAc was added and after washing with a Na$_2$SO$_3$ aqueous solution, water, and Brine, the organic layer was dried over MgSO$_4$; subsequently, the desiccant was filtered off and the filtrate was concentrated under reduced pressure. The resulting residue was purified by silica gel column chromatography (SNAP Cartridge KP-Sil; mobile phase: n-Hexane/EtOAc=90/10-60/40; v/v) to give the titled compound (2.1 g as a pale yellow solid).

MS (ESI pos.) m/z: 301 ([M+H]$^+$).

Reference Example P-C03

Synthesis of 4-[4-(3-chlorophenyl)-3-methyl-1H-pyrazol-1-yl]phenol

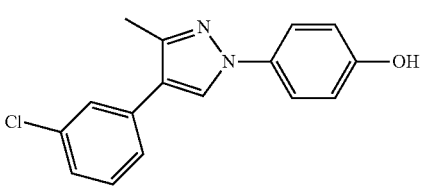

[Chem. 121]

A mixture of the compound (2.1 g) obtained in Reference Example P-C02, (3-chlorophenyl)boronic acid (1.6 g), Pd(PPh$_3$)$_4$ (800 mg), NaHCO$_3$ aqueous solution (2 M, 34 mL) and EtOH (70 mL) was heated under reflux for 2 hours under a nitrogen atmosphere. After leaving the mixture to cool, EtOH was distilled off under reduced pressure and the resulting residue was subjected to extraction with CHCl$_3$. The organic layer was washed with water and Brine and dried over MgSO$_4$; subsequently, the desiccant was filtered off and the filtrate was concentrated under reduced pressure. The resulting residue was purified by column chromatography (SNAP Cartridge KP-NH; mobile phase: CHCl$_3$/MeOH=98/2-90/10; v/v) to give the titled compound (2.0 g as a pale brown solid).

MS (ESI pos.) m/z: 285 ([M+H]$^+$).

Reference Example P-C04

Synthesis of 4-[4-(3-chlorophenyl)-3-methyl-1H-pyrazol-1-yl]phenyl trifluoromethanesulfonate

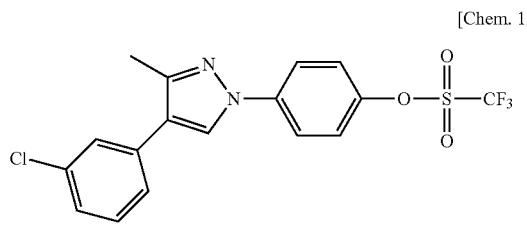

[Chem. 122]

To a CHCl$_3$ solution (16 mL) of the compound (900 mg) obtained in Reference Example P-C03, Et$_3$N (0.80 mL) and Tf$_2$O (0.67 mL) were added under an ice bath and the mixture was stirred at room temperature for 17 hours. The reaction mixture was washed with hydrochloric acid (1 M), a NaHCO$_3$ aqueous solution (1 M) and Brine; after drying over MgSO$_4$, the desiccant was filtered off and the filtrate was concentrated under reduced pressure. The organic layer was filtered with Phase Separator and the solvent was subsequently distilled off under reduced pressure. The resulting residue was purified by column chromatography (SNAP Cartridge HP-Sil; mobile phase: n-Hexane/EtOAc=90/10-70/30; v/v) to give the titled compound (1.1 g as a pale yellow oil).

MS (ESI pos.) m/z: 417 ([M+H]$^+$).

Reference Example P-C05

Synthesis of 4-[3-(bromomethyl)-4-(3-chlorophenyl)-1H-pyrazol-1-yl]phenyl trifluoromethanesulfonate

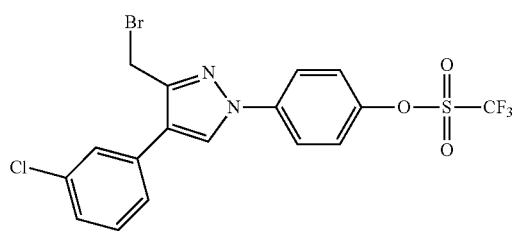

[Chem. 123]

To a CHCl$_3$ solution of the compound (1.1 g) obtained in Reference Example P-C04, NBS (530 mg) and benzoyl peroxide (87 mg) were added and the mixture was heated under reflux for 60 hours. The reaction mixture was washed with water and Brine and dried over MgSO$_4$; thereafter, the desiccant was filtered off and the filtrate was concentrated under reduced pressure to give the titled compound (1.3 g as a pale yellow oil).

MS (ESI pos.) m/z: 495 ([M+H]$^+$).

Reference Example P-C06

Synthesis of 4-[4-(3-chlorophenyl)-3-(cyanomethyl)-1H-pyrazol-1-yl]phenyl trifluoromethanesulfonate

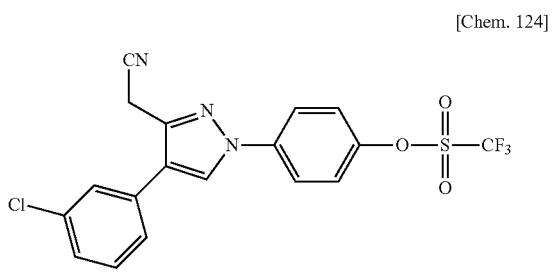 [SMILES: N#CCc1nn(-c2ccc(OS(=O)(=O)C(F)(F)F)cc2)cc1-c1cccc(Cl)c1]

[Chem. 124]

To a DMSO solution (13 mL) of the compound (1.3 g) obtained in Reference Example P-C05, sodium cyanide (200 mg) was added and the mixture was stirred at room temperature for 3 hours. After adding EtOAc to the reaction mixture, it was washed with water and Brine and dried over MgSO$_4$; subsequently, the desiccant was filtered off and the filtrate was concentrated under reduced pressure. The resulting residue was purified by column chromatography (SNAP Cartridge HP-Sil; mobile phase: n-Hexane/EtOAc=90/10-60/40; v/v) to give the titled compound (460 mg as a pale yellow oil).

MS (ESI pos.) m/z: 442 ([M+H]$^+$).

Reference Example P-C07

Synthesis of [4-(3-chlorophenyl)-1-(4-ethenylphenyl)-1H-pyrazol-3-yl]acetonitrile

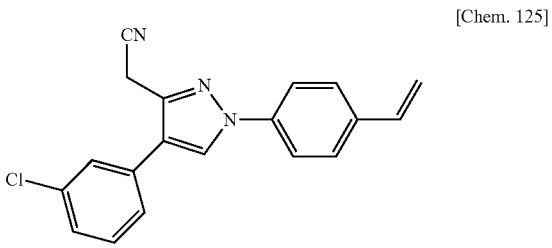 [SMILES: C=Cc1ccc(-n2cc(-c3cccc(Cl)c3)c(CC#N)n2)cc1]

[Chem. 125]

Starting from Reference Example P-C06 (460 mg), the same procedure as in Reference Example P-A03 was applied to give the titled compound (140 mg as a pale yellow solid).

MS (ESI pos.) m/z: 320 ([M+H]$^+$).

Reference Example P-C08

Synthesis of [4-(3-chlorophenyl)-1-(4-ethenylphenyl)-1H-pyrazol-3-yl]acetic acid

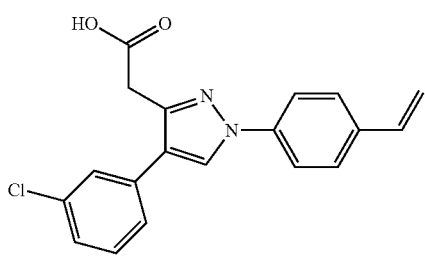

[Chem. 126]

To an EtOH solution (4 mL) of the compound (140 mg) obtained in Reference Example P-C07, a NaOH aqueous solution (2.5 M, 4 mL) was added and the mixture was heated under reflux for 3 hours. After leaving the reaction mixture to cool, hydrochloric acid (1 M) was added and following an adjustment to pH 4, EtOAc was added to separate the organic layer. The resulting organic layer was washed with Brine and dried over MgSO$_4$; subsequently, the desiccant was filtered off and the filtrate was concentrated under reduced pressure to give the titled compound (148 mg as a pale yellow solid).

MS (ESI pos.) m/z: 339 ([M+H]$^+$).

Reference Example P-C09

Synthesis of 2-[4-(3-chlorophenyl)-1-(4-ethenylphenyl)-1H-pyrazol-3-yl]-N-(propan-2-yl)acetamide

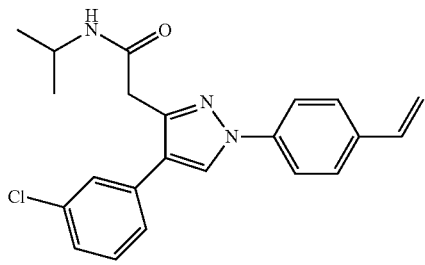

[Chem. 127]

To a THF (4 mL) solution of the compound (148 mg) obtained in Reference Example P-C08, HOBt.H$_2$O (100 mg) and isopropylamine (0.06 mL), EDC.HCl (130 mg) was added under a nitrogen stream and the mixture was stirred at room temperature for 17 hours. After adding CHCl$_3$ to the reaction mixture, it was washed with a saturated aqueous NH$_4$Cl solution, water and Brine and dried over MgSO$_4$; subsequently, the desiccant was filtered off and the filtrate was concentrated under reduced pressure. The resulting residue was purified by silica gel column chromatography (SNAP Cartridge HP-Sil 50 g; mobile phase: n-Hexane/EtOAc=50/50-20/80; v/v) to give the titled compound (130 mg as a colorless solid).

MS (ESI pos.) m/z: 380 ([M+H]$^+$).

Reference Example P-C10

Synthesis of 2-{4-(3-chlorophenyl)-1-[4-(2-hydroxyethyl)phenyl]-1H-pyrazol-3-yl}-N-(propan-2-yl)acetamide

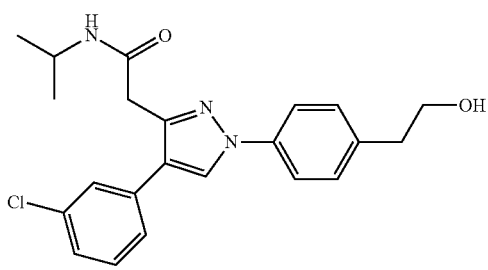

[Chem. 128]

Starting from Reference Example P-C09 (130 mg), the same procedure as in Reference Example P-A04 was applied to give the titled compound (120 mg as a pale yellow solid).

MS (ESI pos.) m/z: 398 ([M+H]$^+$).

Reference Example P-C11

Synthesis of (2E)-1-(4-bromophenyl)-2-[1-(3-chlorophenyl)ethylidene]hydrazine

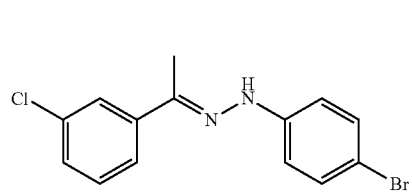

[Chem. 129]

To an EtOH suspension (18 mL) of 1-(3-chlorophenyl)ethanone (1.0 g) and (4-bromophenyl)hydrazine hydrochloride (1.6 g), acetic acid (0.36 mL) was added and the mixture was stirred at an external temperature of 100° C. for 3 hours. After adding EtOAc to the reaction mixture, it was neutralized with a NaHCO$_3$ aqueous solution and the organic layer was subsequently separated. The resulting organic layer was neutralized with a saturated aqueous NaHCO$_3$ solution and the organic layer was separated. After drying the resulting organic layer over MgSO$_4$, the desiccant was filtered off and the filtrate was concentrated under reduced pressure to give the titled compound (3.0 g as a pale brown oil).

MS (ESI neg.) m/z: 323 ([M]$^+$).

Reference Example P-C12

Synthesis of 1-(4-bromophenyl)-3-(3-chlorophenyl)-1H-pyrazole-4-carbaldehyde

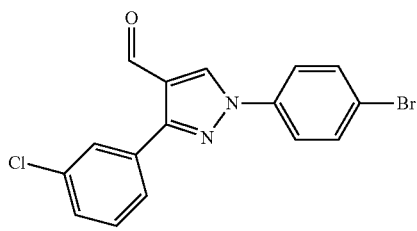

[Chem. 130]

To a DMF (3 mL) solution of phosphorus oxychloride (1.8 mL), a DMF solution (6 mL) of the compound (2.1 g) obtained in Reference Example P-C11 was added under cooling with ice and the mixture was stirred at an external temperature of 80° C. for 3 hours. After cooling with ice, the reaction mixture was added dropwise to a saturated aqueous NaHCO$_3$ solution and the precipitating solid was recovered by filtration and dried to give the titled compound (2.3 g as a pale brown solid).
$^1$H-NMR (600 MHz, CDCl$_3$) δ (ppm); 7.42-7.48 (2H, m), 7.63-7.67 (2H, m), 7.67-7.71 (2H, m), 7.72-7.77 (1H, m), 7.85-7.89 (1H, m), 8.52 (1H, s), 10.05 (1H, s).

Reference Example P-C13

Synthesis of [1-(4-bromophenyl)-3-(3-chlorophenyl)-1H-pyrazol-4-yl]methanol

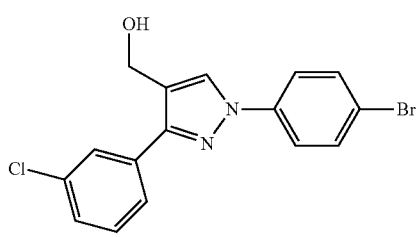

[Chem. 131]

To a MeOH solution (32 mL) of the compound (2.3 g) obtained in Reference Example P-C12, NaBH$_4$ (540 mg) was added in small portions under cooling with ice and the mixture was subsequently stirred at room temperature for an hour. After adding hydrochloric acid (2 M, 60 mL) to the reaction mixture, MeOH was distilled off under reduced pressure. After extracting the aqueous layer with EtOAc, the resulting organic layer was washed with Brine and dried over MgSO$_4$; subsequently, the desiccant was filtered off and the filtrate was concentrated under reduced pressure to give the titled compound (2.4 g as a brown amorphous product).
MS (ESI pos.) m/z: 363 ([M+H]$^+$).

Reference Example P-C14

Synthesis of 1-(4-bromophenyl)-4-(chloromethyl)-3-(3-chlorophenyl)-1H-pyrazole

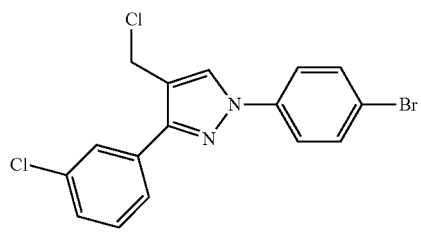

[Chem. 132]

To a CHCl$_3$ solution (32 mL) of the compound (2.4 g) obtained in Reference Example P-C13, thionyl chloride (0.92 mL) was added and the mixture was heated under reflux for 3 hours. The reaction mixture was concentrated under reduced pressure to give the titled compound (2.5 g as a brown amorphous product).
MS (ESI pos.) m/z: 381 ([M+H]$^+$).

Reference Example P-C15

Synthesis of [1-(4-bromophenyl)-3-(3-chlorophenyl)-1H-pyrazol-4-yl]acetonitrile

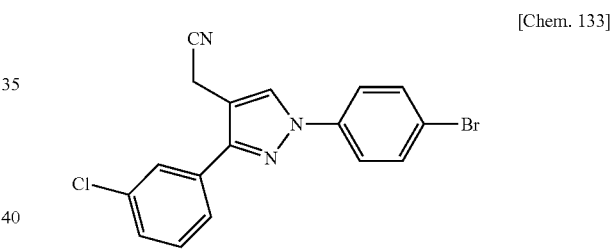

[Chem. 133]

Starting from the compound (2.5 g) obtained in Reference Example P-C14, the same procedure as in Reference Example P-C06 was applied to give the titled compound (1.5 g as a pale yellow solid).
MS (ESI pos.) m/z: 372 ([M+H]$^+$).

Reference Example P-C16

Synthesis of [1-(4-bromophenyl)-3-(3-chlorophenyl)-1H-pyrazol-4-yl]acetic acid

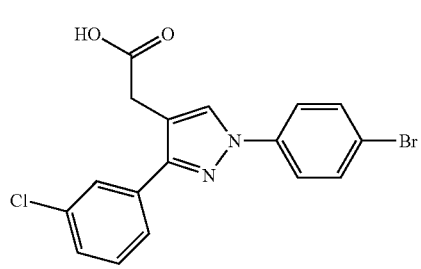

[Chem. 134]

To a dioxane solution (16 mL) of the compound (1.5 g) obtained in Reference Example P-C15, hydrochloric acid (6 M, 8 mL) was added and the mixture was heated under reflux for 48 hours. After additional supply of a HCl-dioxane solution (4 M, 8 mL), the mixture was heated under reflux for 72 hours. To the reaction mixture, EtOAc was added and the organic layer was separated; subsequently, the organic layer was washed with water and Brine and dried over MgSO$_4$; thereafter, the desiccant was filtered off and the filtrate was concentrated under reduced pressure to give the titled compound (1.6 g as a pale brown solid).

MS (ESI neg.) m/z: 389 ([M−H]$^−$).

Reference Example P-C17

Synthesis of 2-[1-(4-bromophenyl)-3-(3-chlorophenyl)-1H-pyrazol-4-yl]-N-(propan-2-yl)acetamide

[Chem. 135]

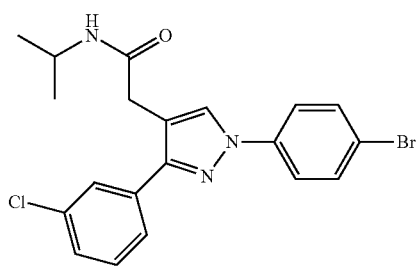

Starting from the compound (1.4 g) obtained in Reference Example P-C16, the same procedure as in Reference Example P-C09 was applied to give the titled compound (1.1 g as a pale brown solid).

MS (ESI pos.) m/z: 432 ([M+H]$^+$).

Reference Example P-C18

Synthesis of 2-[3-(3-chlorophenyl)-1-(4-ethenylphenyl)-1H-pyrazol-4-yl]-N-(propan-2-yl)acetamide

[Chem. 136]

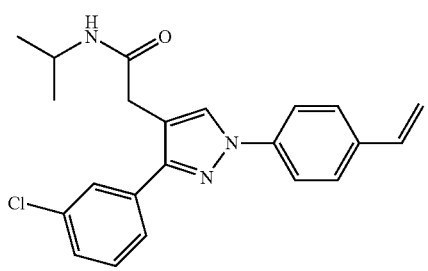

Starting from the compound (1.6 g) obtained in Reference Example P-C17, the same procedure as in Reference Example P-A03 was applied to give the titled compound (1.4 g as a pale yellow solid).

MS (ESI pos.) m/z: 380 ([M+H]$^+$).

Reference Example P-C19

Synthesis of 2-{3-(3-chlorophenyl)-1-[4-(2-hydroxyethyl)phenyl]-1H-pyrazol-4-yl}-N-(propan-2-yl)acetamide

[Chem. 137]

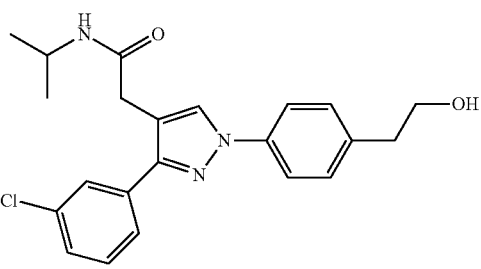

Starting from the compound (1.1 g) obtained in Reference Example P-C18, the same procedure as in Reference Example P-A04 was applied to give the titled compound (1.1 g as a pale brown amorphous product).

MS (ESI pos.) m/z: 420 ([M+Na]$^+$).

Reference Example P-C20

Synthesis of 1-(4-methoxyphenyl)prop-2-yn-1-one

[Chem. 138]

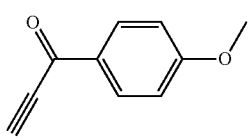

To a CHCl$_3$ solution (160 m L) of 1-(4-methoxyphenyl)prop-2-yn-1-ol (12 g), manganese dioxide (85 g) was added and the mixture was stirred at room temperature for 2 hours. The insoluble matter was removed by filtration through Celite (registered trademark) and the filtrate was concentrated under reduced pressure; thereafter, the resulting residue was washed with n-Hexane under stirring to give the titled compound (7.8 g as a yellow solid).

MS (ESI pos.) m/z: 161 ([M+H]$^+$).

Reference Example P-C21

Synthesis of 1-(3-chlorophenyl)-3-(4-methoxyphenyl)-1H-pyrazole

[Chem. 139]

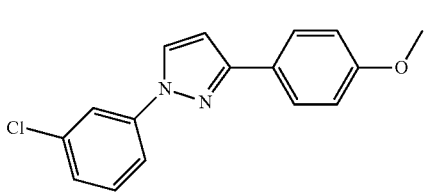

To a MeOH suspension (120 mL) of the compound (3.0 g) obtained in Reference Example P-C19 and (3-chlorophenyl)hydrazine hydrochloride (3.4 g), conc. hydrochloric acid (1.8 mL) was added and the mixture was stirred at room temperature for 26 hours, then stirred at an external temperature of 60° C. for 2 hours. After concentrating the reaction mixture under reduced pressure, EtOAc was added to the resulting residue and the mixture was washed with water and Brine. After drying the organic layer over MgSO$_4$, the desiccant was filtered off and the filtrate was concentrated under reduced pressure; thereafter, the resulting residue was purified by silica gel column chromatography (SNAP Cartridge HP-Sil 50 g; mobile phase: n-Hexane/ EtOAc=100/0-85/15; v/v) to give the titled compound (2.8 g as a pale yellow solid).

MS (ESI pos.) m/z: 285 ([M+H]$^+$).

Reference Example P-C22

Synthesis of 1-(3-chlorophenyl)-3-(4-methoxyphenyl)-1H-pyrazole-5-carboxylic acid

[Chem. 140]

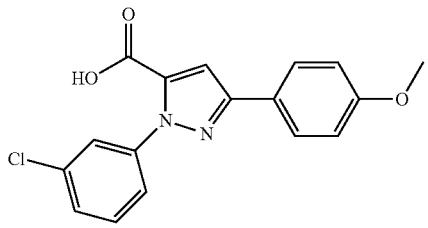

To a THF solution (40 mL) of diisopropylamine (870 mg), 2.6 M n-BuLi (3.3 mL) in hexane was added dropwise under cooling with ice and the mixture was stirred for 10 minutes. After cooling the reaction mixture to −60° C., a THF solution (10 mL) of the compound (2.2 g) obtained in Reference Example P-C21 was added and the mixture was stirred for 30 minutes. To a mixture of Dry Ice with Et$_2$O, the reaction mixture was added dropwise through a cannula and the mixture was stirred overnight. After adding water and EtOAc to the reaction mixture, it was subjected to extradition with a 1 M NaOH aqueous solution. The resulting aqueous layer was adjusted to pH=4 with 1 M hydrochloric acid and subjected to extraction with EtOAc. After drying the organic layer over MgSO$_4$, the desiccant was filtered off and the filtrate was concentrated under reduced pressure to give the titled compound (1.2 g as a pale yellow solid).

MS (ESI pos.) m/z: 329 ([M+H]$^+$).

Reference Example P-C23

Synthesis of [1-(3-chlorophenyl)-3-(4-methoxyphenyl)-1H-pyrazol-5-yl]acetic acid

[Chem. 141]

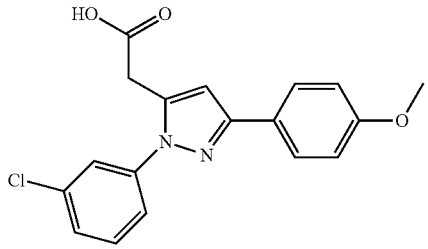

To a CHCl$_3$ (45 mL) suspension of the compound (1.5 g) obtained in Reference Example P-C22, oxalyl chloride (0.78 mL) and DMF (one drop) were added in an ice bath and the mixture was stirred for an hour. After concentrating the reaction mixture, a THF/MeCN liquid mixture (1/1; v/v, 45 mL) was added to the resulting residue and at 0° C., TMSCH$_2$N$_2$ (2 mol/L Et$_2$O solution, 4.5 mL) was also added and the mixture was stirred for an hour. After concentrating the stirred mixture, a 1,4-dioxane/water liquid mixture (1/1; v/v, 45 mL) was added and following the addition of silver acetate (230 mg), the mixture was stirred at 60° C. for an hour. After concentrating the stirred mixture, a saturated NaHCO$_3$ aqueous solution was added and the mixture was stirred at room temperature for an hour. After filtering the reaction mixture through Celite (registered trademark), the filtrate was diluted with added EtOAc; thereafter, the organic layer was washed with water and Brine and dried over MgSO$_4$; subsequently, the desiccant was filtered off and the filtrate was concentrated under reduced pressure to give the titled compound (1.6 g as a pale brown solid).

MS (ESI pos.) m/z: 343 ([M+H]$^+$).

Reference Example P-C24

Synthesis of 2-[1-(3-chlorophenyl)-3-(4-methoxyphenyl)-1H-pyrazol-5-yl]-N-(propan-2-yl)acetamide

[Chem. 142]

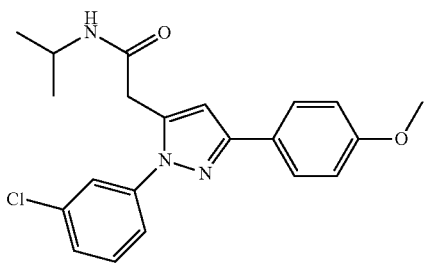

Starting from the compound (1.6 g) obtained in Reference Example P-C23, the same procedure as in Reference Example P-C09 was applied to give the titled compound (780 mg as a pale yellow solid).

MS (ESI pos.) m/z: 384 ([M+H]$^+$).

Reference Example P-C25

Synthesis of 2-[1-(3-chlorophenyl)-3-(4-hydroxyphenyl)-1H-pyrazol-5-yl]-N-(propan-2-yl)acetamide

[Chem. 143]

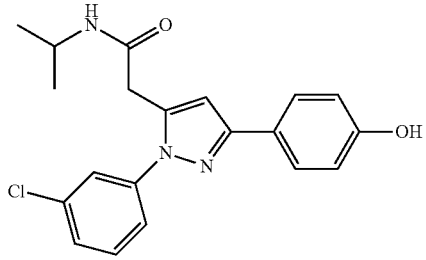

Starting from the compound (780 mg) obtained in Reference Example P-C24, the same procedure as in Reference Example P-A27 was applied to give the titled compound (750 mg as a pale brown solid).

MS (ESI pos.) m/z: 370 ([M+H]⁺).

Reference Example P-C26

Synthesis of 4-{1-(3-chlorophenyl)-5-[2-oxo-2-(propan-2-ylamino)ethyl]-1H-pyrazol-3-yl}phenyl trifluoromethanesulfonate

[Chem. 144]

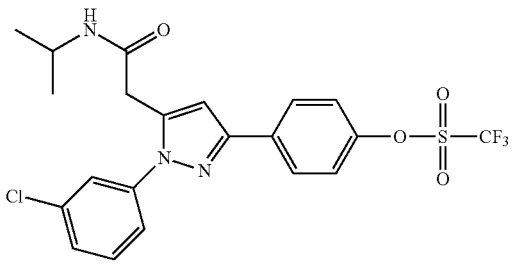

Starting from the compound (750 mg) obtained in Reference Example P-C25, the same procedure as in Reference Example P-C04 was applied to give the titled compound (270 mg as a pale yellow oil).

MS (ESI pos.) m/z: 502 ([M+H]⁺).

Reference Example P-C27

Synthesis of 2-[1-(3-chlorophenyl)-3-(4-ethenylphenyl)-1H-pyrazol-5-yl]-N-(propan-2-yl)acetamide

[Chem. 145]

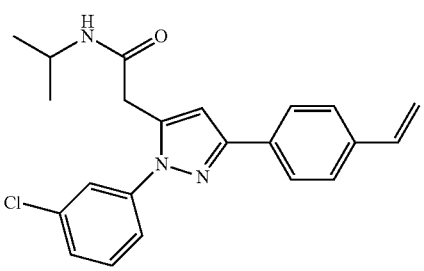

Starting from the compound (270 mg) obtained in Reference Example P-C26, the same procedure as in Reference Example P-A03 was applied to give the titled compound (75 mg as a pale yellow solid).

MS (ESI pos.) m/z: 380 ([M+H]⁺).

Reference Example P-C28

Synthesis of 2-{1-(3-chlorophenyl)-3-[4-(2-hydroxyethyl)phenyl]-1H-pyrazol-5-yl}-N-(propan-2-yl)acetamide

[Chem. 146]

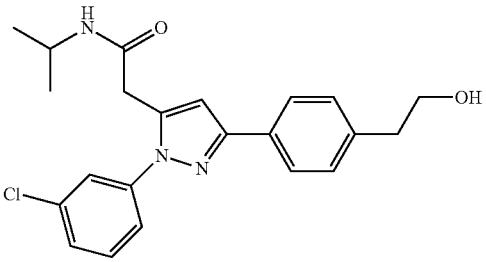

Starting from the compound (75 mg) obtained in Reference Example P-C27, the same procedure as in Reference Example P-A04 was applied to give the titled compound (79 mg as a pale yellow solid).

MS (ESI pos.) m/z: 398 ([M+H]⁺).

Reference Example P-C29

Synthesis of (2E)-1-(4-bromophenyl)-3-(3-chlorophenyl)prop-2-en-1-one

[Chem. 147]

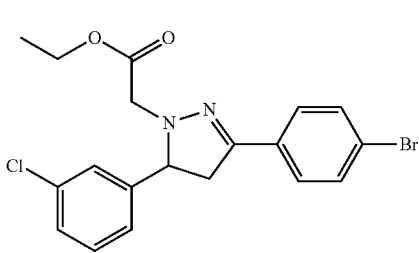

To a MeOH solution (125 mL) of 3-chlorobenzaldehyde (3.0 g) and 1-(4-bromophenyl)ethanone (4.5 g), sodium methoxide (1.2 g) was added and the mixture was stirred at room temperature for 60 hours. To the reaction mixture, dilute hydrochloric acid (0.5 M, 125 mL) was added and the precipitating solid was recovered by filtration and dried to give the titled compound (6.8 g as a pale yellow solid).

MS (ESI pos.) m/z: 321 ([M+H]⁺).

Reference Example P-C30

Synthesis of ethyl [3-(4-bromophenyl)-5-(3-chlorophenyl)-4,5-dihydro-1H-pyrazol-1-yl]acetate

[Chem. 148]

An EtOH solution (70 mL) of the compound (4.4 g) obtained in Reference Example P-C29 and ethyl 2-hydrazinyl acetate hydrochloride (2.2 g) was heated under reflux for 4 hours. After concentrating the reaction mixture under reduced pressure, it was stirred at an external temperature of 60° C. for 2 hours. After concentrating the reaction mixture under reduced pressure, EtOAc was added to the resulting residue and the mixture was washed with water and Brine. After drying the organic layer over MgSO$_4$, the desiccant was filtered off and the filtrate was concentrated under reduced pressure to give the titled compound (5.7 g as a pale yellow oil).

MS (ESI pos.) m/z: 421 ([M+H]$^+$).

Reference Example P-C31

Synthesis of ethyl [3-(4-bromophenyl)-5-(3-chlorophenyl)-1H-pyrazol-1-yl]acetate

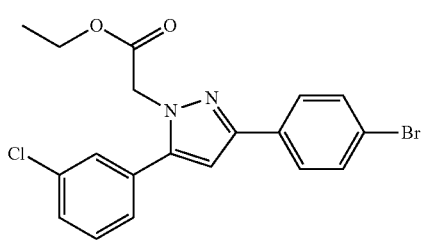

[Chem. 149]

To a toluene solution (130 mL) of the compound (5.7 g) obtained in Reference Example P-C30, 2,3-dichloro-5,6-dicyano-p-benzoquinone (5.2 g) was added and the mixture was stirred at an external temperature of 100° C. for an hour. After filtering the reaction mixture, the filtrate was diluted with added EtOAc and washed with water and Brine. After drying the organic layer over MgSO$_4$, the desiccant was filtered off and the filtrate was concentrated under reduced pressure; thereafter, the resulting residue was purified by silica gel column chromatography in sequential stages (SNAP Cartridge KP-NH; mobile phase: n-Hexane/EtOAc=90/10-70/30; v/v, and SNAP Cartridge HP-Sil 50 g; mobile phase: n-Hexane/EtOAc=80/20-70/30; v/v) to give the titled compound (3.6 g as a pale yellow solid).

MS (ESI pos.) m/z: 419 ([M+H]$^+$).

Reference Example P-C32

Synthesis of [3-(4-bromophenyl)-5-(3-chlorophenyl)-1H-pyrazol-1-yl]acetic acid

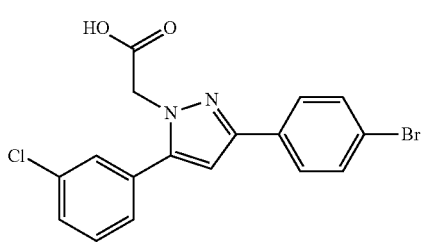

[Chem. 150]

To a THF solution (40 mL) of the compound (3.6 g) obtained in Reference Example P-C31, a NaOH aqueous solution (2.5 M, 8 mL) was added and the mixture was stirred at room temperature for 2 hours. To the reaction mixture, hydrochloric acid (2.0 M) was added for adjustment to pH 4 and extraction was conducted with EtOAc. After drying the organic layer over MgSO$_4$, the desiccant was filtered off and the filtrate was concentrated under reduced pressure to give the titled compound (3.3 g as a pale yellow solid).

MS (ESI pos.) m/z: 391 ([M+H]$^+$).

Reference Example P-C33

Synthesis of 2-[3-(4-bromophenyl)-5-(3-chlorophenyl)-1H-pyrazol-1-yl]-N-(propan-2-yl)acetamide

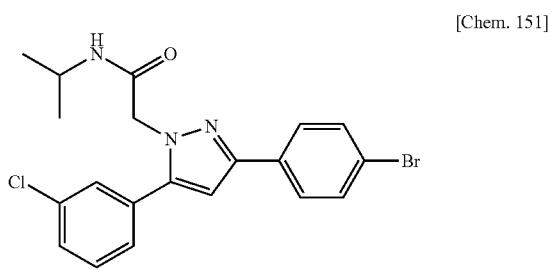 [SMILES: CC(C)NC(=O)Cn1nc(-c2ccc(Br)cc2)cc1-c1cccc(Cl)c1]

[Chem. 151]

Starting from the compound (3.3 g) obtained in Reference Example P-C32, the same procedure as in Reference Example P-C09 was applied to give the titled compound (3.1 g as a colorless solid).

MS (ESI pos.) m/z: 432 ([M+H]$^+$).

Reference Example P-C34

Synthesis of 2-[5-(3-chlorophenyl)-3-(4-ethenylphenyl)-1H-pyrazol-1-yl]-N-(propan-2-yl)acetamide

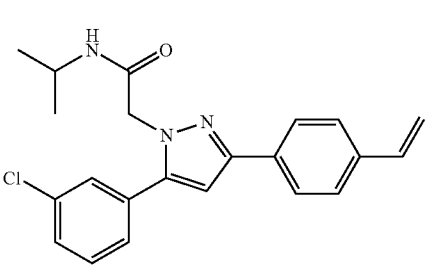

[Chem. 152]

Starting from the compound (3.1 g) obtained in Reference Example P-C33, the same procedure as in Reference Example P-A03 was applied to give the titled compound (1.3 g as a pale brown solid).

MS (ESI pos.) m/z: 380 ([M+H]$^+$).

Reference Example P-C35

Synthesis of 2-{5-(3-chlorophenyl)-3-[4-(2-hydroxyethyl)phenyl]-1H-pyrazol-1-yl}-N-(propan-2-yl)acetamide

[Chem. 153]

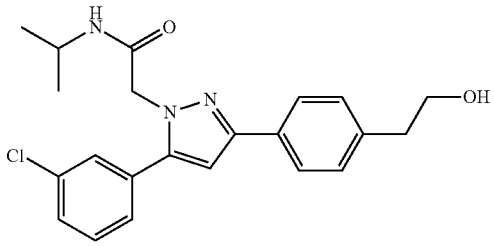

Starting from the compound (1.3 g) obtained in Reference Example P-C34, the same procedure as in Reference Example P-A04 was applied to give the titled compound (1.4 g as a pale yellow solid).
MS (ESI pos.) m/z: 398 ([M+H]$^+$).

Reference Example P-C36

Synthesis of 4-bromo-N-[2-(3-chlorophenyl)-2-oxoethyl]benzamide

[Chem. 154]

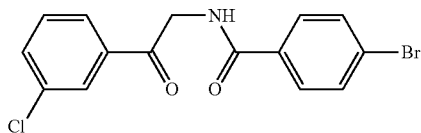

To a CHCl$_3$ solution (24 mL) of 2-amino1-(3-chlorophenyl)ethanone hydrochloride (2.0 g), a saturated aqueous NaHCO$_3$ solution (48 mL) and 4-bromobenzoyl chloride (3.2 g) were added under cooling with ice and the mixture was stirred for 2 hours. The organic layer was separated and dried over MgSO$_4$; subsequently, the desiccant was filtered off and the filtrate was concentrated under reduced pressure to give the titled compound (3.2 g as a colorless solid).
MS (ESI pos.) m/z: 352 ([M+H]$^+$).

Reference Example P-C37

Synthesis of ethyl 3-[(4-bromobenzoyl)amino]-4-(3-chlorophenyl)-4-oxobutanoate

[Chem. 155]

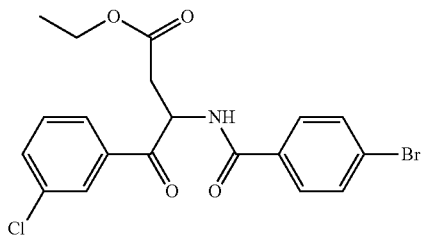

To a DMF solution (10 mL) of the compound (1.1 g) obtained in Reference Example P-C36, sodium hydride (160 mg) was added at −50° C. and the mixture was stirred for 30 minutes; subsequently, 2-bromoacetic acid ethyl ester (0.39 mL) was added and the mixture was stirred for 30 minutes under cooling with ice. After adding water to the reaction mixture, it was diluted with added EtOAc. The organic layer was separated and subsequently washed with Brine. After drying the organic layer over MgSO$_4$, the desiccant was filtered off and the filtrate was concentrated under reduced pressure; the resulting residue was purified by silica gel column chromatography in sequential stages (SNAP Cartridge HP-Sil; mobile phase: n-Hexane/EtOAc/CHCl$_3$=80/20/3-70/30/3; v/v/v) to give the titled compound (460 mg as a pale yellow oil).
MS (ESI pos.) m/z: 438 ([M+H]$^+$).

Reference Example P-C38

Synthesis of ethyl [2-(4-bromophenyl)-5-(3-chlorophenyl)-1,3-oxazol-4-yl]acetate

[Chem. 156]

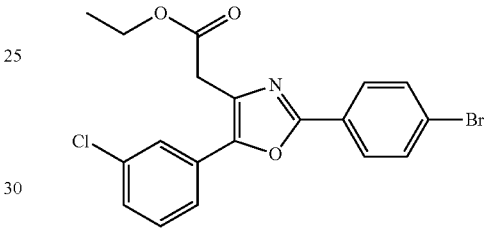

To a DMF solution (10 mL) of the compound (460 mg) obtained in Reference Example P-C37, phosphorus oxychloride (0.39 mL) was added under cooling with ice and the mixture was stirred for 4 hours. The reaction mixture was added to a mixture of EtOAc and ice water. The organic layer was separated and subsequently washed with Brine. After drying the organic layer over MgSO$_4$, the desiccant was filtered off and the filtrate was concentrated under reduced pressure to give the titled compound (441 mg as a pale yellow solid).
MS (ESI pos.) m/z: 420 ([M+H]$^+$).

Reference Example P-C39

Synthesis of [2-(4-bromophenyl)-5-(3-chlorophenyl)-1,3-oxazol-4-yl]acetic acid

[Chem. 157]

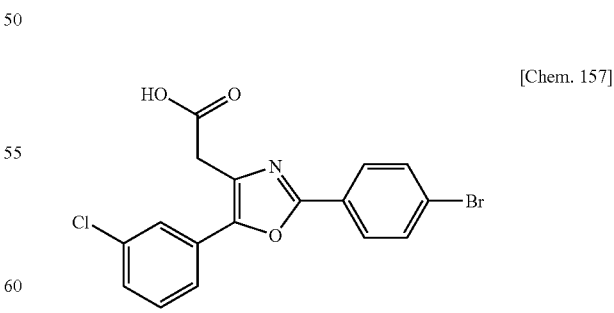

Starting from the compound (3.2 g) obtained in Reference Example P-C38, the same procedure as in Reference Example P-C32 was applied to give the titled compound (3.0 g as a pale yellow solid).
MS (ESI pos.) m/z: 392 ([M+H]$^+$).

Reference Example P-C40

Synthesis of 2-[2-(4-bromophenyl)-5-(3-chlorophenyl)-1,3-oxazol-4-yl]-N-(propan-2-yl)acetamide

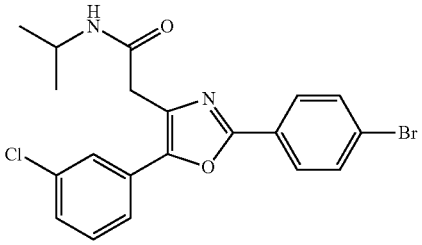
[Chem. 158]

Starting from the compound (3.0 g) obtained in Reference Example P-C39, the same procedure as in Reference Example P-C09 was applied to give the titled compound (2.3 g as a colorless solid).
MS (ESI pos.) m/z: 433 ([M+H]$^+$).

Reference Example P-C41

Synthesis of 2-[5-(3-chlorophenyl)-2-(4-ethenylphenyl)-1,3-oxazol-4-yl]-N-(propan-2-yl)acetamide

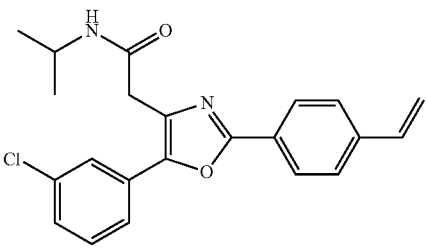
[Chem. 159]

Starting from the compound (2.3 g) obtained in Reference Example P-C40, the same procedure as in Reference Example P-A03 was applied to give the titled compound (1.3 g as a pale brown solid).
MS (ESI pos.) m/z: 381 ([M+H]$^+$).

Reference Example P-C42

Synthesis of 2-{5-(3-chlorophenyl)-2-[4-(2-hydroxyethyl)phenyl]-1,3-oxazol-4-yl}-N-(propan-2-yl)acetamide

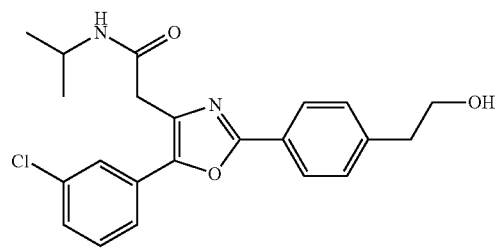
[Chem. 160]

Starting from the compound (1.3 g) obtained in Reference Example P-C41, the same procedure as in Reference Example P-A04 was applied to give the titled compound (1.3 g as a pale yellow solid).
MS (ESI pos.) m/z: 399 ([M+H]$^+$).

Reference Example P-C43

Synthesis of methyl 4-(3-chlorophenyl)-4-hydroxybut-2-ynoate

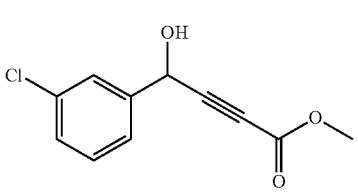
[Chem. 161]

To a THF solution (100 mL) of methyl propargylate (3.6 g), n-BuLi (2.7 M, 16 mL) was added at −78° C. and after stirring the mixture for 30 minutes, a THF solution (20 mL) of 3-chlorobenzaldehyde (4.0 g) was added dropwise. After 1-hour stirring, acetic acid (20 mL) was added and the reaction mixture was subsequently washed with water. After extracting the aqueous layer with EtOAc, the combined organic layer was washed with a saturated aqueous NaHCO$_3$ solution and Brine. After drying the organic layer over MgSO$_4$, the desiccant was filtered off and the filtrate was concentrated under reduced pressure; the resulting residue was purified by silica gel column chromatography (SNAP Cartridge HP-Sil; mobile phase: n-Hexane/EtOAc=90/10-70/30; v/v) to give the titled compound (4.6 g as a pale red oil).
$^1$H NMR (600 MHz, CHLOROFORM-d) δ (ppm); 2.43-2.52 (1H, m) 3.79 (3H, s) 5.55 (1H, d, J=6.4 Hz) 7.29-7.35 (2H, m) 7.36-7.42 (1H, m) 7.47-7.57 (1H, m).

Reference Example P-C44

Synthesis of methyl [4-(3-chlorophenyl)-2-(4-iodophenyl)-1,3-oxazol-5-yl]acetate

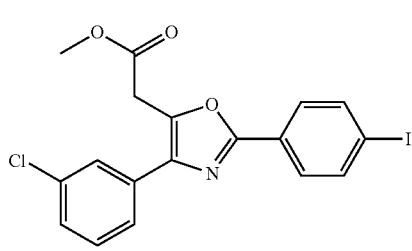
[Chem. 162]

To a mixture of the compound (4.4 g) obtained in Reference Example P-C43 and 4-iodobenzonitrile (4.5 g), conc. sulfuric acid (2.1 mL) was added under cooling with ice and the mixture was stirred at room temperature for 3 hours. After adding CHCl$_3$ to the reaction mixture, it was washed with water and Brine. After drying the organic layer over MgSO$_4$, the desiccant was filtered off and the filtrate was concentrated under reduced pressure; the resulting residue was purified by silica gel column chromatography (SNAP Cartridge HP-Sil; mobile phase: n-Hexane/EtOAc=95/5-80/20; v/v) to give the titled compound (2.3 g as a pale red oil).
MS (ESI pos.) m/z: 454 ([M+H]$^+$).

Reference Example P-C45

Synthesis of [4-(3-chlorophenyl)-2-(4-iodophenyl)-1,3-oxazol-5-yl]acetic acid

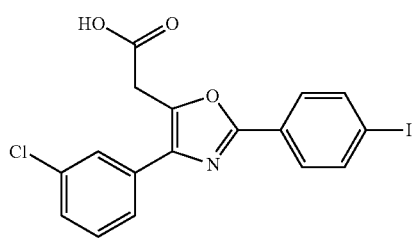

[Chem. 163]

Starting from the compound (3.5 g) obtained in Reference Example P-C44, the same procedure as in Reference Example P-C32 was applied to give the titled compound (3.3 g as a pale yellow solid).
MS (ESI pos.) m/z: 440 ([M+H]$^+$).

Reference Example P-C46

Synthesis of 3-chlorophenyl)-2-(4-iodophenyl)-1,3-oxazol-5-yl]-N-(propan-2-yl)acetamide

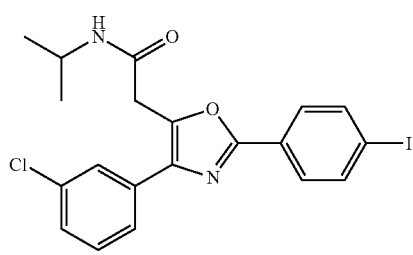

[Chem. 164]

Starting from the compound (3.3 g) obtained in Reference Example P-C45, the same procedure as in Reference Example P-C09 was applied to give the titled compound (3.1 g as a colorless solid).
MS (ESI pos.) m/z: 481 ([M+H]$^+$).

Reference Example P-C47

Synthesis of 2-[4-(3-chlorophenyl)-2-(4-ethenylphenyl)-1,3-oxazol-5-yl]-N-(propan-2-yl)acetamide

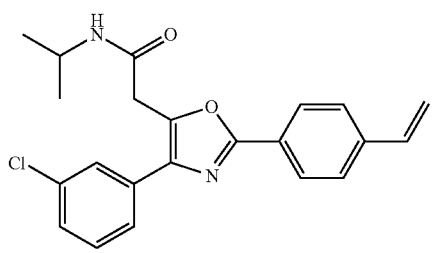

[Chem. 165]

Starting from the compound (3.1 g) obtained in Reference Example P-C46, the same procedure as in Reference Example P-A03 was applied to give the titled compound (1.6 g as a pale brown solid).
MS (ESI pos.) m/z: 381 ([M+H]$^+$).

Reference Example P-C48

Synthesis of 2-{4-(3-chlorophenyl)-2-[4-(2-hydroxyethyl)phenyl]-1,3-oxazol-5-yl}-N-(propan-2-yl)acetamide

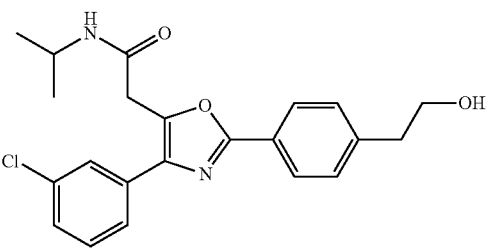

[Chem. 166]

Starting from the compound (1.6 g) obtained in Reference Example P-C47, the same procedure as in Reference Example P-A04 was applied to give the titled compound (1.7 g as a pale yellow solid).
MS (ESI pos.) m/z: 399 ([M+H]$^+$).

Reference Example P-C49

Synthesis of methyl 3-chloro3-(3-chlorophenyl)-2-oxopropanoate

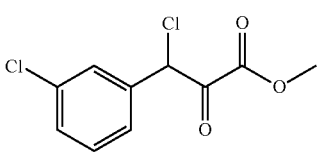

[Chem. 167]

To a tert-butyl methyl ether solution (70 mL) of 3-chlorobenzaldehyde (10 g) and methyl 3,3-dichloro-2-oxopropanoate (9.6 mL), sodium methoxide (4.8 g) was added under cooling with ice and the mixture was stirred at 70° C. for 17 hours. After adding EtOAc to the reaction mixture, it was washed with water and Brine. After drying the organic layer over MgSO$_4$, the desiccant was filtered off and the filtrate was concentrated under reduced pressure to give the titled compound (18 g as a brown oil).
MS (ESI neg.) m/z: 245 ([M−H]$^−$).

Reference Example P-C50

Synthesis of methyl 2-(4-bromophenyl)-5-(3-chlorophenyl)-1,3-thiazole-4-carboxylate

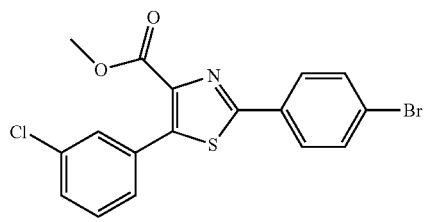

[Chem. 168]

To a MeOH solution (150 mL) of the compound (7.0 g) obtained in Reference Example P-C49, 4-bromobenzothioamide (6.1 g) was added and the mixture was stirred at 70° C. for 2 hours. After leaving the mixture to cool, the precipitating solid was recovered by filtration to give the titled compound (4.9 g as a colorless solid).
MS (ESI pos.) m/z: 408 ([M+H]$^+$).

Reference Example P-C51

Synthesis of 2-(4-bromophenyl)-5-(3-chlorophenyl)-1,3-thiazole-4-carboxylic acid

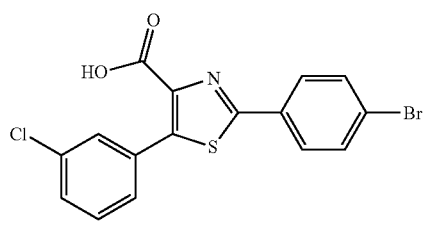

[Chem. 169]

Starting from the compound (4.9 g) obtained in Reference Example P-C50, the same procedure as in Reference Example P-C32 was applied to give the titled compound (4.7 g as a pale yellow solid).
MS (ESI pos.) m/z: 394 ([M+H]$^+$).

Reference Example P-C52

Synthesis of [2-(4-bromophenyl)-5-(3-chlorophenyl)-1,3-thiazol-4-yl]acetic acid

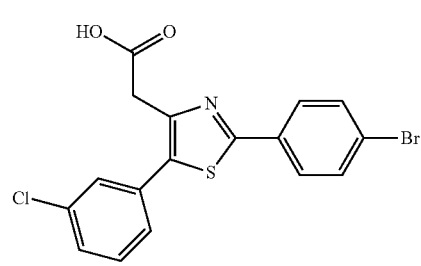

[Chem. 170]

Starting from the compound (210 mg) obtained in Reference Example P-C51, the same procedure as in Reference Example P-C23 was applied to give the titled compound (220 mg as a pale brown solid).
MS (ESI pos.) m/z: 408 ([M+H]$^+$).

Reference Example P-C53

Synthesis of 2-[2-(4-bromophenyl)-5-(3-chlorophenyl)-1,3-thiazol-4-yl]-N-(propan-2-yl)acetamide

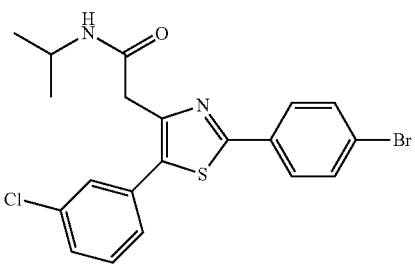

[Chem. 171]

Starting from the compound (220 mg) obtained in Reference Example P-C52, the same procedure as in Reference Example P-C09 was applied to give the titled compound (85 mg as a pale yellow solid).
MS (ESI pos.) m/z: 449 ([M+H]$^+$).

Reference Example P-C54

Synthesis of 2-[5-(3-chlorophenyl)-2-(4-ethenylphenyl)-1,3-thiazol-4-yl]-N-(propan-2-yl)acetamide

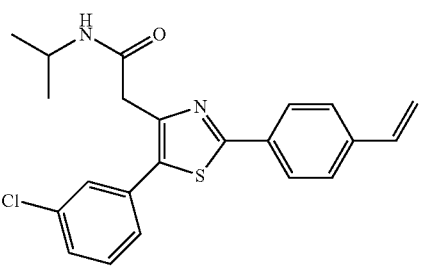

[Chem. 172]

Starting from the compound (1.9 g) obtained in Reference Example P-C53, the same procedure as in Reference Example P-A03 was applied to give the titled compound (820 mg as a pale yellow solid).
MS (ESI pos.) m/z: 397 ([M+H]$^+$).

Reference Example P-C55

Synthesis of 2-{5-(3-chlorophenyl)-2-[4-(2-hydroxyethyl)phenyl]-1,3-thiazol-4-yl}-N-(propan-2-yl)acetamide

[Chem. 173]

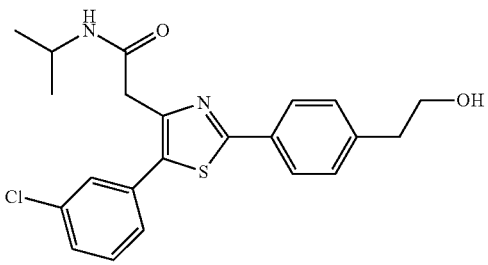

Starting from the compound (820 mg) obtained in Reference Example P-C54, the same procedure as in Reference Example P-A04 was applied to give the titled compound (830 mg as a pale yellow solid).
MS (ESI pos.) m/z: 415 ([M+H]$^+$).

Reference Example P-C56

Synthesis of methyl 2-(3-bromophenyl)-5-(3-chlorophenyl)thiazole-4-carboxylate

[Chem. 174]

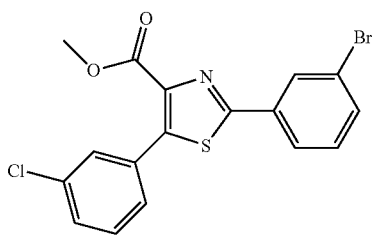

Starting from the compound (7.0 g) obtained in Reference Example P-C49 and 3-bromobenzothioamide (4.9 g), the same procedure as in Reference Example P-C50 was applied to give the titled compound (4.1 g as a colorless solid).
MS (ESI pos.) m/z: 408 ([M+H]$^+$).

Reference Example P-C57

Synthesis of 2-(3-bromophenyl)-5-(3-chlorophenyl)thiazole-4-carboxylic acid

[Chem. 175]

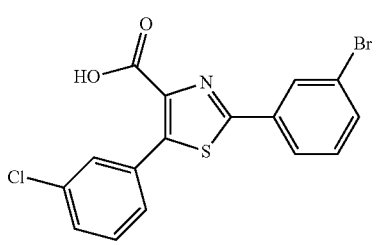

Starting from the compound (4.1 g) obtained in Reference Example P-C56, the same procedure as in Reference Example P-C32 was applied to give the titled compound (3.9 g as a pale yellow solid).
MS (ESI pos.) m/z: 394 ([M+H]$^+$).

Reference Example P-C58

Synthesis of 2-(2-(3-bromophenyl)-5-(3-chlorophenyl)thiazol-4-yl)acetic acid

[Chem. 176]

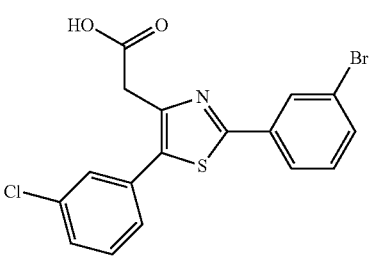

Starting from the compound (3.9 g) obtained in Reference Example P-C57, the same procedure as in Reference Example P-C23 was applied to give the titled compound (4.1 g as a pale brown solid).
MS (ESI pos.) m/z: 408 ([M+H]$^+$).

Reference Example P-C59

Synthesis of 2-(2-(3-bromophenyl)-5-(3-chlorophenyl)thiazol-4-yl)-N-isopropylacetamide

[Chem. 177]

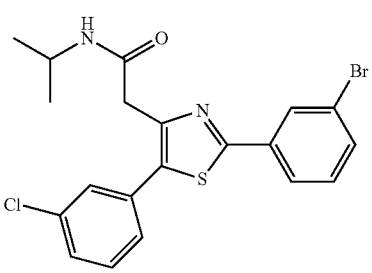

Starting from the compound (4.1 g) obtained in Reference Example P-C58, the same procedure as in Reference Example P-C09 was applied to give the titled compound (2.3 g as a pale yellow solid).
MS (ESI pos.) m/z: 449 ([M+H]$^+$).

Reference Example P-C60

Synthesis of 2-(5-(3-chlorophenyl)-2-(3-vinylphenyl)thiazol-4-yl)-N-isopropylacetamide

[Chem. 178]

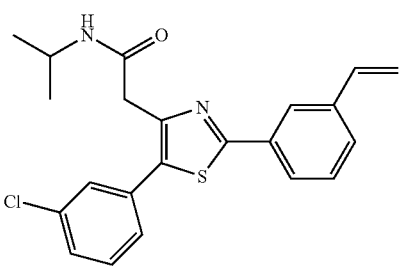

Starting from the compound (2.3 g) obtained in Reference Example P-C59, the same procedure as in Reference Example P-A03 was applied to give the titled compound (650 mg as a pale yellow solid).
MS (ESI pos.) m/z: 397 ([M+H]$^+$).

Reference Example P-C61

Synthesis of 2-(5-(3-chlorophenyl)-2-(3-(2-hydroxyethyl)phenyl)thiazol-4-yl)-N-isopropylacetamide

[Chem. 179]

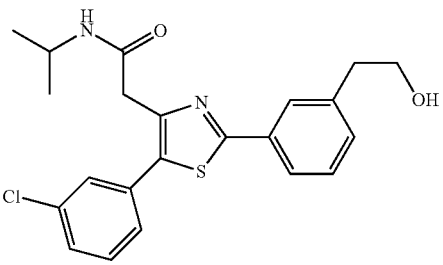

Starting from the compound (650 mg) obtained in Reference Example P-C60, the same procedure as in Reference Example P-A04 was applied to give the titled compound (660 mg as a pale yellow solid).
MS (ESI pos.) m/z: 415 ([M+H]$^+$).

Reference Example P-C62

Synthesis of 4-(2-{[tert-butyl(diphenyl)silyl]oxy}ethyl)aniline

[Chem. 180]

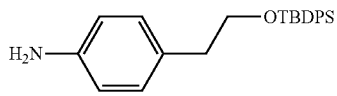

To a DMF solution (15 mL) of 2-(4-aminophenyl)ethanol (1.0 g) and iPr2NEt (1.5 mL), tert-butyl(chloro)diphenylsilane (2.1 mL) was added and the mixture was stirred at room temperature for 17 hours. After adding EtOAc to the reaction mixture, it was washed with water and Brine. After drying the organic layer over MgSO$_4$, the desiccant was filtered off and the filtrate was concentrated under reduced pressure; the resulting residue was purified by silica gel column chromatography (SNAP Cartridge HP-Sil; mobile phase: n-Hexane/EtOAc=90/10-70/30; v/v) to give the titled compound (2.1 g as a pale yellow oil).
MS (ESI pos.) m/z: 376 ([M+H]$^+$).

Reference Example P-C63

Synthesis of 3-bromo1-[4-(2-{[tert-butyl(diphenyl)silyl]oxy}ethyl)phenyl]-1H-pyrrole-2,5-dione

[Chem. 181]

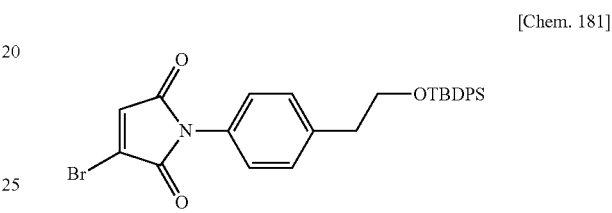

To an acetic acid solution (45 mL) of the compound (5.0 g) obtained in Reference Example P-C62, 3-bromofuran-2,5-dione (2.6 g) was added and the mixture was stirred at 80° C. for 4 hours. The reaction mixture was concentrated under reduced pressure and the resulting residue was purified by silica gel column chromatography (SNAP Cartridge HP-Sil; mobile phase: n-Hexane/EtOAc=95/5-85/15; v/v) to give the titled compound (4.5 g as a pale brown oil).
MS (ESI pos.) m/z: 534, 536 ([M+H]$^+$).

Reference Example P-C64

Synthesis of tributyl(3-chlorophenyl)stannane

[Chem. 182]

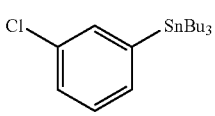

To a THF solution (0.5 M, 30 mL) of (3-chlorophenyl)magnesium bromide, tributyltin chloride (4.3 mL) was added under cooling with ice and the mixture was stirred at room temperature for 5 hours. To the reaction mixture, a saturated aqueous ammonium chloride solution and EtOAc were added and the organic layer was separated. After drying the resulting organic layer over MgSO$_4$, the desiccant was filtered off and the filtrate was concentrated under reduced pressure; the resulting residue was purified by silica gel column chromatography (SNAP Cartridge HP-Sil; mobile phase: n-Hexane) to give the titled compound (5.6 g as a colorless oil).
1H NMR (600 MHz, CHLOROFORM-d) δ (ppm); 0.82-0.92 (34H, m), 0.97-1.13 (24H, m), 1.32 (24H, dq, J=14.7, 7.4 Hz), 1.43-1.63 (27H, m), 7.20-7.27 (12H, m), 7.28-7.32 (3H, m), 7.39 (3H, d, J=2.1 Hz)

Reference Example P-C65

Synthesis of 1-[4-(2-{[tert-butyl(diphenyl) silyl]oxy}ethyl)phenyl]-3-(3-chlorophenyl)-1H-pyrrole-2,5-dione

[Chem. 183]

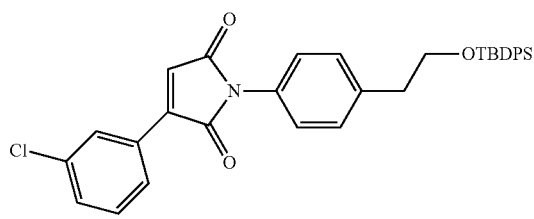

To a dioxane solution (18 mL) of the compound (2.0 g) obtained in Reference Example P-C63 and the compound (2.3 g) obtained in Reference Example P-C64, Pd(PPh$_3$)$_4$ (430 mg) was added and the mixture was stirred at 100° C. for 17 hours. After filtering the reaction mixture through Celite (registered trademark), the filtrate was diluted with added tEtOAc; subsequently, the organic layer was washed with water and Brine and dried over MgSO$_4$; the desiccant was then filtered off and the filtrate was concentrated under reduced pressure. The resulting residue was purified by silica gel column chromatography (SNAP Cartridge HP-Sil; mobile phase: n-Hexane/EtOAc=90/10-70/30; v/v) to give the titled compound (1.0 g as a pale red oil).

MS (ESI pos.) m/z: 588 ([M+Na]$^+$).

Reference Example P-C66

Synthesis of 1-[4-(2-{[tert-butyl(diphenyl)silyl]oxy}ethyl)phenyl]-3-chloro-4-(3-chlorophenyl)-1H-pyrrole-2,5-dione

[Chem. 184]

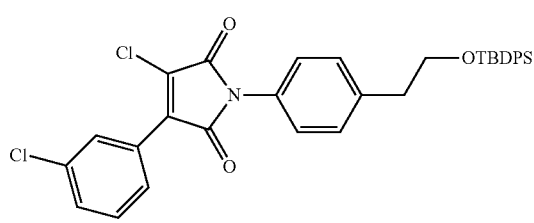

To a thionyl chloride solution (8.0 mL) of the compound (900 mg) obtained in Reference Example P-C65, pyridine (0.26 mL) was added and the mixture was stirred at 60° C. for an hour. After concentrating the reaction mixture under reduced pressure, toluene was added and the insoluble matter was filtered off, with the resulting filtrate being concentrated under reduced pressure. The resulting residue was purified by silica gel column chromatography (SNAP Cartridge HP-Sil; mobile phase: n-Hexane/EtOAc=90/10-80/20; v/v) to give the titled compound (630 mg as a pale yellow amorphous product).

MS (ESI pos.) m/z: 622 ([M+Na]$^+$).

Reference Example P-C67

Synthesis of di-tert-butyl {1-[4-(2-{[tert-butyl(diphenyl)silyl]oxy}ethyl)phenyl]-4-(3-chlorophenyl)-2,5-dioxo-2,5-dihydro-1H-pyrrol-3-yl}propanedioate

[Chem. 185]

To a THF solution (5.0 mL) of di-tert-butyl malonate (480 mg), sodium hydride (88 mg) was added under cooling with ice and the mixture was stirred for 30 minutes; subsequently, a THF solution (5.0 mL) of the compound (630 mg) obtained in Reference Example P-C66 was added dropwise. After 1-hr stirring at room temperature, CHCl$_3$ and water were added to the reaction mixture. The organic layer was separated and dried over MgSO$_4$; subsequently, the desiccant was filtered off and the filtrate was concentrated under reduced pressure. The resulting residue was purified by silica gel column chromatography (SNAP Cartridge HP-Sil; mobile phase: n-Hexane/EtOAc=90/10-80/20; v/v) to give the titled compound (770 mg as a pale yellow oil).

MS (ESI neg.) m/z: 778 ([M−H]$^-$).

Reference Example P-C68

Synthesis of {4-(3-chlorophenyl)-1-[4-(2-hydroxyethyl)phenyl]-2,5-dioxo-2,5-dihydro-1H-pyrrol-3-yl}acetic acid

[Chem. 186]

To a CHCl$_3$ solution (4.50 mL) of the compound (669 mg) obtained in Reference Example P-C67, trifluoroacetic acid (4.50 mL) was added and the mixture was stirred at room temperature for 17 hours. The reaction mixture was concentrated to give the titled compound as a crude product (535 mg as a pale yellow oil).

MS (ESI pos.) m/z: 386 ([M+H]$^+$).

Reference Example P-C69

Synthesis of 2-{4-(3-chlorophenyl)-1-[4-(2-hydroxyethyl)phenyl]-2,5-dioxo-2,5-dihydro-1H-pyrrol-3-yl}-N-(propan-2-yl)acetamide

[Chem. 187]

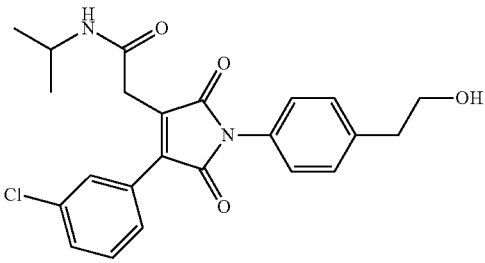

Starting from the compound (49 mg) obtained in Reference Example P-C68, the same procedure as in Reference Example P-C09 was applied to give the titled compound (16 mg as a pale yellow oil).

MS (ESI pos.) m/z: 427 ([M+H]$^+$).

Reference Example P-C70

Synthesis of 2-[(4-bromophenyl)amino]-1-(3-chlorophenyl)ethanone

[Chem. 188]

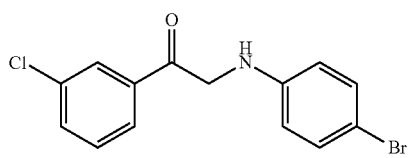

A MeCN (30 mL) suspension of 3-chlorophenacyl bromide (3.0 g), 4-bromoaniline (2.2 g) and NaHCO$_3$ (1.1 g) was stirred first at room temperature for 14 hours, then at an external temperature of 60° C. for 4 hours. After leaving the reaction mixture to cool, water and EtOAc were added for phase separation, followed by washing with Brine. The aqueous layer was extracted with EtOAc twice and the organic layer was dried over Na$_2$SO$_4$; subsequently, the desiccant was filtered off and the filtrate was concentrated under reduced pressure. To the resulting solids, n-Hexane was added and the mixture was stirred at an external temperature of 60° C. for an hour. After leaving the mixture to cool, the solids were recovered by filtration and dried to give the titled compound (3.5 g as a pale brown solid).

MS (ESI pos.) m/z: 324, 326 ([M+H]$^+$).

Reference Example P-C71

Synthesis of 1-(4-bromophenyl)-4-(3-chlorophenyl)-1,3-dihydro-2H-imidazol-2-one

[Chem. 189]

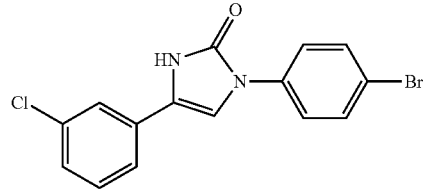

To the compound (4.1 g) obtained in Reference ExampleP-C70 and potassium cyanide (17 g), acetic acid (115 mL) was added and the mixture was stirred at an external temperature of 60° C. for 2 hours. After leaving the reaction mixture to cool, water was added and the resulting solids were recovered by filtration and dried to give the titled the compound (4.8 g as a colorless solid).

MS (ESI pos.) m/z: 351 ([M+H]$^+$).

Reference Example P-C72

Synthesis of 2-[3-(4-bromophenyl)-5-(3-chlorophenyl)-2-oxo-2,3-dihydro-1H-imidazol-1-yl]-N-(propan-2-yl)acetamide

[Chem. 190]

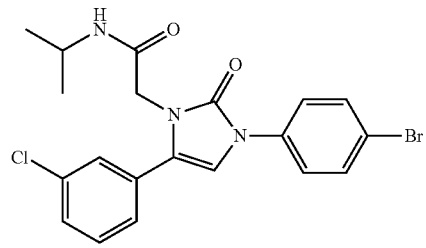

Starting from the compound (1.7 g) obtained in Reference Example P-C71, the same procedure as in Reference Example P-A02 was applied to give the titled the compound (1.7 g as a pale brown solid).

MS (ESI pos.) m/z: 448, 450 ([M+H]$^+$).

Reference Example P-C73

Synthesis of 2-[5-(3-chlorophenyl)-3-(4-ethenylphenyl)-2-oxo-2,3-dihydro-1H-imidazol-1-yl]-N-(propan-2-yl)acetamide

[Chem. 191]

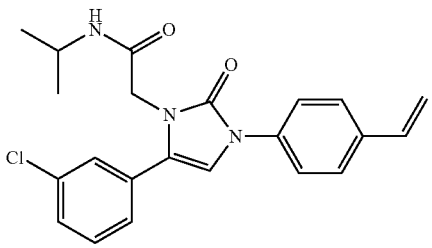

Starting from the compound (1.7 g) obtained in Reference Example P-C72, the same procedure as in Reference Example P-A03 was applied to give the titled the compound (0.69 g as a pale brown solid).

MS (ESI pos.) m/z: 396 ([M+H]$^+$).

Reference Example P-C74

Synthesis of 2-{5-(3-chlorophenyl)-3-[4-(2-hydroxyethyl)phenyl]-2-oxo-2,3-dihydro-1H-imidazol-1-yl}-N-(propan-2-yl)acetamide

[Chem. 192]

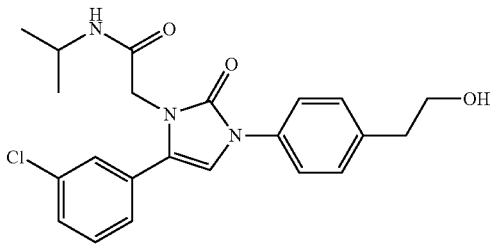

Starting from the compound (0.69 g) obtained in Reference Example P-C73, the same procedure as in Reference Example P-A04 was applied to give the titled the compound (0.24 g as a pale brown solid).

MS (ESI pos.) m/z: 414 ([M+H]$^+$).

Reference Example P-C75

Synthesis of (1E)-1-(3-chlorophenyl)-1-(hydroxyimino)propan-2-one

[Chem. 193]

To a solution of 3-chlorophenylacetone (5.0 g) in EtOH (100 mL), a 20% sodium ethoxide-EtOH solution (14 mL) was added and under cooling with ice, isoamyl nitrite (5.9 mL) was gradually added and the mixture was stirred for 2 hours under cooling with ice. To the reaction mixture, diethyl ether and water were added for phase separation. After adjusting the aqueous layer to about pH 3 with 1 M aqueous hydrochloric acid, extraction was conducted with EtOAc, followed by washing with Brine. After drying the organic layer over Na$_2$SO$_4$, the desiccant was filtered off and the filtrate was concentrated under reduced pressure. The resulting residue was purified by column chromatography (SNAP Cartridge KP-NH 55 g; mobile phase: CHCl$_3$/MeOH=100/0-95/5; v/v) to give the titled compound (4.2 g as a colorless solid).

MS (ESI neg.) m/z: 196 ([M−H]$^−$).

Reference Example P-C76

Synthesis of 1,3,5-tris(4-bromophenyl)-1,3,5-triazinane

[Chem. 194]

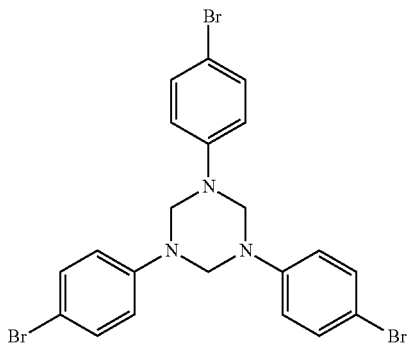

To 4-bromoaniline (5.0 g) and paraformaldehyde (1.2 g), toluene (50 mL) was added and the mixture was stirred at an external temperature of 110° C. for 2 hours. After leaving the reaction mixture to cool, it was concentrated under reduced pressure. After adding EtOAc and heating under reflux for 30 minutes, the reaction mixture was left to cool and the resulting solids were recovered by filtration and dried to give the titled compound (1.8 g as a colorless solid). The mother liquor was concentrated under reduced pressure and following the addition of a hexane/EtOAc mixed solvent (6/1; v/v), the mixture was stirred at 60° C. for 30 minutes; thereafter, the reaction mixture was left to cool and stirred at room temperature for 16 hours. The resulting solids were recovered by filtration and dried to give the titled compound (2.2 g as a colorless solid).

MS (ESI pos.) m/z: 550, 552 ([M+H]$^+$).

Reference Example P-C77

Synthesis of 1-(4-bromophenyl)-4-(3-chlorophenyl)-5-methyl-1,3-dihydro-2H-imidazol-2-one

[Chem. 195]

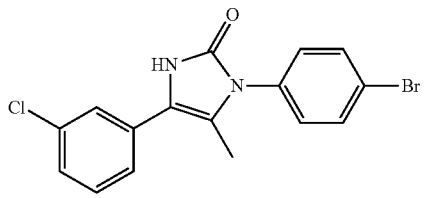

To the compound (2.0 g) obtained in Reference Example P-C75 as well as the compound (1.9 g) obtained in Reference Example P-C76, EtOH (60 mL) was added and the mixture was stirred at an external temperature of 100° C. for 16 hours. After leaving the mixture to cool, it was concentrated under reduced pressure and EtOH (15 mL) was added, followed by stirring the mixture at an external temperature of 100° C. for 30 hours. After leaving the mixture to cool, the resulting solids were recovered by filtration, washed with cold EtOH, and dried to give the titled compound (1.4 g as a colorless solid).

MS (ESI pos.) m/z: 363 ([M+H]$^+$).

Reference Example P-C78

Synthesis of 2-[3-(4-bromophenyl)-5-(3-chlorophenyl)-4-methyl-2-oxo-2,3-dihydro-1H-imidazol-1-yl]-N-(propan-2-yl)acetamide

[Chem. 196]

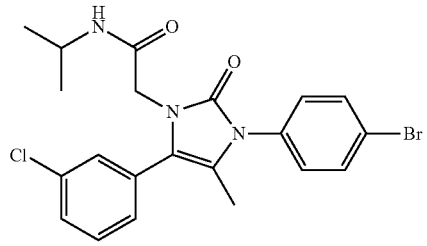

Starting from the compound (0.70 g) obtained in Reference Example P-C77, the same procedure as in Reference Example P-A02 was applied to give the titled compound (0.94 g as a pale brown solid).
MS (ESI pos.) m/z: 462, 464 ([M+H]$^+$).

Reference Example P-C79

Synthesis of 2-[5-(3-chlorophenyl)-3-(4-ethenylphenyl)-4-methyl-2-oxo-2,3-dihydro-1H-imidazol-1-yl]-N-(propan-2-yl)acetamide

[Chem. 197]

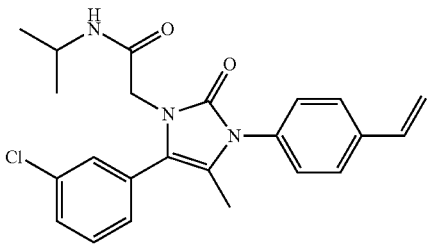

Starting from the compound (0.42 g) obtained in Reference Example P-C78, the same procedure as in Reference Example P-A03 was applied to give the titled compound (0.29 g as a pale brown solid).
MS (ESI pos.) m/z: 410 ([M+H]$^+$).

Reference Example P-C80

Synthesis of 2-{5-(3-chlorophenyl)-3-[4-(2-hydroxyethyl)phenyl]-4-methyl-2-oxo-2,3-dihydro-1H-imidazol-1-yl}-N-(propan-2-yl)acetamide

[Chem. 198]

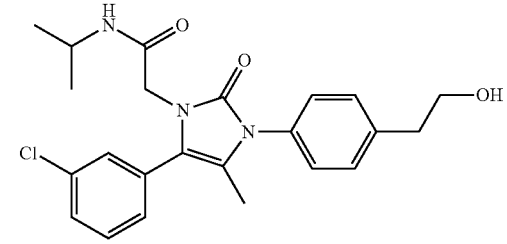

Starting from the compound (0.29 g) obtained in Reference Example P-C79, the same procedure as in Reference Example P-A04 was applied to give the titled compound (0.11 g as a colorless solid).
MS (ESI pos.) m/z: 428 ([M+H]$^+$).

Reference Example P-C81

Synthesis of 4-bromo-N'-(3-chlorophenyl)benzohydrazide

[Chem. 199]

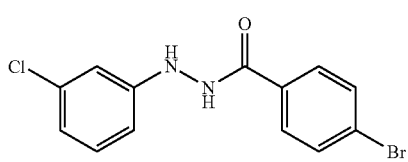

To a CHCl$_3$ solution (80 mL) of (3-chlorophenyl)hydrazine hydrochloride (5.0 g) and Et$_3$N (8.6 mL), a CHCl$_3$ suspension (40 mL) of 4-bromobenzoyl chloride (6.1 g) was added under an ice bath and the mixture was stirred overnight at room temperature. To the reaction mixture, water (100 mL) and a saturated aqueous NaHCO$_3$ solution (30 mL) were added in an ice bath and after separating the organic layer, the aqueous layer was extracted with CHCl$_3$ twice. The organic layers were combined and concentrated under reduced pressure. The resulting residue was washed with IPE (80 mL) under stirring and recovered by filtration to give the titled compound (6.3 g as a pale pink solid).
MS (ESI pos.) m/z: 327 ([M+H]$^+$).

Reference Example P-C82

Synthesis of 4-bromo-N-(3-chlorophenyl)benzenecarbohydrazonoyl chloride

[Chem. 200]

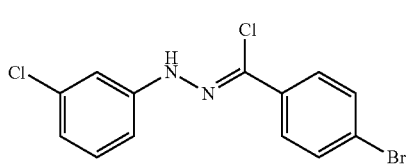

To a MeCN suspension (40 mL) of the compound (2.0 g) obtained in Reference Example P-C81, triphenylphosphine (1.9 g) and carbon tetrachloride (1.1 g) were added and the mixture was stirred overnight at room temperature. After heating the reaction mixture to 40° C., it was left to cool and following the addition of triphenylphosphine (1.6 g) and carbon tetrachloride (0.6 mL), the mixture was stirred at room temperature for 24 hours. The reaction mixture was concentrated under reduced pressure and the resulting residue was purified by silica gel column chromatography (SNAP Cartridge HP-Sil 50 g; mobile phase: n-Hexane/EtOAc=95/5-80/20; v/v) to give the titled compound (1.9 g as a colorless solid).
MS (ESI neg.) m/z: 341, 343 ([M−H]$^−$).

Reference Example P-C83

Synthesis of 2-[3-(4-bromophenyl)-1-(3-chlorophenyl)-1H-1,2,4-triazol-5-yl]-N-(propan-2-yl)acetamide

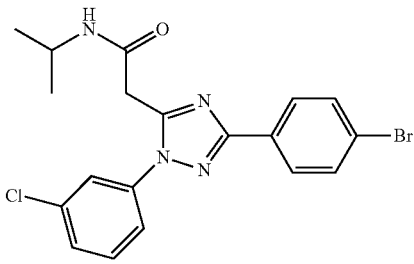

[Chem. 201]

To a MeCN suspension (55 mL) of the compound (1.1 g) obtained in Reference Example P-C82, Et₃N (1.1 mL) and 3-amino-N-(propan-2-yl)propanamide hydrochloride (0.64 g) were added and the mixture was stirred at room temperature for 3 hours. The reaction mixture was concentrated under reduced pressure and after adding MeCN (50 mL) and silver carbonate (1.3 g) to the resulting residue, the mixture was stirred with light shielded, first at 50° C. for 4 hours, then at 60° C. for 4 hours. After leaving the mixture to cool, silver carbonate (0.44 g) was added and the mixture was stirred at 60° C. for 4 hours. After leaving the reaction mixture to cool, it was concentrated under reduced pressure; subsequently, the resulting residue was purified by silica gel column chromatography (SNAP Cartridge HP-Sil 25 g; mobile phase: n-Hexane/EtOAc=88/12-0/100; v/v) and the resulting compound was washed with IPE; the solids were recovered by filtration to give the titled compound (990 mg as a colorless solid).

MS (ESI pos.) m/z: 433 ([M+H]⁺).

Reference Example P-C84

Synthesis of 2-[1-(3-chlorophenyl)-3-(4-ethenylphenyl)-1H-1,2,4-triazol-5-yl]-N-(propan-2-yl)acetamide

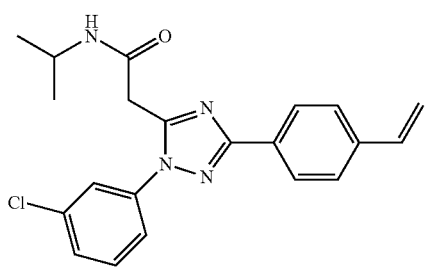

[Chem. 202]

Starting from the compound (282 mg) obtained in Reference Example P-C83, the same procedure as in Reference Example P-A03 was applied to give the titled compound (65 mg as a colorless solid).

MS (ESI pos.) m/z: 381 ([M+H]⁺).

Reference Example P-C85

Synthesis of 2-{1-(3-chlorophenyl)-3-[4-(2-hydroxyethyl)phenyl]-1H-1,2,4-triazol-5-yl}-N-(propan-2-yl)acetamide

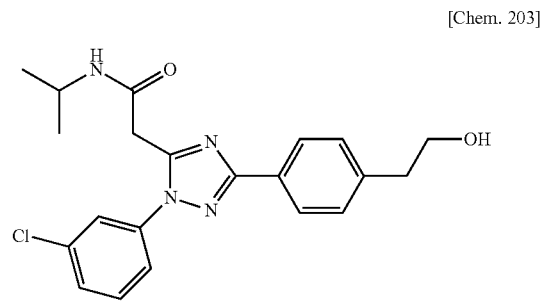 [SMILES: CC(C)NC(=O)Cc1nc(-c2ccc(CCO)cc2)nn1-c1cccc(Cl)c1]

[Chem. 203]

Starting from the compound (65 mg) obtained in Reference Example P-C84, the same procedure as in Reference Example P-A04 was applied to give the titled compound (57 mg as a colorless solid).

MS (ESI pos.) m/z: 399 ([M+H]⁺).

Reference Example P-D01

Synthesis of 1-fluoro-4-isocyanato-2-methoxybenzene

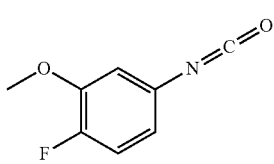

[Chem. 204]

To a toluene solution (60 mL) of 4-fluoro3-methoxyaniline (3.0 g), triphosgene (4.5 g) was added under cooling with ice and the mixture was stirred overnight at 110° C. The reaction mixture was concentrated to give the titled the compound as a crude product (dark purple oil).

Reference Example P-D02

Synthesis of ethyl 3-{2-[(4-fluoro-3-methoxyphenyl)carbamoyl]hydrazinyl}-3-oxopropanoate

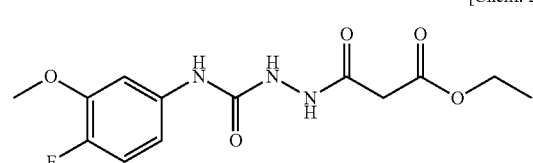

[Chem. 205]

To a THF solution (80 mL) of ethyl 3-hydrazinyl-3-oxopropanoate (3.2 g), the crude product (3.7 g) obtained in Reference Example P-D01 was added under cooling with ice and the mixture was stirred overnight at room temperature. The reaction mixture was concentrated and the resulting residue was purified by silica gel column chromatography (SNAP Cartridge HP-Sil 100 g; mobile phase: CHCl$_3$/MeOH=99/1-80/20; v/v) to give the titled compound (3.8 g as a pale purple solid).

1H NMR (600 MHz, DMSO-d$_6$) δ (ppm); 1.12-1.22 (3H, m) 3.27-3.32 (4H, m) 3.75 (3H, s) 4.02-4.14 (2H, m) 6.82-6.95 (1H, m) 7.05 (1H, dd, J=11.4, 8.9 Hz) 7.30 (1H, dd, J=8.1, 2.3 Hz) 8.22 (1H, br. s.) 8.64 (1H, br. s.) 9.87 (1H, br. s.)

Reference Example P-D03

Synthesis of [4-(4-fluoro3-methoxyphenyl)-5-oxo-4,5-dihydro-1H-1,2,4-triazol-3-yl]acetic acid

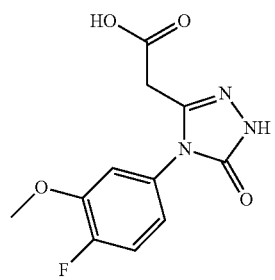

[Chem. 206]

A 3.0 M NaOH aqueous solution (30 mL) of the compound (3.7 g) obtained in Reference Example P-D02 was stirred at 120° C. for 3 days. After leaving the reaction mixture to cool, conc. hydrochloric acid was added for an adjustment to pH=1 and the mixture was stirred at 0° C. for an hour. The resulting solids were recovered by filtration, washed with water and subsequently dried to give the titled compound (2.9 g as a pale yellow solid).

MS (ESI pos.) m/z: 268 ([M+H]$^+$).

Reference Example P-D04

Synthesis of 2-[4-(4-fluoro-3-methoxyphenyl)-5-oxo-4,5-dihydro-1H-1,2,4-triazol-3-yl]-N-(propan-2-yl)acetamide

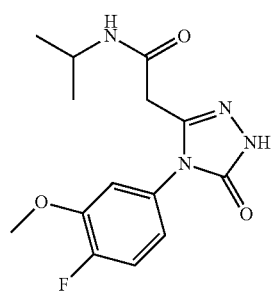

[Chem. 207]

To a DMF suspension (8 mL) of the compound (800 mg) obtained in Reference Example P-D03, HOBt H$_2$O (590 mg) and EDC HCl (740 mg) were added at room temperature and the mixture was stirred for 15 minutes. After adding isopropylamine (0.60 mL) to it, the reaction mixture was stirred at 50° C. for 3 hours. After leaving the reaction mixture to cool, water and CHCl$_3$ were added under cooling with ice and the organic layer was subsequently separated. The resulting organic layer was filtered with Phase Separator and the filtrate was concentrated under reduced pressure. The resulting residue was purified by silica gel column chromatography (SNAP Cartridge HP-Sil 25 g; mobile phase: CHCl$_3$/MeOH=99/1-85/15; v/v) to give the titled compound (400 mg as a colorless solid).

MS (ESI pos.) m/z: 309 ([M+H]$^+$).

Reference Example P-D05

Synthesis of N-tert-butyl-2-[4-(4-fluoro-3-methoxyphenyl)-5-oxo-4,5-dihydro-1H-1,2,4-triazol-3-yl]acetamide

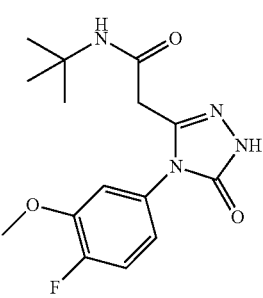

[Chem. 208]

A mixture of the compound (100 mg) obtained in Reference Example P-D03, tert-butylamine (0.08 mL), HATU (210 mg), iPr$_2$NEt (0.13 mL) and THF (1.5 mL) was stirred at room temperature for 5 hours. To the reaction mixture, a saturated aqueous ammonium chloride solution (20 mL) and CHCl$_3$ were added for phase separation; subsequently, the aqueous layer was extracted with CHCl$_3$ (20 mL×3 times). The combined organic layer was dried over MgSO$_4$ and, subsequently, the desiccant was filtered off and the filtrate was concentrated under reduced pressure. The resulting residue was purified by silica gel column chromatography (SNAP Cartridge KP-Sil; mobile phase: CHCl$_3$/MeOH/NH$_4$OH=99/1/0.1-95/5/0.5; v/v/v) to give the titled compound (65 mg as a pale purple amorphous product).

MS (ESI pos.) m/z: 323 ([M+H]$^+$).

Reference Example P-D06

Synthesis of ethyl 3-{2-[(3-chlorophenyl)carbamoyl]hydrazinyl}-3-oxopropanoate

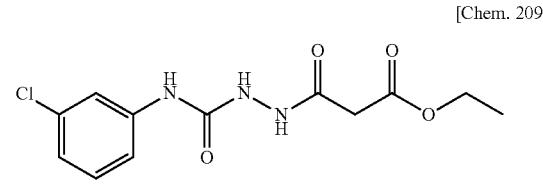

[Chem. 209]

Starting from 1-chloro-3-isocyanatobenzene (5.0 mL) and ethyl 3-hydrazinyl-3-oxopropanoate (6.0 g), the same procedure as in Reference Example P-D02 was applied to give the titled compound (12 g as a pale brown solid).

MS (ESI pos.) m/z: 300 ([M+H]$^+$).

Reference Example P-D07

Synthesis of [4-(3-chlorophenyl)-5-oxo-4,5-dihydro-1H-1,2,4-triazol-3-yl]acetic acid

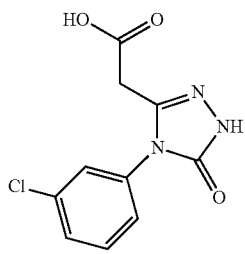

[Chem. 210]

Starting from the compound (3.0 g) obtained in Reference Example P-D06, the same procedure as in Reference Example P-D03 was applied to give the titled compound (1.2 g as a colorless solid).

MS (ESI pos.) m/z: 254 ([M+H]$^+$).

Reference Example P-D08

Synthesis of 2-[4-(3-chlorophenyl)-5-oxo-4,5-dihydro-1H-1,2,4-triazol-3-yl]-N-(propan-2-yl)acetamide

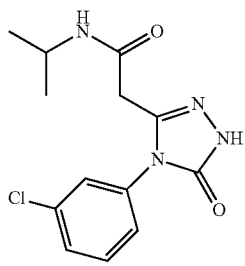

[Chem. 211]

Starting from the compound (1.0 g) obtained in Reference Example P-D07, the same procedure as in Reference Example P-D04 was applied to give the titled compound (960 mg as a colorless solid).

MS (ESI pos.) m/z: 295 ([M+H]$^+$).

Reference Example P-D09

Synthesis of N-tert-butyl-2-[4-(3-chlorophenyl)-5-oxo-4,5-dihydro-1H-1,2,4-triazol-3-yl]acetamide

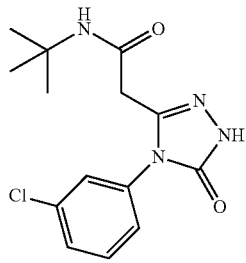

[Chem. 212]

A mixture of the compound (400 mg) obtained in Reference Example P-D07, tert-butylamine (0.26 mL), HATU (900 mg), iPr$_2$NEt (0.81 mL) and DMF (10 mL) was stirred overnight at room temperature and left to stand at room temperature for 5 days. After adding 1 M hydrochloric acid (40 mL) and EtOAc (20 mL) for phase separation, the aqueous layer was extracted with EtOAc (20 mL×5 times). The combined organic layer was washed with 1 M hydrochloric acid (30 mL), water (30 mL) and Brine, followed by concentrating under reduced pressure. The resulting residue was purified by silica gel column chromatography (SNAP Cartridge HP-Sil 25 g; mobile phase: CHCl$_3$/MeOH=99/1-90/10; v/v) and the resulting solids were washed with a mixed solvent of EtOAc and n-Hexane (EtOAc/n-Hexane=1/1; v/v) under stirring and recovered by filtration to give the titled compound (310 mg as a colorless solid).

MS (ESI pos.) m/z: 309 ([M+H]$^+$).

Reference Example P-D10

Synthesis of ethyl 3-{2-[(3-chloro-4-fluorophenyl)carbamoyl]hydrazinyl}-3-oxopropanoate

[Chem. 213]

Starting from 2-chloro-1-fluoro-4-isocyanatobenzene (11 g) and ethyl 3-hydrazinyl-3-oxopropanoate (9.4 g), the same procedure as in Reference Example P-D02 was applied to give the titled compound (15 g as a colorless solid).

1H NMR (600 MHz, DMSO-d$_6$) δ (ppm); 1.16 (3H, t, J=7.0 Hz), 3.26 (2H, s), 4.07 (2H, q, J=7.0 Hz), 7.17-7.46 (2H, m), 7.63-7.84 (1H, m), 8.39 (1H, br. s), 8.84 (1H, br. s), 9.90 (1H, br. s)

Reference Example P-D11

Synthesis of [4-(3-chloro-4-fluorophenyl)-5-oxo-4,5-dihydro-1H-1,2,4-triazol-3-yl]acetic acid

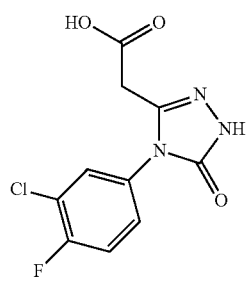

[Chem. 214]

A 3.0 M NaOH aqueous solution (14 mL) of the compound (650 mg) obtained in Reference Example P-D10 was stirred at 120° C. for 2 hours. After leaving the reaction mixture to cool, it was washed with Et$_2$O. To the aqueous layer, conc. hydrochloric acid was added for an adjustment to pH=1 and the mixture was subsequently stirred at 0° C. for 30 minutes. The resulting solids were recovered by filtration, washed with water and subsequently dried to give the titled compound (400 mg as a pale orange-colored solid).

1H NMR (600 MHz, DMSO-d$_6$) δ (ppm); 3.60 (2H, s), 7.36-7.45 (1H, m), 7.56 (1H, t, J=8.9 Hz), 7.67 (1H, dd, J=6.6, 2.9 Hz), 11.87 (1H, s), 12.52-12.89 (1H, m)

Reference Example P-D12

Synthesis of 2-[4-(3-chloro-4-fluorophenyl)-5-oxo-4,5-dihydro-1H-1,2,4-triazol-3-yl]-N-(propan-2-yl)acetamide

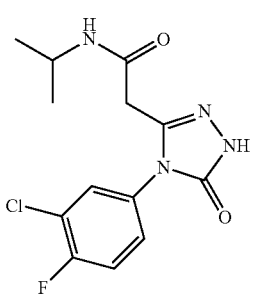

[Chem. 215]

Starting from the compound (3.0 g) obtained in Reference Example P-D07, the same procedure as in Reference Example P-D04 was applied to give the titled compound (2.5 g as a colorless solid).

MS (ESI pos.) m/z: 313 ([M+H]$^+$).

Reference Example P-D13

Synthesis of N-tert-butyl-2-[4-(3-chloro-4-fluorophenyl)-5-oxo-4,5-dihydro-1H-1,2,4-triazol-3-yl]acetamide

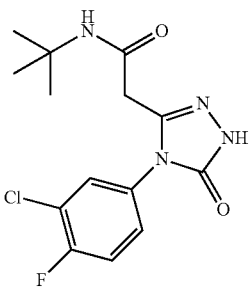

[Chem. 216]

Starting from the compound (1.8 g) obtained in Reference Example P-D07, the same procedure as in Reference Example P-D05 was applied to give the titled compound (1.3 g as a colorless solid).

MS (ESI pos.) m/z: 327 ([M+H]$^+$).

Reference Example P-D14

Synthesis of ethyl 3-{2-[(3-methoxyphenyl)carbamoyl]hydrazinyl}-3-oxopropanoate

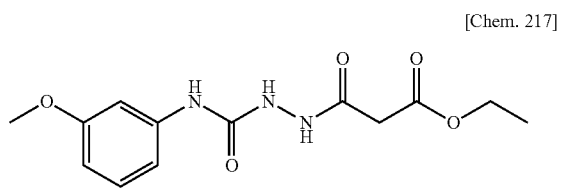 [SMILES: CCOC(=O)CC(=O)NNC(=O)Nc1cccc(OC)c1]

[Chem. 217]

Starting from 1-isocyanato-3-methoxybenzene (5.0 g) and ethyl 3-hydrazinyl-3-oxopropanoate (4.4 g), the same procedure as in Reference Example P-D02 was applied to give the titled compound (8.5 g as a colorless amorphous product).

MS (ESI pos.) m/z: 296 ([M+H]$^+$).

Reference Example P-D15

Synthesis of [4-(3-methoxyphenyl)-5-oxo-4,5-dihydro-1H-1,2,4-triazol-3-yl]acetic acid

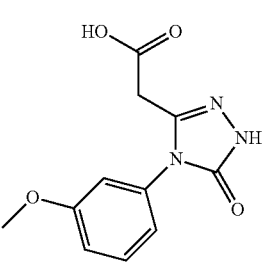

[Chem. 218]

Starting from the compound (8.4 g) obtained in Reference Example P-D14, the same procedure as in Reference Example P-D03 was applied to give the titled compound (3.8 g as a pale yellow solid).

MS (ESI pos.) m/z: 250 ([M+H]+).

Reference Example P-D16

Synthesis of 2-[4-(3-methoxyphenyl)-5-oxo-4,5-dihydro-1H-1,2,4-triazol-3-yl]-N-(propan-2-yl)acetamide

[Chem. 219]

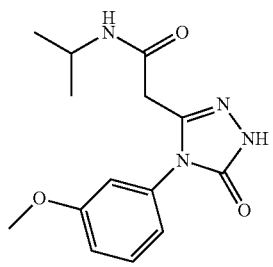

Starting from the compound (800 mg) obtained in Reference Example P-D15, the same procedure as in Reference Example P-D04 was applied to give the titled compound (720 mg as a colorless solid).

MS (ESI pos.) m/z: 291 ([M+H]+).

Reference Example P-D17

Synthesis of N-tert-butyl-2-[4-(3-methoxyphenyl)-5-oxo-4,5-dihydro-1H-1,2,4-triazol-3-yl]acetamide

[Chem. 220]

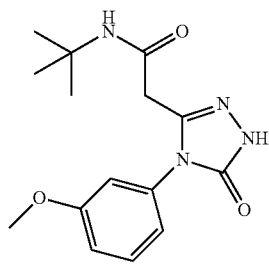

Starting from the compound (400 mg) obtained in Reference Example P-D15, the same procedure as in Reference Example P-D09 was applied to give the titled compound (370 mg as a colorless amorphous product).

MS (ESI pos.) m/z: 305 ([M+H]+).

Reference Example P-D18

Synthesis of ethyl 3-oxo-3-(2-{[3-(trifluoromethyl)phenyl]carbamoyl}hydrazinyl)propanoate

[Chem. 221]

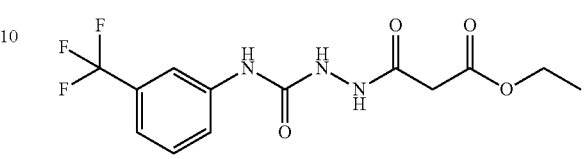

Starting from 1-isocyanato-3-(trifluoromethyl)benzene (5.0 g) and ethyl 3-hydrazinyl-3-oxopropanoate (3.9 g), the same procedure as in Reference Example P-D02 was applied to give the titled compound (7.0 g as a colorless amorphous product).

Reference Example P-D19

Synthesis of {5-oxo-4-[3-(trifluoromethyl)phenyl]-4,5-dihydro-1H-1,2,4-triazol-3-yl}acetic acid

[Chem. 222]

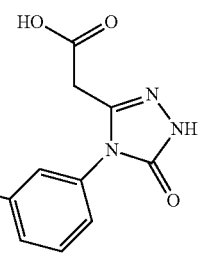

Starting from the compound (6.8 g) obtained in Reference Example P-D06, the same procedure as in Reference Example P-D03 was applied to give the titled compound (1.5 g as a colorless solid).

MS (ESI pos.) m/z: 288 ([M+H]+).

Reference Example P-D20

Synthesis of 2-{5-oxo-4-[3-(trifluoromethyl)phenyl]-4,5-dihydro-1H-1,2,4-triazol-3-yl}-N-(propan-2-yl)acetamide

[Chem. 223]

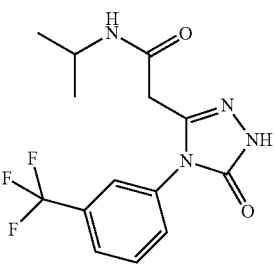

Starting from the compound (800 mg) obtained in Reference Example P-D07, the same procedure as in Reference Example P-D04 was applied to give the titled compound (520 mg as a colorless solid).

MS (ESI pos.) m/z: 329 ([M+H]+).

Reference Example P-D21

Synthesis of 2-{4-(3-chlorophenyl)-1-[4-(2-hydroxyethyl)phenyl]-5-oxo-4,5-dihydro-1H-1,2,4-triazol-3-yl}-N-(propan-2-yl)acetamide

[Chem. 224]

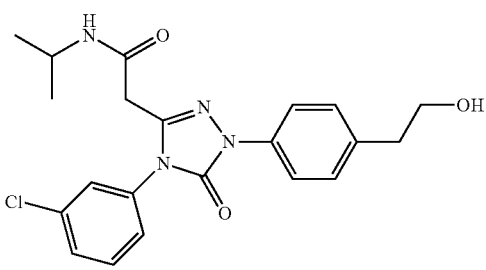

A 1,4-dioxane (70 mL) suspension of the compound (2.8 g) obtained in Reference Example P-D08, 2-(4-bromophenyl)ethanol (1.4 mL), copper iodide (1.8 g), tripotassium phosphate (4.0 g) and trans-N,N'-bismethyl-1,2-cyclohexanediamine (1.5 mL) was stirred at an external temperature of 100° C. for 4 hours under a nitrogen stream. After leaving the mixture to cool, 20% aqueous ammonia and CHCl$_3$ were added to separate the organic layer, with the aqueous layer being subsequently extracted with CHCl$_3$ twice. The combined organic layer was washed with water and 20% aqueous ammonia and subsequently dried over MgSO$_4$; thereafter, the desiccant was filtered off and the filtrate was concentrated under reduced pressure. The resulting residue was purified by silica gel column chromatography (REVELERIS 80 g Silica Cartridge; mobile phase: n-Hexane/CHCl$_3$/MeOH=50/50/0-0/100/0-0/90/10; v/v/v). The resulting crudely purified product was washed with a mixed solvent of EtOAc and n-Hexane (EtOAc/n-Hexane=1/1; v/v) under stirring to give the titled compound (2.5 g as a pale gray solid).

MS (ESI pos.) m/z: 415 ([M+H]+).

Reference Example P-D22

Synthesis of 2-(4-(3-chloro-4-fluorophenyl)-1-(4-(2-hydroxyethyl)phenyl]-5-oxo-4,5-dihydro-1H-1,2,4-triazol-3-yl)-N-isopropylacetamide

[Chem. 225]

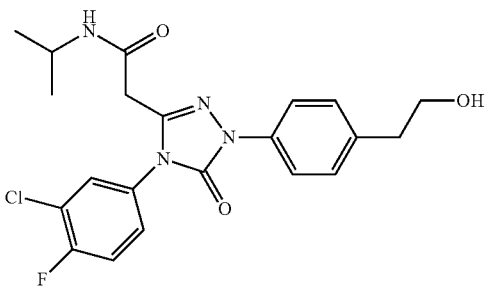

Starting from the compound (500 mg) obtained in Reference Example P-D12, the same procedure as in Reference Example P-D21 was applied to give the titled compound (430 mg as a colorless solid).

MS (ESI pos.) m/z: 433 ([M+H]+).

Example A-01

Synthesis of 2-[2-(3-chlorophenyl)-4-{4-[2-(piperidin-1-yl)ethyl]phenyl}-1H-imidazol-1-yl]-N-(propan-2-yl)acetamide

[Chem. 226]

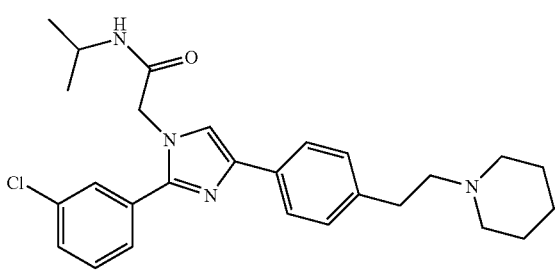

To a CHCl$_3$ (11 mL) solution of the compound (533 mg) obtained in Reference Example P-A04, Et$_3$N (0.28 mL) was added and after adding MsCl (0.12 mL) under cooling with ice, the mixture was stirred at room temperature for 2 hours and a half. Under cooling with ice, water was added, extraction was conducted with CHCl$_3$, and the filtrate was concentrated under reduced pressure. The resulting residue was purified by silica gel (OH) column chromatography (mobile phase: CHCl$_3$/EtOAc=70/30; v/v) to yield a mesyl form (414 mg as a colorless solid).

A mixture of the obtained mesyl form (102 mg), piperidine (0.042 mL), iPr$_2$NEt (0.073 mL) and MeCN (2.0 mL) was subjected to microwave for a reaction (100° C.×1.5 hr). The reaction mixture was purified by reverse-phase column chromatography (mobile phase: 0.1% TFA MeCN/H$_2$O=10/90-90/10; v/v). The fractions were neutralized with a saturated aqueous NaHCO$_3$ solution, extracted with CHCl$_3$, and filtered with Phase Separator. The solvent was distilled off under reduced pressure to give the titled compound (65 mg as a colorless solid).

MS (ESI pos.) m/z: 465 ([M+H]+).

$^1$H-NMR (600 MHz, CDCl$_3$) δ (ppm); 1.12 (6H, d, J=6.4 Hz), 1.43-1.51 (2H, m), 1.60-1.67 (4H, m), 2.48 (4H, br. s.), 2.55-2.62 (2H, m), 2.80-2.87 (2H, m), 4.09-4.19 (1H, m), 4.65 (2H, s), 5.33-5.40 (1H, m), 7.23-7.26 (2H, m), 7.28 (1H, s), 7.38-7.47 (3H, m), 7.67 (1H, s), 7.74-7.78 (2H, m).

Starting from Reference Example P-A04, Reference Example P-A08 and Reference Example P-A12, the same procedure as in Example A-01 was applied to synthesize the following compounds:

Example A-02

2-[2-(3-chlorophenyl)-4-{4-[2-(morpholin-4-yl)ethyl]phenyl}-1H-imidazol-1-yl]-N-(propan-2-yl)acetamide

[Chem. 227]

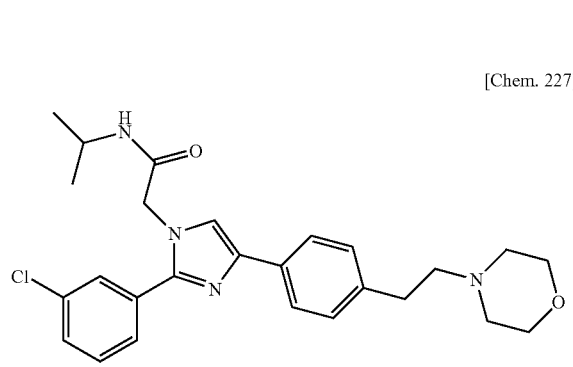 [SMILES: CC(C)NC(=O)Cn1cc(-c2ccc(CCN3CCCCC3)cc2)nc1-c1cccc(Cl)c1]

MS (ESI pos.) m/z: 467 ([M+H]$^+$).

$^1$H-NMR (600 MHz, CDCl$_3$) δ (ppm); 1.12 (6H, d, J=6.9 Hz), 2.54 (4H, br. s.), 2.59-2.67 (2H, m), 2.79-2.87 (2H, m), 3.75 (4H, br. s.), 4.15 (1H, dt, J=7.9, 6.8 Hz), 4.65 (2H, s), 5.37 (1H, d, J=7.8 Hz), 7.24-7.26 (2H, m), 7.28 (1H, s), 7.38-7.48 (3H, m), 7.65-7.68 (1H, m), 7.75-7.79 (2H, m).

Example A-03

2-[2-(3-chlorophenyl)-4-{4-[2-(2-oxa-6-azaspiro[3.3]hept-6-yl)ethyl]phenyl}-1H-imidazol-1-yl]-N-(propan-2-yl)acetamide

[Chem. 228]

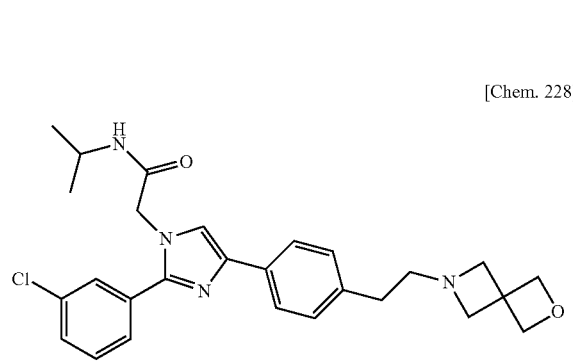 [SMILES: CC(C)NC(=O)Cn1cc(-c2ccc(CCN3CC4(COC4)C3)cc2)nc1-c1cccc(Cl)c1]

MS (ESI pos.) m/z: 479 ([M+H]$^+$).

$^1$H-NMR (600 MHz, CDCl$_3$) δ (ppm); 1.12 (6H, d, J=6.4 Hz), 2.63-2.66 (4H, m), 3.34 (4H, s), 4.11-4.18 (1H, m), 4.64 (2H, s), 4.73 (4H, s), 5.38 (1H, d, J=7.8 Hz), 7.20-7.23 (2H, m), 7.28 (1H, s), 7.38-7.47 (3H, m), 7.66-7.68 (1H, m), 7.74-7.78 (2H, m).

Example A-04

2-[2-(3-chlorophenyl)-4-{4-[2-(4-hydroxypiperidin-1-yl)ethyl]phenyl}-1H-imidazol-1-yl]-N-(propan-2-yl)acetamide

[Chem. 229]

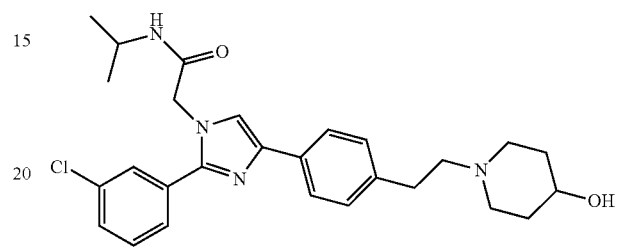

MS (ESI pos.) m/z: 481 ([M+H]$^+$).

$^1$H-NMR (600 MHz, CDCl$_3$) δ (ppm); 1.12 (6H, d, J=6.9 Hz), 1.61-1.67 (2H, m), 1.90-1.97 (2H, m), 2.19-2.27 (2H, m), 2.58-2.64 (2H, m), 2.80-2.91 (4H, m), 3.72 (1H, br. s.), 4.11-4.19 (1H, m), 4.64 (2H, s), 5.39 (1H, d, J=8.3 Hz), 7.23-7.26 (2H, m), 7.28 (1H, s), 7.38-7.47 (3H, m), 7.66 (1H, s), 7.74-7.78 (2H, m).

Example A-05

2-[2-(3-chlorophenyl)-4-{4-[2-(3-hydroxypiperidin-1-yl)ethyl]phenyl}-1H-imidazol-1-yl]-N-(propan-2-yl)acetamide

[Chem. 230]

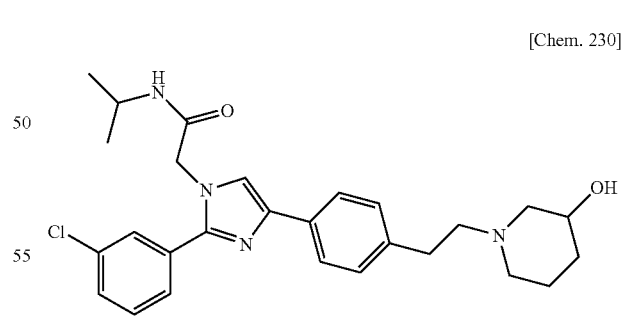

MS (ESI pos.) m/z: 481 ([M+H]$^+$).

$^1$H-NMR (600 MHz, CDCl$_3$) δ (ppm); 1.12 (6H, d, J=6.9 Hz), 1.50-1.59 (3H, m), 1.77-1.86 (1H, m), 2.30-2.39 (1H, m), 2.50-2.67 (5H, m), 2.78-2.84 (2H, m), 3.84 (1H, br. s.), 4.11-4.19 (1H, m), 4.65 (2H, s), 5.39 (1H, d, J=7.8 Hz), 7.22-7.25 (2H, m), 7.28 (1H, s), 7.38-7.47 (3H, m), 7.66-7.68 (1H, m), 7.75-7.79 (2H, m).

Example A-06

2-[2-(3-chlorophenyl)-4-{4-[2-(3-hydroxypyrrolidin-1-yl)ethyl]phenyl}-1H-imidazol-1-yl]-N-(propan-2-yl)acetamide

[Chem. 231]

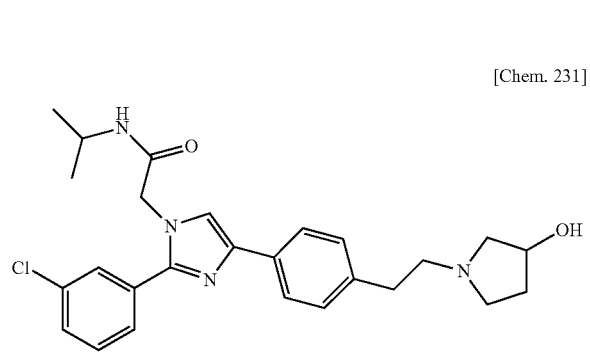 [SMILES: CC(C)NC(=O)Cn1cc(-c2ccc(CCN3CCC(O)C3)cc2)nc1-c1cccc(Cl)c1]

MS (ESI pos.) m/z: 467 ([M+H]$^+$).

$^1$H-NMR (600 MHz, CDCl$_3$) δ (ppm); 1.12 (6H, d, J=6.4 Hz), 1.73-1.80 (1H, m), 2.16-2.24 (1H, m), 2.32-2.38 (1H, m), 2.57 (1H, dd, J=10.1, 5.0 Hz), 2.71-2.79 (3H, m), 2.82-2.88 (2H, m), 2.94-2.99 (1H, m), 4.11-4.19 (1H, m), 4.33-4.37 (1H, m), 4.65 (2H, s), 5.39 (1H, d, J=7.8 Hz), 7.24-7.26 (2H, m), 7.28 (1H, s), 7.38-7.47 (3H, m), 7.65-7.68 (1H, m), 7.75-7.79 (2H, m).

Example A-07

2-[2-(3-chlorophenyl)-4-(4-{2-[3-(hydroxymethyl)pyrrolidin-1-yl]ethyl}phenyl)-1H-imidazol-1-yl]-N-(propan-2-yl)acetamide

[Chem. 232]

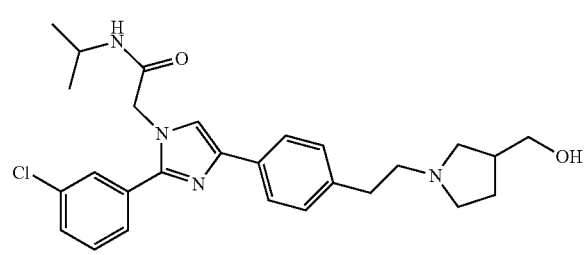

MS (ESI pos.) m/z: 481 ([M+H]$^+$).

$^1$H-NMR (600 MHz, CDCl$_3$) δ (ppm); 1.12 (6H, d, J=6.9 Hz), 1.67-1.75 (1H, m), 1.98-2.05 (1H, m), 2.32-2.38 (2H, m), 2.53-2.58 (1H, m), 2.67-2.75 (3H, m), 2.81-2.86 (2H, m), 2.89-2.95 (1H, m), 3.53 (1H, dd, J=9.9, 4.8 Hz), 3.69 (1H, dd, J=10.1, 4.1 Hz), 4.10-4.19 (1H, m), 4.64 (2H, s), 5.42 (1H, d, J=7.8 Hz), 7.23-7.26 (2H, m), 7.27 (1H, s), 7.38-7.46 (3H, m), 7.65-7.67 (1H, m), 7.75-7.79 (2H, m).

Example A-08

2-[2-(3-chlorophenyl)-4-{4-[2-(3-oxa-8-azabicyclo[3.2.1]oct-8-yl)ethyl]phenyl}-1H-imidazol-1-yl]-N-(propan-2-yl)acetamide

[Chem. 233]

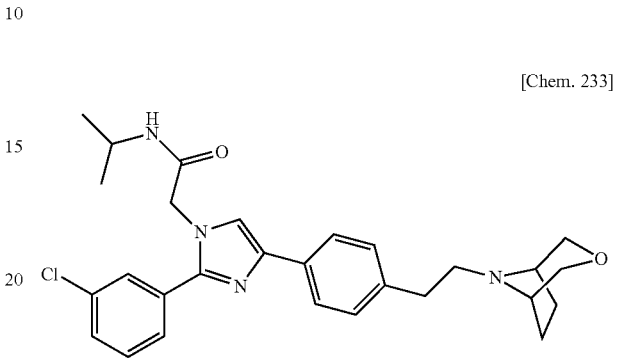

MS (ESI pos.) m/z: 493 ([M+H]$^+$).

$^1$H-NMR (600 MHz, CDCl$_3$) δ (ppm); 1.12 (6H, d, J=6.6 Hz), 1.85-1.95 (4H, m), 2.51-2.57 (2H, m), 2.78-2.84 (2H, m), 3.10 (2H, br. s.), 3.53 (2H, dd, J=10.3, 1.7 Hz), 3.74 (2H, d, J=10.3 Hz), 4.11-4.20 (1H, m), 4.65 (2H, s), 5.37 (1H, d, J=7.8 Hz), 7.25-7.28 (2H, m), 7.29 (1H, s), 7.38-7.47 (3H, m), 7.67 (1H, t, J=1.7 Hz), 7.75-7.79 (2H, m).

Example A-09

2-[2-(4-fluoro-3-methoxyphenyl)-4-{4-[2-(piperidin-1-yl)ethyl]phenyl}-1H-imidazol-1-yl]-N-(propan-2-yl)acetamide

[Chem. 234]

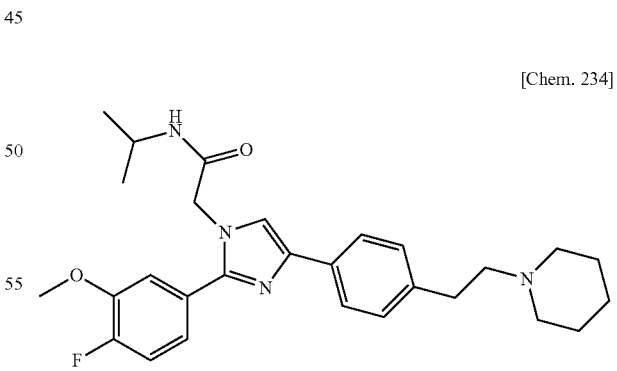

MS (ESI pos.) m/z: 479 ([M+H]$^+$).

$^1$H-NMR (600 MHz, CDCl$_3$) δ (ppm); 1.04-1.17 (6H, m), 1.39-1.72 (7H, m), 2.39-2.94 (7H, m), 3.93 (3H, s), 4.07-4.21 (1H, m), 4.64 (2H, s), 5.35-5.46 (1H, m), 7.01-7.10 (1H, m), 7.12-7.19 (1H, m), 7.21-7.35 (4H, m), 7.69-7.82 (2H, m).

Example A-10

2-[2-(4-fluoro-3-methoxyphenyl)-4-{4-[2-(morpholin-4-yl)ethyl]phenyl}1H-imidazol-1-yl]-N-(propan-2-yl)acetamide

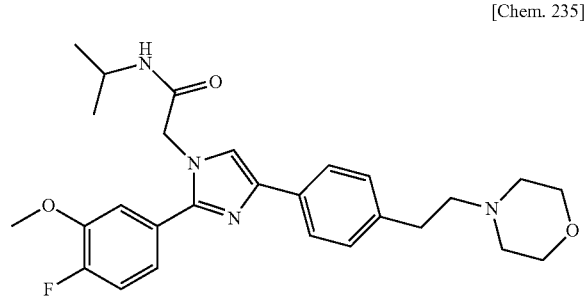 [SMILES: COc1cc(-c2nc(-c3ccc(CCN4CCOCC4)cc3)cn2CC(=O)NC(C)C)ccc1F]

MS (ESI pos.) m/z: 481 ([M+H]⁺).

¹H-NMR (600 MHz, CDCl₃) δ (ppm); 1.11 (6H, d, J=6.4 Hz), 2.47-2.57 (4H, m), 2.58-2.67 (2H, m), 2.75-2.89 (2H, m), 3.68-3.83 (4H, m), 3.93 (3H, s), 4.08-4.21 (1H, m), 4.64 (2H, s), 5.40 (1H, d, J=7.8 Hz), 7.03-7.10 (1H, m), 7.12-7.20 (1H, m), 7.20-7.34 (4H, m), 7.73-7.82 (2H, m).

Example A-11

2-[2-(4-fluoro-3-methoxyphenyl)-4-{4-[2-(pyrrolidin-1-yl)ethyl]phenyl}-1H-imidazol-1-yl]-N-(propan-2-yl)acetamide

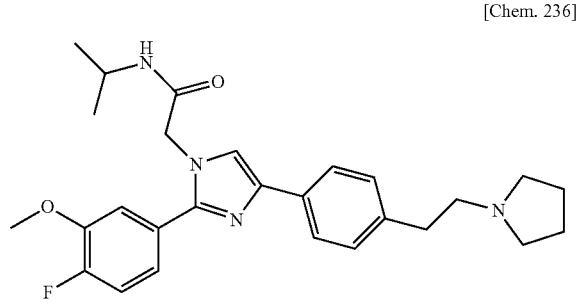 [SMILES: COc1cc(-c2nc(-c3ccc(CCN4CCCC4)cc3)cn2CC(=O)NC(C)C)ccc1F]

MS (ESI pos.) m/z: 465 ([M+H]⁺).

¹H-NMR (600 MHz, CDCl₃) δ (ppm); 1.12 (6H, d, J=6.9 Hz), 1.92 (4H, br. s.), 2.46-3.21 (8H, m), 3.94 (3H, s), 4.07-4.21 (1H, m), 4.64 (2H, s), 5.41 (1H, d, J=7.8 Hz), 7.00-7.10 (1H, m), 7.16 (1H, dd, J=11.0, 8.3 Hz), 7.22-7.31 (4H, m), 7.78 (2H, d, J=8.3 Hz).

Example A-12

2-[2-(4-fluoro-3-methoxyphenyl)-4-(4-{2-[(2R)-2-methylpyrrolidin-1-yl]ethyl}phenyl)-1H-imidazol-1-yl]-N-(propan-2-yl)acetamide

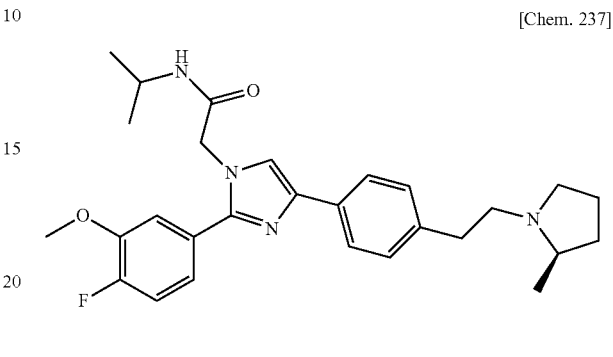

MS (ESI pos.) m/z: 479 ([M+H]⁺).

¹H-NMR (600 MHz, CDCl₃) δ (ppm); 1.11 (9H, d, J=6.4 Hz), 1.45 (1H, br. s.), 1.66-1.87 (2H, m), 1.89-2.00 (1H, m), 2.13-2.25 (1H, m), 2.27-2.40 (2H, m), 2.79-2.94 (2H, m), 2.98-3.10 (1H, m), 3.19-3.32 (1H, m), 3.94 (3H, s), 4.09-4.20 (1H, m), 4.65 (2H, s), 5.40 (1H, d, J=8.3 Hz), 7.02-7.10 (2H, m), 7.16 (2H, dd, J=10.8, 8.5 Hz), 7.21-7.34 (4H, m), 7.78 (2H, d, J=8.3 Hz).

Example A-13

2-[4-{4-[2-(3-cyanopiperidin-1-yl)ethyl]phenyl}-2-(4-fluoro-3-methoxyphenyl)-1H-imidazol-1-yl]-N-(propan-2-yl)acetamide

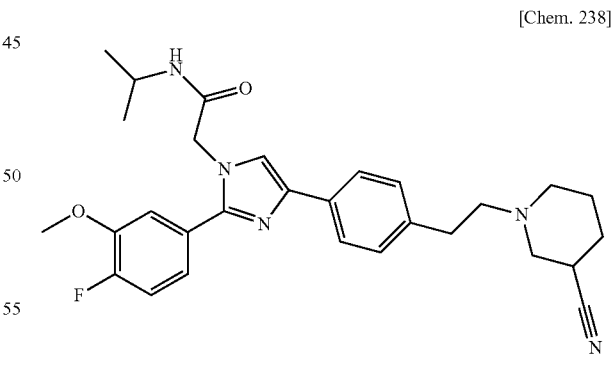

MS (ESI pos.) m/z: 504 ([M+H]⁺).

¹H-NMR (600 MHz, CDCl₃) δ (ppm); 1.12 (6H, d, J=6.9 Hz), 1.56-1.76 (2H, m), 1.78-1.96 (2H, m), 2.38 (1H, br. s.), 2.56 (1H, br. s.), 2.61-2.69 (3H, m), 2.74-2.90 (4H, m), 3.94 (3H, s), 4.07-4.20 (1H, m), 4.64 (2H, s), 5.40 (1H, d, J=8.3 Hz), 7.02-7.10 (1H, m), 7.16 (1H, dd, J=10.8, 8.5 Hz), 7.22-7.33 (4H, m), 7.78 (2H, d, J=8.3 Hz).

145

Example A-14

2-[4-{4-[2-(4-cyanopiperidin-1-yl)ethyl]phenyl}-2-(4-fluoro-3-methoxyphenyl)-1H-imidazol-1-yl]-N-(propan-2-yl)acetamide

[Chem. 239]

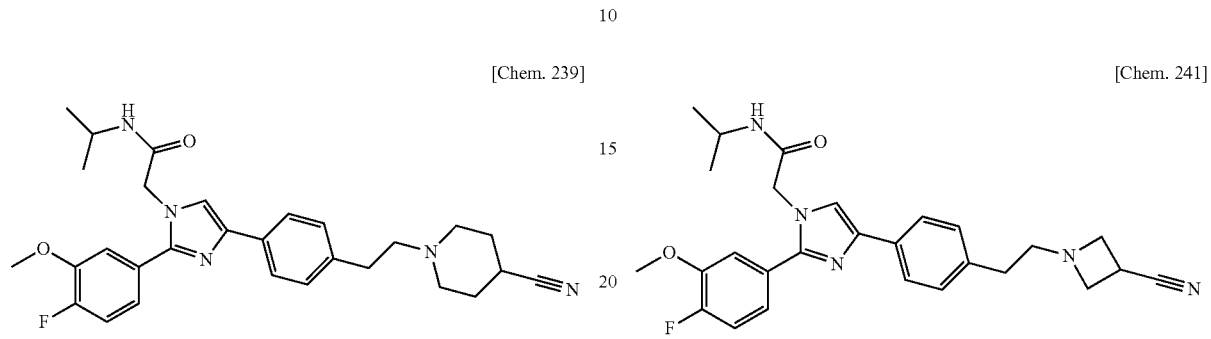

MS (ESI pos.) m/z: 504 ([M+H]$^+$).

$^1$H-NMR (600 MHz, CDCl$_3$) δ (ppm); 1.12 (6H, d, J=6.9 Hz), 1.84-2.02 (4H, m), 2.42 (2H, br. s.), 2.58-2.78 (5H, m), 2.78-2.86 (2H, m), 3.94 (3H, s), 4.08-4.20 (1H, m), 4.64 (2H, s), 5.40 (1H, d, J=7.8 Hz), 6.99-7.10 (1H, m), 7.16 (1H, dd, J=11.0, 8.3 Hz), 7.22-7.34 (4H, m), 7.77 (2H, d, J=7.8 Hz).

Example A-15

2-[2-(4-fluoro-3-methoxyphenyl)-4-{4-[2-(3-hydroxy-8-azabicyclo[3.2.1]oct-8-yl)ethyl]phenyl}-1H-imidazol-1-yl]-N-(propan-2-yl)acetamide

[Chem. 240]

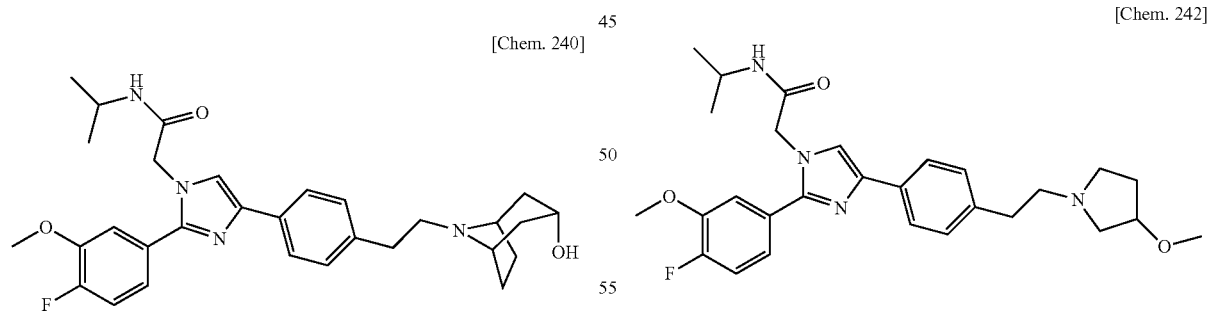

MS (ESI pos.) m/z: 521 ([M+H]$^+$).

$^1$H-NMR (500 MHz, CDCl$_3$) δ (ppm); 1.12 (6H, d, J=6.5 Hz), 1.18-1.33 (1H, m), 1.63-1.74 (2H, m), 1.89-2.01 (2H, m), 2.03-2.20 (4H, m), 2.54-2.68 (2H, m), 2.78-2.89 (2H, m), 3.22-3.31 (2H, m), 3.94 (3H, s), 4.05-4.10 (1H, m), 4.10-4.20 (1H, m), 4.65 (2H, s), 5.35-5.46 (1H, m), 7.02-7.09 (1H, m), 7.17 (1H, dd, J=10.9, 8.2 Hz), 7.23-7.33 (4H, m), 7.78 (2H, d, J=8.4 Hz).

146

Example A-16

2-[4-{4-[2-(3-cyanoazetidin-1-yl)ethyl]phenyl}-2-(4-fluoro-3-methoxyphenyl)-1H-imidazol-1-yl]-N-(propan-2-yl)acetamide

[Chem. 241]

MS (ESI pos.) m/z: 476 ([M+H]$^+$).

$^1$H-NMR (500 MHz, CDCl$_3$) δ (ppm); 1.13 (6H, d, J=6.5 Hz), 2.63-2.79 (4H, m), 3.21-3.32 (3H, m), 3.55-3.63 (2H, m), 3.94 (3H, s), 4.09-4.22 (1H, m), 4.65 (2H, s), 5.37-5.45 (1H, m), 7.04-7.10 (1H, m), 7.17 (1H, dd, J=10.7, 8.4 Hz), 7.20-7.33 (4H, m), 7.79 (2H, d, J=8.0 Hz).

Example A-17

2-[2-(4-fluoro-3-methoxyphenyl)-4-{4-[2-(3-methoxypyrrolidin-1-yl)ethyl]phenyl}-1H-imidazol-1-yl]-N-(propan-2-yl)acetamide

[Chem. 242]

MS (ESI pos.) m/z: 495 ([M+H]$^+$).

$^1$H-NMR (600 MHz, CDCl$_3$) δ (ppm); 1.11 (6H, d, J=6.6 Hz), 1.27-1.37 (1H, m), 1.73-1.85 (1H, m), 1.94 (1H, d, J=9.5 Hz), 2.08-2.25 (2H, m), 2.55-2.67 (2H, m), 2.68-2.77 (1H, m), 2.78-2.89 (2H, m), 2.97 (1H, d, J=8.3 Hz), 3.29-3.42 (3H, m), 3.93 (3H, s), 4.09-4.19 (1H, m), 4.64 (2H, s), 5.41 (1H, d, J=7.8 Hz), 7.03-7.10 (1H, m), 7.16 (1H, dd, J=10.7, 8.3 Hz), 7.24 (2H, s), 7.28-7.32 (2H, m), 7.77 (2H, d, J=8.3 Hz).

Example A-18

2-[2-(4-fluoro-3-methoxyphenyl)-4-{4-[2-(3-methoxypiperidin-1-yl)ethyl]phenyl}-1H-imidazol-1-yl]-N-(propan-2-yl)acetamide

[Chem. 243]

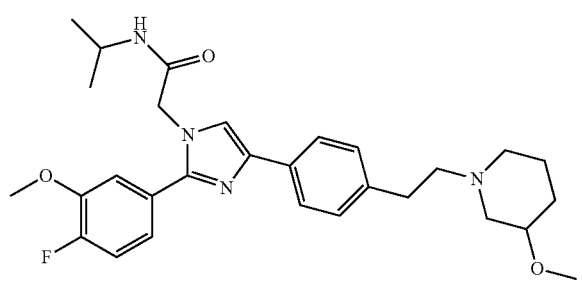

MS (ESI pos.) m/z: 509 ([M+H]$^+$).

$^1$H-NMR (600 MHz, CDCl$_3$) δ (ppm); 1.12 (6H, d, J=6.6 Hz), 1.85 (2H, br. s.), 2.04-2.15 (1H, m), 2.46-2.57 (1H, m), 2.63-2.81 (5H, m), 2.82-2.92 (2H, m), 3.30 (3H, s), 3.94 (5H, s), 4.10-4.19 (1H, m), 4.64 (2H, s), 5.40 (1H, d, J=7.8 Hz), 7.03-7.10 (1H, m), 7.16 (2H, dd, J=10.7, 8.3 Hz), 7.25 (2H, br. s.), 7.29 (1H, dd, J=8.3, 2.1 Hz), 7.77 (2H, d, J=8.3 Hz).

Example A-19

2-[4-{4-[2-(3-fluoroazetidin-1-yl)ethyl]phenyl}-2-(4-fluoro-3-methoxyphenyl)-1H-imidazol-1-yl]-N-(propan-2-yl)acetamide

[Chem. 244]

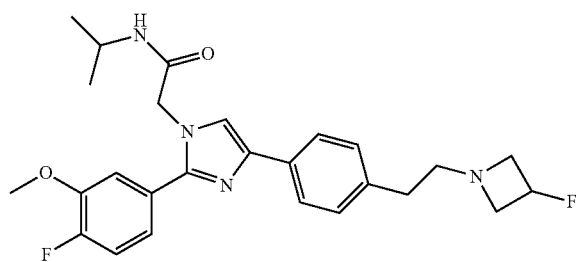

MS (ESI pos.) m/z: 469 ([M+H]$^+$).

$^1$H-NMR (600 MHz, CDCl$_3$) δ (ppm); 1.12 (6H, d, J=6.6 Hz), 2.60-2.81 (4H, m), 3.06-3.19 (2H, m), 3.60-3.74 (2H, m), 3.94 (3H, s), 4.09-4.20 (1H, m), 4.64 (2H, s), 5.02-5.20 (1H, m), 5.40 (1H, d, J=8.3 Hz), 7.02-7.10 (1H, m), 7.16 (1H, dd, J=10.7, 8.3 Hz), 7.20-7.33 (4H, m), 7.77 (2H, d, J=8.3 Hz).

Example A-20

2-[4-{4-[2-(2,6-dimethylmorpholin-4-yl)ethyl]phenyl}-2-(4-fluoro-3-methoxyphenyl)-1H-imidazol-1-yl]-N-(propan-2-yl)acetamide

[Chem. 245]

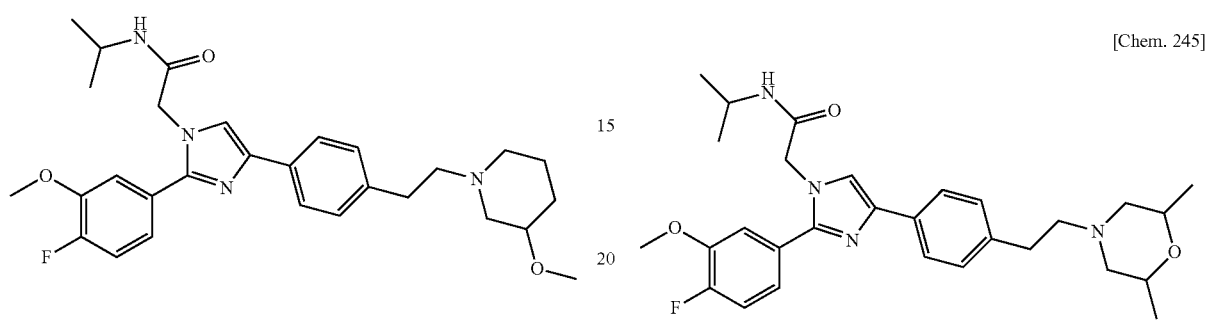

MS (ESI pos.) m/z: 509 ([M+H]$^+$).

$^1$H-NMR (600 MHz, CDCl$_3$) δ (ppm); 1.12 (6H, d, J=6.6 Hz), 1.18 (6H, d, J=6.6 Hz), 1.81 (2H, t, J=10.7 Hz), 2.55-2.65 (2H, m), 2.83 (4H, d, J=10.3 Hz), 3.66-3.77 (2H, m), 3.94 (3H, s), 4.10-4.20 (1H, m), 4.64 (2H, s), 5.40 (1H, d, J=7.8 Hz), 7.02-7.09 (1H, m), 7.16 (1H, dd, J=10.7, 8.3 Hz), 7.22-7.27 (3H, m), 7.28-7.32 (1H, m), 7.77 (2H, d, J=7.8 Hz).

Example A-21

2-[2-(4-fluoro-3-methoxyphenyl)-4-{4-[2-(3-methylpyrrolidin-1-yl)ethyl]phenyl}-1H-imidazol-1-yl]-N-(propan-2-yl)acetamide

[Chem. 246]

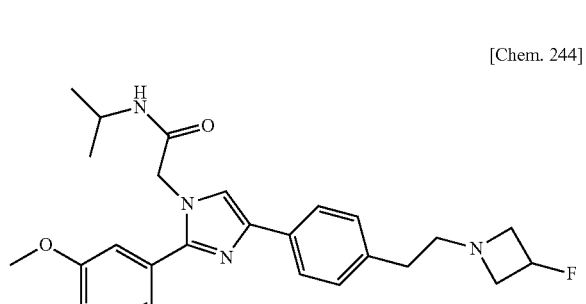

MS (ESI pos.) m/z: 479 ([M+H]$^+$).

$^1$H-NMR (600 MHz, CDCl$_3$) δ (ppm); 1.11 (6H, d, J=6.6 Hz), 1.94 (2H, d, J=10.3 Hz), 2.24 (2H, br. s.), 2.56-2.67 (2H, m), 2.79-2.90 (4H, m), 3.24 (1H, br. s.), 3.35 (3H, s), 3.93 (3H, s), 4.08-4.22 (1H, m), 4.64 (2H, s), 5.40 (1H, d, J=7.8 Hz), 7.02-7.07 (1H, m), 7.16 (1H, dd, J=10.7, 8.3 Hz), 7.22-7.31 (4H, m), 7.77 (2H, d, J=8.3 Hz).

Example A-22

2-[2-(4-fluoro-3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide

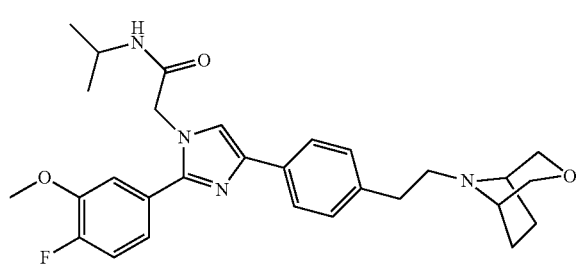

MS (ESI pos.) m/z: 507 ([M+H]$^+$).

$^1$H-NMR (600 MHz, CDCl$_3$) δ (ppm); 1.12 (6H, d, J=6.4 Hz), 1.82-2.00 (4H, m), 2.49-2.60 (2H, m), 2.77-2.88 (2H, m), 3.06-3.17 (2H, m), 3.49-3.58 (2H, m), 3.69-3.81 (2H, m), 3.94 (3H, s), 4.07-4.24 (1H, m), 4.65 (2H, s), 5.36-5.48 (1H, m), 7.01-7.11 (1H, m), 7.17 (1H, dd, J=11.0, 8.3 Hz), 7.24-7.29 (3H, m), 7.30 (1H, dd, J=8.0, 2.1 Hz), 7.78 (2H, d, J=8.3 Hz).

Example A-23

2-[2-(4-fluoro-3-methoxyphenyl)-4-{4-[2-(1,4-oxazepan-4-yl)ethyl]phenyl}-1H-imidazol-1-yl]-N-(propan-2-yl)acetamide

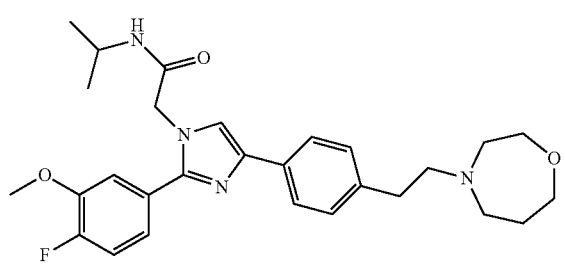

MS (ESI pos.) m/z: 495 ([M+H]$^+$).

$^1$H-NMR (600 MHz, CDCl$_3$) δ (ppm); 1.12 (6H, d, J=6.6 Hz), 1.92 (2H, quin, J=5.8 Hz), 2.73-2.87 (8H, m), 3.72-3.78 (2H, m), 3.82 (2H, t, J=6.0 Hz), 3.94 (3H, s), 4.08-4.19 (1H, m), 4.64 (2H, s), 5.40 (1H, d, J=8.3 Hz), 7.01-7.10 (1H, m), 7.16 (1H, dd, J=10.7, 8.3 Hz), 7.21-7.34 (4H, m), 7.77 (2H, d, J=8.3 Hz).

Example A-24

2-[2-(4-fluoro-3-methoxyphenyl)-4-{4-[2-(4-methoxypiperidin-1-yl)ethyl]phenyl}-1H-imidazol-1-yl]-N-(propan-2-yl)acetamide

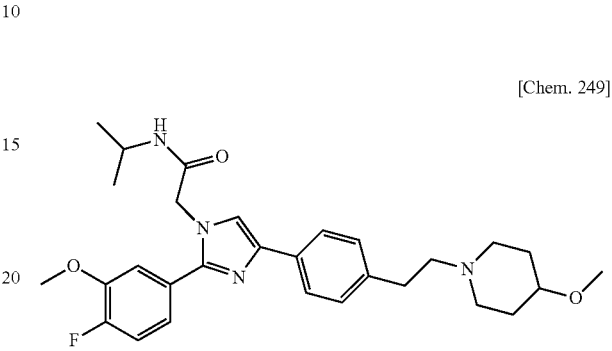

MS (ESI pos.) m/z: 509 ([M+H]$^+$).

$^1$H-NMR (600 MHz, CDCl$_3$) δ (ppm); 1.04 (3H, s), 1.11 (6H, d, J=6.6 Hz), 1.37 (1H, td, J=12.5, 6.0 Hz), 1.97-2.14 (2H, m), 2.23-2.35 (1H, m), 2.52 (1H, br. s.), 2.61-2.98 (8H, m), 3.93 (3H, s), 4.08-4.20 (1H, m), 4.64 (2H, s), 5.41 (1H, d, J=7.8 Hz), 7.02-7.11 (1H, m), 7.16 (1H, dd, J=10.7, 8.3 Hz), 7.21-7.33 (4H, m), 7.77 (2H, d, J=7.8 Hz).

Example A-25

2-[4-{4-[2-(3,5-dimethylmorpholin-4-yl)ethyl]phenyl}-2-(4-fluoro-3-methoxyphenyl)-1H-imidazol-1-yl]-N-(propan-2-yl)acetamide

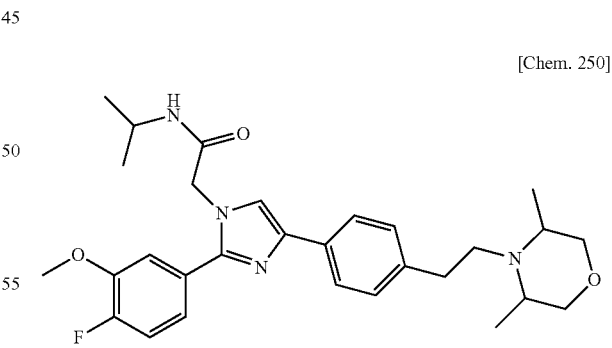

MS (ESI pos.) m/z: 509 ([M+H]$^+$).

$^1$H-NMR (600 MHz, CDCl$_3$) δ (ppm); 1.02-1.10 (6H, m), 1.13 (6H, d, J=6.6 Hz), 2.50-2.58 (1H, m), 2.65-2.75 (1H, m), 2.80-2.99 (4H, m), 3.40-3.46 (2H, m), 3.68-3.75 (2H, m), 3.95 (3H, s), 4.11-4.20 (1H, m), 4.66 (2H, s), 5.37-5.44 (1H, m), 7.05-7.10 (1H, m), 7.14-7.20 (1H, m), 7.21-7.33 (4H, m), 7.79 (2H, d, J=8.3 Hz).

Example A-26

2-[2-(3-chlorophenyl)-4-{5-[2-(morpholin-4-yl)ethyl]pyridin-2-yl}-1H-imidazol-1-yl]-N-(propan-2-yl)acetamide

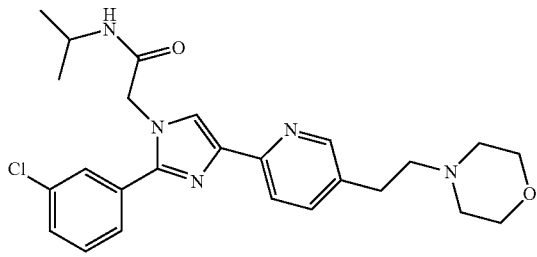

[Chem. 251]

MS (ESI pos.) m/z: 468 ([M+H]$^+$).

$^1$H-NMR (600 MHz, DMSO-d$_6$) δ (ppm); 1.04-1.07 (6H, m), 3.07-3.20 (4H, m), 3.39-3.46 (2H, m), 3.47-3.53 (2H, m), 3.77-3.87 (3H, m), 3.97-4.03 (2H, m), 4.82 (2H, s), 7.55-7.59 (1H, m), 7.59-7.63 (1H, m), 7.63-7.66 (1H, m), 7.69-7.71 (1H, m), 7.91-8.22 (3H, m), 8.26-8.35 (1H, m), 8.50-8.61 (1H, m).

Example A-27

2-[2-(3-chlorophenyl)-4-{5-[2-(3-oxa-8-azabicyclo[3.2.1]oct-8-yl)ethyl]pyridin-2-yl}-1H-imidazol-1-yl]-N-(propan-2-yl)acetamide

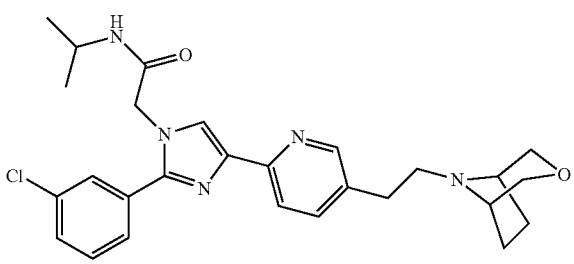

[Chem. 252]

MS (ESI pos.) m/z: 494 ([M+H]$^+$).

$^1$H-NMR (600 MHz, DMSO-d$_6$) δ (ppm); 1.05 (6H, d, J=6.6 Hz), 2.02-2.06 (2H, m), 2.18-2.23 (2H, m), 3.27 (4H, s), 3.71 (2H, d, J=11.1 Hz), 3.79-3.86 (1H, m), 4.01-4.06 (2H, m), 4.13-4.19 (2H, m), 4.85 (2H, s), 7.57-7.62 (1H, m), 7.62-7.68 (2H, m), 7.72 (1H, s), 8.10-8.24 (2H, m), 8.29-8.37 (1H, m), 8.58-8.65 (1H, m).

Example A-28

Synthesis of 2-[2-(6-methoxypyridin-2-yl)-4-{4-[2-(piperidin-1-yl)ethyl]phenyl}-1H-imidazol-1-yl]-N-(propan-2-yl)acetamide

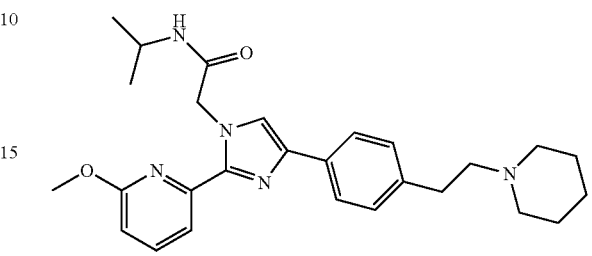

[Chem. 253]

To a CHCl$_3$ (4 mL) solution of the compound (90 mg) obtained in Reference Example P-A16, piperidine (0.06 mL) and acetic acid (0.06 mL) were added and the mixture was stirred for a while at room temperature; subsequently, sodium triacetoxyborohydride (136 mg) was added and the mixture was immediately subjected to stirring which continued overnight. The mixture in an ice bath was then neutralized with a saturated aqueous NaHCO$_3$ solution and extracted with CHCl$_3$. The organic layer was filtered with Phase Separator and the solvent was distilled off under reduced pressure. The resulting residue was purified by silica gel column chromatography (SNAP Cartridge HP-Sil 10 g; mobile phase: CHCl$_3$/MeOH=99/1-90/10; v/v). The purified product was washed with a mixed solvent (EtOAc/n-Hexane=1/6; v/v) and the solids were recovered by filtration to give the titled compound (20 mg as a colorless solid).

MS (ESI pos.) m/z: 462 ([M+H]$^+$).

$^1$H-NMR (600 MHz, CDCl$_3$) δ (ppm); 0.99 (6H, d, J=6.4 Hz), 1.42-1.51 (2H, m), 1.61-1.68 (4H, m), 2.44-2.54 (4H, m), 2.56-2.63 (2H, m), 2.82-2.88 (2H, m), 3.95 (3H, s), 4.03-4.11 (1H, m), 5.28 (2H, s), 5.57-5.64 (1H, m), 6.72-6.78 (1H, m), 7.24-7.28 (3H, m), 7.68-7.73 (1H, m), 7.79 (2H, d, J=8.3 Hz), 7.95-7.99 (1H, m).

Starting from the compounds obtained in Reference Example P-A16, Reference Example P-A20 and Reference Example P-A22, the same procedure as in Example A-28 was applied to give the following compounds:

Example A-29

2-[2-(6-methoxypyridin-2-yl)-4-{4-[2-(morpholin-4-yl)ethyl]phenyl}-1H-imidazol-1-yl]-N-(propan-2-yl)acetamide

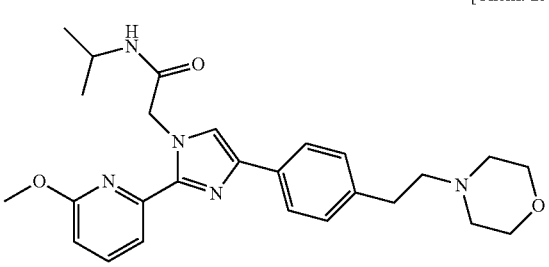

[Chem. 254]

MS (ESI pos.) m/z: 464 ([M+H]+).

¹H-NMR (600 MHz, CDCl₃) δ (ppm); 0.99 (6H, d, J=6.4 Hz), 2.51-2.58 (4H, m), 2.61-2.66 (2H, m), 2.82-2.87 (2H, m), 3.73-3.79 (4H, m), 3.95 (3H, s), 4.03-4.11 (1H, m), 5.28 (2H, s), 5.60-5.65 (1H, m), 6.75 (1H, d, J=8.3 Hz), 7.25-7.29 (3H, m), 7.68-7.74 (1H, m), 7.80 (2H, d, J=8.3 Hz), 7.95-7.99 (1H, m).

Example A-30

2-[2-(3-chlorophenyl)-4-{6-[2-(morpholin-4-yl)ethyl]pyridin-3-yl}-1H-imidazol-1-yl]-N-(propan-2-yl)acetamide

[Chem. 255]

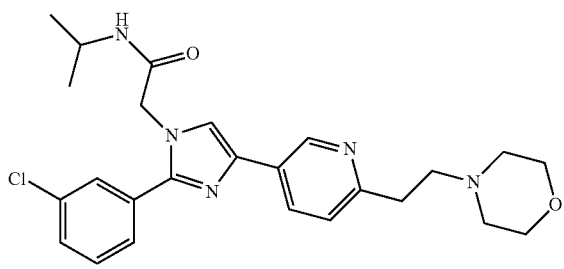

MS (ESI pos.) m/z: 468 ([M+H]+).

¹H-NMR (600 MHz, CDCl₃) δ (ppm); 1.14 (6H, d, J=6.4 Hz), 2.55 (4H, br. s.), 2.77-2.82 (2H, m), 3.00-3.04 (2H, m), 3.73 (4H, t, J=4.6 Hz), 4.11-4.20 (1H, m), 4.65 (2H, s), 5.36 (1H, d, J=7.8 Hz), 7.24 (1H, d, J=8.3 Hz), 7.37 (1H, s), 7.40-7.49 (3H, m), 7.65 (1H, s), 8.11 (1H, dd, J=8.0, 2.1 Hz), 8.92 (1H, d, J=2.3 Hz).

Example A-31

2-[4-{4-[2-(diethylamino)ethyl]phenyl}-2-(4-fluoro-3-methoxyphenyl)-1H-imidazol-1-yl]-N-(propan-2-yl)acetamide

[Chem. 256]

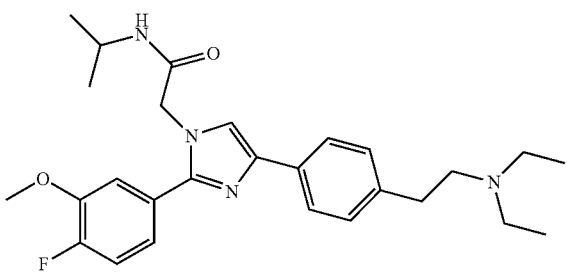

MS (ESI pos.) m/z: 467 ([M+H]+).

¹H-NMR (600 MHz, CDCl₃) δ (ppm); 1.09 (6H, t, J=7.0 Hz), 1.12 (6H, d, J=6.2 Hz), 2.59-2.67 (4H, m), 2.70-2.83 (4H, m), 3.94 (3H, s), 4.11-4.20 (1H, m), 4.65 (2H, s), 5.38-5.45 (1H, m), 7.04-7.09 (1H, m), 7.17 (1H, dd, J=11.1, 8.3 Hz), 7.22-7.34 (4H, m), 7.78 (2H, d, J=8.3 Hz).

Example A-32

2-[4-(4-{2-[ethyl(2-methoxyethyl)amino]ethyl}phenyl)-2-(4-fluoro-3-methoxyphenyl)-1H-imidazol-1-yl]-N-(propan-2-yl)acetamide

[Chem. 257]

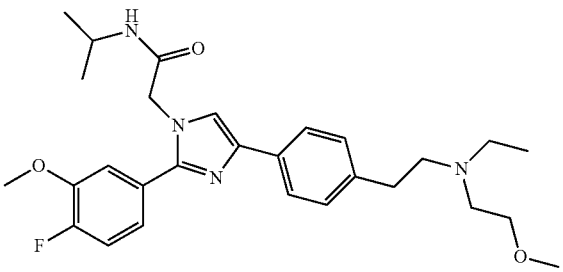

MS (ESI pos.) m/z: 497 ([M+H]+).

¹H-NMR (600 MHz, CDCl₃) δ (ppm); 1.08 (3H, t, J=7.0 Hz), 1.12 (6H, d, J=6.6 Hz), 2.64-2.83 (8H, m), 3.38 (3H, s), 3.47-3.54 (2H, m), 3.94 (3H, s), 4.11-4.21 (1H, m), 4.65 (2H, s), 5.39-5.44 (1H, m), 7.04-7.10 (1H, m), 7.13-7.19 (1H, m), 7.23-7.28 (3H, m), 7.28-7.33 (1H, m), 7.78 (2H, d, J=8.3 Hz).

Example A-33

Synthesis of 2-[2-(3-chlorophenyl)-4-{4-[2-(piperidin-1-yl)ethoxy]phenyl}-1H-imidazol-1-yl]-N-(propan-2-yl)acetamide

[Chem. 258]

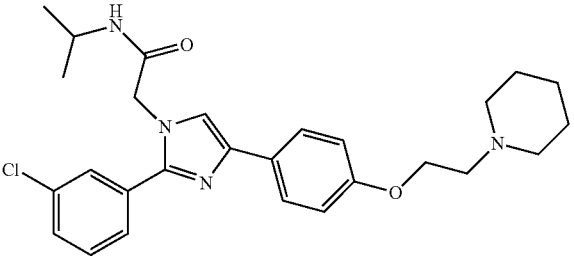

A mixture of the compound (60 mg) obtained in Reference Example P-A24, 1-piperidineethanol (0.06 mL), cyanomethylenetributylphosphorane (94 mg) and toluene (2.0 mL) was stirred at an external temperature of 90° C. for 4 hours under a nitrogen atmosphere. After leaving the mixture to cool, 1-piperidineethanol (0.03 mL) and cyanomethylenetributylphosphorane (47 mg) were further added and the mixture was stirred at an external temperature of 90° C. for 6 hours. After leaving the mixture to cool, the solvent was distilled off under reduced pressure and the resulting residue was purified by column chromatography (SNAP Cartridge KP-Sil 25 g: mobile phase: CHCl₃/MeOH=98/2-90/10; v/v). The resulting crudely refined product was washed with Et₂O to give the titled compound (39 mg as a colorless solid).

MS (ESI pos.) m/z: 481 ([M+H]+).

¹H-NMR (600 MHz, CDCl₃) δ (ppm); 1.13 (6H, d, J=6.4 Hz), 1.44-1.50 (2H, m), 1.60-1.67 (4H, m), 2.48-2.59 (4H, m), 2.76-2.83 (2H, m), 4.11-4.20 (3H, m), 4.65 (2H, s), 5.36-5.42 (1H, m), 6.94-6.99 (2H, m), 7.22 (1H, s), 7.38-7.47 (3H, m), 7.66-7.69 (1H, m), 7.75-7.80 (2H, m).

Starting from Reference Example P-A27, the same procedure as in Example A-33 was applied to synthesize the following compounds.

Example A-34

2-[2-(3-chlorophenyl)-4-{3-[2-(piperidin-1-yl)ethoxy]phenyl}-1H-imidazol-1-yl]-N-(propan-2-yl)acetamide

[Chem. 259]

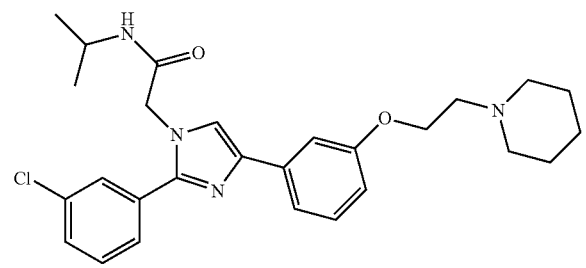

MS (ESI pos.) m/z: 481 ([M+H]+).

¹H-NMR (600 MHz, CDCl₃) δ (ppm); 1.13 (6H, d, J=6.4 Hz), 1.41-1.50 (2H, m), 1.61-1.67 (4H, m), 2.37-2.61 (4H, m), 2.79-2.85 (2H, m), 4.12-4.23 (3H, m), 4.66 (2H, s), 5.37-5.42 (1H, m), 6.84-6.88 (1H, m), 7.29-7.34 (2H, m), 7.40-7.48 (5H, m), 7.67-7.70 (1H, m).

Example A-35

2-[2-(3-chlorophenyl)-4-{3-[3-(piperidin-1-yl)propoxy]phenyl}-1H-imidazol-1-yl]-N-(propan-2-yl)acetamide

[Chem. 260]

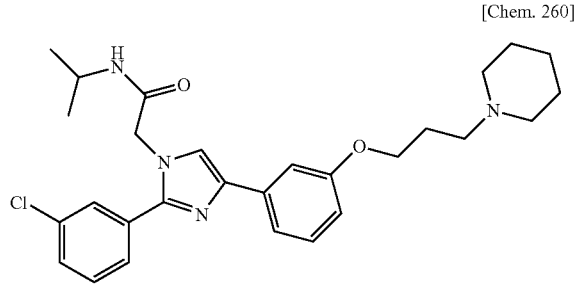 [SMILES: CC(C)NC(=O)Cn1cc(-c2cccc(OCCCN3CCCCC3)c2)nc1-c1cccc(Cl)c1]

MS (ESI pos.) m/z: 495 ([M+H]+).

¹H-NMR (600 MHz, CDCl₃) δ (ppm); 1.13 (6H, d, J=6.4 Hz), 1.43-1.50 (2H, m), 1.63-1.71 (4H, m), 2.00-2.10 (2H, m), 2.35-2.63 (6H, m), 4.08-4.12 (2H, m), 4.13-4.21 (1H, m), 4.66 (2H, s), 5.37-5.42 (1H, m), 6.83-6.87 (1H, m), 7.29-7.34 (2H, m), 7.38-7.49 (5H, m), 7.67-7.70 (1H, m).

Example A-36

Synthesis of 2-[2-(3-methoxyphenyl)-5-methyl-4-{4-[2-(morpholin-4-yl)ethyl]phenyl}-1H-imidazol-1-yl]-N-(propan-2-yl)acetamide

[Chem. 261]

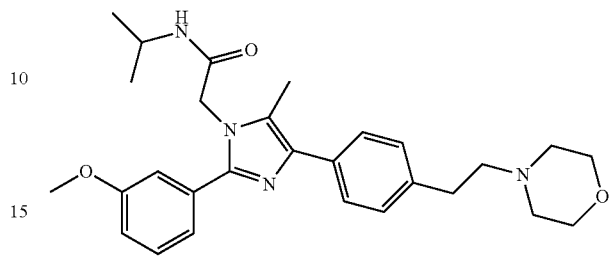

A mixture of the compound (86 mg) obtained in Reference Example P-A30, 4-(2-morpholinoethyl)phenylboronic acid (166 mg), Pd(PPh₃)₄ (54 mg), 2 M Na₂CO₃ aqueous solution (0.24 mL) and a mixed solvent (2.5 mL; toluene/MeOH=5/3; v/v) was stirred at an external temperature of 100° C. for 17 hours. After leaving the mixture to cool, 4-(2-morpholinoethyl)phenylboronic acid (83 mg) and Pd(PPh₃)₄ (27 mg) were further added and the mixture was stirred at an external temperature of 100° C. for 5 hours. After leaving the mixture to cool, it was diluted with CHCl₃ and washed with water. The organic layer was dried over MgSO₄ and subsequently concentrated under reduced pressure. The resulting residue was purified by silica gel (neutral OH form) column chromatography (mobile phase: CHCl₃/MeOH=97/3-90/10; v/v) and washed with IPE to give the titled compound (12 mg as a colorless solid).

MS (ESI pos.) m/z: 477 ([M+H]+).

¹H-NMR (600 MHz, CDCl₃) δ (ppm); 1.13 (6H, d, J=6.0 Hz), 2.43 (3H, s), 2.48-2.58 (4H, m), 2.59-2.69 (2H, m), 2.79-2.90 (2H, m), 3.69-3.77 (4H, m), 3.83 (3H, s), 4.13-4.23 (1H, m), 4.60 (2H, s), 5.32-5.41 (1H, m), 6.92-7.16 (3H, m), 7.21-7.30 (2H, m), 7.31-7.41 (1H, m), 7.59-7.71 (2H, m).

Starting from the compounds obtained in Reference Example P-A32, Reference Example P-A33, Reference Example P-A34, Reference Example P-A35, Reference Example P-A36, Reference Example P-A43, Reference Example P-A46 and Reference Example P-A65, the same procedure as in Example A-36 was applied to synthesize the following compounds:

Example A-37

2-[2-(3-methoxyphenyl)-4-{4-[2-(piperidin-1-yl)ethyl]phenyl}-1H-imidazol-1-yl]-N-(propan-2-yl)acetamide

[Chem. 262]

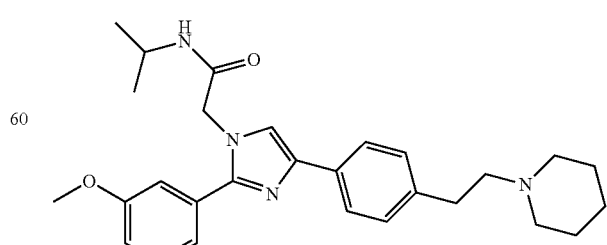

MS (ESI pos.) m/z: 461 ([M+H]⁺).

¹H-NMR (600 MHz, CDCl₃) δ (ppm); 1.09 (6H, d, J=6.4 Hz), 1.45 (1H, br. s.), 1.53-1.67 (5H, m), 2.39-2.53 (4H, m), 2.52-2.62 (2H, m), 2.73-2.90 (2H, m), 3.71-3.89 (3H, m), 4.04-4.20 (1H, m), 4.66 (2H, s), 5.40 (1H, d, J=7.8 Hz), 6.95-7.02 (1H, m), 7.07-7.20 (2H, m), 7.18-7.29 (3H, m), 7.32-7.41 (1H, m), 7.67-7.84 (2H, m).

Example A-38

2-[2-(3-methoxyphenyl)-4-{4-[2-(morpholin-4-yl)ethyl]phenyl}-1H-imidazol-1-yl]-N-(propan-2-yl)acetamide

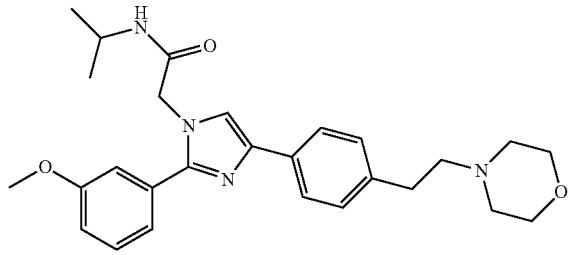

[Chem. 263]

MS (ESI pos.) m/z: 463 ([M+H]⁺).

¹H-NMR (600 MHz, CDCl₃) δ (ppm); 1.11 (6H, s), 2.54 (4H, br. s.), 2.58-2.67 (2H, m), 2.75-2.90 (2H, m), 3.70-3.79 (4H, m), 3.85 (3H, s), 4.06-4.20 (1H, m), 4.67 (2H, s), 5.40 (1H, d, J=7.8 Hz), 6.93-7.03 (1H, m), 7.09-7.19 (2H, m), 7.22-7.29 (3H, m), 7.32-7.42 (1H, m), 7.71-7.87 (2H, m).

Example A-39

2-[2-(3-chloro-4-fluorophenyl)-4-{4-[2-(morpholin-4-yl)ethyl]phenyl}-1H-imidazol-1-yl]-N-(propan-2-yl)acetamide

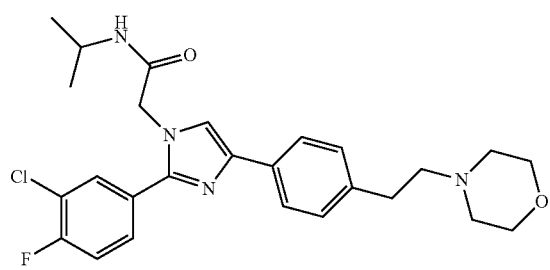

[Chem. 264]

MS (ESI pos.) m/z: 485 ([M+H]⁺).

¹H-NMR (600 MHz, CDCl₃) δ (ppm); 1.13 (6H, d, J=6.4 Hz), 2.54 (4H, br. s.), 2.59-2.68 (2H, m), 2.76-2.89 (2H, m), 3.67-3.81 (4H, m), 4.09-4.22 (1H, m), 4.62 (2H, s), 5.37 (1H, d, J=7.8 Hz), 7.14-7.34 (4H, m), 7.40-7.51 (1H, m), 7.63-7.84 (3H, m).

Example A-40

2-[2-(5-methoxypyridin-3-yl)-4-{4-[2-(morpholin-4-yl)ethyl]phenyl}-1H-imidazol-1-yl]-N-(propan-2-yl)acetamide

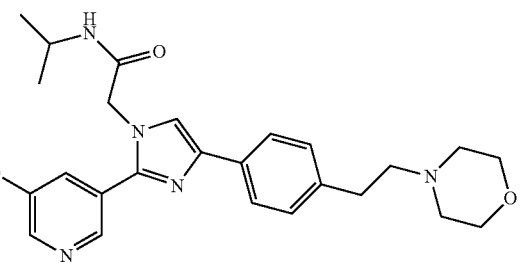

[Chem. 265]

MS (ESI pos.) m/z: 464 ([M+H]).

¹H-NMR (600 MHz, CDCl₃) δ (ppm); 1.12 (6H, d, J=6.4 Hz), 2.54 (4H, br. s.), 2.58-2.66 (2H, m), 2.78-2.90 (2H, m), 3.71-3.78 (4H, m), 3.91 (3H, s), 4.08-4.20 (1H, m), 4.66 (2H, s), 5.39 (1H, d, J=7.8 Hz), 7.21-7.29 (2H, m), 7.32 (1H, s), 7.47-7.52 (1H, m), 7.74-7.80 (2H, m), 8.36-8.45 (2H, m).

Example A-41

2-[2-(2-methoxypyridin-4-yl)-4-{4-[2-(morpholin-4-yl)ethyl]phenyl}-1H-imidazol-1-yl]-N-(propan-2-yl)acetamide

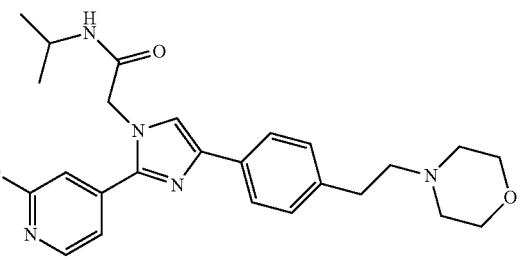

[Chem. 266]

MS (ESI pos.) m/z: 464 ([M+H]⁺).

¹H-NMR (600 MHz, CDCl₃) δ (ppm); 1.11 (6H, d, J=6.4 Hz), 2.54 (4H, br. s.), 2.59-2.65 (2H, m), 2.80-2.89 (2H, m), 3.71-3.78 (4H, m), 3.98 (3H, s), 4.10-4.20 (1H, m), 4.70 (2H, s), 5.35 (1H, d, J=8.3 Hz), 6.98 (1H, s), 7.12-7.17 (1H, m), 7.23-7.28 (2H, m), 7.31 (1H, s), 7.77 (2H, d, J=8.3 Hz), 8.26 (1H, d, J=5.0 Hz).

Example A-42

2-[2-(3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide

[Chem. 267]

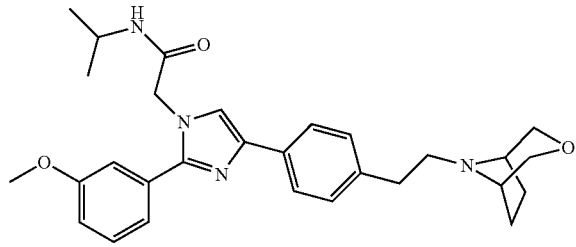

MS (ESI pos.) m/z: 489 ([M+H]⁺).

¹H-NMR (600 MHz, CDCl₃) δ (ppm); 1.11 (6H, d, J=6.6 Hz), 1.84-1.97 (4H, m), 2.51-2.59 (2H, m), 2.79-2.85 (2H, m), 3.11 (2H, br. s.), 3.53 (2H, d, J=9.1 Hz), 3.75 (2H, d, J=10.3 Hz), 3.86 (3H, s), 4.10-4.20 (1H, m), 4.68 (2H, s), 5.36-5.43 (1H, m), 6.97-7.04 (1H, m), 7.13 (1H, d, J=7.4 Hz), 7.16-7.20 (1H, m), 7.23-7.30 (3H, m), 7.38 (1H, t, J=8.1 Hz), 7.79 (2H, d, J=7.8 Hz).

Example A-43

2-[2-(3-chlorophenyl)-4-{2-fluoro-4-[2-(morpholin-4-yl)ethyl]phenyl}-1H-imidazol-1-yl]-N-(propan-2-yl)acetamide

[Chem. 268]

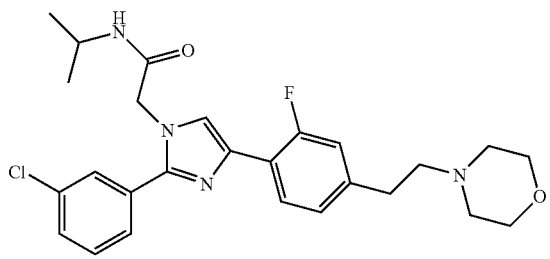

MS (ESI pos.) m/z: 485 ([M+H]⁺).

¹H-NMR (600 MHz, CDCl₃) δ (ppm); 1.12 (6H, d, J=6.6 Hz), 2.53 (4H, br. s.), 2.60-2.65 (2H, m), 2.80-2.85 (2H, m), 3.74 (4H, t, J=4.5 Hz), 4.10-4.19 (1H, m), 4.65 (2H, s), 5.42 (1H, d, J=7.8 Hz), 6.99 (1H, dd, J=12.2, 1.4 Hz), 7.07 (1H, dd, J=8.1, 1.4 Hz), 7.38-7.50 (4H, m), 7.66-7.69 (1H, m), 8.15 (1H, t, J=8.1 Hz).

Example A-44

2-[2-(3-chlorophenyl)-4-{4-[2-(morpholin-4-yl)propyl]phenyl}-1H-imidazol-1-yl]-N-(propan-2-yl)acetamide

[Chem. 269]

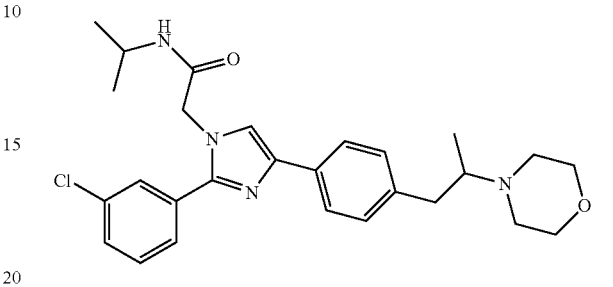

MS (ESI pos.) m/z: 481 ([M+H]⁺).

¹H-NMR (600 MHz, CDCl₃) δ (ppm); 0.98 (3H, d, J=6.6 Hz), 1.12 (6H, d, J=6.6 Hz), 2.42-2.48 (1H, m), 2.59-2.65 (4H, m), 2.76-2.83 (1H, m), 2.99-3.05 (1H, m), 3.71-3.77 (4H, m), 4.10-4.20 (1H, m), 4.65 (2H, s), 5.38 (1H, d, J=7.8 Hz), 7.22 (2H, d, J=8.3 Hz), 7.29 (1H, s), 7.38-7.47 (3H, m), 7.67 (1H, t, J=11.7 Hz), 7.75-7.79 (2H, m).

Example A-45

Synthesis of 2-[2-(3-chlorophenyl)-4-{4-[2-(morpholin-4-yl)ethyl]-2-oxopyridin-1(2H)-yl}-1H-imidazol-1-yl]-N-(propan-2-yl)acetamide

[Chem. 270]

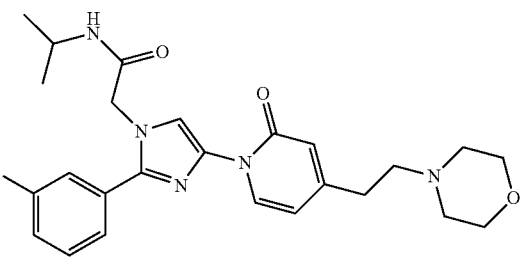

A mixture in DMF (8.0 mL) of the compound (481 mg) obtained in Reference Example P-A36, the compound obtained in Reference Example P-A69, copper iodide (52 mg), tripotassium phosphate (516 mg) and 4,7-dimethoxy-1,10-phenanthroline (98 mg) was stirred at an external temperature of 100° C. for 2 days. After leaving the mixture to cool, it was purified by reverse-phase column chromatography (mobile phase: 0.1% TFA MeCN/H₂O=10/90-90/10; v/v). The fractions were neutralized with a saturated aqueous NaHCO₃ solution, extracted with CHCl₃ and filtered with Phase Separator. The solvent was distilled off under reduced pressure to give the titled compound (155 mg as a colorless solid).

MS (ESI pos.) m/z: 484 ([M+H]⁺).

¹H-NMR (600 MHz, CDCl₃) δ (ppm); 1.13 (6H, d, J=6.6 Hz), 2.32-2.90 (8H, m), 3.73 (4H, br. s.), 4.05-4.22 (1H, m), 4.65 (2H, s), 5.49 (1H, d, J=7.4 Hz), 6.25 (1H, d, J=7.4 Hz), 6.49 (1H, s), 7.36-7.51 (3H, m), 7.66 (1H, t, J=1.7 Hz), 8.03 (1H, s), 8.54 (1H, d, J=7.0 Hz).

Example A-46

Synthesis of 2-[2-(3-chlorophenyl)-4-{4-[2-(morpholin-4-yl)ethyl]-2-oxopiperazin-1-yl}-1H-imidazol-1-yl]-N-(propan-2-yl)acetamide

[Chem. 271]

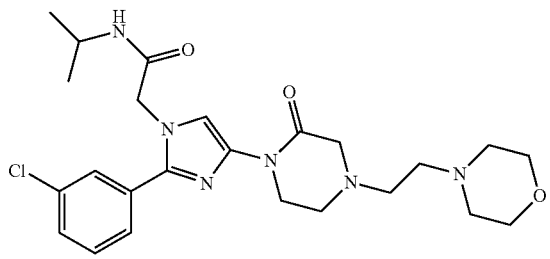

A mixture of the compound (100 mg) obtained in Reference Example P-A37, 4-(2-chloroethyl)morpholine hydrochloride (52 mg), iPr$_2$NEt (0.14 mL) and MeCN (2.0 mL) was stirred overnight at an external temperature of 100° C. After leaving the mixture to cool, the solvent was distilled off under reduced pressure. The resulting residue was purified by silica gel column chromatography (SNAP Cartridge HP-Sil 10 g; mobile phase: CHCl$_3$/MeOH=98/2-90/10; v/v); and after washing with a mixed solvent (EtOAc/n-Hexane=1/6; v/v), the solids were recovered by filtration to give the titled compound (25 mg as a colorless solid).

MS (ESI pos.) m/z: 489 ([M+H]$^+$).
$^1$H-NMR (600 MHz, CDCl$_3$) δ (ppm); 1.13 (6H, d, J=6.6 Hz), 2.52 (4H, br. s.), 2.55-2.60 (2H, m), 2.63-2.68 (2H, m), 2.87-2.92 (2H, m), 3.40 (2H, s), 3.69-3.77 (4H, m), 4.07-4.18 (3H, m), 4.61 (2H, s), 5.37-5.43 (1H, m), 7.37-7.43 (3H, m), 7.59-7.63 (1H, m), 7.69 (1H, s).

Example A-47

Synthesis of 2-(3-chlorophenyl)-N-[4-(morpholin-4-yl)cyclohexyl]-1-[2-oxo-2-(propan-2-ylamino)ethyl]-1H-imidazole-4-carboxamide

[Chem. 272]

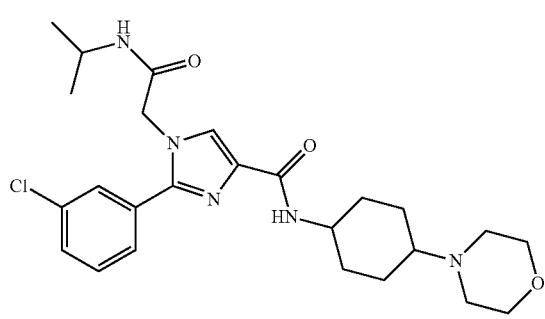

Starting from the compound (61 mg) obtained in Reference Example P-A39, the same procedure as in Example A-28 was applied to give the titled compound (45 mg as a colorless solid).

MS (ESI pos.) m/z: 488 ([M+H]$^+$).
$^1$H-NMR (600 MHz, CDCl$_3$) δ (ppm); 1.14 (6H, d, J=6.6 Hz), 1.23-1.61 (3H, m), 1.64-1.77 (4H, m), 1.85-2.03 (2H, m), 2.12-2.21 (1H, m), 2.47-2.61 (4H, m), 3.73 (4H, br. s.), 4.09-4.22 (2H, m), 4.56-4.62 (2H, m), 5.27-5.35 (1H, m), 7.39-7.50 (3H, m), 7.59-7.66 (2H, m).

Example A-48

Synthesis of 2-(3-chlorophenyl)-N-methyl-N-[4-(morpholin-4-yl)cyclohexyl]-1-[2-oxo-2-(propan-2-ylamino)ethyl]-1H-imidazole-4-carboxamide

[Chem. 273]

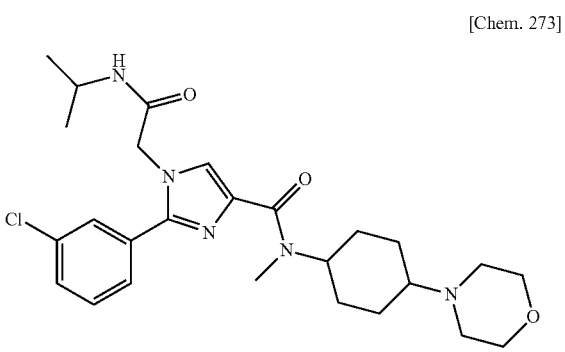 [SMILES: CC(C)NC(=O)Cn1cc(C(=O)N(C)C2CCC(N3CCOCC3)CC2)nc1-c1cccc(Cl)c1]

Starting from the compound (105 mg) obtained in Reference Example P-A40, the same procedure as in Example A-28 was applied to give the titled compound (56 mg as a colorless solid).

MS (ESI pos.) m/z: 502 ([M+H]$^+$).
$^1$H-NMR (600 MHz, CDCl$_3$) δ (ppm); 1.14 (6H, d, J=6.6 Hz), 1.36-1.69 (6H, m), 1.84-2.19 (4H, m), 2.45 (2H, br. s.), 2.57 (2H, br. s.), 2.93-3.05 (1H, m), 3.36 (1H, br. s.), 3.67-3.79 (4H, m), 4.08-4.18 (1H, m), 4.63 (2H, d, J=12.0 Hz), 7.37-7.49 (3H, m), 7.58-7.66 (2H, m).

Example A-49

Synthesis of 2-[2-(3-chlorophenyl)-4-({3-[2-(morpholin-4-yl)ethyl]pyrrolidin-1-yl}carbonyl)-1H-imidazol-1-yl]-N-(propan-2-yl)acetamide

[Chem. 274]

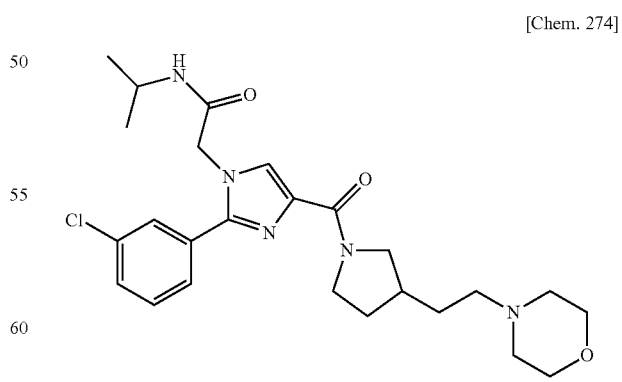

Starting from the compound (98 mg) obtained in Reference Example P-A41, the same procedure as in Example A-01 was applied to give the titled compound (50 mg as a colorless amorphous product).

MS (ESI pos.) m/z: 488 ([M+H]+).
1H-NMR (600 MHz, CDCl3) δ (ppm); 1.13 (6H, d, J=6.6 Hz), 1.50-1.72 (5H, m), 2.04-2.30 (2H, m), 2.35-2.52 (4H, m), 3.19-3.63 (1H, m), 3.66-3.84 (5H, m), 3.86-4.00 (1H, m), 4.08-4.17 (1H, m), 4.30-4.46 (1H, m), 4.63 (2H, s), 5.65-5.78 (1H, m), 7.37-7.50 (3H, m), 7.64 (1H, s), 7.71 (1H, s).

Starting from the compound obtained in Reference Example P-B02, together with the compound obtained in Reference Example P-A43, 4-(2-morpholinoethyl)phenylboronic acid, and 4-(4-methyl-1-piperazinylmethyl)benzeneboronic acid pinacol ester, the same procedure as in Example A-36 was applied to synthesize the following compounds:

Example B-01

2-[5-(3-chlorophenyl)-3-{4-[2-(3-oxa-8-azabicyclo[3.2.1]oct-8-yl)ethyl]phenyl}-1H-1,2,4-triazol-1-yl]-N-(propan-2-yl)acetamide

[Chem. 275]

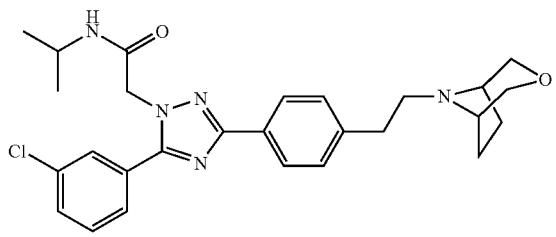

MS (ESI pos.) m/z: 494 ([M+H]+).
1H-NMR (600 MHz, CDCl3) δ (ppm); 1.17 (6H, d, J=6.6 Hz), 1.85-1.97 (4H, m), 2.54-2.60 (2H, m), 2.83-2.88 (2H, m), 3.11 (2H, br. s.), 3.54 (2H, d, J=9.1 Hz), 3.75 (2H, d, J=10.3 Hz), 4.11-4.18 (1H, m), 4.85 (2H, s), 6.15-6.20 (1H, m), 7.34 (2H, d, J=7.8 Hz), 7.46-7.50 (1H, m), 7.51-7.55 (1H, m), 7.55-7.58 (1H, m), 7.78-7.80 (1H, m), 8.09 (2H, d, J=8.3 Hz).

Example B-02

2-[5-(3-chlorophenyl)-3-{4-[2-(morpholin-4-yl)ethyl]phenyl}-1H-1,2,4-triazol-1-yl]-N-(propan-2-yl)acetamide

[Chem. 276]

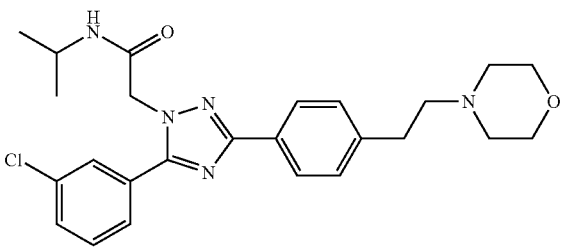

MS (ESI pos.) m/z: 468 ([M+H]+).
1H-NMR (600 MHz, CDCl3) δ (ppm); 1.16 (6H, d, J=6.6 Hz), 2.52-2.57 (4H, m), 2.62-2.68 (2H, m), 2.85-2.90 (2H, m), 3.75 (4H, t, J=4.5 Hz), 4.11-4.17 (1H, m), 4.85 (2H, s), 6.14-6.19 (1H, m), 7.31-7.34 (2H, m), 7.46-7.50 (1H, m), 7.51-7.53 (1H, m), 7.54-7.57 (1H, m), 7.77-7.79 (1H, m), 8.08 (2H, d, J=8.3 Hz).

Example B-03

2-[5-(3-chlorophenyl)-3-{4-[(4-methylpiperazin-1-yl)methyl]phenyl}-1H-1,2,4-triazol-1-yl]-N-(propan-2-yl)acetamide

[Chem. 277]

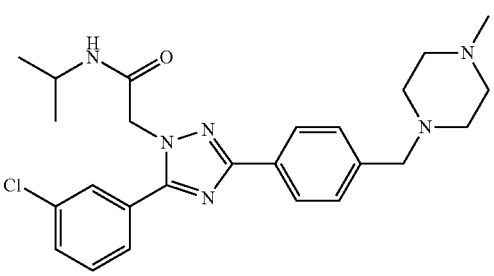

MS (ESI pos.) m/z: 467 ([M+H]+).
1H-NMR (600 MHz, DMSO-d6) δ (ppm); 1.08 (6H, d, J=6.6 Hz), 2.15 (3H, s), 3.50 (2H, s), 3.81-3.88 (1H, m), 4.93 (2H, s), 7.40 (2H, d, J=8.3 Hz), 7.58-7.62 (1H, m), 7.63-7.66 (1H, m), 7.76-7.79 (1H, m), 7.83-7.85 (1H, m), 7.98 (2H, d, J=8.3 Hz), 8.34 (1H, d, J=7.4 Hz).

Example B-04

Synthesis of 2-[5-(3-chlorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide

[Chem. 278]

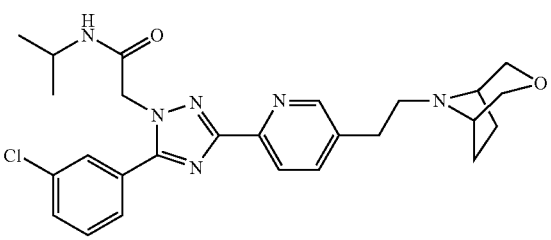

A mixture of the compound (99 mg) obtained in Reference Example P-A62, the compound (70 mg) obtained in Reference Example P-B04, Pd(PPh3)4 (23 mg) and DMF (3.0 mL) was stirred at an external temperature of 95° C. for 3 hours under a nitrogen atmosphere. After leaving the mixture to cool, Pd(PPh3)4 (23 mg) was further added and the mixture was stirred at an external temperature of 95° C. for 4 hours. After leaving the mixture to cool, Pd(PPh3)4 (23 mg) was further added and the mixture was stirred at an external temperature of 95° C. for 2 days. After leaving the mixture to cool, water and a saturated aqueous NaHCO3 solution were added and extraction was conducted with CHCl3. The organic layer was filtered with Phase Separator and the solvent was distilled off under reduced pressure. The resulting residue was purified by silica gel column chromatography (SNAP Cartridge HP-Sil 50 g; mobile phase: CHCl₃/MeOH=98/2-85/15; v/v). The purified product was washed with Et₂O to give the titled compound (27 mg as a colorless solid).

MS (ESI pos.) m/z: 495 ([M+H]⁺).
¹H-NMR (600 MHz, CDCl₃) δ (ppm); 1.16 (6H, d, J=6.6 Hz), 1.86-1.94 (4H, m), 2.55-2.60 (2H, m), 2.82-2.87 (2H, m), 3.08 (2H, br. s.), 3.53 (2H, d, J=9.1 Hz), 3.72 (2H, d, J=10.3 Hz), 4.11-4.18 (1H, m), 4.92 (2H, s), 5.96-6.02 (1H, m), 7.46-7.51 (1H, m), 7.52-7.55 (1H, m), 7.62-7.66 (1H, m), 7.70-7.74 (1H, m), 7.86-7.89 (1H, m), 8.15 (1H, d, J=7.8 Hz), 8.66 (1H, d, J=1.7 Hz).

Starting from the compounds obtained in Reference Example P-A60, Reference Example P-A62, Reference Example P-B02, Reference Example P-B03, Reference Example P-B04, Reference Example P-B05, Reference Example P-B07 and Reference Example P-B08, the same procedure as in Example B-04 was applied to synthesize the following compounds.

Example B-05

2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide

[Chem. 279]

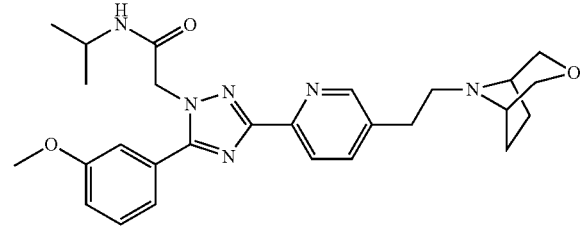

MS (ESI pos.) m/z: 491 ([M+H]⁺).
¹H-NMR (600 MHz, CDCl₃) δ (ppm); 1.14 (6H, d, J=6.6 Hz), 1.91 (4H, br. s.), 2.49-2.61 (2H, m), 2.84 (2H, t, J=7.4 Hz), 3.08 (2H, br. s.), 3.52 (2H, d, J=10.7 Hz), 3.71 (2H, d, J=9.9 Hz), 3.88 (3H, s), 4.07-4.19 (1H, m), 4.93 (2H, s), 6.03 (1H, d, J=9.5 Hz), 7.02-7.12 (1H, m), 7.28-7.35 (2H, m), 7.39-7.49 (1H, m), 7.71 (1H, d, J=9.9 Hz), 8.16 (1H, d, J=8.3 Hz), 8.66 (1H, s).

Example B-06

2-[5-(4-fluoro-3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide

[Chem. 280]

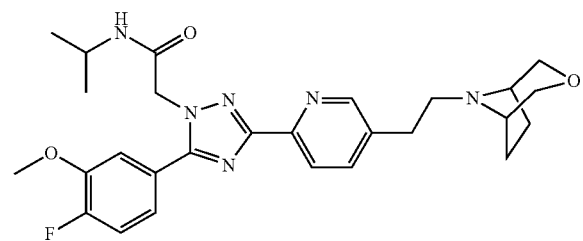

MS (ESI pos.) m/z: 509 ([M+H]⁺).
¹H-NMR (600 MHz, CDCl₃) δ (ppm); 1.16 (6H, d, J=6.2 Hz), 1.83-1.97 (4H, m), 2.51-2.61 (2H, m), 2.81-2.88 (2H, m), 3.08 (2H, br. s.), 3.53 (2H, d, J=9.9 Hz), 3.71 (2H, d, J=10.3 Hz), 3.98 (3H, s), 4.09-4.18 (1H, m), 4.91 (2H, s), 6.02-6.12 (1H, m), 7.23 (1H, dd, J=10.7, 8.3 Hz), 7.29-7.33 (1H, m), 7.48 (1H, dd, J=7.8, 2.1 Hz), 7.69-7.75 (1H, m), 8.15 (1H, d, J=7.8 Hz), 8.66 (1H, d, J=2.1 Hz).

Example B-07

N-tert-butyl-2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]acetamide

[Chem. 281]

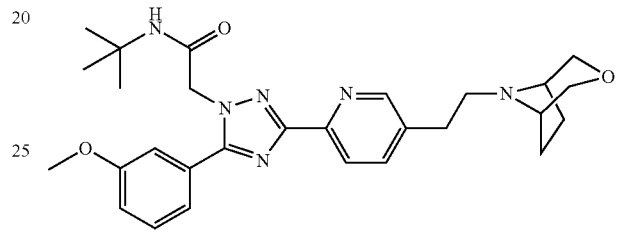

MS (ESI pos.) m/z: 505 ([M+H]⁺).
¹H-NMR (600 MHz, CDCl₃) δ (ppm); 1.34 (9H, s), 1.90 (4H, br. s.), 2.56 (2H, t, J=7.6 Hz), 2.84 (2H, t, J=7.4 Hz), 3.07 (2H, br. s.), 3.52 (2H, d, J=9.1 Hz), 3.71 (2H, d, J=10.3 Hz), 3.88 (3H, s), 4.87 (2H, s), 6.05 (1H, s), 7.08 (1H, dd, J=8.3, 2.5 Hz), 7.28-7.34 (2H, m), 7.44 (1H, t, J=7.8 Hz), 7.70 (1H, dd, J=8.1, 1.9 Hz), 8.16 (1H, d, J=8.3 Hz), 8.65 (1H, d, J=2.1 Hz).

Example B-08

2-[5-(3-chloro-4-fluorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide

[Chem. 282]

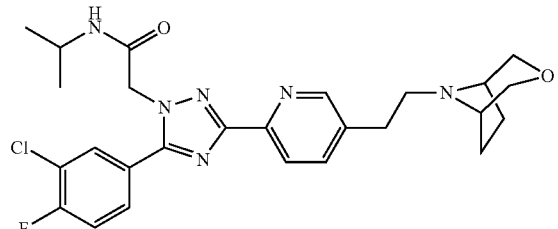

MS (ESI pos.) m/z: 513 ([M+H]⁺).
¹H-NMR (600 MHz, CDCl₃) δ (ppm); 1.16 (6H, d, J=6.6 Hz), 1.90 (4H, s), 2.56 (2H, t, J=7.4 Hz), 2.84 (2H, t, J=7.6 Hz), 3.07 (2H, br. s.), 3.52 (2H, dd, J=10.5, 1.9 Hz), 3.70 (2H, d, J=10.3 Hz), 4.05-4.18 (1H, m), 4.89 (2H, s), 6.03 (1H, d, J=7.8 Hz), 7.31 (1H, t, J=8.5 Hz), 7.64-7.74 (2H, m), 7.98 (1H, dd, J=7.0, 2.1 Hz), 8.13 (1H, d, J=7.8 Hz), 8.65 (1H, d, J=1.7 Hz).

Example B-09

N-tert-butyl-2-[5-(3-chlorophenyl)-3-{5-[2-(3-oxa-8-azabicyclo[3.2.1]oct-8-yl)ethyl]pyridin-2-yl}-1H-1,2,4-triazol-1-yl]acetamide

[Chem. 283]

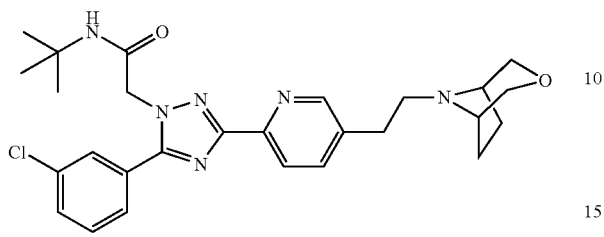

MS (ESI pos.) m/z: 509 ([M+H]$^+$).
$^1$H-NMR (600 MHz, CDCl$_3$) δ (ppm); 1.35 (9H, s), 1.91 (4H, br. s.), 2.57 (2H, t, J=7.6 Hz), 2.84 (2H, t, J=7.2 Hz), 3.08 (2H, br. s.), 3.53 (2H, d, J=10.7 Hz), 3.71 (2H, d, J=9.9 Hz), 4.86 (2H, s), 6.00 (1H, br. s.), 7.40-7.58 (2H, m), 7.60-7.76 (2H, m), 7.86 (1H, s), 8.14 (1H, d, J=8.3 Hz), 8.65 (1H, s).

Example B-10

2-[5-(3-chlorophenyl)-3-{5-[2-(morpholin-4-yl)ethyl]pyridin-2-yl}-1H-1,2,4-triazol-1-yl]-N-(propan-2-yl)acetamide

[Chem. 284]

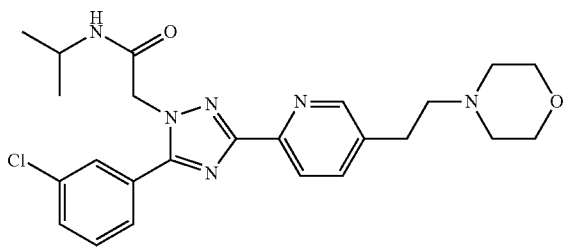

MS (ESI pos.) m/z: 469 ([M+H]$^+$).
$^1$H-NMR (600 MHz, CDCl$_3$) δ (ppm); 1.16 (6H, d, J=6.6 Hz), 2.95 (2H, br. s.), 3.20-3.29 (2H, m), 3.35-3.46 (2H, m), 3.56 (2H, br. s.), 3.93-4.18 (3H, m), 4.26 (2H, br. s.), 4.92 (2H, s), 6.07 (1H, d, J=7.0 Hz), 7.45-7.58 (2H, m), 7.65 (1H, d, J=7.8 Hz), 7.77-7.90 (2H, m), 8.21 (1H, d, J=8.3 Hz), 8.64 (1H, s).

Example B-11

N-tert-butyl-2-[5-(3-chlorophenyl)-3-{5-[2-(morpholin-4-yl)ethyl]pyridin-2-yl}-1H-1,2,4-triazol-1-yl]acetamide

[Chem. 285]

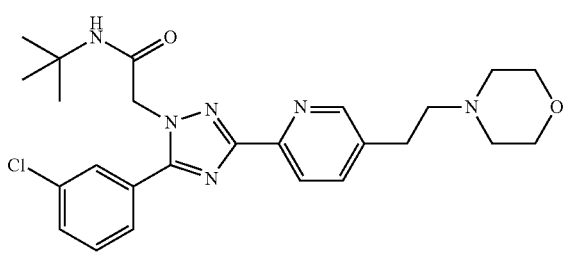

MS (ESI pos.) m/z: 483 ([M+H]$^+$).
$^1$H-NMR (600 MHz, CDCl$_3$) δ (ppm); 1.33 (9H, s), 2.52 (4H, br. s.), 2.58-2.69 (2H, m), 2.81-2.90 (2H, m), 3.72 (4H, t, J=4.7 Hz), 4.84 (2H, s), 5.97 (1H, s), 7.44-7.53 (2H, m), 7.59-7.70 (2H, m), 7.84 (1H, t, J=1.9 Hz), 8.13 (1H, d, J=7.8 Hz), 8.61 (1H, d, J=2.1 Hz).

Example B-12

2-[5-(3-chloro-4-fluorophenyl)-3-{5-[2-(morpholin-4-yl)ethyl]pyridin-2-yl}-1H-1,2,4-triazol-1-yl]-N-(propan-2-yl)acetamide

[Chem. 286]

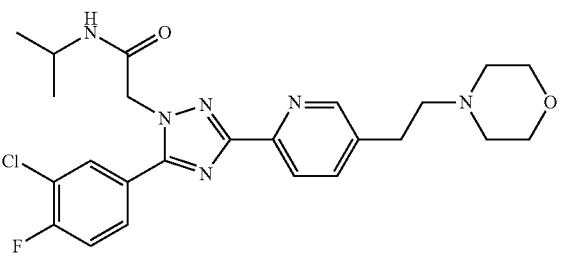

MS (ESI pos.) m/z: 487 ([M+H]$^+$).
$^1$H-NMR (600 MHz, CDCl$_3$) δ (ppm); 1.16 (6H, d, J=6.6 Hz), 2.53 (4H, br. s.), 2.65 (2H, t, J=7.6 Hz), 2.87 (2H, t, J=7.6 Hz), 3.73 (4H, t, J=4.3 Hz), 4.07-4.17 (1H, m), 4.89 (2H, s), 6.01 (1H, d, J=8.7 Hz), 7.31 (1H, t, J=8.7 Hz), 7.64-7.73 (2H, m), 7.98 (1H, dd, J=6.8, 2.3 Hz), 8.13 (1H, d, J=7.8 Hz), 8.63 (1H, d, J=1.7 Hz).

Example B-13

2-[5-(4-fluoro-3-methoxyphenyl)-3-{5-[2-(morpholin-4-yl)ethyl]pyridin-2-yl}-1H-1,2,4-triazol-1-yl]-N-(propan-2-yl)acetamide

[Chem. 287]

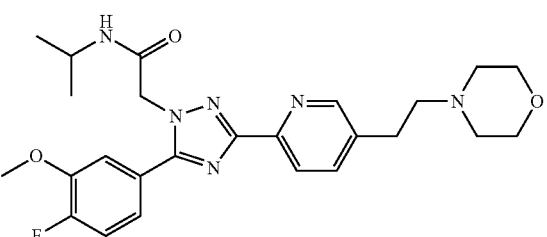

MS (ESI pos.) m/z: 483 ([M+H]$^+$).
$^1$H-NMR (600 MHz, CDCl$_3$) δ (ppm); 1.15 (6H, d, J=6.6 Hz), 2.53 (4H, br. s.), 2.65 (2H, t, J=7.6 Hz), 2.88 (2H, t, J=7.6 Hz), 3.74 (4H, t, J=4.5 Hz), 3.97 (3H, s), 4.12 (1H, dq, J=13.5, 6.6 Hz), 4.91 (2H, s), 6.01-6.13 (1H, m), 7.23 (1H, dd, J=10.5, 8.5 Hz), 7.28-7.35 (1H, m), 7.47 (1H, dd, J=7.8, 1.7 Hz), 7.69 (1H, dd, J=8.1, 1.9 Hz), 8.15 (1H, d, J=8.3 Hz), 8.63 (1H, d, J=2.1 Hz).

Example B-14

N-tert-butyl-2-[5-(3-methoxyphenyl)-3-{5-[2-(morpholin-4-yl)ethyl]pyridin-2-yl}-1H-1,2,4-triazol-1-yl]acetamide

[Chem. 288]

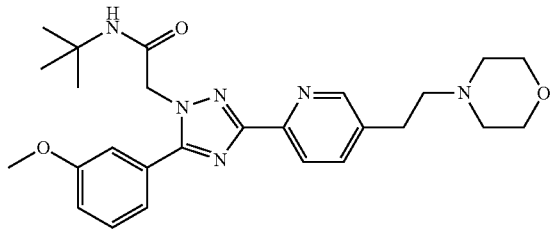

MS (ESI pos.) m/z: 479 ([M+H]$^+$).

$^1$H-NMR (600 MHz, CDCl$_3$) δ (ppm); 1.34 (9H, s), 2.54 (4H, br. s.), 2.61-2.69 (2H, m), 2.84-2.90 (2H, m), 3.74 (4H, t, J=4.7 Hz), 3.87 (3H, s), 4.87 (2H, s), 6.04 (1H, s), 7.08 (1H, dd, J=8.9, 3.1 Hz), 7.28-7.35 (2H, m), 7.40-7.47 (1H, m), 7.68 (1H, dd, J=8.1, 2.3 Hz), 8.16 (1H, d, J=8.3 Hz), 8.63 (1H, d, J=2.1 Hz).

Example B-15

Synthesis of 2-[5-(3-methoxyphenyl)-3-{5-[2-(morpholin-4-yl)ethyl]pyridin-2-yl}-1H-1,2,4-triazol-1-yl]-N-(propan-2-yl)acetamide

[Chem. 289]

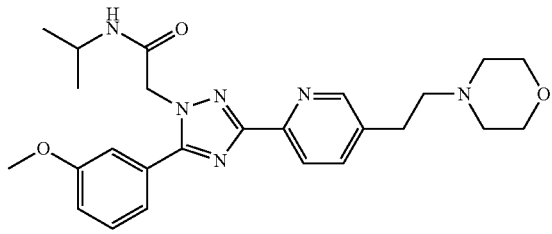

A mixture of the compound (100 mg) obtained in Reference Example P-B04, hexamethylditin (370 mg), Pd(PPh$_3$)$_4$ (33 mg) and toluene (3.0 mL) was stirred at an external temperature of 100° C. for 3 days. After leaving the mixture to cool, water was added and extraction was conducted with EtOAc. The organic layer was washed with Brine and dried over Na$_2$SO$_4$; subsequently, the desiccant was filtered off and the solvent was distilled off under reduced pressure.

A mixture of the resulting residue, the compound (95 mg) obtained in Reference Example P-A59, Pd(PPh$_3$)$_4$ (80 mg) and DMF (2.5 mL) was stirred at an external temperature of 95° C. for 2 days. After leaving the mixture to cool, water and a saturated aqueous NaHCO$_3$ solution were added and extraction was conducted with CHCl$_3$. The organic layer was washed with Brine and filtered with Phase Separator; subsequently, the solvent was distilled off under reduced pressure. The resulting residue was purified by silica gel column chromatography (SNAP Cartridge HP-Sil; mobile phase: CHCl$_3$/MeOH=98/2-85/15; v/v). The purified product was washed with a mixed solvent (EtOAc/n-Hexane=1/4; v/v) to give the titled compound (68 mg as a colorless solid).

MS (ESI pos.) m/z: 465 ([M+H]$^+$).

$^1$H-NMR (600 MHz, CDCl$_3$) δ (ppm); 1.14 (6H, d, J=6.6 Hz), 2.53 (4H, br. s.), 2.60-2.70 (2H, m), 2.82-2.91 (2H, m), 3.74 (4H, t, J=4.5 Hz), 3.87 (3H, s), 4.07-4.19 (1H, m), 4.93 (2H, s), 6.04 (1H, d, J=7.4 Hz), 7.04-7.11 (1H, m), 7.27-7.35 (2H, m), 7.44 (1H, t, J=7.8 Hz), 7.68 (1H, dd, J=8.3, 2.1 Hz), 8.16 (1H, d, J=8.3 Hz), 8.63 (1H, d, J=1.7 Hz).

Starting from the compound obtained in Reference Example P-B04, together with 4-(4-bromophenethyl)morpholine, Reference Example P-A42, Reference Example P-A45, Reference Example P-A49 and Reference Example P-A64, the same procedure as in Example B-15 was applied to synthesize the following compounds.

Example B-16

2-[5-(3-methoxyphenyl)-3-{4-[2-(morpholin-4-yl)ethyl]phenyl}-1H-1,2,4-triazol-1-yl]-N-(propan-2-yl)acetamide

[Chem. 290]

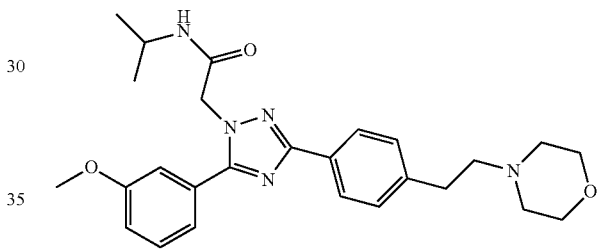

MS (ESI pos.) m/z: 464 ([M+H]$^+$).

$^1$H-NMR (600 MHz, CDCl$_3$) δ (ppm); 1.10-1.18 (6H, m), 2.55 (4H, br. s.), 2.62-2.68 (2H, m), 2.83-2.91 (2H, m), 3.75 (4H, t, J=4.5 Hz), 3.81-3.90 (3H, m), 4.07-4.18 (1H, m), 4.76 (2H, s), 6.19 (1H, d, J=7.0 Hz), 7.00-7.10 (1H, m), 7.14-7.25 (2H, m), 7.32 (1H, d, J=7.8 Hz), 7.42-7.47 (1H, m), 8.06 (1H, s), 8.10 (2H, d, J=8.3 Hz).

Example B-17

2-[5-(3-methoxyphenyl)-3-{4-[2-(3-oxa-8-azabicyclo[3.2.1]oct-8-yl)ethyl]phenyl}-1H-1,2,4-triazol-1-yl]-N-(propan-2-yl)acetamide

[Chem. 291]

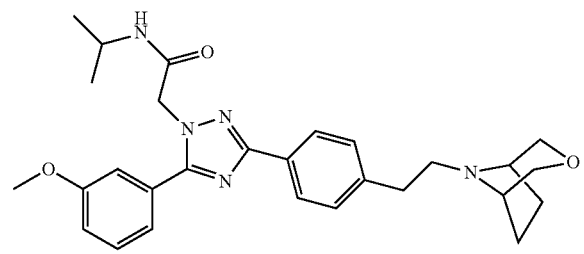

MS (ESI pos.) m/z: 490 ([M+H]+).

¹H-NMR (600 MHz, CDCl₃) δ (ppm); 1.17 (1H, d, J=6.6 Hz), 1.83-1.98 (4H, m), 2.54-2.61 (2H, m), 2.82-2.89 (2H, m), 3.08-3.15 (2H, m), 3.52-3.57 (2H, m), 3.72-3.78 (2H, m), 3.88 (3H, s), 4.11-4.18 (1H, m), 4.87 (2H, s), 6.17-6.23 (1H, m), 7.06-7.11 (1H, m), 7.22-7.26 (2H, m), 7.31-7.36 (2H, m), 7.42-7.46 (1H, m), 8.08-8.13 (2H, m).

Example B-18

2-[3-{2-fluoro-4-[2-(morpholin-4-yl)ethyl]phenyl}-5-(3-methoxyphenyl)-1H-1,2,4-triazol-1-yl]-N-(propan-2-yl)acetamide

[Chem. 292]

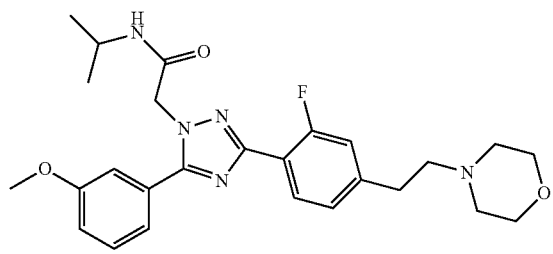

MS (ESI pos.) m/z: 482 ([M+H]+).

¹H-NMR (600 MHz, CDCl₃) δ (ppm); 1.10-1.21 (6H, m), 2.53 (4H, br. s.), 2.60-2.70 (2H, m), 2.80-2.92 (2H, m), 3.74 (4H, t, J=4.7 Hz), 3.81-3.91 (3H, m), 4.04-4.18 (1H, m), 4.90 (2H, s), 6.54 (1H, d, J=7.4 Hz), 7.01-7.25 (4H, m), 7.34-7.48 (2H, m), 7.97-8.11 (1H, m).

Example B-19

2-[3-{3-fluoro-4-[2-(morpholin-4-yl)ethyl]phenyl}-5-(3-methoxyphenyl)-1H-1,2,4-triazol-1-yl]-N-(propan-2-yl)acetamide

[Chem. 293]

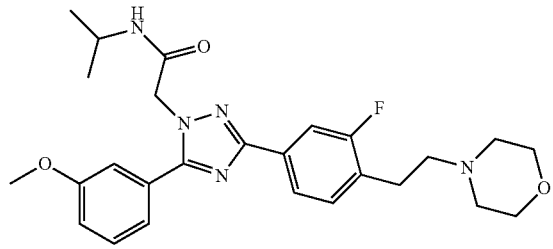

MS (ESI pos.) m/z: 482 ([M+H]+).

¹H-NMR (600 MHz, CDCl₃) δ (ppm); 1.10-1.20 (6H, m), 2.55 (4H, br. s.), 2.60-2.68 (2H, m), 2.84-2.94 (2H, m), 3.74 (2H, t, J=4.5 Hz), 3.82-3.90 (5H, m), 4.14 (1H, d, J=7.4 Hz), 4.86 (2H, d, J=5.0 Hz), 6.12 (1H, d, J=7.4 Hz), 7.00-7.11 (1H, m), 7.17-7.21 (1H, m), 7.32 (1H, t, J=7.6 Hz), 7.43 (1H, q, J=8.1 Hz), 7.75-7.93 (2H, m), 8.06 (1H, s).

Example B-20

2-[5-(3-methoxyphenyl)-3-{4-[2-(3-oxa-8-azabicyclo[3.2.1]oct-8-yl)propyl]phenyl}-1H-1,2,4-triazol-1-yl]-N-(propan-2-yl)acetamide

[Chem. 294]

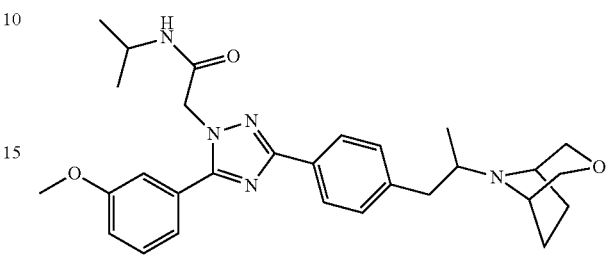

MS (ESI pos.) m/z: 504 ([M+H]+).

¹H-NMR (600 MHz, CDCl₃) δ (ppm); 1.17 (6H, d, J=6.6 Hz), 2.42-2.51 (2H, m), 2.55-2.62 (2H, m), 3.04 (2H, dd, J=12.6, 2.3 Hz), 3.36 (2H, d, J=7.0 Hz), 3.47 (2H, d, J=5.0 Hz), 3.57 (2H, dd, J=8.1, 2.3 Hz), 3.68-3.83 (3H, m), 3.88 (3H, s), 4.06-4.21 (2H, m), 4.87 (2H, s), 6.20 (1H, d, J=7.4 Hz), 7.00-7.12 (2H, m), 7.19-7.26 (3H, m), 7.39-7.49 (1H, m), 8.09 (2H, d, J=8.3 Hz).

Starting from the compound obtained in Reference Example P-B09, the same procedure as in Example A-01 was applied to synthesize the following compounds:

Example B-21: 2-[5-(3-methoxyphenyl)-3-{4-[2-(pyrrolidin-1-yl)ethyl]phenyl}-1H-1,2,4-triazol-1-yl]-N-(propan-2-yl)acetamide;

Example B-22: 2-[3-{4-[2-(3,6-dihydropyridin-1(2H)-yl)ethyl]phenyl}-5-(3-methoxyphenyl)-1H-1,2,4-triazol-1-yl]-N-(propan-2-yl)acetamide;

Example B-23: 2-[5-(3-methoxyphenyl)-3-{4-[2-(4-methylpiperidin-1-yl)ethyl]phenyl}-1H-1,2,4-triazol-1-yl]-N-(propan-2-yl)acetamide;

Example B-24: 2-[3-{4-[2-(4-cyanopiperidin-1-yl)ethyl]phenyl}-5-(3-methoxyphenyl)-1H-1,2,4-triazol-1-yl]-N-(propan-2-yl)acetamide;

Example B-25: 2-[5-(3-methoxyphenyl)-3-{4-[2-(3-methoxypiperidin-1-yl)ethyl]phenyl}-1H-1,2,4-triazol-1-yl]-N-(propan-2-yl)acetamide;

Example B-26: 2-[3-(4-{2-[4-(dimethylamino)piperidin-1-yl]ethyl}phenyl)-5-(3-methoxyphenyl)-1H-1,2,4-triazol-1-yl]-N-(propan-2-yl)acetamide;

Example B-27: 2-[5-(3-methoxyphenyl)-3-{4-[2-(octahydroisoquinolin-2(1H)-yl)ethyl]phenyl}-1H-1,2,4-triazol-1-yl]-N-(propan-2-yl)acetamide;

Example B-28: 2-[5-(3-methoxyphenyl)-3-{4-[2-(thiomorpholin-4-yl)ethyl]phenyl}-1H-1,2,4-triazol-1-yl]-N-(propan-2-yl)acetamide;

Example B-29: 2-[3-(4-{2-[(2R,6S)-2,6-dimethylmorpholin-4-yl]ethyl}phenyl)-5-(3-methoxyphenyl)-1H-1,2,4-triazol-1-yl]-N-(propan-2-yl)acetamide;

Example B-30: 2-[5-(3-methoxyphenyl)-3-{4-[2-(3-methylmorpholin-4-yl)ethyl]phenyl}-1H-1,2,4-triazol-1-yl]-N-(propan-2-yl)acetamide;

Example B-31: 2-[3-{4-[2-(3-ethylmorpholin-4-yl)ethyl]phenyl}-5-(3-methoxyphenyl)-1H-1,2,4-triazol-1-yl]-N-(propan-2-yl)acetamide;

Example B-32: 2-[5-(3-methoxyphenyl)-3-{4-[2-(4-methylpiperazin-1-yl)ethyl]phenyl}-1H-1,2,4-triazol-1-yl]-N-(propan-2-yl)acetamide;

Example B-33: 2-[3-{4-[2-(4-acetylpiperazin-1-yl)ethyl]phenyl}-5-(3-methoxyphenyl)-1H-1,2,4-triazol-1-yl]-N-(propan-2-yl)acetamide;

Example B-34: 1-[2-(4-{5-(3-methoxyphenyl)-1-[2-oxo-2-(propan-2-ylamino)ethyl]-1H-1,2,4-triazol-3-yl}phenyl)ethyl]piperidine-4-carboxamide;

Example B-35: 2-[3-(4-{2-[4-(acetylamino)piperidin-1-yl]ethyl}phenyl)-5-(3-methoxyphenyl)-1H-1,2,4-triazol-1-yl]-N-(propan-2-yl)acetamide;

Example B-36: 2-[3-{4-[2-(4-hydroxy-4-methylpiperidin-1-yl)ethyl]phenyl}-5-(3-methoxyphenyl)-1H-1,2,4-triazol-1-yl]-N-(propan-2-yl)acetamide;

Example B-37: 2-[5-(3-methoxyphenyl)-3-{4-[2-(7-oxa-2-azaspiro[3.5]non-2-yl)ethyl]phenyl}-1H-1,2,4-triazol-1-yl]-N-(propan-2-yl)acetamide;

Example B-38: 2-[5-(3-methoxyphenyl)-3-(4-{2-[4-(trifluoromethyl)piperidin-1-yl]ethyl}phenyl)-1H-1,2,4-triazol-1-yl]-N-(propan-2-yl)acetamide;

Example B-39: 2-[3-{4-[2-(4-fluoropiperidin-1-yl)ethyl]phenyl}-5-(3-methoxyphenyl)-1H-1,2,4-triazol-1-yl]-N-(propan-2-yl)acetamide;

Example B-40: 2-[3-{4-[2-(4,4-difluoropiperidin-1-yl)ethyl]phenyl}-5-(3-methoxyphenyl)-1H-1,2,4-triazol-1-yl]-N-(propan-2-yl)acetamide;

Example B-41: 2-[3-{4-[2-(3,5-dimethylmorpholin-4-yl)ethyl]phenyl}-5-(3-methoxyphenyl)-1H-1,2,4-triazol-1-yl]-N-(propan-2-yl)acetamide;

Example B-42: 2-[5-(3-methoxyphenyl)-3-{4-[2-(2-oxa-6-azaspiro[3.3]hept-6-yl)ethyl]phenyl}-1H-1,2,4-triazol-1-yl]-N-(propan-2-yl)acetamide.

Tables 1-1 to 1-4 show the results of measurements of the retention time (hereinafter RT) and MS in LCMS as performed in Examples B-21 to B-42.

TABLE 1-1

| Example | Structure | Conditions for LC-MS measurement | RT (min) | MS (ESI pos.) m/z([M + H]$^+$) |
|---|---|---|---|---|
| B-21 | 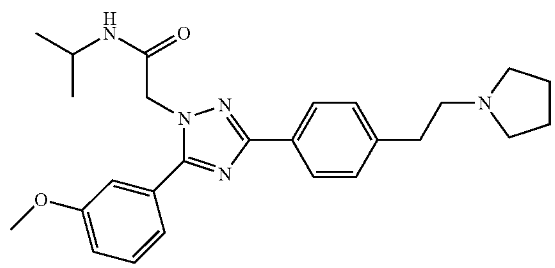 [SMILES: COc1cccc(-c2nc(-c3ccc(CCN4CCCC4)cc3)nn2CC(=O)NC(C)C)c1] | 2-1 | 0.47 | 448 |
| B-22 | 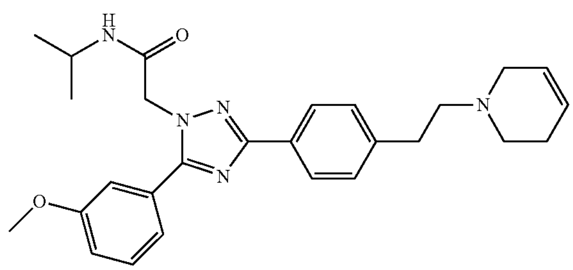 [SMILES: COc1cccc(-c2nc(-c3ccc(CCN4CC=CCC4)cc3)nn2CC(=O)NC(C)C)c1] | 2-1 | 0.48 | 460 |
| B-23 | 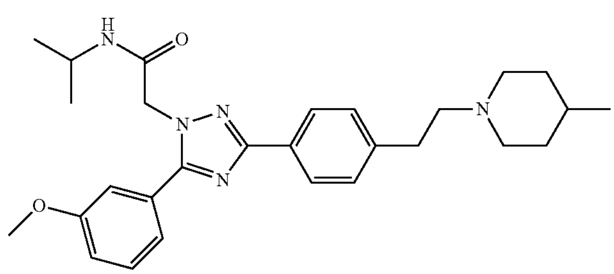 | 2-1 | 0.54 | 476 |
| B-24 | 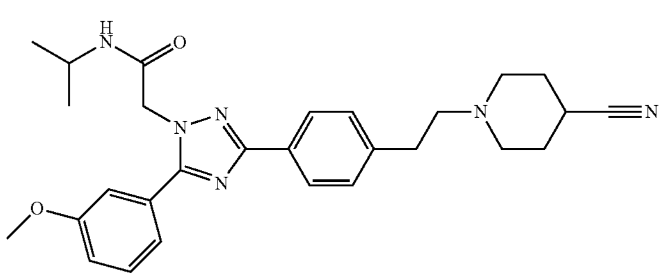 [SMILES: COc1cccc(-c2nc(-c3ccc(CCN4CCC(C#N)CC4)cc3)nn2CC(=O)NC(C)C)c1] | 2-1 | 0.47 | 487 |

TABLE 1-1-continued

| Example | Structure | Conditions for LC-MS measurement | RT (min) | MS (ESI pos.) m/z([M + H]+) |
|---|---|---|---|---|
| B-25 | 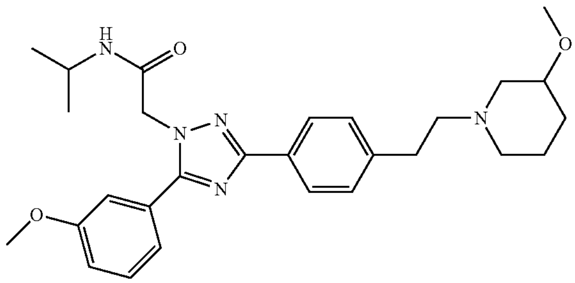 [SMILES: COc1cccc(-c2nc(-c3ccc(CCN4CCCC(OC)C4)cc3)nn2CC(=O)NC(C)C)c1] | 2-1 | 0.49 | 492 |
| B-26 | 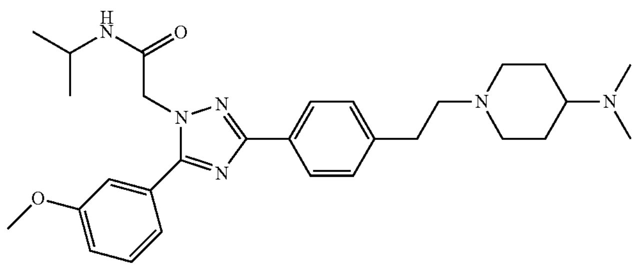 | 2-2 | 0.60 | 505 |

TABLE 1-2

| Example | Structure | Conditions for LC-MS measurement | RT (min) | MS (ESI pos.) m/z([M + H]+) |
|---|---|---|---|---|
| B-27 | 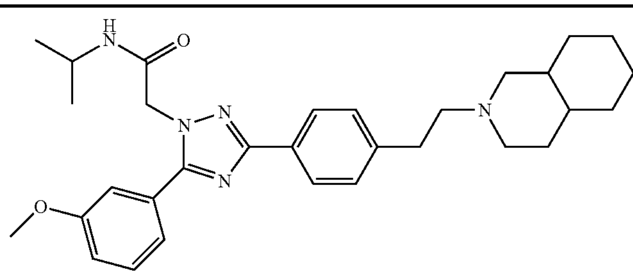 | 2-1 | 0.63 | 516 |
| B-28 | 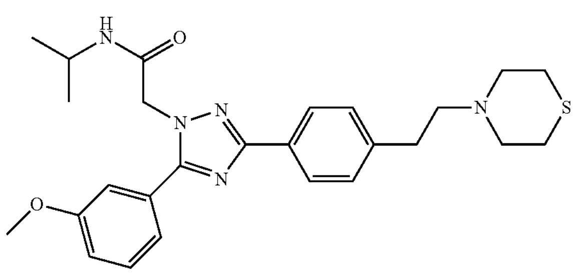 [SMILES: COc1cccc(-c2nc(-c3ccc(CCN4CCSCC4)cc3)nn2CC(=O)NC(C)C)c1] | 2-1 | 0.48 | 480 |
| B-29 | 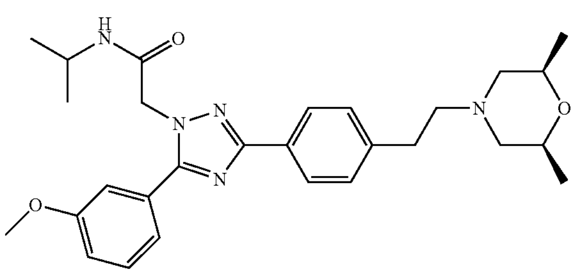 | 2-1 | 0.51 | 492 |

TABLE 1-2-continued

| Example | Structure | Conditions for LC-MS measurement | RT (min) | MS (ESI pos.) m/z([M + H]+) |
|---|---|---|---|---|
| B-30 | 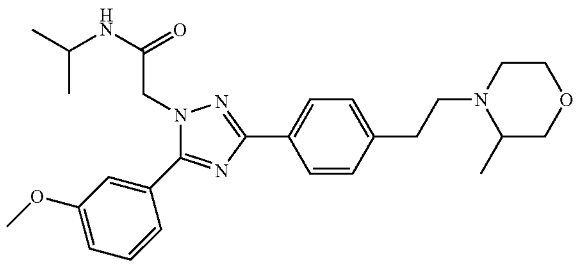 [SMILES: COc1cccc(-c2nc(-c3ccc(CCN4CCOCC4C)cc3)nn2CC(=O)NC(C)C)c1] | 2-1 | 0.46 | 478 |
| B-31 | 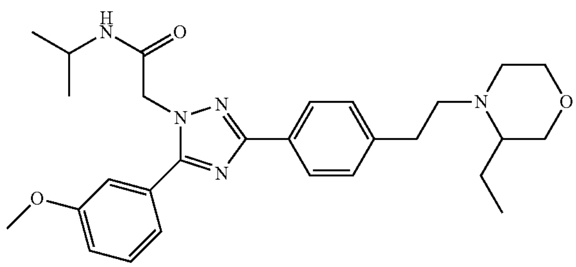 [SMILES: CCC1COCCN1CCc1ccc(-c2nc(-c3cccc(OC)c3)n(CC(=O)NC(C)C)n2)cc1] | 2-1 | 0.50 | 492 |
| B-32 | 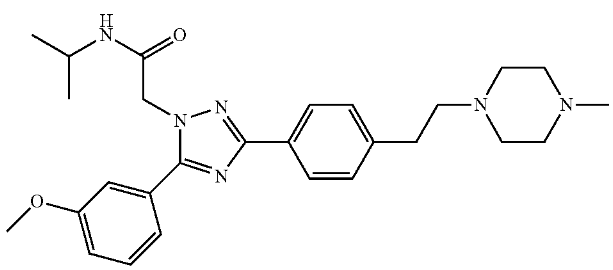 | 2-1 | 0.30 | 477 |

TABLE 1-3

| Example | Structure | Conditions for LC-MS measurement | RT (min) | MS (ESI pos.) m/z([M + H]+) |
|---|---|---|---|---|
| B-33 | 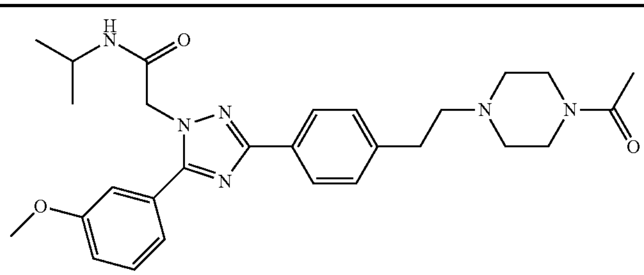 | 2-1 | 0.42 | 505 |
| B-34 | 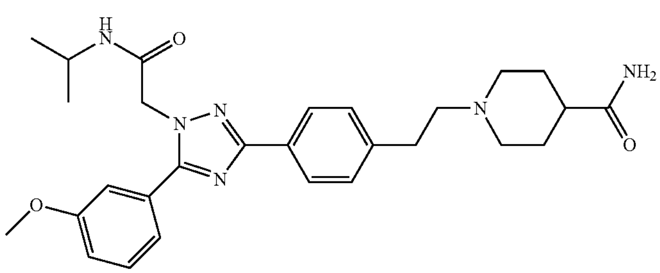 [SMILES: COc1cccc(-c2nc(-c3ccc(CCN4CCC(C(N)=O)CC4)cc3)nn2CC(=O)NC(C)C)c1] | 2-1 | 0.42 | 505 |

TABLE 1-3-continued

| Example | Structure | Conditions for LC-MS measurement | RT (min) | MS (ESI pos.) m/z([M + H]+) |
|---|---|---|---|---|
| B-35 | 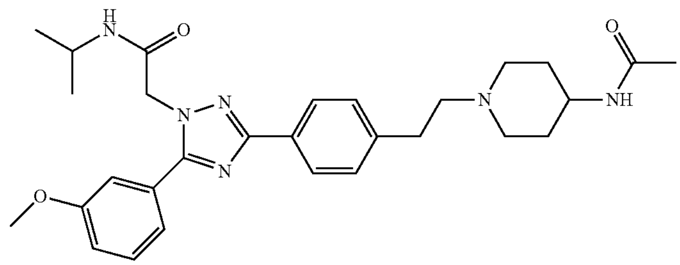 [SMILES: COc1cccc(-c2nc(-c3ccc(CCN4CCC(NC(C)=O)CC4)cc3)nn2CC(=O)NC(C)C)c1] | 2-1 | 0.43 | 519 |
| B-36 | 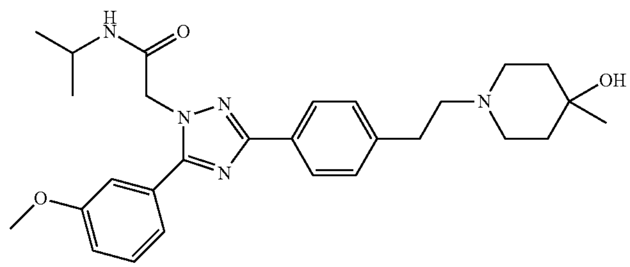 | 2-1 | 0.46 | 492 |
| B-37 | 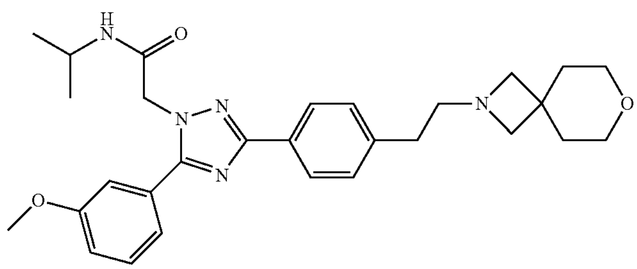 [SMILES: COc1cccc(-c2nc(-c3ccc(CCN4CC5(CCOCC5)C4)cc3)nn2CC(=O)NC(C)C)c1] | 2-1 | 0.48 | 504 |
| B-38 | 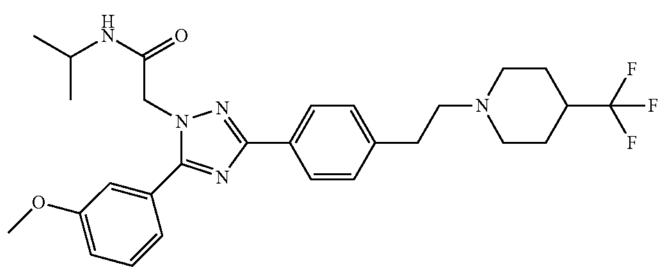 [SMILES: COc1cccc(-c2nc(-c3ccc(CCN4CCC(C(F)(F)F)CC4)cc3)nn2CC(=O)NC(C)C)c1] | 2-1 | 0.56 | 530 |

TABLE 1-4

| Example | Structure | Conditions for LC-MS measurement | RT (min) | MS (ESI pos.) m/z([M + H]+) |
|---|---|---|---|---|
| B-39 | 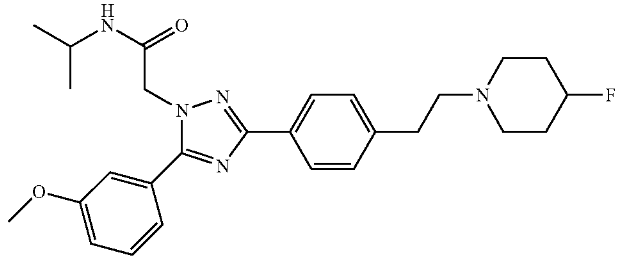 [SMILES: COc1cccc(-c2nc(-c3ccc(CCN4CCC(F)CC4)cc3)nn2CC(=O)NC(C)C)c1] | 2-1 | 0.49 | 480 |

TABLE 1-4-continued

| Example | Structure | Conditions for LC-MS measurement | RT (min) | MS (ESI pos.) m/z([M + H]+) |
|---|---|---|---|---|
| B-40 | 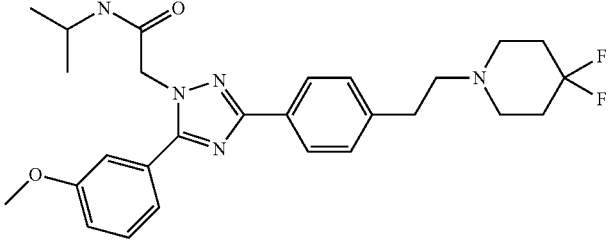 | 2-1 | 0.51 | 498 |
| B-41 | 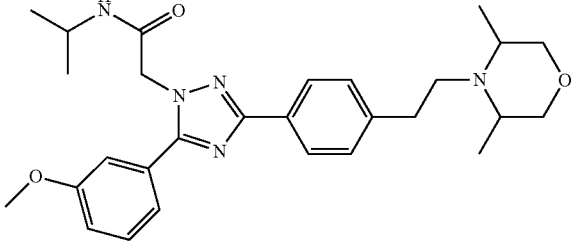 | 2-1 | 0.49 | 492 |
| B-42 | 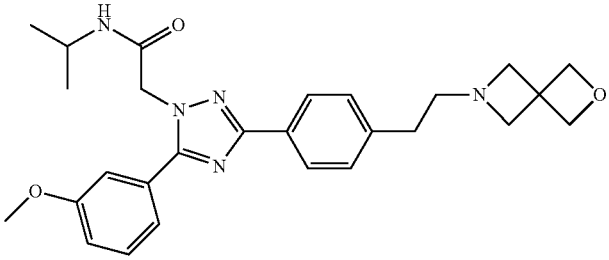 [SMILES: COc1cccc(-c2nc(-c3ccc(CCN4CC5(COC5)C4)cc3)nn2CC(=O)NC(C)C)c1] | 2-1 | 0.43 | 476 |

Starting from the compounds obtained in Reference Examples P-C10, P-C19, P-C28, P-C35, P-C42, P-C48, P-C55, P-C61, P-C69, P-C74, P-C80 and P-C85, the same procedure as in Example A-01 was applied to synthesize the following compounds of Examples C-01 to C-22:

Example C-01: 2-[4-(3-chlorophenyl)-1-{4-[2-(piperidin-1-yl)ethyl]phenyl}-1H-pyrazol-3-yl]-N-(propan-2-yl)acetamide;

Example C-02: 2-[3-(3-chlorophenyl)-1-{4-[2-(piperidin-1-yl)ethyl]phenyl}-1H-pyrazol-4-yl]-N-(propan-2-yl)acetamide;

Example C-03: 2-[3-(3-chlorophenyl)-1-{4-[2-(morpholin-4-yl)ethyl]phenyl}-1H-pyrazol-4-yl]-N-(propan-2-yl)acetamide;

Example C-04: 2-[3-(3-chlorophenyl)-1-{4-[2-(2-oxa-6-azaspiro[3.3]hept-6-yl)ethyl]phenyl}-1H-pyrazol-4-yl]-N-(propan-2-yl)acetamide;

Example C-05: 2-[1-(3-chlorophenyl)-3-{4-[2-(morpholin-4-yl)ethyl]phenyl}-1H-pyrazol-5-yl]-N-(propan-2-yl)acetamide;

Example C-06: 2-[5-(3-chlorophenyl)-3-{4-[2-(piperidin-1-yl)ethyl]phenyl}-1H-pyrazol-1-yl]-N-(propan-2-yl)acetamide;

Example C-07: 2-[5-(3-chlorophenyl)-3-{4-[2-(morpholin-4-yl)ethyl]phenyl}-1H-pyrazol-1-yl]-N-(propan-2-yl)acetamide;

Example C-08: 2-[5-(3-chlorophenyl)-2-{4-[2-(piperidin-1-yl)ethyl]phenyl}-1,3-oxazol-4-yl]-N-(propan-2-yl)acetamide;

Example C-09: 2-[5-(3-chlorophenyl)-2-{4-[2-(morpholin-4-yl)ethyl]phenyl}-1,3-oxazol-4-yl]-N-(propan-2-yl)acetamide;

Example C-10: 2-[4-(3-chlorophenyl)-2-{4-[2-(piperidin-1-yl)ethyl]phenyl}-1,3-oxazol-5-yl]-N-(propan-2-yl)acetamide;

Example C-11: 2-[4-(3-chlorophenyl)-2-{4-[2-(morpholin-4-yl)ethyl]phenyl}-1,3-oxazol-5-yl]-N-(propan-2-yl)acetamide;

Example C-12: 2-[4-(3-chlorophenyl)-2-{4-[2-(2-oxa-6-azaspiro[3.3]hept-6-yl)ethyl]phenyl}-1,3-oxazol-5-yl]-N-(propan-2-yl)acetamide;

Example C-13: 2-[5-(3-chlorophenyl)-2-{4-[2-(piperidin-1-yl)ethyl]phenyl}-1,3-thiazol-4-yl]-N-(propan-2-yl)acetamide;

Example C-14: 2-[5-(3-chlorophenyl)-2-{4-[2-(morpholin-4-yl)ethyl]phenyl}-1,3-thiazol-4-yl]-N-(propan-2-yl)acetamide;

Example C-15: 2-[5-(3-chlorophenyl)-2-{4-[2-(2-oxa-6-azaspiro[3.3]hept-6-yl)ethyl]phenyl}-1,3-thiazol-4-yl]-N-(propan-2-yl)acetamide;

Example C-16: 2-[5-(3-chlorophenyl)-2-{3-[2-(piperidin-1-yl)ethyl]phenyl}-1,3-thiazol-4-yl]-N-(propan-2-yl)acetamide;

Example C-17: 2-[5-(3-chlorophenyl)-2-{3-[2-(morpholin-4-yl)ethyl]phenyl}-1,3-thiazol-4-yl]-N-(propan-2-yl)acetamide;

Example C-18: 2-[4-(3-chlorophenyl)-1-{4-[2-(morpholin-4-yl)ethyl]phenyl}-2,5-dioxo-2,5-dihydro-1H-pyrrol-3-yl]-N-(propan-2-yl)acetamide;

Example C-19: 2-[5-(3-chlorophenyl)-3-{4-[2-(morpholin-4-yl)ethyl]phenyl}-2-oxo-2,3-dihydro-1H-imidazol-1-yl]-N-(propan-2-yl)acetamide;

Example C-20: 2-[5-(3-chlorophenyl)-4-methyl-3-{4-[2-(morpholin-4-yl)ethyl]phenyl}-2-oxo-2,3-dihydro-1H-imidazol-1-yl]-N-(propan-2-yl)acetamide;

Example C-21: 2-[1-(3-chlorophenyl)-3-{4-[2-(morpholin-4-yl)ethyl]phenyl}-1H-1,2,4-triazol-5-yl]-N-(propan-2-yl)acetamide;

Example C-22: 2-[1-(3-chlorophenyl)-3-{4-[2-(3-oxa-8-azabicyclo[3.2.1]oct-8-yl)ethyl]phenyl}-1H-1,2,4-triazol-5-yl]-N-(propan-2-yl)acetamide Tables 2-1 to 2-4 show the results of $^1$H-NMR and MS measurements in Examples C-01 to C-22.

TABLE 2-1

| Example | Structure | $^1$H NMR | MS (ESI pos.) m/z ([M + H]$^+$) |
|---|---|---|---|
| C-01 | 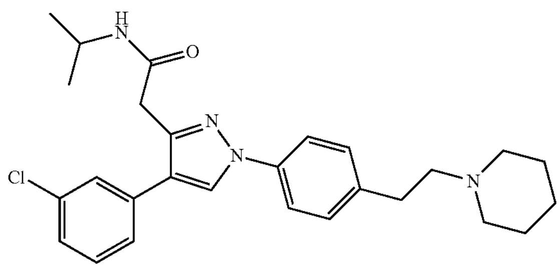 [SMILES: CC(C)NC(=O)Cc1nn(-c2ccc(CCN3CCCCC3)cc2)cc1-c1cccc(Cl)c1] | $^1$H NMR (600 MHz, CHLOROFORM-d) δ ppm; 1.10 (6 H, d, J = 6.4 Hz), 1.43-1.50 (2 H, m), 1.59-1.68 (4 H, m), 2.42-2.53 (4 H, m), 2.54-2.63 (2 H, m), 2.80-2.91 (2 H, m), 3.74 (2 H, s), 3.97-4.15 (1 H, m), 6.36 (1 H, br. s.), 7.27-7.38 (5 H, m), 7.42 (1 H, s), 7.55-7.63 (2 H, m), 7.99 (1 H, s) | 465 |
| C-02 | 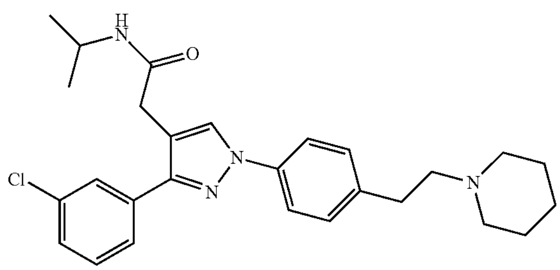 [SMILES: CC(C)NC(=O)Cc1cn(-c2ccc(CCN3CCCCC3)cc2)nc1-c1cccc(Cl)c1] | $^1$H NMR (600 MHz, CHLOROFORM-d) δ ppm; 1.04 (6 H, d, J = 6.9 Hz), 1.42-1.72 (7 H, m), 2.38-2.69 (5 H, m), 2.81-2.93 (2 H, m), 3.59 (2 H, s), 4.01-4.11 (1 H, m), 5.35 (1 H, br. s.), 7.29-7.33 (2 H, m), 7.33-7.40 (2 H, m), 7.49-7.56 (1 H, m), 7.63-7.69 (2 H, m), 7.71-7.75 (1 H, m), 7.96 (1 H, s) | 465 |
| C-03 | 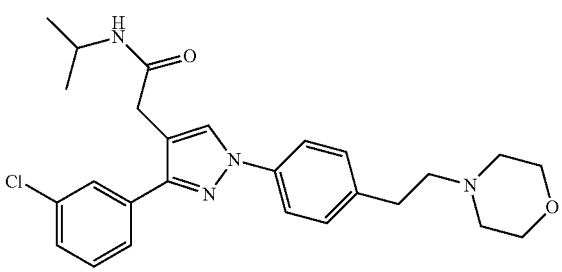 [SMILES: CC(C)NC(=O)Cc1cn(-c2ccc(CCN3CCOCC3)cc2)nc1-c1cccc(Cl)c1] | $^1$H NMR (600 MHz, CHLOROFORM-d) δ ppm; 1.04 (6 H, d, J = 6.9 Hz), 2.46-2.58 (4 H, m), 2.59-2.66 (2 H, m), 2.80-2.90 (2 H, m), 3.59 (2 H, s), 3.71-3.80 (4 H, m), 3.98-4.15 (1 H, m), 5.36 (1 H, m, J = 6.9 Hz), 7.29-7.33 (2 H, m), 7.33-7.40 (2 H, m), 7.50-7.57 (1 H, m), 7.63-7.69 (2 H, m), 7.73 (1 H, s), 7.97 (1 H, s) | 467 |
| C-04 | 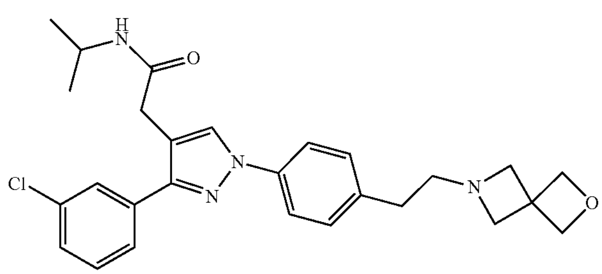 [SMILES: CC(C)NC(=O)Cc1cn(-c2ccc(CCN3CC4(COC4)C3)cc2)nc1-c1cccc(Cl)c1] | $^1$H NMR (600 MHz, CHLOROFORM-d) δ ppm; 1.07 (6 H, d, J = 6.4 Hz), 3.07-3.22 (4 H, m), 3.27-3.41 (4 H, m), 3.57 (2 H, s), 3.98-4.16 (1 H, m), 4.69 (4H, s), 5.20-5.44 (1 H, m), 7.38 (4 H, d, J = 6.9 Hz), 7.54 (1 H, s), 7.62-7.83 (3 H, m), 8.02 (1 H, s) | 479 |

TABLE 2-1-continued

| Example | Structure | ¹H NMR | MS (ESI pos.) m/z ([M + H]⁺) |
|---|---|---|---|
| C-05 | 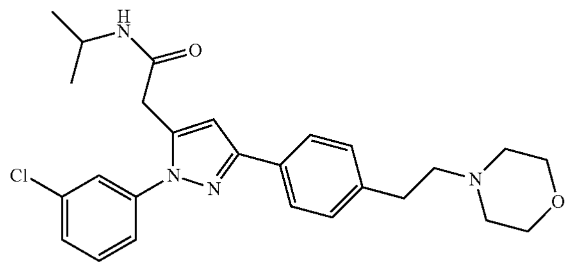 [SMILES: CC(C)NC(=O)Cc1cc(-c2ccc(CCN3CCOCC3)cc2)nn1-c1cccc(Cl)c1] | ¹H NMR (600 MHz, CHLOROFORM-d) δ ppm; 1.10 (6 H, d, J = 6.9 Hz), 2.54 (4 H, br. s.), 2.60-2.65 (2 H, m), 2.80-2.88 (2 H, m), 3.64 (2 H, s), 3.75 (4 H, br. s.), 4.00-4.13 (1 H, m), 5.33 (1 H, d, J = 5.0 Hz), 6.69 (1 H, s), 7.23-7.29 (2 H, m), 7.34-7.45 (3 H, m), 7.56 (1 H, s), 7.76-7.81 (2 H, m) | 467 |

TABLE 2-2

| Example | Structure | ¹H NMR | MS (ESI pos.) m/z ([M + H]⁺) |
|---|---|---|---|
| C-06 | 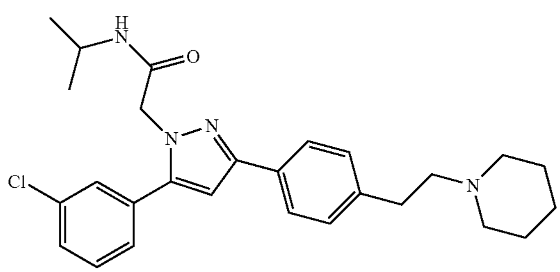 [SMILES: CC(C)NC(=O)Cn1nc(-c2ccc(CCN3CCCCC3)cc2)cc1-c1cccc(Cl)c1] | ¹H NMR (600 MHz, CHLOROFORM-d) δ ppm; 1.12 (6 H, d, J = 6.4 Hz), 1.34-1.74 (6 H, m), 2.50 (4 H, br. s.), 2.61 (2 H, br. s.), 2.87 (2 H, br. s.), 3.92-4.23 (1 H, m), 4.75 (2 H, s), 6.20 (1 H, d, J = 6.4 Hz), 6.67 (1 H, s), 7.21-7.32 (3 H, m), 7.37-7.45 (3 H, m), 7.69-7.79 (2 H, m) | 465 |
| C-07 | 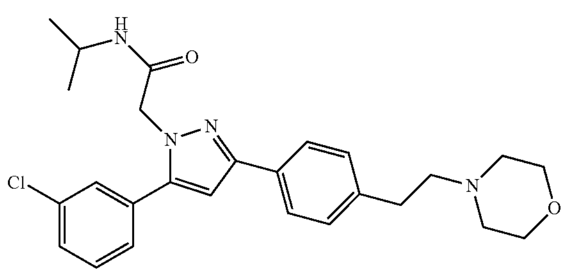 [SMILES: CC(C)NC(=O)Cn1nc(-c2ccc(CCN3CCOCC3)cc2)cc1-c1cccc(Cl)c1] | ¹H NMR (600 MHz, CHLOROFORM-d) δ ppm; 1.13 (6 H, d, J = 6.4 Hz), 2.55 (4 H, br. s.), 2.64 (2 H, br. s.), 2.78-2.94 (2 H, m), 3.76 (4 H, br. s.), 4.03-4.14 (1 H, m), 4.76 (2 H, s), 6.19 (1 H, d, J = 7.3 Hz), 6.67 (1 H, s), 7.26-7.33 (3 H, m), 7.37-7.46 (3 H, m), 7.72-7.81 (2 H, m) | 467 |
| C-08 | 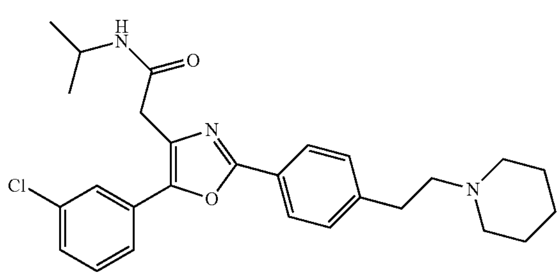 [SMILES: CC(C)NC(=O)Cc1nc(-c2ccc(CCN3CCCCC3)cc2)oc1-c1cccc(Cl)c1] | ¹H NMR (600 MHz, CHLOROFORM-d) δ ppm; 1.15 (6 H, d, J = 6.4 Hz), 1.43-1.51 (2 H, m), 1.53-1.69 (6 H, m), 2.44-2.54 (3 H, m), 2.56-2.67 (2 H, m), 2.82-2.96 (2 H, m), 3.70 (2 H, s), 3.99-4.16 (1 H, m), 6.56 (1 H, br. s.), 7.31-7.37 (3 H, m), 7.38-7.43 (1 H, m), 7.61 (1 H, d, J = 7.8 Hz), 7.68-7.75 (1 H, m), 7.96-8.03 (2 H, m) | 466 |

TABLE 2-2-continued

| Example | Structure | ¹H NMR | MS (ESI pos.) m/z ([M + H]⁺) |
|---|---|---|---|
| C-09 | 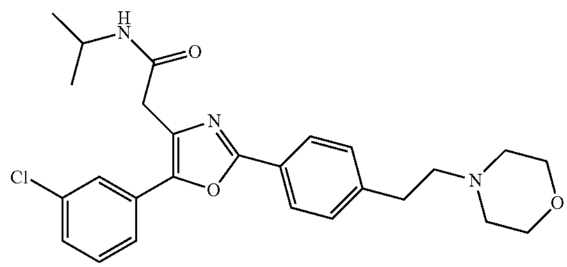 | ¹H NMR (600 MHz, CHLOROFORM-d) δ ppm; 1.15 (6 H, d, J = 6.9 Hz), 2.48-2.57 (4 H, m), 2.60-2.68 (2 H, m), 2.84-2.91 (2 H, m), 3.70 (2 H, s), 3.72-3.78 (4 H, m), 4.10 (1 H, dd, J = 14.0, 6.6 Hz), 6.53 (1 H, br. s.), 7.32-7.37 (3 H, m), 7.38-7.44 (1 H, m), 7.58-7.65 (1 H, m), 7.69-7.75 (1 H, m), 7.96-8.04 (2 H, m) | 468 |
| C-10 | 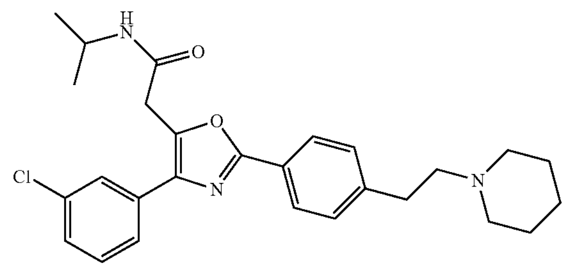 [SMILES: CC(C)NC(=O)Cc1oc(-c2ccc(CCN3CCCCC3)cc2)nc1-c1cccc(Cl)c1] | ¹H NMR (600 MHz, CHLOROFORM-d) δ ppm; 1.11 (6 H, d, J = 6.4 Hz), 1.42-1.52 (2 H, m), 1.54-1.71 (4 H, m), 2.45-2.66 (6 H, m), 2.85-2.94 (2 H, m), 3.85 (2 H, s), 4.12 (1 H, m, J = 7.8, 6.6, 6.6 Hz), 5.45 (1 H, m, J = 7.3 Hz), 7.30-7.36 (3 H, m), 7.36-7.41 (1 H, m), 7.59-7.64 (1 H, m), 7.81 (1 H, t, J = 1.8 Hz), 7.96-8.02 (2 H, m) | 466 |
| C-11 | 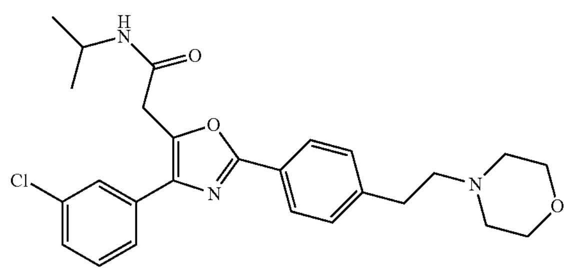 [SMILES: CC(C)NC(=O)Cc1oc(-c2ccc(CCN3CCOCC3)cc2)nc1-c1cccc(Cl)c1] | ¹H NMR(600 MHz, CHLOROFORM-d) δ ppm; 1.12 (6 H, d, J = 6.9 Hz), 2.48-2.58 (4 H, m), 2.60-2.67 (2 H, m), 2.83-2.91 (2 H, m), 3.71-3.77 (4 H, m), 3.85 (2 H, s), 4.05-4.18 (1 H, m), 5.45 (1 H, m, J = 7.8 Hz), 7.30-7.36 (3 H, m), 7.36-7.41 (1 H, m), 7.58-7.65 (1 H, m), 7.81 (1 H, m, J = 1.6, 1.6 Hz), 7.98-8.03 (2 H, m) | 468 |

TABLE 2-3

| Example | Structure | ¹H NMR | MS (ESI pos.) m/z ([M + H]⁺) |
|---|---|---|---|
| C-12 | 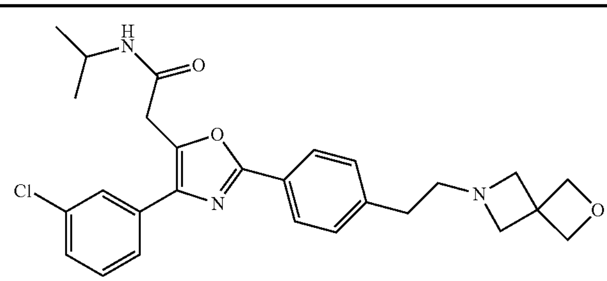 | ¹H NMR (600 MHz, CHLOROFORM-d) δ ppm; 1.12 (6 H, d, J = 6.9 Hz), 2.70 (4 H, br. s.), 3.37 (4 H, br. s.), 3.85 (2 H, s), 4.07-4.16 (1 H, m), 4.73 (4 H, s), 5.38-5.48 (1 H, m), 7.27-7.41 (4 H, m), 7.59-7.64 (1 H, m), 7.79-7.83 (1 H, m), 7.98-8.03 (2 H, m) | 480 |

TABLE 2-3-continued

| Example | Structure | ¹H NMR | MS (ESI pos.) m/z ([M + H]⁺) |
|---|---|---|---|
| C-13 | 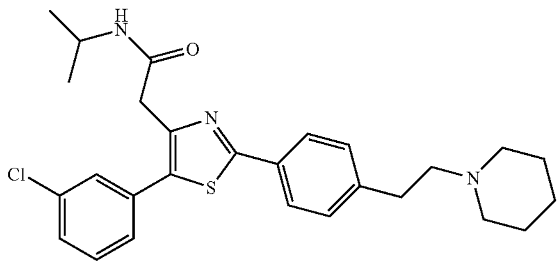 [SMILES: CC(C)NC(=O)Cc1nc(-c2ccc(CCN3CCCCC3)cc2)sc1-c1cccc(Cl)c1] | ¹H NMR (600 MHz, CHLOROFORM-d) δ ppm; 1.17 (6 H, d, J = 6.4 Hz), 1.44-1.51 (2 H, m), 1.61-1.70 (4 H, m), 2.40-2.55 (4 H, m), 2.57-2.66 (2 H, m), 2.82-2.94 (2 H, m), 3.70 (2 H, s), 4.02-4.16 (1 H, m), 6.86 (1 H, br. s.), 7.29-7.34 (2 H, m), 7.35-7.45 (3 H, m), 7.48-7.53 (1 H, m), 7.81-7.87 (2 H, m) | 482 |
| C-14 | 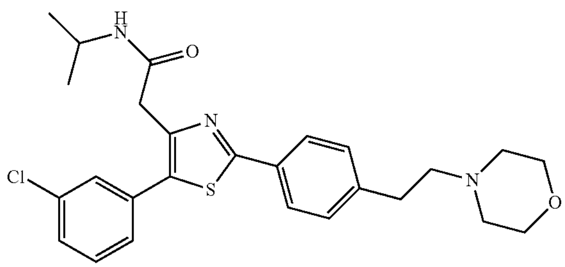 | ¹H NMR (600 MHz, CHLOROFORM-d) δ ppm; 1.17 (6 H, d, J = 6.4 Hz), 2.47-2.58 (4 H, m), 2.60-2.69 (2 H, m), 2.81-2.92 (2 H, m), 3.70 (2 H, s), 3.73-3.77 (4 H, m), 4.03-4.15 (1 H, m), 6.83 (1 H, br. s.), 7.30-7.34 (2 H, m), 7.35-7.41 (2 H, m), 7.42-7.46 (1 H, m), 7.49-7.53 (1 H, m), 7.83-7.88 (2 H, m) | 484 |
| C-15 | 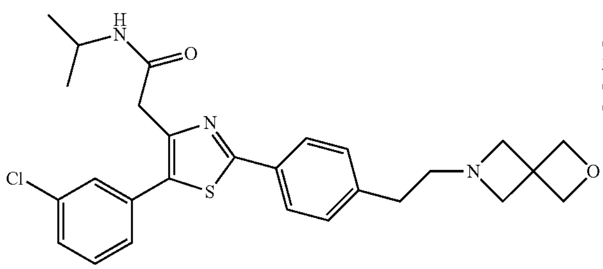 [SMILES: CC(C)NC(=O)Cc1nc(-c2ccc(CCN3CC4(COC4)C3)cc2)sc1-c1cccc(Cl)c1] | ¹H NMR (600 MHz, CHLOROFORM-d) δ ppm; 1.17 (6 H, d, J = 6.9 Hz), 2.70 (4 H, br. s.), 3.40 (4 H, s), 3.70 (2 H, s), 4.03-4.13 (1 H, m), 4.74 (4 H, s), 6.81 (1 H, br. s.), 7.29 (2 H, s), 7.35-7.46 (3 H, m), 7.51 (1 H, t, J = 1.6 Hz), 7.82-7.87 (2 H, m) | 496 |
| C-16 | 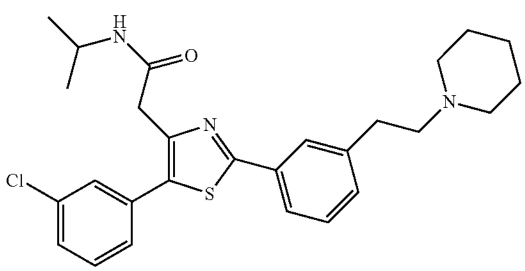 [SMILES: CC(C)NC(=O)Cc1nc(-c2cccc(CCN3CCCCC3)c2)sc1-c1cccc(Cl)c1] | ¹H NMR (600 MHz, CHLOROFORM-d) δ ppm; 1.18 (6 H, d, J = 6.4 Hz), 1.44-1.52 (2 H, m), 1.60-1.68 (4 H, m), 2.42-2.55 (4 H, m), 2.57-2.67 (2 H, m), 2.83-2.96 (2 H, m), 3.71 (2 H, s), 4.01-4.14 (1 H, m), 6.85 (1 H, br. s.), 7.29-7.33 (1 H, m), 7.35-7.42 (3 H, m), 7.42-7.47 (1 H, m), 7.50-7.54 (1 H, m), 7.73-7.77 (1 H, m), 7.79 (1 H, s) | 482 |
| C-17 | 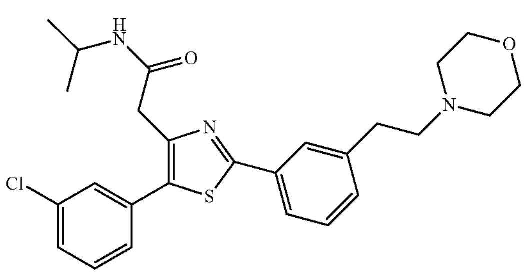 [SMILES: CC(C)NC(=O)Cc1nc(-c2cccc(CCN3CCOCC3)c2)sc1-c1cccc(Cl)c1] | ¹H NMR (600 MHz, CHLOROFORM-d) δ ppm; 1.18 (6 H, d, J = 6.9 Hz), 2.49-2.59 (4 H, m), 2.62-2.71 (2 H, m), 2.85-2.94 (2 H, m), 3.71 (2 H, s), 3.73-3.78 (4 H, m), 3.98-4.19 (1 H, m), 6.80 (1 H, br. s.), 7.32 (1 H, d, J = 7.8 Hz), 7.35-7.42 (3 H, m), 7.43-7.46 (1 H, m), 7.50-7.54 (1 H, m), 7.75-7.78 (1 H, m), 7.78-7.81 (1 H, m) | 484 |

TABLE 2-4

| Example | Structure | ¹H NMR | MS (ESI pos.) m/z ([M + H]⁺) |
|---|---|---|---|
| C-18 | 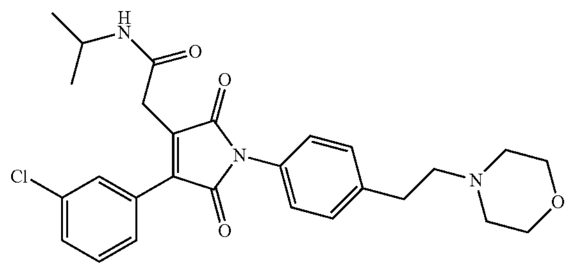 [SMILES: CC(C)NC(=O)CC1=C(c2cccc(Cl)c2)C(=O)N(c2ccc(CCN3CCOCC3)cc2)C1=O] | ¹H NMR (600 MHz, CHLOROFORM-d) δ ppm; 1.18 (6 H, d, J = 6.6 Hz), 2.54 (4 H, br. s.), 2.58-2.66 (2 H, m), 2.81-2.90 (2 H, m), 3.49 (2 H, s), 3.71-3.77 (4 H, m), 4.00-4.13 (1 H, m), 6.09 (1 H, d, J = 7.8 Hz), 7.28-7.37 (4 H, m), 7.42-7.50 (2 H, m), 7.84-7.91 (1 H, m), 7.95 (1 H, s) | 496 |
| C-19 | 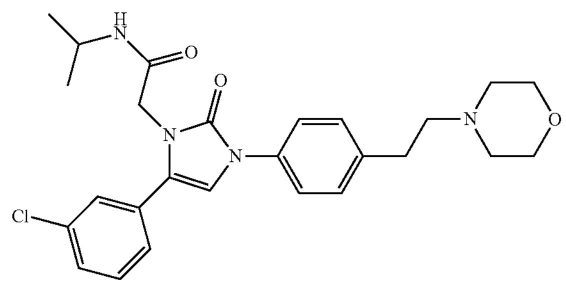 [SMILES: CC(C)NC(=O)Cn1c(-c2cccc(Cl)c2)cn(-c2ccc(CCN3CCOCC3)cc2)c1=O] | ¹H NMR (600 MHz, DMSO-d6) δ ppm; 1.01 (6 H, d, J = 6.6 Hz), 2.43 (4 H, br. s.), 2.73-2.79 (2 H, m), 3.28 (2 H, s), 3.55-3.61 (4 H, m), 3.76-3.83 (1 H, m), 4.27 (2 H, s), 7.33 (2 H, d, J = 8.7 Hz), 7.37 (1 H, s), 7.40-7.49 (3 H, m), 7.52-7.55 (1 H, m), 7.69 (2 H, d, J = 8.7 Hz), 8.04 (1 H, d, J = 7.4 Hz) | 483 |
| C-20 | 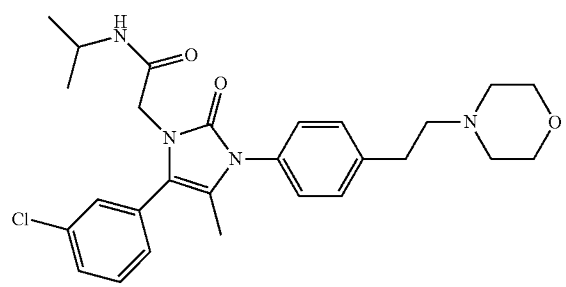 [SMILES: Cc1c(-c2cccc(Cl)c2)n(CC(=O)NC(C)C)c(=O)n1-c1ccc(CCN2CCOCC2)cc1] | ¹H NMR (600 MHz, DMSO-d6) δ ppm; 1.08 (6 H, d, J = 6.6 Hz), 2.15 (3 H, s), 3.50 (2 H, s), 3.81-3.88 (1 H, m), 4.93 (2 H, s), 7.40 (2 H, d, J = 8.3 Hz), 7.58-7.62 (1 H, m), 7.63-7.66 (1 H, m), 7.76-7.79 (1 H, m), 7.83-7.85 (1 H, m), 7.98 (2 H, d, J = 8.3 Hz), 8.34 (1 H, d, J = 7.4 Hz) | 497 |
| C-21 | 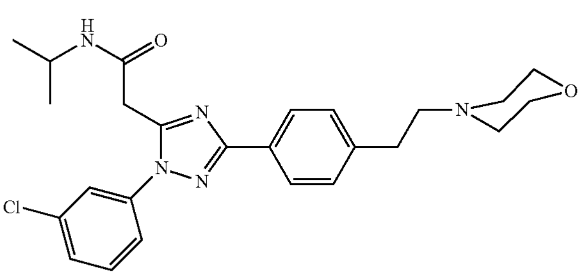 [SMILES: CC(C)NC(=O)Cc1nc(-c2ccc(CCN3CCOCC3)cc2)nn1-c1cccc(Cl)c1] | ¹H NMR (600 MHz, CHLOROFORM-d) δ ppm; 1.22 (6 H, d, J = 6.6 Hz), 2.55 (4 H, br. s.), 2.63-2.69 (2 H, m), 2.85-2.91 (2 H, m), 3.73-3.80 (6 H, m), 4.07-4.14 (1 H, m), 7.33 (2 H, d, J = 8.3 Hz), 7.39-7.50 (4 H, m), 7.61-7.63 (1 H, m), 8.06 (2 H, d, J = 8.3 Hz). | 468 |
| C-22 | 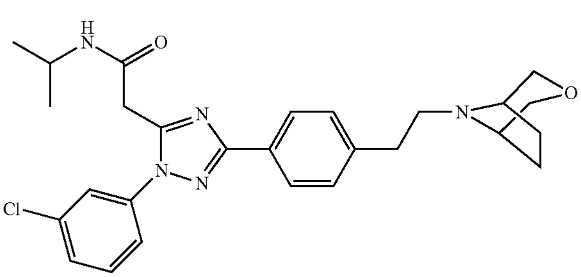 [SMILES: CC(C)NC(=O)Cc1nc(-c2ccc(CCN3C4CCC3COC4)cc2)nn1-c1cccc(Cl)c1] | ¹H NMR (600 MHz, CHLOROFORM-d) δ ppm; 1.22 (6 H, d, J = 6.6 Hz), 1.85-1.97 (4 H,. m), 2.53-2.62 (2 H, m), 2.82-2.90 (2 H, m), 3.08-3.15 (2 H, m), 3.51-3.57 (2 H, m), 3.72-3.77 (2 H, m), 3.79 (2 H, s), 4.07-4.14 (1 H, m), 7.34 (2 H, d, J = 8.3 Hz), 7.39-7.51 (4 H, m), 7.60-7.63 (1 H, m), 8.06 (2 H, d, J = 7.8 Hz). | 494 |

Example D-01

Synthesis of 2-[4-(3-chlorophenyl)-1-{4-[2-(morpholin-4-yl)ethyl]phenyl}-5-oxo-4,5-dihydro-1H-1,2,4-triazol-3-yl]-N-(propan-2-yl)acetamide

[Chem. 295]

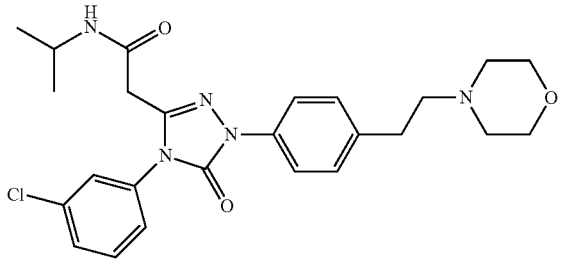

A 1,4-dioxane (1.8 mL) suspension of the compound (90 mg) obtained in Reference Example P-D08, 4-(4-bromophenethyl)morpholine (91 mg), copper iodide (64 mg), tripotassium phosphate (130 mg) and trans-N,N'-bismethyl-1,2-cyclohexanediamine (0.055 mL) was stirred overnight at an external temperature of 100° C. under a nitrogen stream. After leaving the reaction mixture to cool, it was filtered through Celite (registered trademark) and the remaining solids were washed with $CHCl_3$. The filtrate was concentrated and the resulting residue was purified by silica gel column chromatography (SNAP Cartridge KP-NH 28 g; mobile phase: n-Hexane/$CHCl_3$=25/75; v/v) and the resulting compound was washed in a mixed solvent (n-Hexane/EtOAc=6/1; v/v); subsequently, the solids were recovered by filtration to give the titled compound (77 mg as a colorless solid).

$^1$H-NMR (600 MHz, $CDCl_3$) δ (ppm); 1.14 (6H, d, J=6.6 Hz), 2.53 (4H, br. s.), 2.58-2.64 (2H, m), 2.78-2.87 (2H, m), 3.47 (2H, s), 3.75 (4H, t, J=4.5 Hz), 3.96-4.09 (1H, m), 5.92 (1H, d, J=6.6 Hz), 7.27-7.33 (3H, m), 7.37-7.50 (3H, m), 7.81-7.93 (2H, m).

MS (ESI pos.) m/z: 484 ([M+H]$^+$).

Starting from the compounds obtained in Reference Example P-D04, Reference Example P-D05, Reference Example P-D08, Reference Example P-D09, Reference Example P-D12, Reference Example P-D13, Reference Example P-D16, Reference Example P-D17, Reference Example P-D20, Reference Example P-A42, Reference Example P-A47, Reference Example P-A49, Reference Example P-A50, Reference Example P-A52, Reference Example P-A54, Reference Example P-A55, Reference Example P-A56, Reference Example P-A57, Reference Example P-A59, Reference Example P-A61, Reference Example P-A63, Reference Example P-A64, Reference Example P-A66 and Reference Example P-A67, as well as from 4-(4-bromophenethyl)morpholine, the same procedure as in Example D-01 was applied to synthesize the following compounds:

Example D-02: 2-[4-(3-chlorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]-N-(propan-2-yl)acetamide;

Example D-03: 2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-04: 2-[4-(3-chlorophenyl)-1-{5-[2-(morpholin-4-yl)ethyl]pyridin-2-yl}-5-oxo-4,5-dihydro-1H-1,2,4-triazol-3-yl]-N-(propan-2-yl)acetamide;

Example D-05: N-tert-butyl-2-[4-(4-fluoro-3-methoxyphenyl)-1-{4-[2-(morpholin-4-yl)ethyl]phenyl}-5-oxo-4,5-dihydro-1H-1,2,4-triazol-3-yl]acetamide;

Example D-06: N-tert-butyl-2-[4-(3-methoxyphenyl)-1-{4-[2-(morpholin-4-yl)ethyl]phenyl}-5-oxo-4,5-dihydro-1H-1,2,4-triazol-3-yl]acetamide;

Example D-07: N-tert-butyl-2-[4-(3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

Example D-08: N-tert-butyl-2-[4-(3-methoxyphenyl)-1-{5-[2-(morpholin-4-yl)ethyl]pyridin-2-yl}-5-oxo-4,5-dihydro-1H-1,2,4-triazol-3-yl]acetamide;

Example D-09: N-tert-butyl-2-[4-(3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

Example D-10: N-tert-butyl-2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

Example D-11: N-tert-butyl-2-[4-(4-fluoro-3-methoxyphenyl)-1-{5-[2-(morpholin-4-yl)ethyl]pyridin-2-yl}-5-oxo-4,5-dihydro-1H-1,2,4-triazol-3-yl]acetamide;

Example D-12: N-tert-butyl-2-[4-(4-fluoro-3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

Example D-13: N-tert-butyl-2-[4-(3-chlorophenyl)-1-{4-[2-(morpholin-4-yl)ethyl]phenyl}-5-oxo-4,5-dihydro-1H-1,2,4-triazol-3-yl]acetamide;

Example D-14: N-tert-butyl-2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

Example D-15: N-tert-butyl-2-[4-(3-chlorophenyl)-1-{5-[2-(morpholin-4-yl)ethyl]pyridin-2-yl}-5-oxo-4,5-dihydro-1H-1,2,4-triazol-3-yl]acetamide;

Example D-16: N-tert-butyl-2-[4-(3-chlorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

Example D-17: 2-[4-(3-chlorophenyl)-1-{4-[2-(morpholin-4-yl)propyl]phenyl}-5-oxo-4,5-dihydro-1H-1,2,4-triazol-3-yl]-N-(propan-2-yl)acetamide;

Example D-18: 2-[4-(3-chlorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

Example D-19: 2-[4-(3-chlorophenyl)-1-{5-[2-(morpholin-4-yl)propyl]pyridin-2-yl}-5-oxo-4,5-dihydro-1H-1,2,4-triazol-3-yl]-N-(propan-2-yl)acetamide;

Example D-20: 2-[4-(3-chlorophenyl)-1-{3-fluoro-4-[2-(morpholin-4-yl)ethyl]phenyl}-5-oxo-4,5-dihydro-1H-1,2,4-triazol-3-yl]-N-(propan-2-yl)acetamide;

Example D-21: 2-[4-(3-chlorophenyl)-1-{3-fluoro-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-22: 2-[4-(3-chlorophenyl)-1-{3-methoxy-4-[2-(morpholin-4-yl)ethyl]phenyl}-5-oxo-4,5-dihydro-1H-1,2,4-triazol-3-yl]-N-(propan-2-yl)acetamide;

Example D-23: 2-[4-(3-chlorophenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-24: 2-[4-(3-chlorophenyl)-1-{2-fluoro-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-25: 2-[4-(3-chlorophenyl)-1-{2-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-26: 2-[4-(3-chloro-4-fluorophenyl)-1-{4-[2-(morpholin-4-yl)ethyl]phenyl}-5-oxo-4,5-dihydro-1H-1,2,4-triazol-3-yl]-N-(propan-2-yl)acetamide;

Example D-27: 2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-28: 2-[4-(3-chloro-4-fluorophenyl)-1-{5-[2-(morpholin-4-yl)ethyl]pyridin-2-yl}-5-oxo-4,5-dihydro-1H-1,2,4-triazol-3-yl]-N-(propan-2-yl)acetamide;

Example D-29: 2-[4-(3-chloro-4-fluorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]-N-(propan-2-yl)acetamide;

Example D-30: N-tert-butyl-2-[4-(3-chloro-4-fluorophenyl)-1-{4-[2-(morpholin-4-yl)ethyl]phenyl}-5-oxo-4,5-dihydro-1H-1,2,4-triazol-3-yl]acetamide;

Example D-31: N-tert-butyl-2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

Example D-32: N-tert-butyl-2-[4-(3-chloro-4-fluorophenyl)-1-{5-[2-(morpholin-4-yl)ethyl]pyridin-2-yl}-5-oxo-4,5-dihydro-1H-1,2,4-triazol-3-yl]acetamide;

Example D-33: N-tert-butyl-2-[4-(3-chloro-4-fluorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

Example D-34: 2-[4-(3-chlorophenyl)-1-{5-[2-(3-oxa-8-azabicyclo[3.2.1]oct-8-yl)propyl]pyridin-2-yl}-5-oxo-4,5-dihydro-1H-1,2,4-triazol-3-yl]-N-(propan-2-yl)acetamide;

Example D-35: 2-(1-{4-[2-(morpholin-4-yl)ethyl]phenyl}-5-oxo-4-[3-(trifluoromethyl)phenyl]-4,5-dihydro-1H-1,2,4-triazol-3-yl)-N-(propan-2-yl)acetamide;

Example D-36: 2-[4-(3-chloro-4-fluorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

Example D-37: 2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-38: 2-[4-(4-fluoro-3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]-N-(propan-2-yl)acetamide;

Example D-39: 2-[4-(3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-40: 2-[4-(3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]-N-(propan-2-yl)acetamide;

Example D-41: 2-[4-(4-fluoro-3-methoxyphenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

Example D-42: 2-[1-{3-methoxy-4-[2-(3-oxa-8-azabicyclo[3.2.1]oct-8-yl)ethyl]phenyl}-4-(3-methoxyphenyl)-5-oxo-4,5-dihydro-1H-1,2,4-triazol-3-yl]-N-(propan-2-yl)acetamide.

Tables 3-1 to 3-7 show the results of $^1$H-NMR and MS measurements in Examples D-02 to D-42.

TABLE 3-1

| Example | Structure | $^1$H NMR | MS (ESI pos.) m/z ([M + H]$^+$) |
|---|---|---|---|
| D-02 | 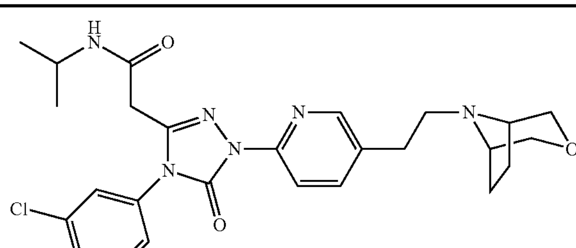 | $^1$H NMR (600 MHz, CHLOROFORM-d) δ ppm; 1.11 (6 H, d, J = 6.6 Hz), 1.89 (4 H, s), 2.53 (2 H, t, J = 7.4 Hz), 2.80 (2 H, t, J = 7.2 Hz), 3.06 (2 H, br. s.), 3.45-3.59 (4 H, m), 3.70 (2 H, d, J = 10.3 Hz), 3.93-4.05 (1 H, m), 5.70 (1 H, d, J = 7.4 Hz), 7.30-7.39 (1 H, m), 7.41-7.54 (3 H, m), 7.72 (1 H, dd, J = 8.3, 2.5 Hz), 8.12 (1 H, d, J = 8.7 Hz), 8.45 (1 H, d, J = 1.7 Hz) | 511 |
| D-03 | 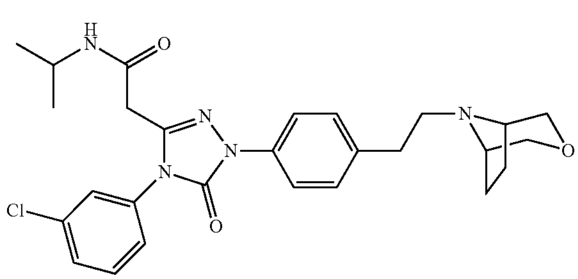 [SMILES: CC(C)NC(=O)Cc1nn(-c2ccc(CCN3C4CCC3COC4)cc2)c(=O)n1-c1cccc(Cl)c1] | $^1$H NMR (600 MHz, CHLOROFORM-d) δ ppm; 1.14 (6 H, d, J = 6.6 Hz), 1.80-1.97 (4 H, m), 2.48-2.59 (2 H, m), 2.74-2.85 (2 H, m), 3.09 (2 H, br. s.), 3.43-3.57 (4 H, m), 3.73 (2 H, d, J = 10.3 Hz), 3.94-4.10 (1 H, m), 5.91 (1 H, d, J = 9.1 Hz), 7.27-7.35 (3 H, m), 7.37-7.53 (3 H, m), 7.87 (2 H, d, J = 8.7 Hz) | 510 |

TABLE 3-1-continued

| Example | Structure | 1H NMR | MS (ESI pos.) m/z ([M + H]+) |
|---|---|---|---|
| D-04 | 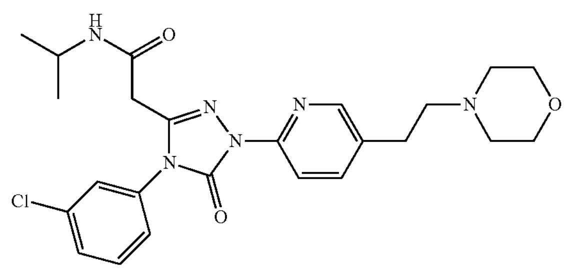 [SMILES: CC(C)NC(=O)Cc1nn(-c2ccc(CCN3CCOCC3)cn2)c(=O)n1-c1cccc(Cl)c1] | 1H NMR (600 MHz, CHLOROFORM-d) δ ppm : 1.12 (6 H, d, J = 6.6 Hz), 2.53 (4 H, br. s.), 2.57-2.66 (2 H, m), 2.84 (2 H, t, J = 7.6 Hz), 3.54 (2 H, s), 3.74 (4 H, t, J = 4.5 Hz), 3.93-4.06 (1 H, m), 5.62-5.75 (1 H, m), 7.32-7.54 (4 H, m), 7.70 (1 H, dd, J = 8.5, 2.3 Hz), 8.13 (1 H, d, J = 8.7 Hz), 8.43 (1 H, d, J = 2.1 Hz). | 485 |
| D-05 | 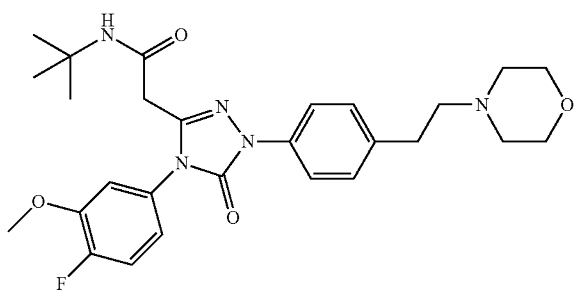 | 1H NMR (600 MHz, CHLOROFORM-D) δ ppm; 1.34 (9 H, s), 2.51-2.57 (4 H, m), 2.60-2.65 (2 H, m), 2.81-2.87 (2 H, m), 3.43 (2 H, s), 3.73-3.78 (4 H, m), 3.92 (3 H, s), 5.89-5.94 (1 H, m), 6.90-6.95 (1 H, m), 7.03-7.07 (1 H, m), 7.18-7.23 (1 H, m), 7.28-7.31 (2 H, m), 7.87-7.91 (2 H, m). | 512 |
| D-06 | 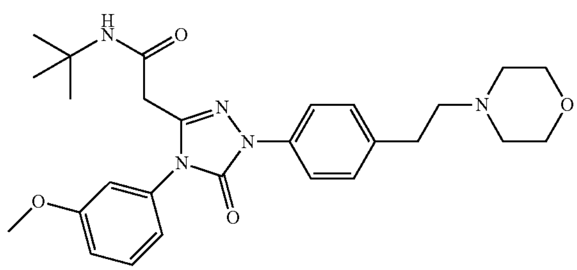 [SMILES: COc1cccc(-n2c(CC(=O)NC(C)(C)C)nn(-c3ccc(CCN4CCOCC4)cc3)c2=O)c1] | 1H NMR (600 MHz, CHLOROFORM-D) δ ppm; 1.33 (9 H, s), 2.47-2.58 (4 H, m), 2.58-2.66 (2 H, m), 2.80-2.89 (2 H, m), 3.44 (2 H, s), 3.72-3.79 (4 H, m), 3.84 (3 H, s), 5.98-6.07 (1 H, m), 6.89-6.93 (1 H, m), 6.93-6.96 (1 H, m), 7.01-7.05 (1 H, m), 7.28-7.32 (2 H, m), 7.39-7.45 (1 H, m), 7.87-7.94 (2 H, m). | 494 |
| D-07 | 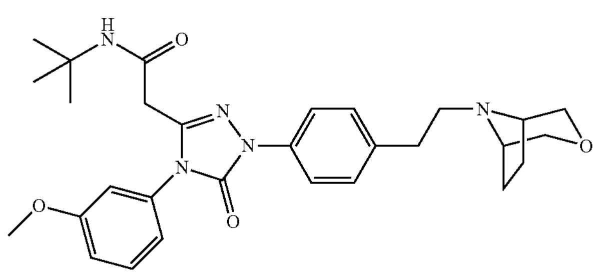 [SMILES: COc1cccc(-n2c(CC(=O)NC(C)(C)C)nn(-c3ccc(CCN4C5CCC4COC5)cc3)c2=O)c1] | 1H NMR (600 MHz, CHLOROFORM-D) δ ppm; 1.33 (9 H, s), 1.84-1.97 (4 H, m), 2.50-2.57 (2 H, m), 2.78-2.84 (2 H, m), 3.06-3.13 (2 H, m), 3.44 (2 H, s), 3.50-3.56 (2 H, m), 3.71-3.77 (2 H, m), 3.84 (3 H, s), 5.99-6.06 (1 H, m), 6.90-6.93 (1 H, m), 6.93-6.96 (1 H, m), 6.99-7.05 (1 H, m), 7.28-7.32 (2 H, m), 7.40-7.45 (1 H, m), 7.88-7.93 (2 H, m). | 520 |

TABLE 3-2

| Example | Structure | $^1$H NMR | MS (ESI pos.) m/z ([M + H]$^+$) |
|---|---|---|---|
| D-08 | 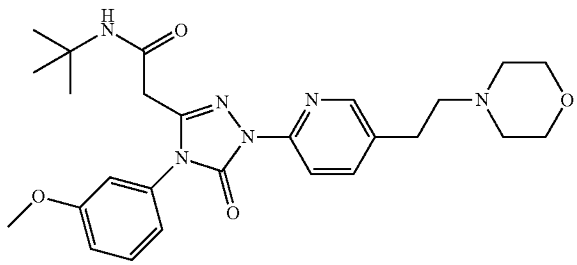 [SMILES: COc1cccc(-n2c(CC(=O)NC(C)(C)C)nn(-c3ccc(CCN4CCOCC4)cn3)c2=O)c1] | $^1$H NMR (600 MHz, CHLOROFORM-D) δ ppm; 1.30 (9 H, s), 2.49-2.57 (4 H, m), 2.59-2.65 (2 H, m), 2.81-2.87 (2 H, m), 3.51 (2 H, s), 3.71-3.77 (4 H, m), 3.84 (3 H, s), 5.69-5.77 (1 H, m), 6.94-7.00 (2 H, m), 7.01-7.05 (1 H, m), 7.40-7.46 (1 H, m), 7.66-7.72 (1 H, m), 8.12-8.18 (1 H, m), 8.40-8.46 (1 H, m). | 495 |
| D-09 | 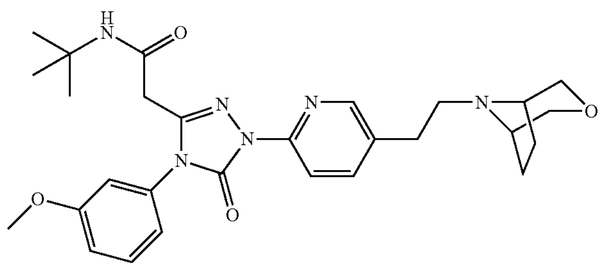 [SMILES: COc1cccc(-n2c(CC(=O)NC(C)(C)C)nn(-c3ccc(CCN4C5CCC4COC5)cn3)c2=O)c1] | $^1$H NMR (600 MHz, CHLOROFORM-D) δ ppm; 1.30 (9 H, s), 1.86-1.96 (4 H, m), 2.48-2.58 (2 H, m), 2.76-2.85 (2 H, m), 3.03-3.10 (2 H, m), 3.48-3.75 (6 H, m), 3.84 (3 H, s), 5.68-5.78 (1 H, m), 6.93-7.00 (2 H, m), 7.01-7.05 (1 H, m), 7.40-7.45 (1 H, m), 7.69-7.75 (1 H, m), 8.11-8.18 (1 H, m), 8.41-8.47 (1 H, m). | 521 |
| D-10 | 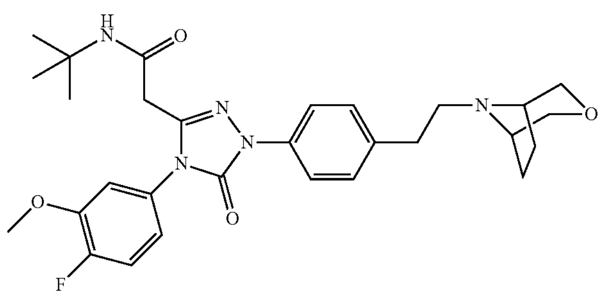 [SMILES: COc1cc(-n2c(CC(=O)NC(C)(C)C)nn(-c3ccc(CCN4C5CCC4COC5)cc3)c2=O)ccc1F] | $^1$H NMR (600 MHz, CHLOROFORM-D) δ ppm; 1.34 (9 H, s), 1.85-1.95 (4 H, m), 2.51-2.57 (2 H, m), 2.78-2.84 (2 H, m), 3.08-3.12 (2 H, m), 3.43 (2 H, s), 3.51-3.56 (2 H, m), 3.72-3.76 (2 H, m), 3.92 (3 H, s), 5.90-5.95 (1 H, m), 6.89-6.95 (1 H, m), 7.03-7.07 (1 H, m), 7.18-7.23 (1 H, m), 7.29-7.33 (2 H, m), 7.85-7.91 (2 H, m). | 538 |
| D-11 | 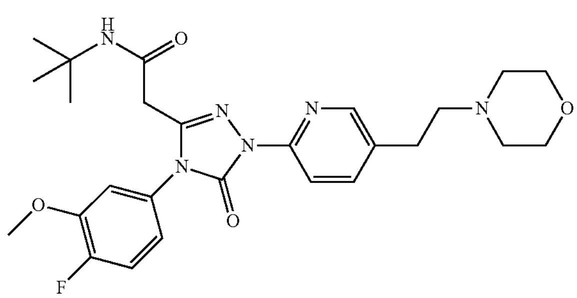 [SMILES: COc1cc(-n2c(CC(=O)NC(C)(C)C)nn(-c3ccc(CCN4CCOCC4)cn3)c2=O)ccc1F] | $^1$H NMR (600 MHz, CHLOROFORM-D) δ ppm; 1.31 (9 H, s), 2.48-2.56 (4 H, m), 2.59-2.66 (2 H, m), 2.81-2.87 (2 H, m), 3.49 (2 H, s), 3.70-3.77 (4 H, m), 3.92 (3 H, s), 5.65-5.71 (1 H, m), 6.94-6.98 (1 H, m), 7.09-7.13 (1 H, m), 7.18-7.24 (1 H, m), 7.67-7.73 (1 H, m), 8.10-8.15 (1 H, m), 8.41-8.45 (1 H, m). | 513 |
| D-12 | 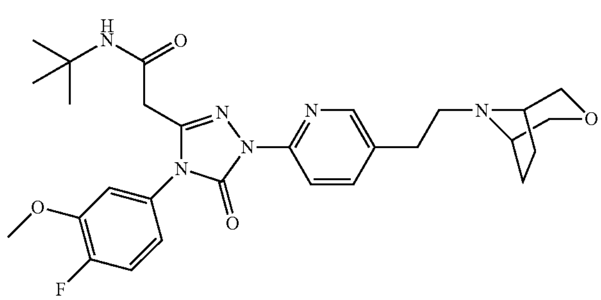 [SMILES: COc1cc(-n2c(CC(=O)NC(C)(C)C)nn(-c3ccc(CCN4C5CCC4COC5)cn3)c2=O)ccc1F] | $^1$H NMR (600 MHz, CHLOROFORM-D) δ ppm; 1.25-1.34 (9 H, m), 1.90 (4 H, br. s.), 2.47-2.58 (2 H, m), 2.75-2.84 (2 H, m), 3.02-3.11 (2 H, m), 3.49 (4 H, s), 3.67-3.73 (2 H, m), 3.92 (3 H, s), 5.64-5.72 (1 H, m), 6.91-7.00 (1 H, m), 7.07-7.13 (1 H, m), 7.18-7.23 (1 H, m), 7.69-7.75 (1 H, m), 8.09-8.15 (1 H, m), 8.42-8.47 (1 H, m). | 539 |

TABLE 3-2-continued

| Example | Structure | ¹H NMR | MS (ESI pos.) m/z ([M + H]⁺) |
|---|---|---|---|
| D-13 | 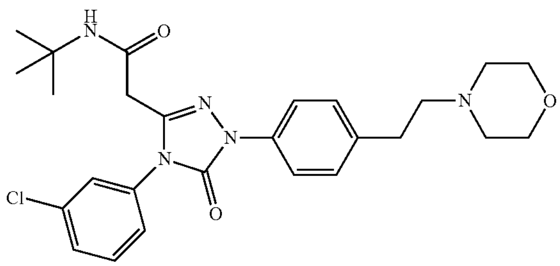 [SMILES: CC(C)(C)NC(=O)Cc1nn(-c2ccc(CCN3CCOCC3)cc2)c(=O)n1-c1cccc(Cl)c1] | ¹H NMR (600 MHz, CHLOROFORM-D) δ ppm; 1.33 (9 H, s), 2.49-2.58 (4 H, m), 2.59-2.65 (2 H, m), 2.80-2.87 (2 H, m), 3.44 (2 H, s), 3.70-3.80 (4 H, m), 5.86-5.92 (1 H, m), 7.28-7.34 (3 H, m), 7.40-7.50 (3 H, m), 7.85-7.93 (2 H, m). | 498 |

TABLE 3-3

| Example | Structure | ¹H NMR | MS (ESI pos.) m/z ([M + H]⁺) |
|---|---|---|---|
| D-14 | 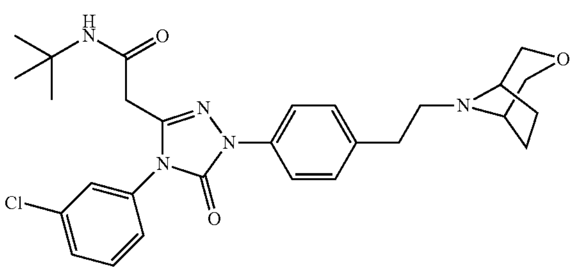 [SMILES: CC(C)(C)NC(=O)Cc1nn(-c2ccc(CCN3C4CCC3COC4)cc2)c(=O)n1-c1cccc(Cl)c1] | ¹H NMR (600 MHz, CHLOROFORM-D) δ ppm; 1.33 (9 H, s), 1.85-1.99 (4 H, m), 2.50-2.63 (2 H, m), 2.77-2.89 (2 H, m), 3.07-3.19 (2 H, m), 3.44 (2 H, s), 3.51-3.57 (2 H, m), 3.71-3.83 (2 H, m), 5.86-5.92 (1 H, m), 7.28-7.34 (3 H, m), 7.42-7.50 (3 H, m), 7.89 (2 H, d, J = 8.7 Hz). | 524 |
| D-15 | 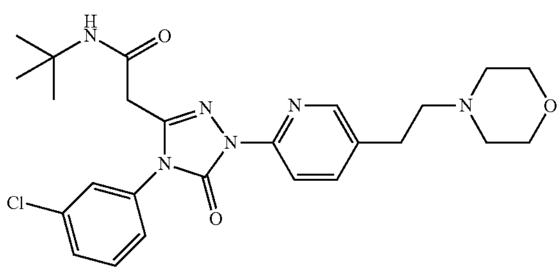 [SMILES: CC(C)(C)NC(=O)Cc1nn(-c2ccc(CCN3CCOCC3)cn2)c(=O)n1-c1cccc(Cl)c1] | ¹H NMR (600 MHz, CHLOROFORM-D) δ ppm; 1.30 (9 H, s), 2.49-2.57 (4 H, m), 2.59-2.66 (2 H, m), 2.80-2.87 (2 H, m), 3.51 (2 H, s), 3.69-3.78 (4 H, m), 5.59-5.68 (1 H, m), 7.34-7.38 (1 H, m), 7.44-7.51 (3 H, m), 7.70 (1 H, dd, J = 8.3, 2.5 Hz), 8.12 (1 H, d, J = 8.3 Hz), 8.41-8.45 (1 H, m). | 499 |
| D-16 | 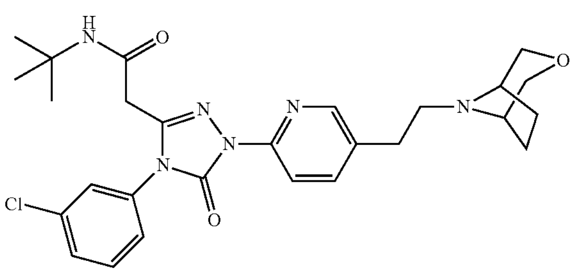 [SMILES: CC(C)(C)NC(=O)Cc1nn(-c2ccc(CCN3C4CCC3COC4)cn2)c(=O)n1-c1cccc(Cl)c1] | ¹H NMR (600 MHz, CHLOROFORM-D) δ ppm; 1.30 (9 H, s), 1.86-1.95 (4 H, m), 2.54 (2 H, t, J = 7.4 Hz), 2.80 (2 H, t, J = 7.4 Hz), 3.07 (2 H, br. s.), 3.48-3.56 (4 H, m), 3.71 (2 H, d, J = 10.3 Hz), 5.59-5.68 (1 H, m), 7.33-7.39 (1 H, m), 7.43-7.51 (3 H, m), 7.72 (1 H, dd, J = 8.3, 2.5 Hz), 8.12 (1 H, d, J = 8.3 Hz), 8.45 (1 H, d, J = 2.5 Hz). | 525 |

TABLE 3-3-continued

| Example | Structure | ¹H NMR | MS (ESI pos.) m/z ([M + H]⁺) |
|---|---|---|---|
| D-17 | 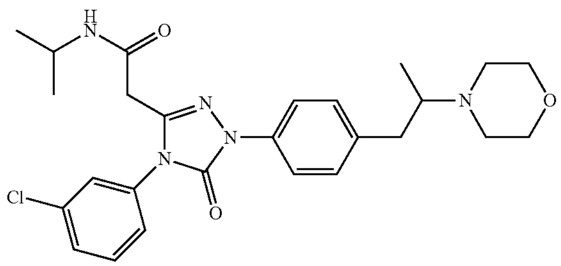 [SMILES: CC(C)NC(=O)Cc1nn(-c2ccc(CC(C)N3CCOCC3)cc2)c(=O)n1-c1cccc(Cl)c1] | ¹H NMR (600 MHz, CHLOROFORM-D) δ ppm; 0.98 (3 H, d, J = 6.6 Hz), 1.15 (6 H, d, J = 6.6 Hz), 2.46 (1 H, dd, J = 13.0, 9.3 Hz), 2.61-2.65 (4 H, m), 2.76-2.83 (1 H, m), 2.99-3.05 (1 H, m), 3.48 (2 H, s), 3.71-3.77 (4 H, m), 4.05 (1 H, d, J = 7.4 Hz), 5.89-5.95 (1 H, m), 7.25-7.28 (2 H, m), 7.30-7.33 (1 H, m), 7.42-7.44 (1 H, m), 7.47-7.50 (2 H, m), 7.88 (2 H, d, J = 8.3 Hz). | 498 |
| D-18 | 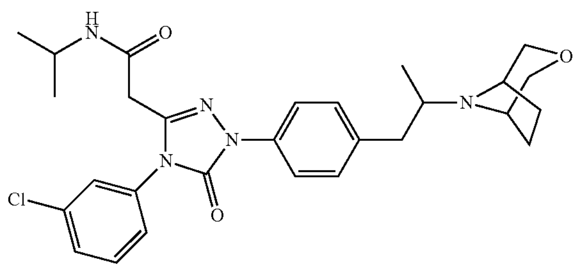 [SMILES: CC(C)NC(=O)Cc1nn(-c2ccc(CC(C)N3C4CCC3COC4)cc2)c(=O)n1-c1cccc(Cl)c1] | ¹H NMR (600 MHz, CHLOROFORM-D) δ ppm; 0.94 (3 H, d, J = 6.2 Hz), 1.15 (6 H, d, J = 6.6 Hz), 1.76-2.01 (4 H, m), 2.45 (1 H, dd, J = 13.2, 9.1 Hz), 2.52-2.59 (1 H, m), 3.01 (1 H, dd, J = 13.4, 3.5 Hz), 3.33-3.37 (1 H, m), 3.44-3.47 (1 H, m), 3.47-3.50 (2 H, m), 3.54-3.59 (2 H, m), 3.78 (2 H, dd, J = 10.3, 3.7 Hz), 4.01-4.09 (1 H, m), 5.90-5.96 (1 H, m), 7.26 (2 H, d, J = 8.3 Hz), 7.30-7.34 (1 H, m), 7.42-7.44 (1 H, m), 7.46-7.49 (2 H, m), 7.89 (2 H, d, J = 8.7 Hz). | 524 |
| D-19 | 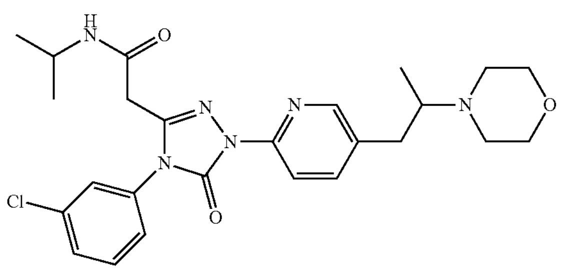 [SMILES: CC(C)NC(=O)Cc1nn(-c2ccc(CC(C)N3CCOCC3)cn2)c(=O)n1-c1cccc(Cl)c1] | ¹H NMR (600 MHz, CHLOROFORM-D) δ ppm; 0.98-1.07 (3 H, m), 1.08-1.14 (6 H, m), 2.48-3.06 (7 H, m), 3.55 (2 H, s), 3.64-3.82 (4 H, m), 3.96-4.05 (1 H, m), 5.69-5.77 (1 H, m), 7.33-7.39 (1 H, m), 7.44-7.51 (3 H, m), 7.65-7.72 (1 H, m), 8.13 (1 H, d, J = 8.3 Hz), 8.37-8.41 (1 H, m). | 499 |

TABLE 3-4

| Example | Structure | ¹H NMR | MS (ESI pos.) m/z ([M + H]⁺) |
|---|---|---|---|
| D-20 | 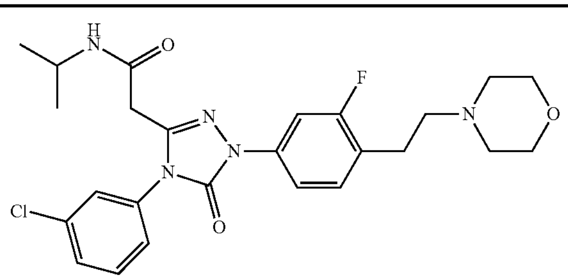 | ¹H NMR (600 MHz, CHLOROFORM-D) δ ppm; 1.15 (6 H, d, J = 6.6 Hz), 2.50-2.58 (4 H, m), 2.59-2.64 (2 H, m), 2.83-2.89 (2 H, m), 3.47 (2 H, s), 3.72-3.78 (4 H, m), 4.01-4.08 (1 H, m), 5.78-5.84 (1 H, m), 7.27-7.34 (2 H, m), 7.41-7.44 (1 H, m), 7.47-7.50 (2 H, m), 7.71-7.76 (2 H, m). | 502 |

TABLE 3-4-continued

| Example | Structure | ¹H NMR | MS (ESI pos.) m/z ([M + H]⁺) |
|---|---|---|---|
| D-21 | 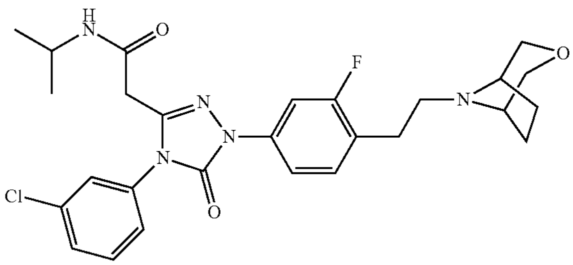 | ¹H NMR (600 MHz, CHLOROFORM-D) δ ppm; 1.15 (6 H, d, J = 6.6 Hz), 1.85-1.96 (4 H, m), 2.47-2.55 (2 H, m), 2.80-2.86 (2 H, m), 3.10 (2 H, br. s.), 3.48 (2 H, s), 3.53 (2 H, d, J = 9.1 Hz), 3.72 (2 H, d, J = 10.3 Hz), 4.01-4.08 (1 H, m), 5.77-5.86 (1 H, m), 7.28-7.34 (2 H, m), 7.41-7.51 (3 H, m), 7.70-7.76 (2 H, m). | 528 |
| D-22 | 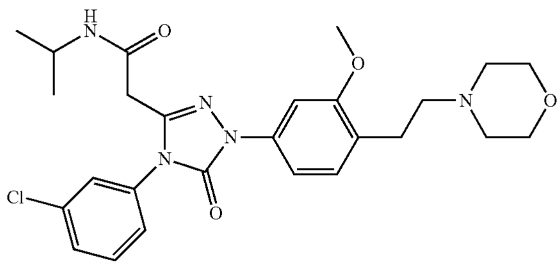 [SMILES: COc1cc(-n2nc(CC(=O)NC(C)C)n(-c3cccc(Cl)c3)c2=O)ccc1CCN1CCOCC1] | ¹H NMR (600 MHz, CHLOROFORM-D) δ ppm; 1.15 (6 H, d, J = 6.6 Hz), 2.50-2.61 (6 H, m), 2.80-2.88 (2 H, m), 3.49 (2 H, s), 3.73-3.79 (4 H, m), 3.88 (3 H, s), 4.01-4.09 (1 H, m), 5.89-5.97 (1 H, m), 7.21 (1 H, d, J = 8.3 Hz), 7.29-7.34 (1 H, m), 7.41-7.51 (4 H, m), 7.60 7.65 (1 H, m). | 514 |
| D-23 | 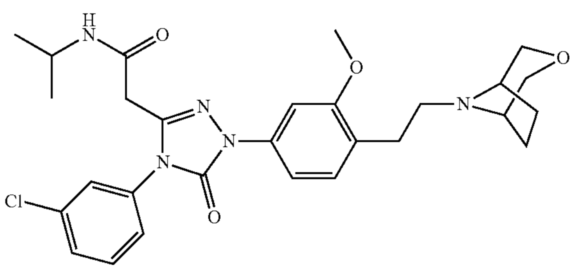 [SMILES: COc1cc(-n2nc(CC(=O)NC(C)C)n(-c3cccc(Cl)c3)c2=O)ccc1CCN1C2CCC1COC2] | ¹H NMR (600 MHz, CHLOROFORM-D) δ ppm; 1.15 (6 H, d, J = 6.6 Hz), 1.85-1.95 (4 H, m), 2.46-2.51 (2 H, m), 2.78-2.84 (2 H, m), 3.12-3.17 (2 H, m), 3.49 (2 H, s), 3.51-3.56 (2 H, m), 3.76 (2 H, d, J = 10.3 Hz), 3.87 (3 H, s), 4.02-4.09 (1 H, m), 5.90-5.97 (1 H, m), 7.22 (1 H, d, J = 8.3 Hz), 7.30-7.33 (1 H, m), 7.42-7.44 (1 H, m), 7.45 (1 H, dd, J = 8.3, 2.1 Hz), 7.47-7.49 (2 H, m), 7.62 (1 H, d, J = 2.1 Hz). | 540 |
| D-24 | 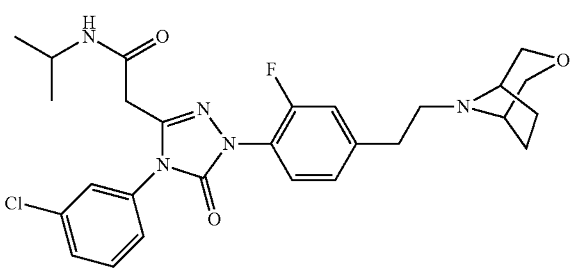 [SMILES: CC(C)NC(=O)Cc1nn(-c2ccc(CCN3C4CCC3COC4)cc2F)c(=O)n1-c1cccc(Cl)c1] | ¹H NMR (600 MHz, CHLOROFORM-D) δ ppm; 1.15 (6 H, d, J = 6.2 Hz), 1.87-1.95 (4 H, m), 2.51-2.57 (2 H, m), 2.79-2.85 (2 H, m), 3.07-3.11 (2 H, m), 3.47 (2 H, s), 3.51-3.56 (2 H, m), 3.70-3.75 (2 H, m), 4.00-4.09 (1 H, m), 6.08-6.14 (1 H, m), 7.10-7.17 (2 H, m), 7.30-7.35 (1 H, m), 7.43-7.54 (4 H, m). | 528 |
| D-25 | 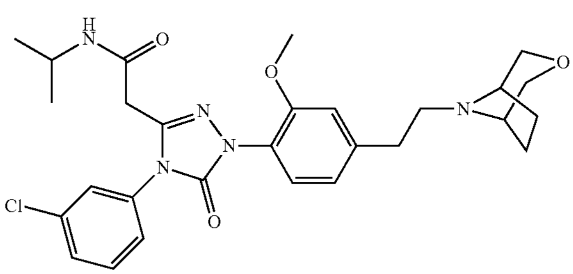 [SMILES: COc1cc(CCN2C3CCC2COC3)ccc1-n1nc(CC(=O)NC(C)C)n(-c2cccc(Cl)c2)c1=O] | ¹H NMR (600 MHz, CHLOROFORM-D) δ ppm; 1.14 (6 H, d, J = 6.6 Hz), 1.87-1.98 (4 H, m), 2.52-2.58 (2 H, m), 2.80-2.86 (2 H, m), 3.09-3.14 (2 H, m), 3.47 (2 H, s), 3.53-3.57 (2 H, m), 3.72-3.77 (2 H, m), 3.88 (3 H, s), 4.02-4.09 (1 H, m), 6.10-6.16 (1 H, m), 6.90-6.93 (1 H, m), 6.94-6.98 (1 H, m), 7.31-7.36 (2 H, m), 7.43-7.49 (3 H, m). | 540 |

TABLE 3-5

| Example | Structure | ¹H NMR | MS (ESI pos.) m/z ([M + H]⁺) |
|---|---|---|---|
| D-26 | 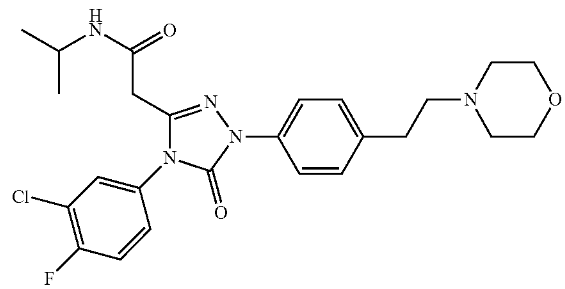 [SMILES: CC(C)NC(=O)Cc1nn(-c2ccc(CCN3CCOCC3)cc2)c(=O)n1-c1ccc(F)c(Cl)c1] | ¹H NMR (600 MHz, DMSO-d6) δ ppm; 0.89 (6 H, d, J = 6.6 Hz), 2.42 (4 H, br. s.), 2.51-2.57 (2 H, m), 2.70-2.81 (2 H, m), 3.53 (2 H, s), 3.55-3.60 (4 H, m), 3.61-3.70 (1 H, m), 7.34 (2 H, d, J = 8.3 Hz), 7.48-7.56 (1 H, m), 7.58-7.67 (1 H, m), 7.72-7.83 (3 H, m), 7.89 (1 H, d, J = 7.4 Hz) | 502 |
| D-27 | 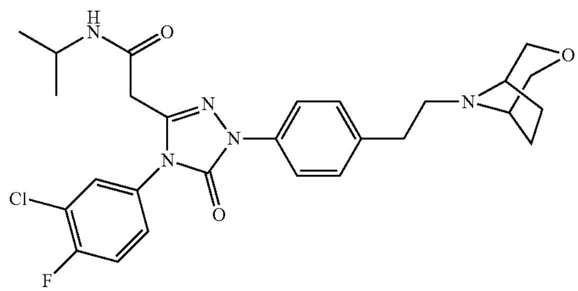 [SMILES: CC(C)NC(=O)Cc1nn(-c2ccc(CCN3C4CCC3COC4)cc2)c(=O)n1-c1ccc(F)c(Cl)c1] | ¹H NMR (600 MHz, DMSO-d6) δ ppm; 0.89 (6 H, d, J = 6.6 Hz), 1.62-1.72 (2 H, m), 1.84 (2 H, dd, J = 7.6, 3.5 Hz), 2.46 (2 H, d, J = 8.3 Hz), 2.68-2.76 (2 H, m), 3.08 (2 H, br. s.), 3.40 (2 H, dd, J = 10.1, 1.9 Hz), 3.47-3.55 (4 H, m), 3.65 (1 H, dq, J = 13.6, 6.8 Hz), 7.36 (2 H, d, J = 8.7 Hz), 7.50-7.56 (1 H, m), 7.58-7.65 (1 H, m), 7.75-7.82 (3 H, m), 7.88 (1 H, d, J = 7.4 Hz) | 528 |
| D-28 | 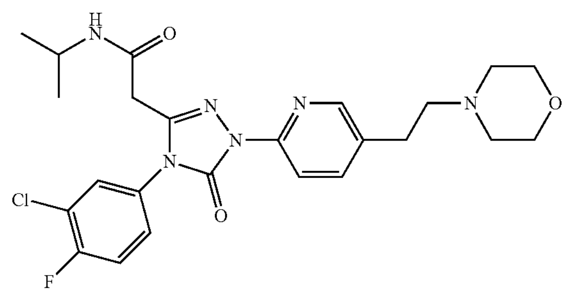 [SMILES: CC(C)NC(=O)Cc1nn(-c2ccc(CCN3CCOCC3)cn2)c(=O)n1-c1ccc(F)c(Cl)c1] | ¹H NMR (600 MHz, DMSO-d6) δ ppm; 0.90 (6 H, d, J = 6.6 Hz), 2.36-2.40 (1 H, m), 2.41-2.46 (2 H, m), 2.51-2.57 (2 H, m), 2.61 (1 H, dt, J = 3.7, 1.9 Hz), 2.79 (2 H, t, J = 7.2 Hz), 3.53 (2 H, s), 3.57 (4 H, t, J = 4.7 Hz), 3.61-3.69 (1 H, m), 7.52-7.56 (1 H, m), 7.59-7.65 (1 H, m), 7.79 (1 H, dd, J = 6.6, 2.5 Hz), 7.83 (2 H, s), 7.89 (1 H, d, J = 7.8 Hz), 8.36-8.40 (1 H, m) | 503 |
| D-29 | 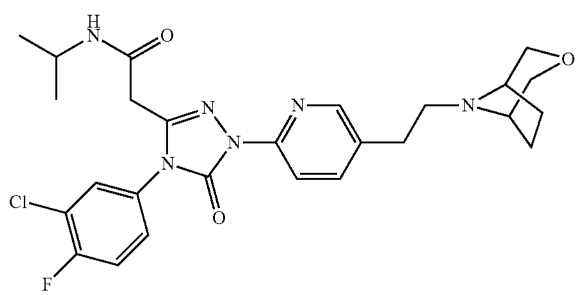 [SMILES: CC(C)NC(=O)Cc1nn(-c2ccc(CCN3C4CCC3COC4)cn2)c(=O)n1-c1ccc(F)c(Cl)c1] | ¹H NMR (600 MHz, DMSO-d6) δ ppm; 0.86-0.92 (6 H, m), 1.66-1.73 (2 H, m), 1.81-1.88 (2 H, m), 2.44-2.48 (2 H, m), 2.75 (2 H, t, J = 7.4 Hz), 3.09 (2 H, br. s.), 3.40 (2 H, dd, J = 9.9, 1.7 Hz), 3.49 (2 H, d, J = 9.9 Hz), 3.53 (2 H, s), 3.61-3.69 (1 H, m), 7.52-7.56 (1 H, m), 7.59-7.66 (1 H, m), 7.80 (1 H, dd, J = 6.6, 2.5 Hz), 7.82-7.92 (3 H, m), 8.40 (1 H, d, J = 1.7 Hz) | 529 |
| D-30 | 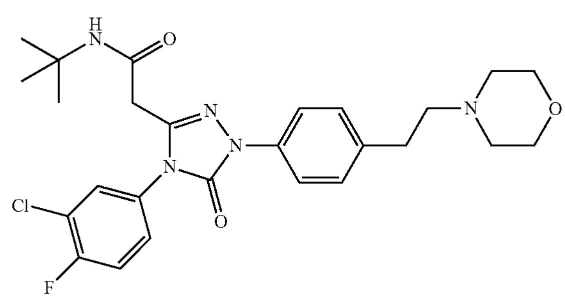 [SMILES: CC(C)(C)NC(=O)Cc1nn(-c2ccc(CCN3CCOCC3)cc2)c(=O)n1-c1ccc(F)c(Cl)c1] | ¹H NMR (600 MHz, DMSO-d6) δ ppm; 1.09 (9 H, s), 2.43 (4 H, br. s.), 2.51-2.55 (2 H, m), 2.72-2.79 (2 H, m), 3.54 (2 H, s), 3.57 (4 H, t, J = 4.7 Hz), 7.34 (2 H, d, J = 8.7 Hz), 7.49-7.56 (1 H, m), 7.59-7.67 (2 H, m), 7.76 (1 H, dd, J = 6.6, 2.5 Hz), 7.79-7.83 (2 H, m) | 516 |

TABLE 3-5-continued

| Example | Structure | ¹H NMR | MS (ESI pos.) m/z ([M + H]⁺) |
|---|---|---|---|
| D-31 | 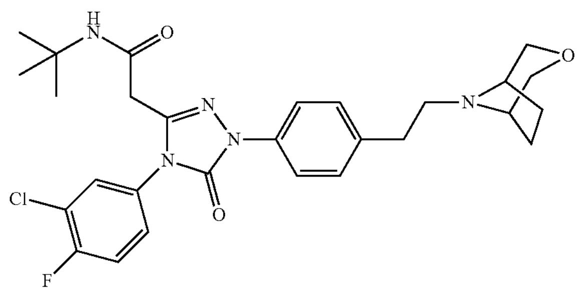 [SMILES: CC(C)(C)NC(=O)Cc1nn(-c2ccc(CCN3C4CCC3COC4)cc2)c(=O)n1-c1ccc(F)c(Cl)c1] | ¹H NMR (600 MHz, DMSO-d6) δ ppm; 1.09 (9 H, s), 1.66-1.72 (2 H, m), 1.81-1.87 (2 H, m), 2.42-2.47 (2 H, m), 2.68-2.76 (2 H, m), 3.08 (2 H, br. s.), 3.40 (2 H, dd, J = 9.9, 1.7 Hz), 3.47-3.57 (4 H, m), 7.36 (2 H, d, J = 8.7 Hz), 7.48-7.57 (1 H, m), 7.59-7.67 (2 H, m), 7.76 (1 H, dd, J = 6.6, 2.5 Hz), 7.78-7.83 (2 H, m) | 542 |

TABLE 3-6

| Example | Structure | ¹H NMR | MS (ESI pos.) m/z ([M + H]⁺) |
|---|---|---|---|
| D-32 | 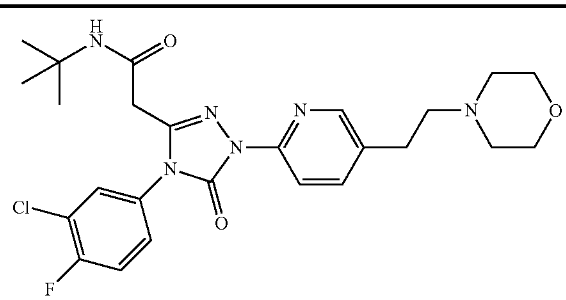 | ¹H NMR (600 MHz, CHLOROFORM-d) δ ppm; 1.30 (9 H, s), 2.52 (4 H, br. s.), 2.57-2.65 (2 H, m), 2.83 (2 H, t, J = 7.6 Hz), 3.48 (2 H, s), 3.73 (4 H, t, J = 4.5 Hz), 5.60 (1 H, br. s.), 7.31 (1 H, d, J = 8.7 Hz), 7.34-7.41 (1 H, m), 7.51-7.57 (1 H, m), 7.64-7.72 (1 H, m), 8.10 (1 H, d, J = 8.3 Hz), 8.42 (1 H, d, J = 2.1 Hz) | 517 |
| D-33 | 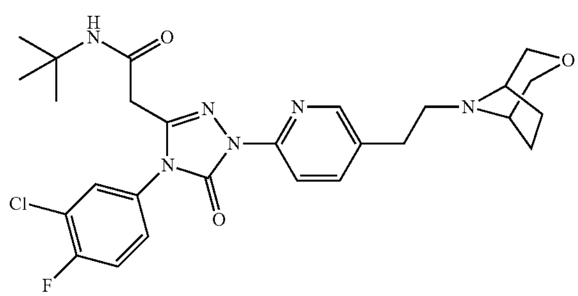 | ¹H NMR (600 MHz, DMSO-d6) δ ppm; 1.09 (9 H, s), 1.67-1.72 (2 H, m), 1.82-1.87 (2 H, m), 2.45-2.48 (2 H, m), 2.75 (2 H, t, J = 7.2 Hz), 3.09 (2 H, d, J = 0.8 Hz), 3.40 (2 H, dd, J = 9.9, 1.7 Hz), 3.50 (2 H, d, J = 9.9 Hz), 3.54 (2 H, s), 7.54 (1 H, ddd, J = 8.9, 4.3, 2.5 Hz), 7.62 (1 H, t, J = 8.9 Hz), 7.66 (1 H, s), 7.77 (1 H, dd, J = 6.6, 2.5 Hz), 7.80-7.84 (1 H, m), 7.84-7.88 (1 H, m), 8.40 (1 H, d, J = 2.1 Hz) | 543 |
| D-34 | 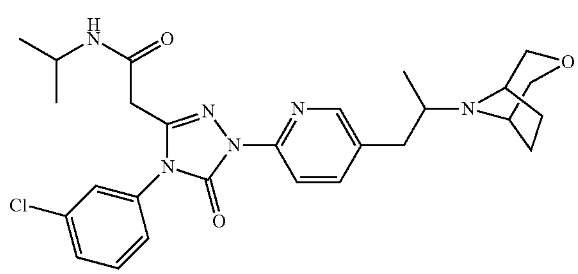 | ¹H NMR (600 MHz, CHLOROFORM-D) δ ppm; 0.92 (3 H, d, J = 6.2 Hz), 1.12 (6 H, d, J = 6.2 Hz), 1.76-1.85 (1 H, m), 1.89-1.98 (3 H, m), 2.56-2.64 (2 H, m), 2.84-2.91 (1 H, m), 3.27-3.32 (1 H, m), 3.41 (1 H, br. s.), 3.51-3.59 (4 H, m), 3.70-3.80 (2 H, m), 3.96-4.06 (1 H, m), 5.65-5.74 (1 H, m), 7.33-7.38 (1 H, m), 7.45-7.51 (3 H, m), 7.69 (1 H, dd, J = 8.5, 2.3 Hz), 8.13 (1 H, d, J = 8.3 Hz), 8.42 (1 H, d, J = 2.1 Hz). | 525 |

TABLE 3-6-continued

| Example | Structure | ¹H NMR | MS (ESI pos.) m/z ([M + H]⁺) |
|---|---|---|---|
| D-35 | 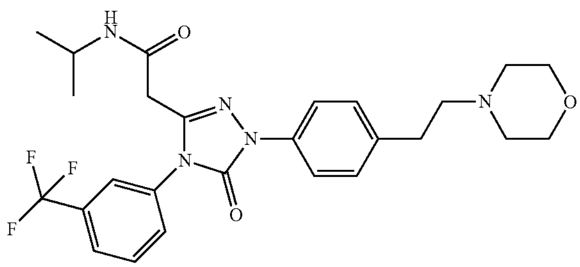 [SMILES: CC(C)NC(=O)Cc1nn(-c2ccc(CCN3CCOCC3)cc2)c(=O)n1-c1cccc(C(F)(F)F)c1] | ¹H NMR (600 MHz, CHLOROFORM-d) δ ppm; 1.08-1.16 (6 H, m), 2.53 (4 H, d, J = 0.8 Hz), 2.58-2.66 (2 H, m), 2.79-2.87 (2 H, m), 3.48 (2 H, s), 3.75 (4 H, t, J = 4.5 Hz), 3.94-4.09 (1 H, m), 5.85 (1 H, d, J = 10.3 Hz), 7.29 (2 H, d, J = 8.7 Hz), 7.57-7.71 (3 H, m), 7.72-7.77 (1 H, m), 7.83-7.93 (2 H, m) | 518 |
| D-36 | 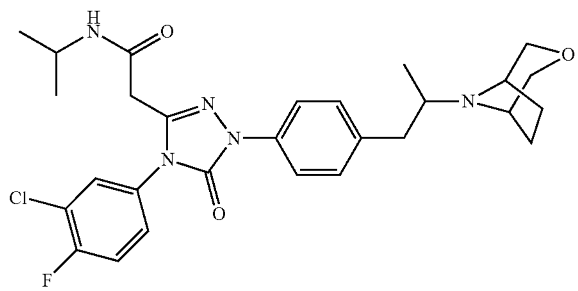 [SMILES: CC(C)NC(=O)Cc1nn(-c2ccc(CC(C)N3C4CCC3COC4)cc2)c(=O)n1-c1ccc(F)c(Cl)c1] | ¹H NMR (600 MHz, CHLOROFORM-d) δ ppm; 0.92 (4 H, d, J = 6.2 Hz), 1.12-1.18 (6 H, m), 1.75-1.97 (3 H, m), 2.44 (1 H, dd, J = 12.6, 8.9 Hz), 2.55 (1 H, d, J = 5.4 Hz), 2.99 (1 H, dd, J = 13.4, 2.7 Hz), 3.34 (1 H, d, J = 5.4 Hz), 3.41-3.48 (3 H, m), 3.56 (2 H, ddd, J = 7.6, 5.4, 2.7 Hz), 3.72-3.80 (2 H, m), 4.00-4.07 (1 H, m), 5.84 (1 H, d, J = 7.8 Hz), 7.22-7.36 (4 H, m), 7.51 (1 H, dd, J = 6.6, 2.5 Hz), 7.83-7.88 (2 H, m) | 542 |
| D-37 | 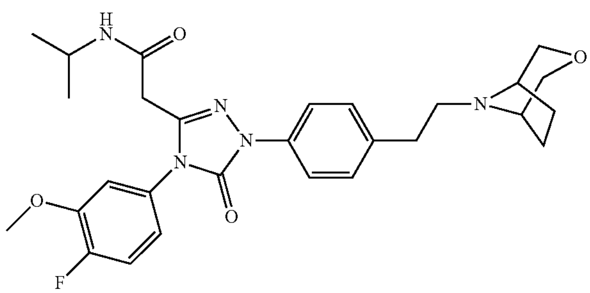 [SMILES: COc1cc(-n2c(CC(=O)NC(C)C)nn(-c3ccc(CCN4C5CCC4COC5)cc3)c2=O)ccc1F] | ¹H NMR (600 MHz, CHLOROFORM-D) δ ppm; 1.16 (6 H, d, J = 6.6 Hz), 1.85-1.97 (4 H, m), 2.49-2.59 (2 H, m), 2.78-2.86 (2 H, m), 3.10 (2 H, br. s.), 3.46 (2 H, s), 3.51-3.56 (2 H, m), 3.70-3.78 (2 H, m), 3.92 (3 H, s), 4.02-4.09 (1 H, m), 5.91-5.97 (1 H, m), 6.90-6.94 (1 H, m), 7.06 (1 H, dd, J = 7.4, 2.5 Hz), 7.21 (1 H, dd, J = 10.5, 8.5 Hz), 7.31 (2 H, d, J = 8.7 Hz), 7.89 (2H, d, J = 8.7 Hz). | 524 |

TABLE 3-7

| Example | Structure | ¹H NMR | MS (ESI pos.) m/z ([M + H]⁺) |
|---|---|---|---|
| D-38 | 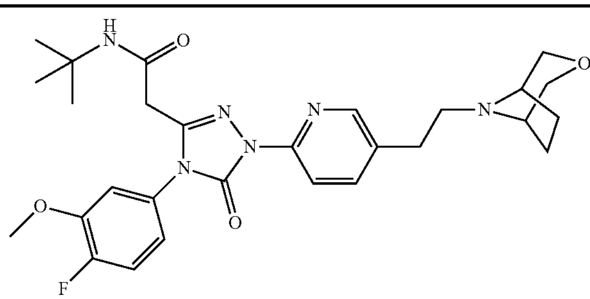 | ¹H NMR (600 MHz, CHLOROFORM-D) δ ppm; 1.13 (6 H, d, J = 6.6 Hz), 1.91 (4 H, br. s.), 2.49-2.59 (2 H, m), 2.76-2.84 (2 H, m), 3.07 (2 H, br. s.), 3.49-3.56 (4 H, m), 3.67-3.74 (2 H, m), 3.92 (3 H, s), 3.98-4.06 (1 H, m), 5.70-5.78 (1 H, m), 6.94-6.99 (1 H, m), 7.11 (1 H, dd, J = 7.4, 2.5 Hz), 7.21 (1 H, dd, J = 10.5, 8.5 Hz), 7.73 (1 H, d, J = 7.0 Hz), 8.13 (1 H, d, J = 8.7 Hz), 8.46 (1 H, d, J = 2.5 Hz). | 525 |

TABLE 3-7-continued

| Example | Structure | ¹H NMR | MS (ESI pos.) m/z ([M + H]⁺) |
|---|---|---|---|
| D-39 | 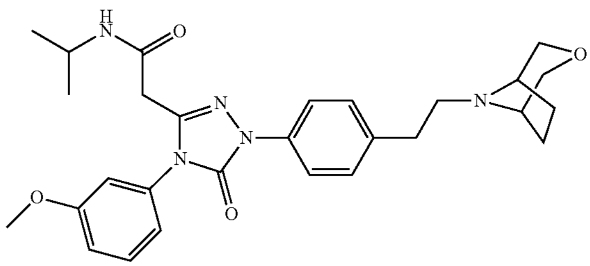 | ¹H NMR (600 MHz, CHLOROFORM-D) δ ppm; 1.15 (6 H, d, J = 6.6 Hz), 1.85-1.97 (4 H, m), 2.51-2.58 (2 H, m), 2.78-2.85 (2 H, m), 3.10 (2 H, br. s.), 3.48 (2 H, s), 3.50-3.56 (2 H, m), 3.70-3.78 (2 H, m), 3.84 (3 H, s), 4.02-4.09 (1 H, m), 6.01-6.08 (1 H, m), 6.89-6.92 (1 H, m), 6.92-6.95 (1 H, m), 7.02 (1 H, dd, J = 8.3, 2.5 Hz), 7.31 (2 H, d, J = 8.3 Hz), 7.42 (1 H, t, J = 8.3 Hz), 7.90 (2 H, d, J = 8.3 Hz). | 506 |
| D-40 | 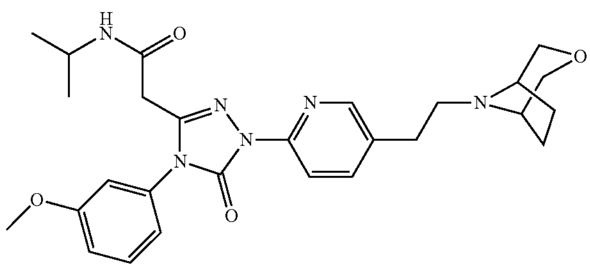 [SMILES: COc1cccc(-n2c(CC(=O)NC(C)C)nn(-c3ccc(CCN4C5CCC4COC5)cn3)c2=O)c1] | ¹H NMR (600 MHz, CHLOROFORM-D) δ ppm; 1.12 (6 H, d, J = 6.2 Hz), 1.90 (4 H, br. s.), 2.51-2.58 (2 H, m), 2.77-2.84 (2 H, m), 3.07 (2 H, br. s.), 3.50-3.57 (4 H, m), 3.71 (2 H, d, J = 9.9 Hz), 3.84 (3 H, s), 3.98-4.05 (1 H, m), 5.74-5.80 (1 H, m), 6.93-6.99 (2 H, m), 7.01-7.05 (1 H, m), 7.43 (1 H, t, J = 8.3 Hz), 7.69-7.75 (1 H, m), 8.15 (1 H, d, J = 8.3 Hz), 8.46 (1 H, d, J = 2.1 Hz). | 507 |
| D-41 | 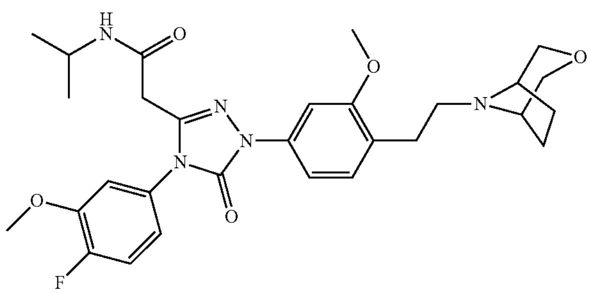 [SMILES: COc1cc(-n2c(CC(=O)NC(C)C)nn(-c3ccc(CCN4C5CCC4COC5)c(OC)c3)c2=O)ccc1F] | ¹H NMR (600 MHz, CHLOROFORM-D) δ ppm; 1.16 (6 H, d, J = 6.6 Hz), 1.84-1.97 (4 H, m), 2.49 (2 H, br. s.), 2.82 (2 H, br. s.), 3.15 (2 H, br. s.), 3.47 (2 H, s), 3.54 (2 H, d, J = 9.5 Hz), 3.72-3.81 (2 H, m), 3.87 (3 H, s), 3.92 (3 H, s), 4.02-4.09 (1 H, m), 5.90-5.97 (1 H, m), 6.90-6.94 (1 H, m), 7.05 (1 H, dd, J = 7.4, 2.5 Hz), 7.18-7.25 (2 H, m), 7.45 (1 H, dd, J = 8.1, 1.9 Hz), 7.62 (1H, d, J = 1.7 Hz). | 554 |
| D-42 | 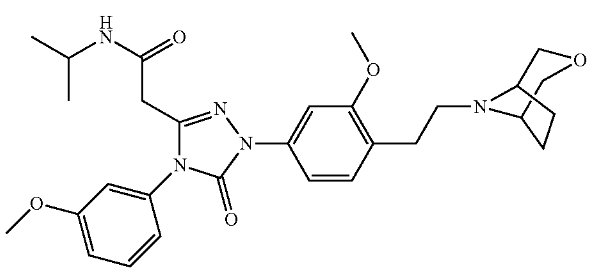 [SMILES: COc1cccc(-n2c(CC(=O)NC(C)C)nn(-c3ccc(CCN4C5CCC4COC5)c(OC)c3)c2=O)c1] | ¹H NMR (600 MHz, CHLOROFORM-D) δ ppm; 1.15 (6 H, d, J = 6.6 Hz), 1.84-1.97 (4 H, m), 2.50 (2 H, br. s.), 2.82 (2 H, br. s.), 3.16 (2 H, br. s.), 3.49 (2 H, s), 3.54 (2 H, d, J = 9.5 Hz), 3.73-3.81 (2 H, m), 3.84 (3 H, s), 3.87 (3 H, s), 4.02-4.09 (1 H, m), 6.02-6.08 (1 H, m), 6.90-6.92 (1 H, m), 6.92-6.95 (1 H, m), 7.03 (1 H, dd, J = 8.7, 2.5 Hz), 7.23 (1 H, d, J = 8.3 Hz), 7.43 (1 H, t, J = 8.1 Hz), 7.46 (1 H, dd, J = 8.3, 1.7 Hz), 7.63-7.67 (1 H, m). | 536 |

Starting from the compounds obtained in Reference Example P-D21 and Reference Example P-D22 as well as from corresponding amines, the same procedure as in Example-01 was applied to synthesize the following compounds:

Example D-43: 2-[4-(3-chloro-4-fluorophenyl)-5-oxo-1-{4-[2-(pyrrolidin-1-yl)ethyl]phenyl}-4,5-dihydro-H-1,2,4-triazol-3-yl]-N-(propan-2-yl)acetamide;

Example D-44: 2-[4-(3-chloro-4-fluorophenyl)-5-oxo-1-{4-[2-(piperidin-1-yl)ethyl]phenyl}-4,5-dihydro-1H-1,2,4-triazol-3-yl]-N-(propan-2-yl)acetamide;

Example D-45: 2-[4-(3-chlorophenyl)-5-oxo-1-{4-[2-(pyrrolidin-1-yl)ethyl]phenyl}-4,5-dihydro-1H-1,2,4-triazol-3-yl]-N-(propan-2-yl)acetamide;

Example D-46: 2-[4-(3-chlorophenyl)-5-oxo-1-{4-[2-(piperidin-1-yl)ethyl]phenyl}-4,5-dihydro-1H-1,2,4-triazol-3-yl]-N-(propan-2-yl)acetamide;

Example D-47: 2-[4-(3-chlorophenyl)-1-{4-[2-(3,6-dihydropyridin-1(2H)-yl)ethyl]phenyl}-5-oxo-4,5-dihydro-1H-1,2,4-triazol-3-yl]-N-(propan-2-yl)acetamide;

Example D-48: 2-[4-(3-chlorophenyl)-5-oxo-1-{4-[2-(thiomorpholin-4-yl)ethyl]phenyl}-4,5-dihydro-1H-1,2,4-triazol-3-yl]-N-(propan-2-yl)acetamide;

Example D-49: 2-[4-(3-chlorophenyl)-1-{4-[2-(4-methylpiperidin-1-yl)ethyl]phenyl}-5-oxo-4,5-dihydro-1H-1,2,4-triazol-3-yl]-N-(propan-2-yl)acetamide;

Example D-50: 2-[4-(3-chlorophenyl)-1-{4-[2-(3-methoxypiperidin-1-yl)ethyl]phenyl}-5-oxo-4,5-dihydro-1H-1,2,4-triazol-3-yl]-N-(propan-2-yl)acetamide;

Example D-51: 2-[4-(3-chlorophenyl)-1-{4-[2-(octahydroisoquinolin-2(1H)-yl)ethyl]phenyl}-5-oxo-4,5-dihydro-1H-1,2,4-triazol-3-yl]-N-(propan-2-yl)acetamide;
Example D-52: 2-[4-(3-chlorophenyl)-1-(4-{2-[(2R,6S)-2,6-dimethylmorpholin-4-yl]ethyl}phenyl)-5-oxo-4,5-dihydro-1H-1,2,4-triazol-3-yl]-N-(propan-2-yl)acetamide;
Example D-53: 2-[4-(3-chlorophenyl)-1-{4-[2-(3-methylmorpholin-4-yl)ethyl]phenyl}-5-oxo-4,5-dihydro-1H-1,2,4-triazol-3-yl]-N-(propan-2-yl)acetamide;
Example D-54: 2-[4-(3-chlorophenyl)-1-{4-[2-(3-ethylmorpholin-4-yl)ethyl]phenyl}-5-oxo-4,5-dihydro-1H-1,2,4-triazol-3-yl]-N-(propan-2-yl)acetamide;
Example D-55: 2-[4-(3-chlorophenyl)-1-{4-[2-(4-hydroxy-4-methylpiperidin-1-yl)ethyl]phenyl}-5-oxo-4,5-dihydro-1H-1,2,4-triazol-3-yl]-N-(propan-2-yl)acetamide;
Example D-56: 2-[4-(3-chlorophenyl)-1-{4-[2-(7-oxa-2-azaspiro[3.5]non-2-yl)ethyl]phenyl}-5-oxo-4,5-dihydro-1H-1,2,4-triazol-3-yl]-N-(propan-2-yl)acetamide;
Example D-57: 2-[4-(3-chlorophenyl)-1-{4-[2-(4-fluoropiperidin-1-yl)ethyl]phenyl}-5-oxo-4,5-dihydro-1H-1,2,4-triazol-3-yl]-N-(propan-2-yl)acetamide;
Example D-58: 2-[4-(3-chlorophenyl)-1-{4-[2-(4,4-difluoropiperidin-1-yl)ethyl]phenyl}-5-oxo-4,5-dihydro-1H-1,2,4-triazol-3-yl]-N-(propan-2-yl)acetamide;
Example D-59: 2-[4-(3-chlorophenyl)-5-oxo-1-(4-{2-[4-(trifluoromethyl)piperidin-1-yl]ethyl}phenyl)-4,5-dihydro-1H-1,2,4-triazol-3-yl]-N-(propan-2-yl)acetamide;
Example D-60: 2-[4-(3-chlorophenyl)-1-{4-[2-(3,5-dimethylmorpholin-4-yl)ethyl]phenyl}-5-oxo-4,5-dihydro-1H-1,2,4-triazol-3-yl]-N-(propan-2-yl)acetamide;
Example D-61: 2-[4-(3-chlorophenyl)-1-{4-[2-(2-oxa-6-azaspiro[3.3]hept-6-yl)ethyl]phenyl}-5-oxo-4,5-dihydro-1H-1,2,4-triazol-3-yl]-N-(propan-2-yl)acetamide.

Table 4 shows the results of $^1$H-NMR and MS measurements in Example D-43 to D-46.

TABLE 4

| Example | Structure | $^1$H NMR | MS (ESI pos.) m/z ([M + H]$^+$) |
|---|---|---|---|
| D-43 | 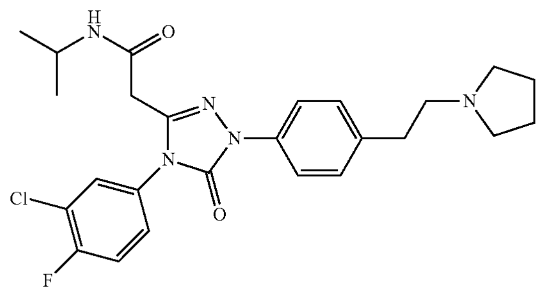 [SMILES: CC(C)NC(=O)Cc1nn(-c2ccc(CCN3CCCC3)cc2)c(=O)n1-c1ccc(F)c(Cl)c1] | $^1$H NMR (600 MHz, CHLOROFORM-d) δ ppm; 1.16 (6 H, d, J = 6.6 Hz), 1.85 (4 H, br. s.), 2.50-2.97 (7 H, m), 3.46 (2 H, s), 4.01 4.09 (1 H, m), 5.83-5.92 (1 H, m), 7.28-7.36 (5 H, m), 7.51-7.54 (1 H, m), 7.87 (2 H, d, J = 8.3 Hz) | 486 |
| D-44 | 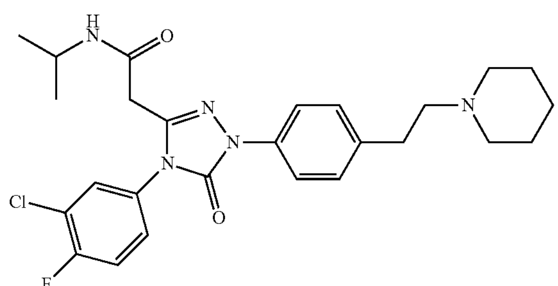 | $^1$H NMR (600 MHz, CHLOROFORM-d) δ ppm; 1.16 (6 H, d, J = 6.6 Hz), 1.43-1.50 (2 H, m), 1-63 (4 H, br. s.), 2.39-2.53 (4 H, m), 2.54-2.62 (2 H, m), 2.78-2.90 (2 H, m), 3.46 (2 H, s), 3.99-4.12 (1 H, m), 5.82-5.93 (1 H, m), 7.28-7.36 (4 H, m), 7.50-7.56 (1 H, m), 7.86 (2 H, d, J = 8.7 Hz) | 500 |
| D-45 | 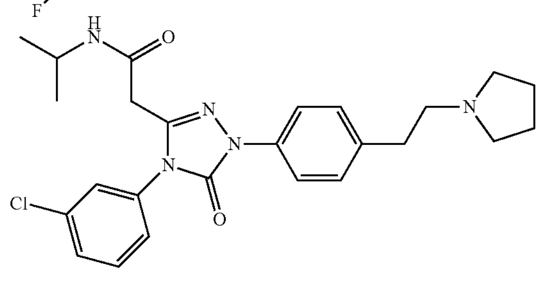 | $^1$H NMR (600 MHz, CHLOROFORM-d) δ ppm; 1.15 (6 H, dd, J = 6.6, 0.8 Hz), 1.81 (4 H, br. s.), 2.58 (4 H, br. s.), 2.67-2.76 (2 H, m), 2.82-2.90 (2 H, m), 3.47 (2 H, s), 3.96-4.12 (1 H, m), 5.89-6.02 (1 H, m), 7.30 (3 H, m), 7.37-7.52 (3 H, m), 7.87 (2 H, d, J = 7.8 Hz) | 468 |
| D-46 | 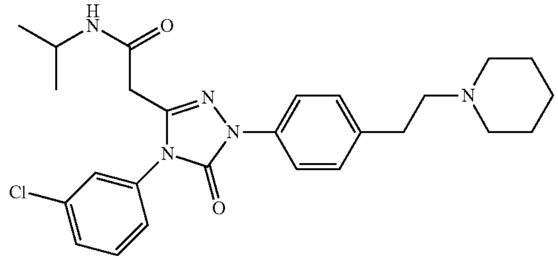 [SMILES: CC(C)NC(=O)Cc1nn(-c2ccc(CCN3CCCCC3)cc2)c(=O)n1-c1cccc(Cl)c1] | $^1$H NMR (600 MHz, CHLOROFORM-d) δ ppm; 1.14 (6 H, d, J = 6.6 Hz), 1.41-1.50 (2 H, m), 1-58-1.67 (4 H, m), 2.40-2.52 (4 H, m), 2.53-2.61 (2 H, m), 2.78-2.89 (2 H, m), 3.47 (2 H, s), 3.98-4.10 (1 H, m), 5.90 6.00 (1 H, m), 7.27-7.34 (3 H, m), 7.38-7.49 (3 H, m), 7.86 (2 H, d, J = 8.7 Hz) | 482 |

Tables 5-1 to 5-3 show the results of measurements of MS and retention time in HPLC as performed in Examples D-47 to D-61.
TABLE 5-1
| Example | Structure | Conditions for LC-MS measurement | RT (min) | MS (ESI pos.) m/z ([M + H]+) |
|---------|-----------|----------------------------------|----------|------------------------------|
| D-47 | 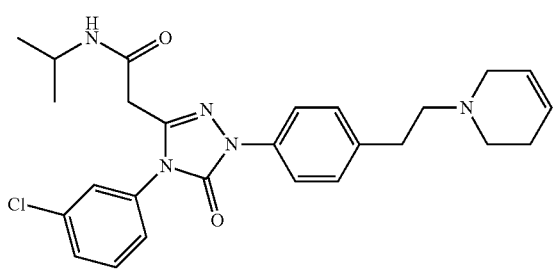 [SMILES: CC(C)NC(=O)Cc1nn(-c2ccc(CCN3CC=CCC3)cc2)c(=O)n1-c1cccc(Cl)c1] | 2-1 | 0.49 | 480 |
| D-48 | 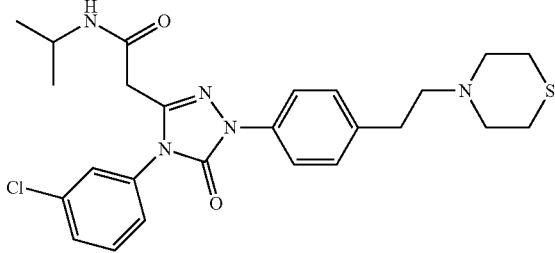 | 2-1 | 0.49 | 500 |
| D-49 | 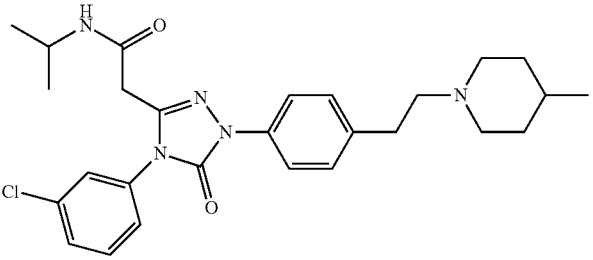 [SMILES: CC1CCN(CCc2ccc(-n3nc(CC(=O)NC(C)C)n(-c4cccc(Cl)c4)c3=O)cc2)CC1] | 2-1 | 0.54 | 496 |
| D-50 | 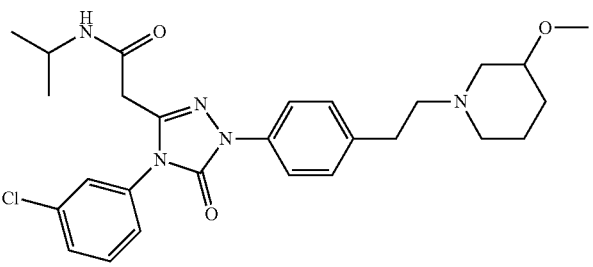 [SMILES: COC1CCCN(CCc2ccc(-n3nc(CC(=O)NC(C)C)n(-c4cccc(Cl)c4)c3=O)cc2)C1] | 2-1 | 0.50 | 512 |
| D-51 | 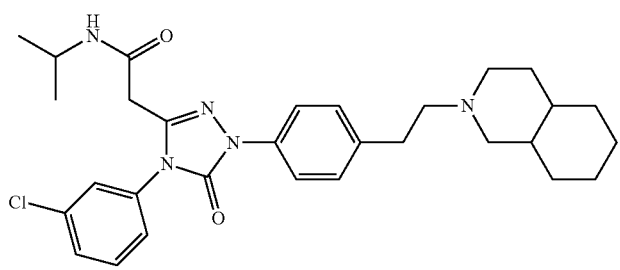 [SMILES: CC(C)NC(=O)Cc1nn(-c2ccc(CCN3CCC4CCCCC4C3)cc2)c(=O)n1-c1cccc(Cl)c1] | 2-1 | 0.63 | 536 |

TABLE 5-1-continued

| Example | Structure | Conditions for LC-MS measurement | RT (min) | MS (ESI pos.) m/z ([M + H]+) |
|---|---|---|---|---|
| D-52 | 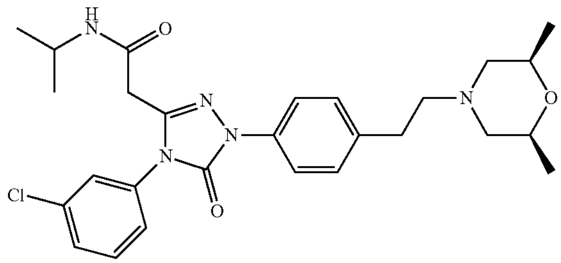 [SMILES: CC(C)NC(=O)Cc1nn(-c2ccc(CCN3C[C@@H](C)O[C@@H](C)C3)cc2)c(=O)n1-c1cccc(Cl)c1] | 2-1 | 0.52 | 512 |

TABLE 5-2

| Example | Structure | Conditions for LC-MS measurement | RT (min) | MS (ESI pos.) m/z ([M + H]+) |
|---|---|---|---|---|
| D-53 | 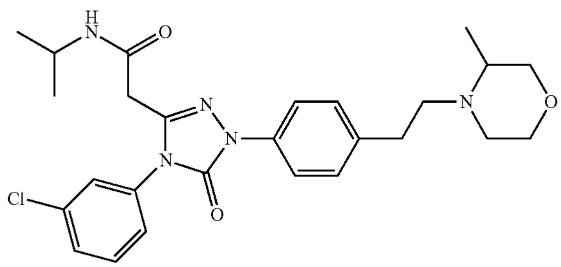 [SMILES: CC(C)NC(=O)Cc1nn(-c2ccc(CCN3CCOCC3C)cc2)c(=O)n1-c1cccc(Cl)c1] | 2-1 | 0.47 | 498 |
| D-54 | 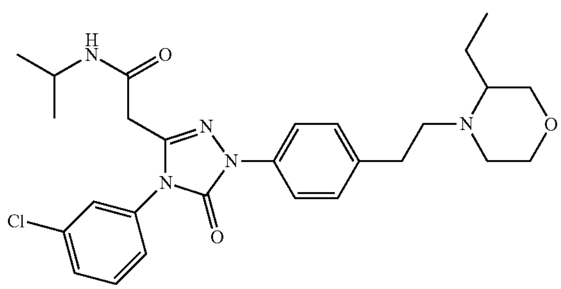 [SMILES: CCC1COCCN1CCc1ccc(-n2nc(CC(=O)NC(C)C)n(-c3cccc(Cl)c3)c2=O)cc1] | 2-1 | 0.51 | 512 |
| D-55 | 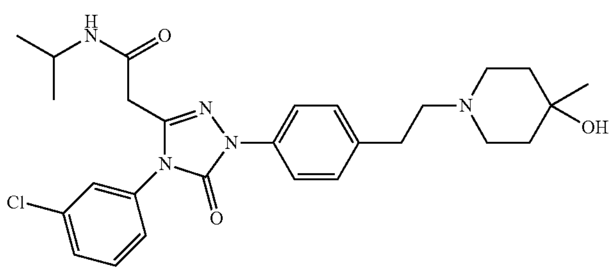 [SMILES: CC(C)NC(=O)Cc1nn(-c2ccc(CCN3CCC(C)(O)CC3)cc2)c(=O)n1-c1cccc(Cl)c1] | 2-1 | 0.46 | 512 |
| D-56 | 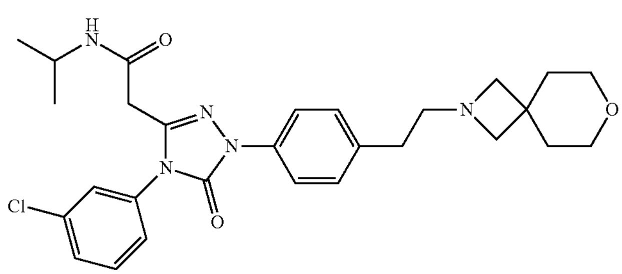 [SMILES: CC(C)NC(=O)Cc1nn(-c2ccc(CCN3CC4(CCOCC4)C3)cc2)c(=O)n1-c1cccc(Cl)c1] | 2-1 | 0.48 | 524 |

TABLE 5-2-continued

| Example | Structure | Conditions for LC-MS measurement | RT (min) | MS (ESI pos.) m/z ([M + H]+) |
|---|---|---|---|---|
| D-57 | 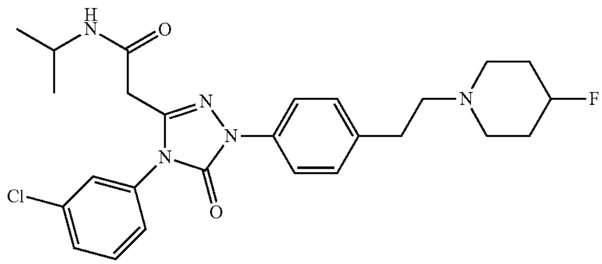 [SMILES: CC(C)NC(=O)Cc1nn(-c2ccc(CCN3CCC(F)CC3)cc2)c(=O)n1-c1cccc(Cl)c1] | 2-1 | 0.50 | 500 |
| D-58 | 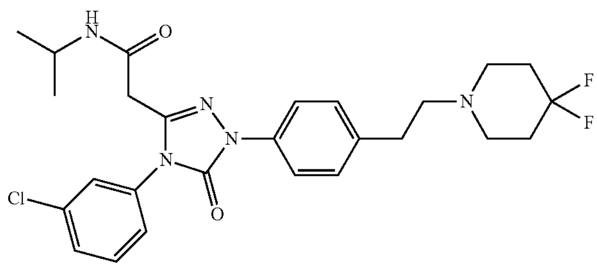 [SMILES: CC(C)NC(=O)Cc1nn(-c2ccc(CCN3CCC(F)(F)CC3)cc2)c(=O)n1-c1cccc(Cl)c1] | 2-1 | 0.52 | 518 |

TABLE 5-3

| Example | Structure | Conditions for LC-MS measurement | RT (min) | MS (ESI pos.) m/z ([M + H]+) |
|---|---|---|---|---|
| D-59 | 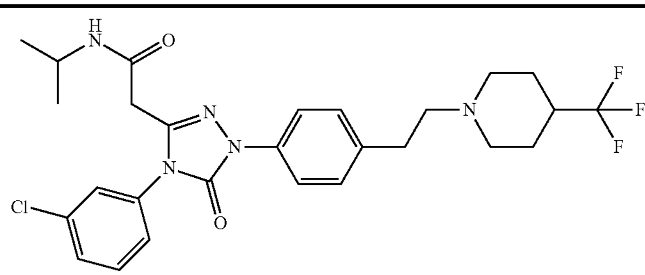 | 2-1 | 0.56 | 550 |
| D-60 | 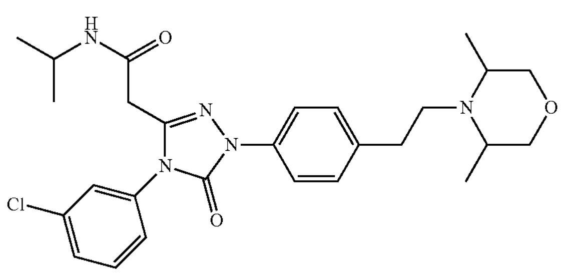 [SMILES: CC(C)NC(=O)Cc1nn(-c2ccc(CCN3C(C)COCC3C)cc2)c(=O)n1-c1cccc(Cl)c1] | 2-1 | 0.49 | 512 |
| D-61 | 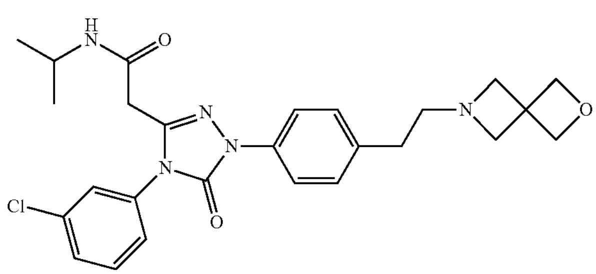 [SMILES: CC(C)NC(=O)Cc1nn(-c2ccc(CCN3CC4(COC4)C3)cc2)c(=O)n1-c1cccc(Cl)c1] | 2-1 | 0.44 | 496 |

Test Example 1

Binding Test for V1b Receptor

Human V1b receptor was transiently expressed in 293FT cells (Invitrogen). The cells were collected and then homogenated in a 15 mmol/L tris-hydrochloric acid buffer (pH 7.4 and containing 2 mmol/L magnesium chloride, 0.3 mmol/L ethylenediaminetetracetic acid, and 1 mmol/L glycol ether diaminetetraacetic acid). The resulting homogenate was centrifuged at 50,000×g at 4° C. for 20 minutes. The precipitate was resuspended in a 75 mmol/L tris-hydrochloric acid buffer (pH 7.4 and containing 12.5 mmol/L magnesium chloride, 0.3 mmol/L ethylenediaminetetracetic acid, 1 mmol/L glycol ether diaminetetraacetic acid, and 250 mmol/L sucrose) to give a crude membrane preparation, which was stored at −80° C. until the binding test was initiated. In the binding test, the crude membrane preparation was diluted with a 50 mmol/L tris-hydrochloric acid buffer (pH 7.4 and containing 10 mmol/L magnesium chloride and 0.1% bovine serum albumin) and mixed with each test compound and [$^3$H]AVP (final concentration: 0.4 to 1 nmol/L), followed by incubation at room temperature for 60 minutes. The test compound was serially diluted with DMSO so that it would have final concentrations of 0.01 nmol/L to 1 μmol/L at the time of mixing. After the incubation, the mixture was suction filtered through a GF/C filter that was preliminarily impregnated with 0.3% polyethyleneimine. The GF/C filter was dried and after adding a scintillator, the residual radioactivity on the filter was measured using TopCount (PerkinElmer Inc.). The radioactivity in the presence of unlabeled AVP at 10 mmol/L was defined as 0%, and the radioactivity in the absence of unlabeled AVP was defined as 100%. A dose-response curve was plotted from radio activities in the presence of a test compound at various concentrations, and the 50% inhibitory concentration (IC$_{50}$ value) of the test compound was calculated. The IC$_{50}$ values of the compounds of the present invention were in the range of 0.1 to 1000 nM. The results are shown in Tables 6-1 and 6.2

TABLE 6-1

| Example No. | IC$_{50}$ value (nmol/L) |
|---|---|
| A-01 | 15 |
| A-02 | 3.7 |
| A-03 | 10~100 |
| A-04 | 10~100 |
| A-05 | 10~100 |
| A-06 | 10~100 |
| A-07 | 18 |
| A-08 | 0.82 |
| A-09 | 16 |
| A-10 | 3.7 |
| A-11 | 10 |
| A-12 | 17 |
| A-13 | 10~100 |
| A-14 | 100~1000 |
| A-15 | 2.4 |
| A-16 | 100~1000 |
| A-17 | 10~100 |
| A-18 | 19 |
| A-19 | 10~100 |
| A-20 | 12 |
| A-21 | 3.2 |
| A-22 | 2.6 |
| A-23 | 11 |
| A-24 | 10~100 |
| A-25 | 14 |
| A-26 | 3.4 |
| A-27 | 3.6 |
| A-28 | 10~100 |
| A-29 | 27 |
| A-30 | 21 |
| A-31 | 10~100 |
| A-32 | 100~1000 |
| A-33 | 100~1000 |
| A-34 | 100~1000 |
| A-35 | 100~1000 |
| A-36 | 20 |
| A-37 | 10~100 |
| A-38 | 10 |
| A-39 | 1.0 |
| A-40 | 10~100 |
| A-41 | 100~1000 |
| A-42 | 6.3 |
| A-43 | 0.49 |
| A-44 | 0.16 |
| A-45 | 34 |
| A-46 | 100~1000 |
| A-47 | 100~1000 |
| A-48 | 100~1000 |
| A-49 | 100~1000 |
| B-01 | 1.4 |
| B-02 | 2.2 |
| B-03 | 100~1000 |
| B-04 | 7.4 |
| B-05 | 11 |
| B-06 | 3.3 |
| B-07 | 4.3 |
| B-08 | 2.8 |
| B-09 | 2.2 |
| B-10 | 12 |
| B-11 | 5.1 |
| B-12 | 6.3 |
| B-13 | 8.9 |
| B-14 | 6.6 |
| B-15 | 31 |
| B-16 | 5.3 |
| B-17 | 1.4 |
| B-18 | 7.2 |
| B-19 | 6.9 |
| B-20 | 0.43 |
| B-21 | 10~100 |
| B-22 | 10~100 |
| B-23 | 10~100 |
| B-24 | 100~1000 |
| B-25 | 10~100 |
| B-26 | 100~1000 |
| B-27 | 10~100 |
| B-28 | <10 |
| B-29 | 10~100 |
| B-30 | 10~100 |
| B-31 | 10~100 |
| B-32 | 100~1000 |
| B-33 | 100~1000 |
| B-34 | 100~1000 |
| B-35 | 100~1000 |
| B-36 | 10~100 |
| B-37 | <10 |
| B-38 | 10~100 |
| B-39 | 10~100 |
| B-40 | 10~100 |
| B-41 | 10~100 |

TABLE 6-2

| Example No. | IC$_{50}$ value (nmol/L) |
|---|---|
| B-42 | <10 |
| C-01 | 21 |
| C-02 | 13 |
| C-03 | 8.6 |
| C-04 | 10~100 |
| C-05 | 21 |
| C-06 | 17 |

TABLE 6-2-continued

| Example No. | IC$_{50}$ value (nmol/L) |
|---|---|
| C-07 | 7.1 |
| C-08 | 10~100 |
| C-09 | 27 |
| C-10 | 6.5 |
| C-11 | 3.9 |
| C-12 | 4.3 |
| C-13 | 16 |
| C-14 | 14 |
| C-15 | 22 |
| C-16 | 100~1000 |
| C-17 | 100~1000 |
| C-18 | 9.0 |
| C-19 | 2.2 |
| C-20 | 10~100 |
| C-21 | 14 |
| C-22 | 8.8 |
| D-01 | 15 |
| D-02 | 10~100 |
| D-03 | 14 |
| D-04 | 100~1000 |
| D-05 | 2.5 |
| D-06 | 4.6 |
| D-07 | 5.5 |
| D-08 | 10~100 |
| D-09 | 10~100 |
| D-10 | 7.1 |
| D-11 | 10~100 |
| D-12 | 7.0 |
| D-13 | 3.5 |
| D-14 | 4.7 |
| D-15 | 10~100 |
| D-16 | 10~100 |
| D-17 | 3.9 |
| D-18 | 1.5 |
| D-19 | 10~100 |
| D-20 | 20 |
| D-21 | 7.5 |
| D-22 | 12 |
| D-23 | 3.3 |
| D-24 | 10~100 |
| D-25 | 100~1000 |
| D-26 | 4.4 |
| D-27 | 5.3 |
| D-28 | 10~100 |
| D-29 | 10~100 |
| D-30 | 2.8 |
| D-31 | 2.9 |
| D-32 | 17 |
| D-33 | 9.1 |
| D-34 | 3.3 |
| D-35 | 18 |
| D-36 | 0.61 |
| D-37 | 12 |
| D-38 | 10~100 |
| D-39 | 10~100 |
| D-40 | 100~1000 |
| D-41 | 2.7 |
| D-42 | 7.9 |
| D-43 | 15 |
| D-44 | 16 |
| D-45 | 10~100 |
| D-46 | 10~100 |
| D-47 | 100~1000 |
| D-48 | 10~100 |
| D-49 | 100~1000 |
| D-50 | 100~1000 |
| D-51 | 100~1000 |
| D-52 | 100~1000 |
| D-53 | 10~100 |
| D-54 | 10~100 |
| D-55 | 100~1000 |
| D-56 | 10~100 |
| D-57 | 10~100 |
| D-58 | 10~100 |
| D-59 | 100~1000 |
| D-60 | 100~1000 |
| D-61 | 10~100 |

Test Example 2

Measurement of V1b Receptor Antagonistic Activity

CHO cells (ATCC) so modified as to express human V1b receptor in a stable manner were cultured in Ham's F-12 medium (containing 10% FBS and 0.5 mg/mL Geneticin). On the day before the test, seeding was conducted at a density of 20,000 cells/well in a 96-well poly-D-lysine coated black plate. On the day of the test, the culture medium was removed, and a loading solution (1×HBSS, 10 mmol/L HEPES, 0.1% bovine serum albumin, 1.25 mmol/L Probenecid, 0.02% Pluronic F-127, 1.5 µmol/L Fluo-4-AM, pH 7.4) was added to each well, followed by incubation in a $CO_2$ incubator for an hour. After the incubation, the loading solution was removed. A test solution (1×HBSS, 10 mmol/L HEPES, 0.1% bovine serum albumin, 1.25 mmol/L Probenecid, pH 7.4) containing any one of test compounds was added to wells, followed by incubation in a $CO_2$ incubator for 30 minutes. The test compound was serially diluted with DMSO so that it would have final concentrations of 0.1 nmol/L to 1 mmol/L at the time of assaying. After the incubation, fluorescence intensity levels were measured and AVP added by means of FDSS (Hamamatsu Photonics K.K.); AVP was added to give a final concentration of 2.5 nmol/L at the time of assaying. At this concentration, AVP shows 70 to 80% of its maximum response. The fluorescence level in a well to which neither test compound nor AVP was added was defined as 0%, and the fluorescence level in a well to which only AVP was added and no test compound was added was defined as 100%. A dose-response curve was plotted from fluorescence levels after the addition of AVP in the presence of a test compound at various concentrations, and the 50% inhibitory concentration (IC$_{50}$ value) of the compound was calculated. The results are shown in Table 7.

TABLE 7

| Example No | IC$_{50}$ value (nmol/L) |
|---|---|
| A-02 | 3.2 |
| B-02 | 10 |
| C-12 | 32 |
| D-01 | 21 |
| D-13 | 13 |
| D-14 | 12 |
| D-18 | 0.65 |

INDUSTRIAL APPLICABILITY

The present invention is able to provide agents for treating or preventing mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, alopecia, and so forth.

The invention claimed is:

1. An azole derivative represented by Formula (I):

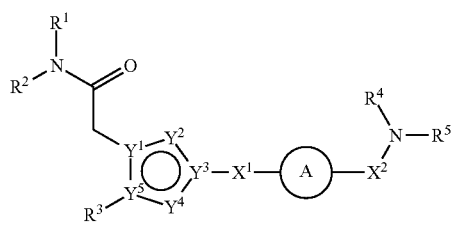

[in Formula (I),

R$^1$ represents a hydrogen atom, C$_{1-5}$ alkyl (the C$_{1-5}$ alkyl is optionally substituted by one to three groups selected from the group consisting of hydroxy, halogen atoms, cyano, C$_{3-7}$ cycloalkyl, and C$_{1-5}$ alkoxy), C$_{3-7}$ cycloalkyl, or 4- to 8-membered saturated heterocycle;

R$^2$ represents a hydrogen atom or C$_{1-5}$ alkyl;

R$^3$ represents aryl or heteroaryl (the aryl and heteroaryl are optionally substituted by one or two groups selected from the group consisting of C$_{1-5}$ alkoxy, C$_{1-5}$ alkyl, halogen atoms, trifluoromethyl, trifluoromethoxy, cyano, hydroxy, difluoromethoxy, and C$_{1-5}$ alkylsulfonyl);

R$^4$ and R$^5$ which may be the same or different each represent a hydrogen atom, C$_{1-5}$ alkyl (the C$_{1-5}$ alkyl is optionally substituted by one to three groups selected from the group consisting of hydroxy, halogen atoms, cyano, C$_{3-7}$ cycloalkyl, and C$_{1-5}$ alkoxy), C$_{3-7}$ cycloalkyl, or a 4- to 8-membered saturated or unsaturated heterocycle containing one or more nitrogen, oxygen or sulfur atoms in the ring (the 4- to 8-membered saturated or unsaturated heterocycle is optionally substituted by one or two groups selected from the group consisting of hydroxy, C$_{1-5}$ alkyl, C$_{1-5}$ alkoxy, halogen atoms, cyano, C$_{2-5}$ alkanoyl, and trifluoromethyl), or R$^4$ and R$^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, C$_{1-5}$ alkyl (the C$_{1-5}$ alkyl is optionally substituted by one or two hydroxyl groups), C$_{1-5}$ alkoxy, halogen atoms, cyano, C$_{2-5}$ alkanoyl, oxo, aminocarbonyl, mono-C$_{1-5}$ alkylaminocarbonyl, di-C$_{1-5}$ alkylaminocarbonyl, trifluoromethyl, amino, mono-C$_{1-5}$ alkylamino, di-C$_{1-5}$ alkylamino and C$_{2-5}$ alkanoylamino, and the 4- to 8-membered saturated or unsaturated heterocycle optionally has a C$_{1-5}$ alkylene group crosslinking two different carbon atoms in the ring) or form 2-oxa-6-azaspiro[3.3]hept-6-yl or 7-oxa-2-azaspiro[3.5]non-2-yl;

the optionally substituted azole ring which is represented by the following formula (α):

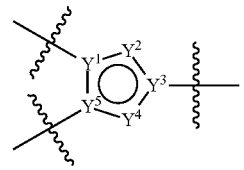

has any one of the structures in the following formula group (II):

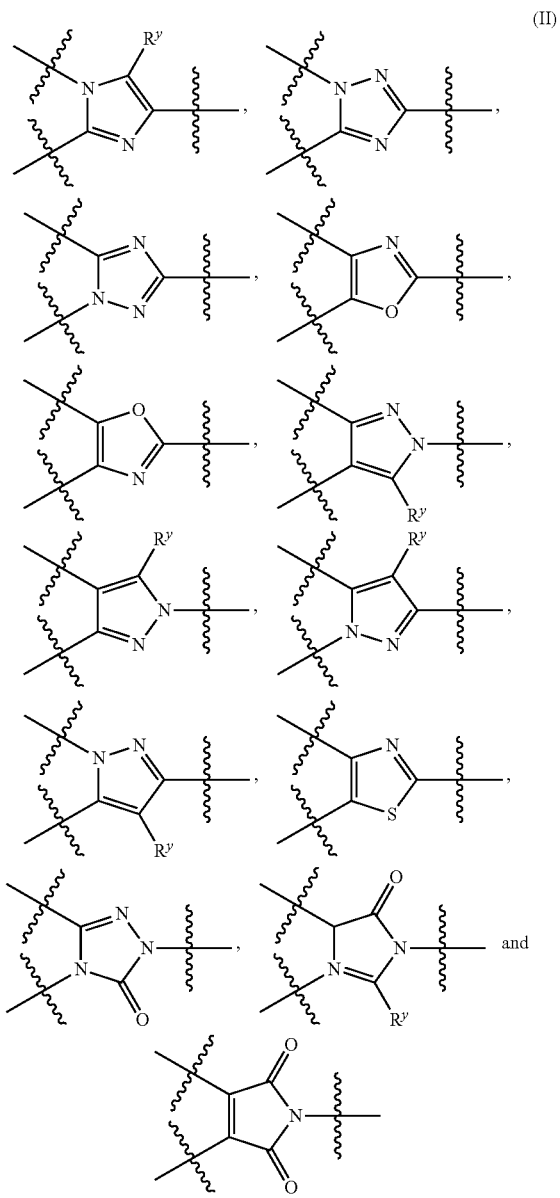

where

R$^y$ represents a hydrogen atom or C$_{1-5}$ alkyl;

X$^1$ and X$^2$ are such that i) when X$^1$ is a single bond or the formula —CO—, X$^2$ represents —C$_{1-5}$ alkylene- or —O—C$_{1-5}$ alkylene-; and ii) when $X^1$ is the formula —$CONR^{x1}$—, $X^2$ represents a single bond;

$R^{x1}$ represents a hydrogen atom or $C_{1-5}$ alkyl; and the ring A represents a benzene ring, a 6-membered aromatic heterocycle (the benzene ring and the 6-membered aromatic heterocycle are optionally substituted by one or two groups selected from the group consisting of halogen atoms and $C_{1-5}$ alkoxy), a 4- to 8-membered saturated or partially unsaturated heterocycle containing one or two nitrogen atoms (the 4- to 8-membered saturated or unsaturated heterocycle is optionally substituted by one oxo) or $C_{3-7}$ cycloalkane] or a pharmaceutically acceptable salt of the azole derivative.

2. The azole derivative or pharmaceutically acceptable salt thereof according to claim 1, wherein in the above Formula (I), $R^4$ and $R^5$ which may be the same or different each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or a 4- to 8-membered saturated or unsaturated heterocycle containing one or more nitrogen, oxygen or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl or 7-oxa-2-azaspiro[3.5]non-2-yl.

3. The azole derivative or pharmaceutically acceptable salt thereof according to claim 1, wherein in the above Formula (I), $X^1$ represents a single bond;

$X^2$ represents —$C_{1-5}$ alkylene- or —O—$C_{1-5}$ alkylene-; and the ring A represents a benzene ring, a 6-membered aromatic heterocycle (the benzene ring and the 6-membered aromatic heterocycle are optionally substituted by one or two groups selected from the group consisting of halogen atoms and $C_{1-5}$ alkoxy) or a 4- to 8-membered saturated or unsaturated heterocycle containing one or two nitrogen atoms (the 4- to 8-membered saturated or unsaturated heterocycle is optionally substituted by one oxo).

4. The azole derivative or pharmaceutically acceptable salt thereof according to claim 1, wherein in the above Formula (I), the ring A represents a benzene ring or a 6-membered aromatic heterocycle (the benzene ring and the 6-membered aromatic heterocycle are optionally substituted by one or two groups selected from the group consisting of halogen atoms and $C_{1-5}$ alkoxy).

5. The azole derivative or pharmaceutically acceptable salt thereof according to claim 1, wherein in the above Formula (I), the ring A represents a benzene ring or a pyridine ring (the benzene ring and the pyridine ring are optionally substituted by one or two groups selected from the group consisting of halogen atoms and $C_{1-5}$ alkoxy).

6. The azole derivative or pharmaceutically acceptable salt thereof according to claim 1, wherein in the above Formula (I), $R^1$ is a $C_{1-5}$ alkyl;

$R^2$ is a hydrogen atom; and $R^3$ is phenyl or pyridyl (the phenyl and pyridyl are optionally substituted by one or two groups selected from the group consisting of $C_{1-5}$ alkyl, $C_{1-5}$ alkoxy, halogen atoms, cyano, trifluoromethyl, difluoromethoxy, trifluoromethoxy, and $C_{1-5}$ alkylsulfonyl).

7. The azole derivative or pharmaceutically acceptable salt thereof according to claim 1, wherein in the above Formula (I), the optionally substituted azole ring which is represented by the following formula (α):

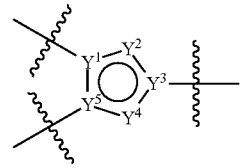

has any one of the structures in the following formula group (III):

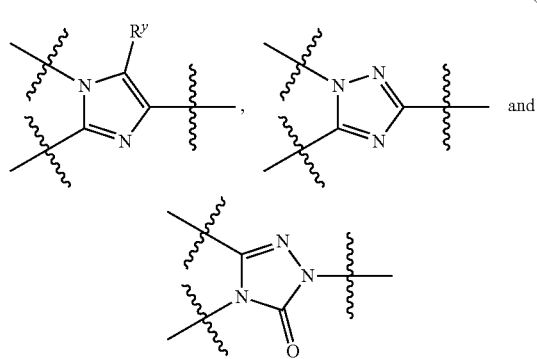

where $R^y$ represents a hydrogen atom or a methyl group.

8. The azole derivative or pharmaceutically acceptable salt thereof according to claim 1, wherein in the above Formula (I), $X^1$ is a single bond;

$X^2$ is ethylene or methylethylene; and $R^4$ and $R^5$, together with the adjoining nitrogen atom, form a 4- to 8-membered saturated or unsaturated heterocycle optionally containing one or more nitrogen, oxygen or sulfur atoms in the ring in addition to the adjoining nitrogen atom (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxyl groups), $C_{1-5}$ alkoxy, halogen atoms, cyano, $C_{2-5}$ alkanoyl and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl.

9. The azole derivative or pharmaceutically acceptable salt thereof according to claim 1, wherein in the above Formula (I), $R^4$ and $R^5$, together with the adjoining nitrogen atom, form a 5- or 6-membered saturated heterocycle optionally containing one or more oxygen atoms in the ring in addition to the adjoining nitrogen atom (the 6-membered saturated heterocycle is optionally substituted by one or two groups selected from the group consisting of hydroxyl and $C_{1-5}$ alkyl, and the 6-membered saturated heterocycle optionally has a $C_{1-5}$ alkylene group crosslinking two different carbon atoms in the ring) or form 2-oxa-6-azaspiro[3.3]hept-6-yl.

10. The azole derivative or pharmaceutically acceptable salt thereof according to claim 1, wherein the azole derivative represented by Formula (1) is selected from the group consisting of:

2-[2-(3-chlorophenyl)-4-{4-[2-(piperidin-1-yl)ethyl]phenyl}-1H-imidazol-1-yl]-N-(propan-2-yl)acetamide;

2-[2-(3-chlorophenyl)-4-{4-[2-(morpholin-4-yl)ethyl]phenyl}-1H-imidazol-1-yl]-N-(propan-2-yl)acetamide;

2-[2-(3-chlorophenyl)-4-(4-{2-[3-(hydroxymethyl)pyrrolidin-1-yl]ethyl}phenyl)-1H-imidazol-1-yl]-N-(propan-2-yl)acetamide;

2-[2-(3-chlorophenyl)-4-{4-[2-(3-oxa-8-azabicyclo[3.2.1]oct-8-yl)ethyl]phenyl}-1H-imidazol-1-yl]-N-(propan-2-yl)acetamide;

2-[2-(4-fluoro-3-methoxyphenyl)-4-{4-[2-(piperidin-1-yl)ethyl]phenyl}-1H-imidazol-1-yl]-N-(propan-2-yl)acetamide;

2-[2-(4-fluoro-3-methoxyphenyl)-4-{4-[2-(morpholin-4-yl)ethyl]phenyl}-1H-imidazol-1-yl]-N-(propan-2-yl)acetamide;

2-[2-(4-fluoro-3-methoxyphenyl)-4-{4-[2-(pyrrolidin-1-yl)ethyl]phenyl}-1H-imidazol-1-yl]-N-(propan-2-yl)acetamide;

2-[2-(4-fluoro-3-methoxyphenyl)-4-(4-{2-[(2R)-2-methylpyrrolidin-1-yl]ethyl}phenyl)-1H-imidazol-1-yl]-N-(propan-2-yl)acetamide;

2-[2-(4-fluoro-3-methoxyphenyl)-4-{4-[2-(3-hydroxy-8-azabicyclo[3.2.1]oct-8-yl)ethyl]phenyl}-1H-imidazol-1-yl]-N-(propan-2-yl)acetamide;

2-[2-(4-fluoro-3-methoxyphenyl)-4-{4-[2-(3-methoxypiperidin-1-yl)ethyl]phenyl}-1H-imidazol-1-yl]-N-(propan-2-yl)acetamide;

2-[4-{4-[2-(2,6-dimethylmorpholin-4-yl)ethyl]phenyl}-2-(4-fluoro-3-methoxyphenyl)-1H-imidazol-1-yl]-N-(propan-2-yl)acetamide;

2-[2-(4-fluoro-3-methoxyphenyl)-4-{4-[2-(3-methylpyrrolidin-1-yl)ethyl]phenyl}-1H-imidazol-1-yl]-N-(propan-2-yl)acetamide;

2-[2-(4-fluoro-3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide;

2-[2-(4-fluoro-3-methoxyphenyl)-4-{4-[2-(1,4-oxazepan-4-yl)ethyl]phenyl}-1H-imidazol-1-yl]-N-(propan-2-yl)acetamide;

2-[4-{4-[2-(3,5-dimethylmorpholin-4-yl)ethyl]phenyl}-2-(4-fluoro-3-methoxyphenyl)-1H-imidazol-1-yl]-N-(propan-2-yl)acetamide;

2-[2-(3-chlorophenyl)-4-{5-[2-(morpholin-4-yl)ethyl]pyridin-2-yl}-1H-imidazol-1-yl]-N-(propan-2-yl)acetamide;

2-[2-(3-chlorophenyl)-4-{5-[2-(3-oxa-8-azabicyclo[3.2.1]oct-8-yl)ethyl]pyridin-2-yl}-1H-imidazol-1-yl]-N-(propan-2-yl)acetamide;

2-[2-(3-chlorophenyl)-4-{6-[2-(morpholin-4-yl)ethyl]pyridin-3-yl}-1H-imidazol-1-yl]-N-(propan-2-yl)acetamide;

2-[2-(3-methoxyphenyl)-5-methyl-4-{4-[2-(morpholin-4-yl)ethyl]phenyl}-1H-imidazol-1-yl]-N-(propan-2-yl)acetamide;

2-[2-(3-methoxyphenyl)-4-{4-[2-(morpholin-4-yl)ethyl]phenyl}-1H-imidazol-1-yl]-N-(propan-2-yl)acetamide;

2-[2-(3-chloro-4-fluorophenyl)-4-{4-[2-(morpholin-4-yl)ethyl]phenyl}-1H-imidazol-1-yl]-N-(propan-2-yl)acetamide;

2-[2-(3-methoxyphenyl)-4-{4-[2-(3-oxa-8-azabicyclo[3.2.1]oct-8-yl)ethyl]phenyl}-1H-imidazol-1-yl]-N-(propan-2-yl)acetamide;

2-[2-(3-chlorophenyl)-4-{2-fluoro-4-[2-(morpholin-4-yl)ethyl]phenyl}-1H-imidazol-1-yl]-N-(propan-2-yl)acetamide;

2-[2-(3-chlorophenyl)-4-{4-[2-(morpholin-4-yl)propyl]phenyl}-1H-imidazol-1-yl]-N-(propan-2-yl)acetamide;

2-[5-(3-chlorophenyl)-3-{4-[2-(3-oxa-8-azabicyclo[3.2.1]oct-8-yl)ethyl]phenyl}-1H-1,2,4-triazol-1-yl]-N-(propan-2-yl)acetamide;

2-[5-(3-chlorophenyl)-3-{4-[2-(morpholin-4-yl)ethyl]phenyl}-1H-1,2,4-triazol-1-yl]-N-(propan-2-yl)acetamide;

2-[5-(3-chlorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;

2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;

2-[5-(4-fluoro-3-methoxyphenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;

N-tert-butyl-2-[5-(3-methoxyphenyl)-3-{5-[2-(3-oxa-8-azabicyclo[3.2.1]oct-8-yl)ethyl]pyridin-2-yl}-1H-1,2,4-triazol-1-yl]acetamide;

2-[5-(3-chloro-4-fluorophenyl)-3-{5-[2-(3-oxa-8-azabicyclo[3.2.1]oct-8-yl)ethyl]pyridin-2-yl}-1H-1,2,4-triazol-1-yl]-N-(propan-2-yl)acetamide;

N-tert-butyl-2-[5-(3-chlorophenyl)-3-{5-[2-(3-oxa-8-azabicyclo[3.2.1]oct-8-yl)ethyl]pyridin-2-yl}-1H-1,2,4-triazol-1-yl]acetamide;

2-[5-(3-chlorophenyl)-3-{5-[2-(morpholin-4-yl)ethyl]pyridin-2-yl}-1H-1,2,4-triazol-1-yl]-N-(propan-2-yl)acetamide;

N-tert-butyl-2-[5-(3-chlorophenyl)-3-{5-[2-(morpholin-4-yl)ethyl]pyridin-2-yl}-1H-1,2,4-triazol-1-yl]acetamide;

2-[5-(3-chloro-4-fluorophenyl)-3-{5-[2-(morpholin-4-yl)ethyl]pyridin-2-yl}-1H-1,2,4-triazol-1-yl]-N-(propan-2-yl)acetamide;

2-[5-(4-fluoro-3-methoxyphenyl)-3-{5-[2-(morpholin-4-yl)ethyl]pyridin-2-yl}-1H-1,2,4-triazol-1-yl]-N-(propan-2-yl)acetamide;

N-tert-butyl-2-[5-(3-methoxyphenyl)-3-{5-[2-(morpholin-4-yl)ethyl]pyridin-2-yl}-1H-1,2,4-triazol-1-yl]acetamide;

2-[5-(3-methoxyphenyl)-3-{4-[2-(morpholin-4-yl)ethyl]phenyl}-1H-1,2,4-triazol-1-yl]-N-(propan-2-yl)acetamide;

2-[5-(3-methoxyphenyl)-3-{4-[2-(3-oxa-8-azabicyclo[3.2.1]oct-8-yl)ethyl]phenyl}-1H-1,2,4-triazol-1-yl]-N-(propan-2-yl)acetamide;

2-[3-{2-fluoro-4-[2-(morpholin-4-yl)ethyl]phenyl}-5-(3-methoxyphenyl)-1H-1,2,4-triazol-1-yl]-N-(propan-2-yl) acetamide;

2-[3-{3-fluoro-4-[2-(morpholin-4-yl)ethyl]phenyl}-5-(3-methoxyphenyl)-1H-1,2,4-triazol-1-yl]-N-(propan-2-yl)acetamide;

2-[5-(3-methoxyphenyl)-3-{4-[2-(3-oxa-8-azabicyclo[3.2.1]oct-8-yl)propyl]phenyl}-1H-1,2,4-triazol-1-yl]-N-(propan-2-yl)acetamide;

2-[5-(3-methoxyphenyl)-3-{4-[2-(7-oxa-2-azaspiro[3.5]non-2-yl)ethyl]phenyl}-1H-1,2,4-triazol-1-yl]-N-(propan-2-yl)acetamide;

2-[5-(3-methoxyphenyl)-3-{4-[2-(2-oxa-6-azaspiro[3.3]hept-6-yl)ethyl]phenyl}-1H-1,2,4-triazol-1-yl]-N-(propan-2-yl)acetamide;

2-[1-(3-chlorophenyl)-3-{4-[2-(morpholin-4-yl)ethyl]phenyl}-1H-1,2,4-triazol-5-yl]-N-(propan-2-yl)acetamide;

2-[1-(3-chlorophenyl)-3-{4-[2-(3-oxa-8-azabicyclo[3.2.1]oct-8-yl)ethyl]phenyl}-1H-1,2,4-triazol-5-yl]-N-(propan-2-yl)acetamide;

2-[5-(3-chlorophenyl)-3-{4-[2-(morpholin-4-yl)ethyl]phenyl}-2-oxo-2,3-dihydro-1H-imidazol-1-yl]-N-(propan-2-yl)acetamide;

2-[4-(3-chlorophenyl)-2-{4-[2-(piperidin-1-yl)ethyl]phenyl}-1,3-oxazol-5-yl]-N-(propan-2-yl)acetamide;

2-[4-(3-chlorophenyl)-2-{4-[2-(morpholin-4-yl)ethyl]phenyl}-1,3-oxazol-5-yl]-N-(propan-2-yl)acetamide;

2-[4-(3-chlorophenyl)-2-{4-[2-(2-oxa-6-azaspiro[3.3]hept-6-yl)ethyl]phenyl}-1,3-oxazol-5-yl]-N-(propan-2-yl) acetamide;

2-[5-(3-chlorophenyl)-2-{4-[2-(piperidin-1-yl)ethyl]phenyl}-1,3-thiazol-4-yl]-N-(propan-2-yl)acetamide;

2-[5-(3-chlorophenyl)-2-{4-[2-(morpholin-4-yl)ethyl]phenyl}-1,3-thiazol-4-yl]-N-(propan-2-yl)acetamide;

2-[3-(3-chlorophenyl)-1-{4-[2-(piperidin-1-yl)ethyl]phenyl}-1H-pyrazol-4-yl]-N-(propan-2-yl)acetamide;

2-[3-(3-chlorophenyl)-1-{4-[2-(morpholin-4-yl)ethyl]phenyl}-1H-pyrazol-4-yl]-N-(propan-2-yl)acetamide;

2-[5-(3-chlorophenyl)-3-{4-[2-(morpholin-4-yl)ethyl]phenyl}-1H-pyrazol-1-yl]-N-(propan-2-yl)acetamide;

2-[4-(3-chlorophenyl)-1-{4-[2-(morpholin-4-yl)ethyl]phenyl}-2,5-dioxo-2,5-dihydro-1H-pyrrol-3-yl]-N-(propan-2-yl)acetamide;

2-[4-(3-chlorophenyl)-1-{4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

N-tert-butyl-2-[4-(4-fluoro-3-methoxyphenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-methoxyphenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(4-fluoro-3-methoxyphenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

N-tert-butyl-2-[4-(3-chlorophenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-chlorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

2-[4-(3-chlorophenyl)-1-{4-[2-(morpholin-4-yl)propyl]phenyl}-5-oxo-4,5-dihydro-1H-1,2,4-triazol-3-yl]-N-(propan-2-yl)acetamide;

2-[4-(3-chlorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

2-[4-(3-chlorophenyl)-1-{3-fluoro-4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{3-fluoro-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[4-(3-chlorophenyl)-1-{3-methoxy-4-[2-(morpholin-4-yl)ethyl]phenyl}-5-oxo-4,5-dihydro-1H-1,2,4-triazol-3-yl]-N-(propan-2-yl)acetamide;

2-[4-(3-chlorophenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[4-(3-chloro-4-fluorophenyl)-1-{4-[2-(morpholin-4-yl)ethyl]phenyl}-5-oxo-4,5-dihydro-1H-1,2,4-triazol-3-yl]-N-(propan-2-yl)acetamide;

2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

N-tert-butyl-2-[4-(3-chloro-4-fluorophenyl)-1-{4-[2-(morpholin-4-yl)ethyl]phenyl}-5-oxo-4,5-dihydro-1H-1,2,4-triazol-3-yl]acetamide;

N-tert-butyl-2-[4-(3-chloro-4-fluorophenyl)-1-{4-[2-(3-oxa-8-azabicyclo[3.2.1]oct-8-yl)ethyl]phenyl}-5-oxo-4,5-dihydro-1H-1,2,4-triazol-3-yl]acetamide;

N-tert-butyl-2-[4-(3-chloro-4-fluorophenyl)-1-{5-[2-(morpholin-4-yl)ethyl]pyridin-2-yl}-5-oxo-4,5-dihydro-1H-1,2,4-triazol-3-yl]acetamide;

N-tert-butyl-2-[4-(3-chloro-4-fluorophenyl)-1-{5-[2-(3-oxa-8-azabicyclo[3.2.1]oct-8-yl)ethyl]pyridin-2-yl}-5-oxo-4,5-dihydro-1H-1,2,4-triazol-3-yl]acetamide;

2-[4-(3-chlorophenyl)-1-{5-[2-(3-oxa-8-azabicyclo[3.2.1]oct-8-yl)propyl]pyridin-2-yl}-5-oxo-4,5-dihydro-1H-1,2,4-triazol-3-yl]-N-(propan-2-yl)acetamide;

2-(1-{4-[2-(morpholin-4-yl)ethyl]phenyl}-5-oxo-4-[3-(trifluoromethyl)phenyl]-4,5-dihydro-1H-1,2,4-triazol-3-yl)-N-(propan-2-yl)acetamide;

2-[4-(3-chloro-4-fluorophenyl)-1-{4-[2-(3-oxa-8-azabicyclo[3.2.1]oct-8-yl)propyl]phenyl}-5-oxo-4,5-dihydro-1H-1,2,4-triazol-3-yl]-N-(propan-2-yl)acetamide;

2-[4-(4-fluoro-3-methoxyphenyl)-1-{4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[4-(4-fluoro-3-methoxyphenyl)-1-{3-methoxy-4-[2-(3-oxa-8-azabicyclo[3.2.1]oct-8-yl)ethyl]phenyl}-5-oxo-4,5-dihydro-1H-1,2,4-triazol-3-yl]-N-(propan-2-yl)acetamide;

2-[1-{3-methoxy-4-[2-(3-oxa-8-azabicyclo[3.2.1]oct-8-yl)ethyl]phenyl}-4-(3-methoxyphenyl)-5-oxo-4,5-dihydro-1H-1,2,4-triazol-3-yl]-N-(propan-2-yl)acetamide;

2-[4-(3-chloro-4-fluorophenyl)-5-oxo-1-{4-[2-(pyrrolidin-1-yl)ethyl]phenyl}-4,5-dihydro-1H-1,2,4-triazol-3-yl]-N-(propan-2-yl)acetamide;

2-[4-(3-chloro-4-fluorophenyl)-5-oxo-1-{4-[2-(piperidin-1-yl)ethyl]phenyl}-4,5-dihydro-1H-1,2,4-triazol-3-yl]-N-(propan-2-yl)acetamide; and 2-[2-(3-chlorophenyl)-4-{4-[2-(2-oxa-6-azaspiro[3.3]hept-6-yl)ethyl]phenyl}-1H-imidazol-1-yl]-N-(propan-2-yl)acetamide, or pharmaceutically acceptable salts of these compounds.

11. A pharmaceutical composition comprising the azole derivative or pharmaceutically acceptable salt thereof according to claim 1 as an active ingredient and a pharmaceutically acceptable carrier.

12. A pharmaceutical composition comprising the azole derivative or pharmaceutically acceptable salt thereof according to claim 10 as an active ingredient and a pharmaceutically acceptable carrier.

13. A method for treating or mood disorder mediated by AVP receptors, anxiety disorder mediated by AVP receptors, hypertension, gastrointestinal disease mediated by AVP receptors, drug addiction, cerebral ischemia, cerebral edema or head injury, comprising administering to a subject in need of said treating an effective amount of the azole derivative or pharmaceutically acceptable salt thereof according to claim 1.

14. A method for treating mood disorder mediated by AVP receptors, anxiety disorder mediated by AVP receptors, hypertension, gastrointestinal disease mediated by AVP receptors, drug addiction, cerebral ischemia, cerebral edema or head injury, comprising administering to a subject in need of said treating an effective amount of the azole derivative or pharmaceutically acceptable salt thereof according to claim 10.

* * * * *